United States Patent
Thakkar et al.

(10) Patent No.: US 9,233,983 B2
(45) Date of Patent: Jan. 12, 2016

(54) SUBSTITUTED HETERO-BICYCLIC COMPOUNDS, COMPOSITIONS AND MEDICINAL APPLICATIONS THEREOF

(71) Applicant: ADVINUS THERAPEUTICS LIMITED, Bangalore (IN)

(72) Inventors: Mahesh Thakkar, Pune (IN); Summon Koul, Pune (IN); Debnath Bhuniya, Pune (IN); Kasim Mookhtiar, Pune (IN); Santosh Kurhade, Pune (IN); Yogesh Munot, Pune (IN); Tanaji Mengawade, Pune (IN); Bheemashankar A. Kulkarni, Pune (IN)

(73) Assignee: ADVINUS THERAPEUTICS LIMITED, Bangalore (IN)

( * ) Notice: Subject to any disclaimer, the term of this patent is extended or adjusted under 35 U.S.C. 154(b) by 0 days.

(21) Appl. No.: 14/509,793

(22) Filed: Oct. 8, 2014

(65) Prior Publication Data
US 2015/0064196 A1    Mar. 5, 2015

Related U.S. Application Data

(63) Continuation-in-part of application No. PCT/IN2013/000259, filed on Apr. 18, 2013.

(30) Foreign Application Priority Data

Apr. 20, 2012 (IN) .......................... 1573/CHE/2012

(51) Int. Cl.
| | |
|---|---|
| C07D 403/04 | (2006.01) |
| C07D 413/14 | (2006.01) |
| C07D 519/00 | (2006.01) |
| C07D 403/14 | (2006.01) |
| A61K 45/06 | (2006.01) |
| A61K 31/519 | (2006.01) |
| A61K 31/5377 | (2006.01) |
| A61K 31/553 | (2006.01) |
| C07D 471/04 | (2006.01) |
| C07D 487/04 | (2006.01) |

(52) U.S. Cl.
CPC ............ *C07D 519/00* (2013.01); *A61K 31/519* (2013.01); *A61K 31/5377* (2013.01); *A61K 31/553* (2013.01); *A61K 45/06* (2013.01); *C07D 403/14* (2013.01); *C07D 413/14* (2013.01); *C07D 471/04* (2013.01); *C07D 487/04* (2013.01)

(58) Field of Classification Search
CPC .......................... C07D 403/04; C07D 413/14
See application file for complete search history.

(56) References Cited

U.S. PATENT DOCUMENTS

| 2007/0129364 A1 | 6/2007 | Dong et al. | |
| 2014/0243306 A1* | 8/2014 | Heng et al. | 514/210.18 |

FOREIGN PATENT DOCUMENTS

| WO | WO-03/000688 A1 | 1/2003 |
| WO | WO-03/000695 A1 | 1/2003 |
| WO | WO-2007/002313 A2 | 1/2007 |
| WO | WO-2007/027729 A1 | 3/2007 |
| WO | WO-2008/078091 A1 | 7/2008 |
| WO | WO-2009/098144 A1 | 8/2009 |
| WO | WO-2010/000633 A1 | 1/2010 |
| WO | WO-2010/003133 A2 | 1/2010 |
| WO | WO-2010/005783 A1 | 1/2010 |

(Continued)

OTHER PUBLICATIONS

Burger et al., Activity and tolerability of the Bruton's tyrosine kinase (BTK) inhibitor PCI-32765 in patients with chronic lymphocytic leukemia/small lymphocytic lymphoma (CLL/SLL): Interim results of a phase Ib/II study, J. Clin. Oncol., 6508 abstract (2011).

(Continued)

*Primary Examiner* — Bruck Kifle
(74) *Attorney, Agent, or Firm* — Marshall, Gerstein & Borun LLP

(57) ABSTRACT

The present disclosure provides hetero-bicyclic compounds of formula (I), their tautomers, polymorphs, stereoisomers, prodrugs, solvates, hydrates, N-oxides, co-crystals, pharmaceutically acceptable salts, pharmaceutical compositions containing them and methods of treating conditions and diseases that are mediated by Bruton's tyrosine kinase (Btk) activity, The disclosure also relates to the process of preparation of compounds of Formula (I).

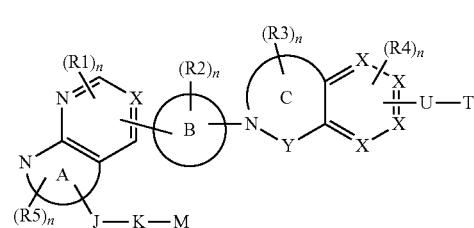

These compounds are useful in the treatment, prevention, prophylaxis, management, or adjunct treatment of all medical conditions related to inhibition of Bruton's tyrosine kinase (Btk), such as inflammatory and/or autoimmune disorder, cell proliferation, rheumatoid arthritis, psoriasis, psoriatic arthritis, transplant rejection, graft-versus-host disease, multiple sclerosis, inflammatory bowel disease, allergic diseases, asthma, type 1 diabetes, myasthenia gravis, hematopoetic disfunction, B-cell malignancies, systemic lupus, erythematosus or other disorders.

6 Claims, No Drawings

(56) References Cited

FOREIGN PATENT DOCUMENTS

| WO | WO-2010/006970 A1 | 1/2010 |
|----|-------------------|--------|
| WO | WO-2010/007114 A2 | 1/2010 |
| WO | WO-2010/048149 A2 | 4/2010 |
| WO | WO-2010/068788 A1 | 6/2010 |
| WO | WO-2010/068806 A1 | 6/2010 |
| WO | WO-2010/068810 A2 | 6/2010 |
| WO | WO-2010/080481 A1 | 7/2010 |
| WO | WO-2010/100070 A1 | 9/2010 |
| WO | WO-2010/122038 A1 | 10/2010 |
| WO | WO-2010/123870 A1 | 10/2010 |
| WO | WO-2010/144647 A1 | 12/2010 |
| WO | WO-2011/019780 A1 | 2/2011 |
| WO | WO-2011/046964 A2 | 4/2011 |
| WO | WO-2011/092140 A1 | 8/2011 |
| WO | WO-2013/008095 A1 | 1/2013 |
| WO | WO-2013/024078 A1 | 2/2013 |

OTHER PUBLICATIONS

Burger, Angiopoietin-2 in CLL, Blood, 116(4):508-9 (2010).
Di Paolo et al., Specific Btk inhibition suppresses B cell- and myeloid cell-mediated arthritis, Nat. Chem. Biol., 7(1):41-50 (2011).
Gustafsson et al., Trimethylaluminium mediated amide bond formation in a continuous flow microreactor as key to the synthesis of rimonabant and efaproxiral, Chem. Commun. (Camb.), 9:1100-2 (2008).
Hartwig, Approaches to catalyst discovery. New carbon-heteroatom and carbon-carbon bond formation, 71(8):1417-23 (1999).
Honingberg et al., The Bruton tyrosine kinase inhibitor PCI-32765 blocks B-cell activation and is efficacious in models of autoimmune disease and B-cell malignancy, Proc. Natl. Acad. Sci. USA, 107(29):13075-80 (2010).
Horwood et al., Bruton's tyrosine kinase is required for lipopolysaccharide-induced tumor necrosis factor alpha production, J. Exp. Med., 197(12):1603-11 (2003).
International Preliminary Report on Patentability, International application No. PCT/IB2013/000259, dated Oct. 21, 2014.
International Search Report and Written Opinion, International Application No. PCT/IN2013/000259, Oct. 4, 2013.
Jansson et al., Genes on the X chromosome affect development of collagen-induced arthritis in mice, Clin. Exp. Immunol., 94(3):459-65 (1993).
Jefferies et al., Bruton's tyrosine kinase is a Toll/interleukin-1 receptor domain-binding protein that participates in nuclear factor kappaB activation by Toll-like receptor 4, J. Biol. Chem., 278(28):26258-64 (2003).
Jester et al., Testing the promiscuity of commercial kinase inhibitors against the AGC kinase group using a split-luciferase screen, J. Med. Chem., 55(4):1526-37 (2012).
Kim et al., Imidazo[1,5-a]quinoxalines as irreversible BTK inhibitors for the treatment of rheumatoid arthritis, Bioorg. Med. Chem. Lett., 21(21):6258-63 (2011).
Klapars et al., A general and efficient copper catalyst for the amidation of aryl halides and the N-arylation of nitrogen heterocycles, J. Am. Chem. Soc., 123(31):7727-9 (2001).
Lou et al., Bruton's tyrosine kinase inhibitors: approaches to potent and selective inhibition, preclinical and clinical evaluation for inflammatory diseases and B cell malignancies, J. Med. Chem., 55(10):4539-50 (2012).
Miyaura et al., Palladium-catalyzed cross-coupling reactions of organoboron compounds, Chem. Rev., 95(7):2457-83 (1995).
Niiro et al., Regulation of B-cell fate by antigen-receptor signals, Nat. Rev. Immunol., 2(12):945-56 (2002).
Pan et al., Discovery of selective irreversible inhibitors for Bruton's tyrosine kinase, ChemMedChem., 2(1):58-61 (2007).
Perez et al., Switching reversibility to irreversibility in glycogen synthase kinase 3 inhibitors: clues for specific design of new compounds, J. Med. Chem., 54(12):4042-56 (2011).
Schaeffer et al., Tec family kinases in lymphocyte signaling and function, Curr. Opin. Immunol., 12(3):282-8 (2000).
Surry et al., Dialkylbiaryl Phosphines in Pd-Catalyzed Amination: A User's Guide, Chem. Sci., 2(1):27-50 (2011).
Zhou et al., Pd(PPh3)4-PEG 400 catalyzed protocol for the atom-efficient Stille cross-coupling reaction of organotin with aryl bromides, J. Org. Chem., 74(15):5599-602 (2009).

\* cited by examiner

SUBSTITUTED HETERO-BICYCLIC COMPOUNDS, COMPOSITIONS AND MEDICINAL APPLICATIONS THEREOF

CROSS-REFERENCE TO RELATED APPLICATION

This application is a Continuation-in-Part of PCT Application No. PCT/IN2013/000259, filed Apr. 18, 2013, entitled "Substituted Hetero-Bicyclic Compounds, Compositions and Medicinal Applications Thereof," which claims priority to Indian Application No. 1573/CHE/2012, filed Apr. 20, 2012, entitled "Substituted Hetero-Bicyclic Compounds, Compositions and Medicinal Applications Thereof," the entire disclosures of which are hereby incorporated by reference herein.

TECHNICAL FIELD

The present disclosure relates to a class of substituted hetero-bicyclic compounds of formula (I), their tautomers, polymorphs, stereoisomers, prodrugs, solvates, hydrates, N-oxides, co-crystals, pharmaceutically acceptable salts and pharmaceutical compositions containing them. The disclosure also relates to the process of preparation of compounds of Formula (I). These compounds are useful in the treatment, prevention, prophylaxis, management, or adjunct treatment of all medical conditions related to inhibition of Bruton's tyrosine kinase (Btk), such as inflammatory and/or autoimmune disorder, cell proliferation, rheumatoid arthritis, psoriasis, psoriatic arthritis, transplant rejection, graft-versus-host disease, multiple sclerosis, inflammatory bowel disease, allergic diseases, asthma, chronic obstructive pulmonary disease (COPD) type 1 diabetes, myasthenia gravis, hematopoetic disfunction, B-cell malignancies, systemic lupus erythematosus, non-Hodgkin's lymphoma, chronic lymphocytic leukemia, Mantle cell lymphoma or other disorders.

BACKGROUND

Bruton's tyrosine kinase (Btk) belongs to tyrosine kinases, a subfamily of protein kinases that phosphorylate protein on the phenolic moiety of tyrosine residue. It is a non-receptor cytoplasmic tyrosine kinase and a key regulator for B-cell development, activation, signaling and survival (Schaeffer and Schwartzberg, Curr. Op. Imm. 2000, 282; Niiro and Clark, Nature Rev. Immumol. 2002, 945; Di Paolo and Currie, Nat. Chem. Biol. 2011, 7). Btk is expressed in all hematopoietic cell types, excluding plasma cells, T lymphocytes and natural killer cells. After activation by upstream B-cell antigen receptor or Toll like receptor-4, Btk induces PLC-γ2 phosphorylation, which ultimately results in activation of nuclear factor κB (NFκB) and nuclear factor of activated T cell dependent pathways. Additionally, Btk is crucial for number of other hematopoetic cell signaling; such as, Fcγ-mediated inflammatory cytokine production (such as TNF-α, IL1β and IL6) in monocytes/macrophages, IgE mediated signaling in mast cells, inhibition of Fas/APO-1 apoptotic signaling in B-lineage lymphoid cells etc (Jeffries et al. J. Biol. Chem. 2003, 26258; Horwood et al., J. Experimental Med. 2003, 1603).

Use of B-cell depleting protein based therapeutics (for example, Rituxan, a CD20 antibody) for the treatment of a number of autoimmune and/or inflammatory diseases provides enough evidence for the role of B-cells and the humoral immune system in the pathogenesis of autoimmune and/or inflammatory disease. And as Btk is essential for B-cell activation, this also provides an indirect rational for the role of Btk in autoimmune and/or inflammatory diseases.

Additional rationales for the involvement of Btk in various autoimmune and/or inflammatory diseases come from Btk deficient mouse models; for example, Btk deficiency has been shown to result in a marked amelioration of disease progression, in murine preclinical model of systemic lupus erythematosus (SLE). BTK deficient mice are resistant to develop collagen-induced arthritis (Jansson and Holmdahl Clin. Exp. Immumol. 1993, 459).

Pharmacological validation for the involvement of Btk in various autoimmune and/or inflammatory diseases comes from two different class of Btk inhibitors, for example, (a) an irreversible Btk inhibitor (Pan et al, Chem. Med. Chem. 2007, 58), and (b) a reversible Btk inhibitor (Di Paolo, Nat. Chem. Biol. 2010, 41). Both the type of inhibitors have demonstrated efficacy in a mouse model of arthritis. PCI-32765 (an irreversible Btk inhibitor), has shown promising clinical activity in chronic lymphocytic leukemia (CLL) and small lymphocytic lymphoma (SLL) (Burger et al, Blood 2010, 32 & J Clin Oncol 2011, 6508). Thus, small molecule Btk inhibitors are expected to be useful to treat disease processes that involve B-cell activation.

Several prior art literature describe the discovery of small molecule Btk inhibitors (for a recent review, Lou et al. J. Med. Chem. 2012). As for example, amino-pyrazolo-pyrimidine (WO2011046964A2) and imidazo[1,5-a]quinoxalines (Kim et al, Bio-org. Med. Chem. Lett., 2011, 6258) based compounds, which utilize its acrylamide functionality for covalent modification of the target protein, are published as irreversible inhibitors. There are literature prior art disclosing reversible Btk inhibitors, such as, substituted amino-pyrimidine analogs (WO2010123870A1); imidazo[1,2-f][1,2,4]triazine core based amide compounds (WO2010068810A2); various heterocyclic (e.g. imidazo[1,2-a]pyrazine, aminopyrimidine, 2-pyridone etc) amide derivatives (WO2010068788A1, WO2010068806A1); benzo[f][1,4]oxazepin analogs (WO2010122038A1); 3,4-dihydro-2H-isoquinoline or 2H-isoquinolin-1-one based analogs (WO2010100070A1, WO2013024078); phenylimidazopyrazine analogs (WO2010006970A1); 3,5-disubstituted pyrid-2-one analogs (WO2007027729A1); azaindazole compounds (WO2011019780A1); nicotinamide compounds (WO2010144647A1); carbazole carboxamide analogs (WO2010080481A1), pyrrolopyrimidine derivatives (WO2013008095).

Despite several discoveries in this area, there is no small molecule Btk inhibitor available in the market. The most advanced compounds in the clinical trials are irreversible inhibitors of Btk. Such an irreversible mechanism of action often encounters nonspecific binding with proteins including off-targets leading to safety concern particularly upon long term used such as off-target related adverse side effects, general hepatotoxicity and organ toxicity, antibody mediated reactions. Therefore, there is a need of Btk inhibitors with safer mechanism of action such as reversible mechanism of inhibition. These compounds will have medical application in the disease area of inflammation, autoimmune disorder and cell proliferation, rheumatoid arthritis, psoriasis, psoriatic arthritis, transplant rejection, graft-versus-host disease, multiple sclerosis, inflammatory bowel disease, allergic diseases and asthma, type 1 diabetes, myasthenia gravis, hematopoetic disfunction, B-cell malignancies, systemic lupus erythematosus.

SUMMARY

The present disclosure provides hetero-bicyclic compounds of formula (I), their tautomers, polymorphs, stereoisomers, prodrugs, solvates, hydrates, N-oxides, co-crystals, pharmaceutically acceptable salts, pharmaceutical compositions containing them and methods of treating conditions and diseases that are mediated by Bruton's tyrosine kinase (Btk) activity.

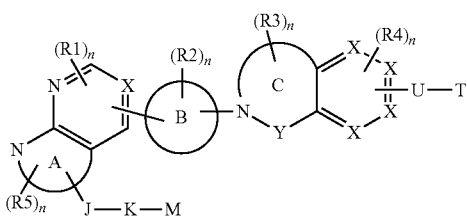

wherein, ring A and ring C are independently a 5-7 membered ring which is unsaturated or partially unsaturated optionally having upto three heteroatom independently selected from O, N or S;

ring B represents a 5-7 membered ring which is saturated, unsaturated or partially unsaturated optionally having upto three heteroatoms independently selected from O, N or S;

each X independently represents N or C(R1);

Y represents —C(O) or —S(O)p-;

J is absent or is selected from the group consisting of cycloalkylene, cycloalkenylene, arylene, heterocyclylene, heteroarylene, spirocyclylene, (C1-6)alkylene, (C1-6)alkenylene or (C1-6)alkynylene;

K is a bond or is selected from the group consisting of —($CR^aR^b$)—, ($C_{1-6}$)alkylene, ($C_{1-6}$)alkenylene and ($C_{1-6}$)alkynylene wherein optionally one or more than one methylene groups of alkylene, alkenylene or alkynylene are independently replaced by hetero atoms or groups such as —O—, —S(O)$_p$—, —N($R^6$)—, —C(O)—, —C(=NR')— or —C(R')=N—, wherein R' is H, alkyl, cyano, hydroxy, hydroxyalkyl, haloalkyl or perhaloalkyl;

M is selected from hydrogen, cyano, halogen, haloalkyl, perhaloalkyl, alkyl, alkenyl, alkynyl, cyanoalkyl, acyl, cyanoalkylcarbonyl, cyanoalkenylcarbonyl, —($CR^aR^b$)$_m$$OR^6$, —$SR^6$, —($CR^aR^b$)$_m$$COOR^6$, —($CR^aR^b$)$_m$$NR^7R^8$, —($CR^aR^b$)$_m$C(O)$NR^7R^8$, —($CR^aR^b$)$_m$$NR^6$C(O)$NR^7R^8$, thiocarbonyl, S(O)$_2$$NR^7R^8$, —$NR^6$S(O)$_2$$R^6$, —S(O)$_p$$R^6$, —$SO_3H$, cycloalkyl, cycloalkenyl, cycloalkylalkyl, aryl, arylalkyl, heterocyclyl, heterocyclylalkyl, heteroaryl, spirocyclyl or heteroarylalkyl;

J, K and M is optionally substituted with one or more substituents independently selected from cyano, nitro, keto, oxo, halogen, haloalkyl, perhaloalkyl, hydroxyamino, —(CRaRb)mOR6, —(CRaRb)mC(O)R6, —OC(O)R6, —SR6, —(CRaRb)mCOOR6, —(CRaRb)mNR7R8, —(CRaRb)mC(O)NR7R8, —(CRaRb)mNR6C(O)NR7R8, —NR6C(O)R6, thiocarbonyl, —S(O)2NR7R8, —NR6S(O)2R6, —S(O)pR6, —SO3H, alkyl, alkenyl, alkynyl, cycloalkyl, cyclkenyl, cycloalkylalkyl, aryl, heterocyclyl or heteroaryl; wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, cyano, alkyl, halogen, haloalkyl, perhaloalkyl, cyano, cyanoalkyl, amino, carboxy, carboxyalkyl, —OC(O)R6, —($CR^aR^b$)$_m$C(O)$NR^7R^8$, —$NR^6$C(O)$R^6$, —$SR^6$, —S(O)$_p$$R^6$, —S(O)$_2$$NR^7R^8$ or —$NR^6$S(O)$_2$$R^6$;

U is a bond or is selected from the group consisting of cycloalkylene, cycloalkenylene, arylene, heterocyclylene, heteroarylene, ($C_{1-6}$)alkylene, ($C_{1-6}$)alkenylene and ($C_{1-6}$)alkynylene, wherein one or more than one methylene groups of alkylene, alkenylene or alkynylene are optionally replaced by hetero atoms or groups such as —O—, —S(O)$_p$—, —N($R^6$)—, —C(O)—C(=NR')— or —C(R')=N—, wherein R' is H, alkyl, cyano, hydroxy, hydroxyalkyl, haloalkyl or perhaloalkyl;

T is selected from hydrogen, cyano, halogen, haloalkyl, perhaloalkyl, alkyl, alkenyl, alkynyl, cyanoalkyl, acyl, cyanoalkylarbonyl, cyanoalkenylcarbonyl, —($CR^aR^b$)$_m$$OR^6$, —$SR^6$, —($CR^aR^b$)$_m$$COOR^6$, —($CR^aR^b$)$_m$$NR^7R^8$, —($CR^aR^b$)$_m$C(O)$NR^7R^8$, —($CR^aR^b$)$_m$$NR^6$C(O)$NR^7R^8$, thiocarbonyl, S(O)$_2$$NR^7R^8$, —$NR^6$S(O)$_2$$R^6$, —S(O)$_p$$R^6$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

U and T is optionally substituted with one or more substituents independently selected from cyano, nitro, keto, oxo, halogen, haloalkyl, perhaloalkyl, hydroxyamino, —($CR^aR^b$)$_m$$OR^6$, —($CR^aR^b$)$_m$C(O)$R^6$, —OC(O)$R^6$, —$SR^6$, —($CR^aR^b$)$_m$$COOR^6$, —($CR^aR^b$)$_m$$NR^7R^8$, —($CR^aR^b$)$_m$C(O)$NR^7R^8$, —($CR^aR^b$)$_m$$NR^6$C(O)$NR^7R^8$, —$NR^6$C(O)$R^6$, thiocarbonyl, —S(O)$_2$$NR^7R^8$, —$NR^6$S(O)$_2$$R^6$, —S(O)$_p$$R^6$, —$SO_3H$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)$R^6$, —($CR^aR^b$)$_m$C(O) $NR^7R^8$, —$NR^6$C(O)$R^6$, —$SR^6$, —S(O)$_p$$R^6$, —S(O)$_2$$NR^7R^8$ or —$NR^6$S(O)$_2$$R^6$;

$R^1$, $R^2$, $R^3$, $R^4$ and $R^5$ are independently selected from hydrogen, alkyl, alkenyl, alkynyl, alkoxy, acyl, acylamino, acyloxy, $R^6$, —($CR^aR^b$)$_m$C(O)$R^6$, —($CR^aR^b$)$_m$$NR^7R^8$, —($CR^aR^b$)$_m$O ($CR^aR^b$)$_n$Si($R^7$)$_3$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —$SO_3H$, —S(O)$_p$$R^6$, —S(O)$_2$$NR^7R^8$ alkylthio, or nitro; or when $R^1$ or $R^2$ or $R^3$ or $R^4$ or $R^5$ are more than one, then any 2$R^1$ or 2$R^2$ or 2$R^3$ or 2$R^4$ or 2$R^5$ independently is optionally, taken together form a monocyclic or a bicyclic ring system which is saturated or partially unsaturated and optionally have additional heteroatoms selected from O, N or S;

$R^6$ is selected from the group consisting of hydrogen, —($CR^aR^b$)$_m$$OR^6$, halogen, haloalkyl, —($CR^aR^b$)$_m$C(O)$R^6$, alkyl, alkenyl, alkynyl, aryl, arylalkyl, heteroaryl, heteroarylalkyl, cycloalkyl, cycloalkylalkyl, heterocyclyl or heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $OR^5$, —OC(O)$R^6$, —($CR^aR^b$)$_m$C(O)$NR^7R^8$, —$NR^6$C(O)$R^6$, —$SR^6$, —S(O)$_p$$R^6$, —S(O)$_2$$NR^7R^8$ or —$NR^6$S(O)$_2$$R^6$;

$R^7$ and $R^8$ are independently selected from the group consisting of hydrogen, —($CR^aR^b$)$_m$$OR^6$, haloalkyl, —($CR^aR^b$)$_m$C (O)$R^6$, alkyl, alkenyl, alkynyl, aryl, arylalkyl, heteroaryl, heteroarylalkyl, cycloalkyl, cycloalkylalkyl, heterocyclyl or heterocyclylalkyl, or $R^7$ and $R^8$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —$(CR^aR^b)_mOR^6$, —$SR^6$, —$(CR^aR^b)_mNR^7R^8$, oxo, alkylsulfonyl, —$(CR^aR^b)_mCOOR^6$, —$(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;

$R^a$ and $R^b$ are independently selected from the group consisting of hydrogen, —$OR^6$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S;

m is 0-6;

n is 0-3;

p is 0, 1 or 2; and q is 1 or 2.

DETAILED DESCRIPTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—CH2CH2-), the propylene isomers (e.g., —CH2CH2CH2- and —CH(CH3)CH2-) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —SO3H, aryl, aryloxy, heteroaryl, aminocarbonylamino, heteroaryloxy, heterocyclyl, heterocyclyloxy, hydroxyamino, alkoxyamino, nitro, —S(O) 2NRaRa, —NRaS(O)2Ra and —S(O)pRb, where each Ra is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where Rb is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently selected from oxygen, sulphur and $NR^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or —$S(O)_pR^c$, in which $R^c$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl(—CH═CH2), 1-propylene or allyl (—CH2CH═CH2), isopropylene (—C(CH3)═CH2), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, SO3H, aryl, aryloxy, heteroaryl, aminocarbonylamino, heteroaryloxy, heterocyclyl, heterocyclyloxy, hydroxyamino, alkoxyamino, nitro, —S(O)2NRaRa, —NRaS(O)2Ra and —S(O)pRb where each Ra is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where Rb is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH2C≡CH), homopropargyl (or but-1-yn-4-yl, —CH2CH2C≡CH) and the like.

The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO3H, aryl, aryloxy, heteroaryl, aminocarbonylamino, heteroaryloxy, heterocyclyl, heterocyclyloxy, hydroxyamino, alkoxyamino, nitro, —S(O)2NRaRa, —NRaS(O)2Ra and —S(O)pRb, where each Ra is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where Rb is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF3, amino, substituted amino, cyano, and —S(O)pRc where Rc is alkyl, aryl, or heteroaryl and p is 0, 1 or 2.

The term "cycloalkyl" refers to unless otherwise mentioned, carbocyclic groups of from 3 to 20 carbon atoms having a single cyclic ring or multiple condensed rings or spirocyclic rings or bridged rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2]octane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "cycloalkylene" refers to a divalent cycloalkyl group as defined above. This term is exemplified by groups such as 1,4-cyclohexylene, 1,3-cyclohexylene, 1,2-cyclohexylene, 1,4-cyclohexenyl and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)pRb, where R is hydrogen, hydroxyl, alkoxy, alkyl and cyclocalkyl, heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'"—O—, where R'" is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, CF3, amino, substituted amino, cyano, or —S(O)pRc, where Rc is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to (C1-6)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3, 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO3H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)2NRaRa, —NRaS(O)2Ra and —S(O)pRb where each Ra is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where Rb is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, CF3, amino, substituted amino, cyano, and —S(O)pRc where Rc is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)ORd where Rd is alkyl, cycloalkyl, where alkyl, cycloalkyl are as defined herein, and may be optionally further substituted by alkyl, halogen, CF3, amino, substituted amino, cyano, or —S(O)pRc, in which Rc is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heteroarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO3H, aryl, aryloxy, heteroaryl, aminocarbonylamino, heteroaryloxy, heterocyclyl, heterocyclyloxy, hydroxyamino, alkoxyamino, nitro, —S(O)2NRaRa, —NRaS(O)2Ra and —S(O)pRb, where each Ra is independently selected from the group consisting of hydrogen, alkyl, cycloalkyl, cycloalkylalkyl, aryl, arylalkyl, heteroaryl heteroarylalkyl, heterocyclyl and heterocyclylalkyl; where Rb is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF3, amino, substituted amino, cyano, and —S(O)nRc, where Rc is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings or spirocyclic rings, or bridged rings unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)pRb, where Rb is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF3, amino, substituted amino, cyano, and —S(O)nRc, where Rc is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —S(O)2R.

The term "substituted sulfone" refers to a group —S(O)2R, in which R is alkyl, aryl, or heteroaryl.

The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the x-ray diffraction patterns, solubility behaviour, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the disclosure are quaternary ammonium compounds wherein an equivalent of an anion (M−) is associated with the positive charge of the N atom. M− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M− is preferably an anion selected from chloride, bromide, iodide, sulphate, nitrate, acetate, maleate, oxalate, succinate or trifluoroacetate. More preferably M− is chloride, bromide, trifluoroacetate or methanesulphonate.

"Co-crystal" refers to a crystalline material comprising two or more compounds at ambient temperature (20 to 25[deg.]C., preferably 20[deg.]C.), of which at least two are held together by weak interaction, wherein at least one of the compounds is a co-crystal former. Weak interaction is being defined as an interaction which is neither ionic nor covalent and includes for example: hydrogen bonds, van der Waals forces, and interactions.

"Pharmaceutical composition" refers to one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition comprising a compound of the present disclosure and a pharmaceutically acceptable carrier.

"Carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

"Drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

"Therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The present disclosure provides hetero-bicyclic compounds of formula (I), their tautomers, polymorphs, stereoisomers, prodrugs, solvates, hydrates, N-oxides, co-crystals, pharmaceutically acceptable salts, pharmaceutical compositions containing them and methods of treating conditions and diseases that are mediated by Bruton's tyrosine kinase (Btk) activity,

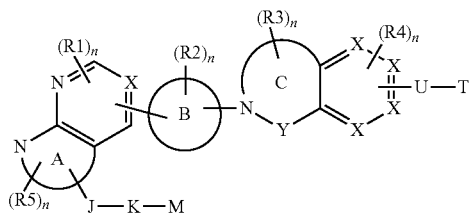

wherein,
ring A and ring C are independently a 5-7 membered ring which is unsaturated or partially unsaturated optionally having upto three heteroatom independently selected from O, N or S;
ring B represents a 5-7 membered ring which is saturated, unsaturated or partially unsaturated optionally having upto three heteroatoms independently selected from O, N or S;
each X independently represents N or C($R^1$);
Y represents —C(O) or —S(O)$_p$—;
J is absent or is selected from the group consisting of cycloalkylene, cycloalkenylene, arylene, heterocyclylene, heteroarylene, spirocyclylene, ($C_{1-6}$)alkylene, ($C_{1-6}$)alkenylene or ($C_{1-6}$)alkynylene;
K is a bond or is selected from the group consisting of —(CR$^a$R$^b$)—, ($C_{1-6}$)alkylene, ($C_{1-6}$)alkenylene and ($C_{1-6}$) alkynylene wherein optionally one or more than one methylene groups of alkylene, alkenylene or alkynylene are independently replaced by hetero atoms or groups such as —O—, —S(O)$_p$—, —N($R^6$)—, —C(O)—, —C(=NR')— or —C(R')=N—, wherein R' is H, alkyl, cyano, hydroxy, hydroxyalkyl, haloalkyl or perhaloalkyl;
M is selected from hydrogen, cyano, halogen, haloalkyl, perhaloalkyl, alkyl, alkenyl, alkynyl, cyanoalkyl, acyl, cyanoalkylcarbonyl, cyanoalkenylcarbonyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, thiocarbonyl, S(O)$_2$NR$^7$R$^8$, —NR$^6$S(O)$_2$R$^6$, —S(O)$_p$R$^6$, —SO$_3$H, cycloalkyl, cycloalkenyl, cycloalkylalkyl, aryl, arylalkyl, heterocyclyl, heterocyclylalkyl, heteroaryl or heteroarylalkyl;
J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O) NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;
wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O) NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;
U is a bond or is selected from the group consisting of cycloalkylene, cycloalkenylene, arylene, heterocyclylene, heteroarylene, ($C_{1-6}$)alkylene, ($C_{1-6}$)alkenylene and ($C_{1-6}$)

alkynylene, wherein one or more than one methylene groups of alkylene, alkenylene or alkynylene are optionally replaced by hetero atoms or groups such as —O—, —S(O)$_p$—, —N(R$^6$)—, —C(O)—C(=NR')— or —C(R')=N—, wherein R' is H, alkyl, cyano, hydroxy, hydroxyalkyl, haloalkyl or perhaloalkyl;

T is selected from hydrogen, cyano, halogen, haloalkyl, perhaloalkyl, alkyl, alkenyl, alkynyl, cyanoalkyl, acyl, cyanoalkylarbonyl, cyanoalkenylcarbonyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, thiocarbonyl, S(O)$_2$NR$^7$R$^8$, —NR$^6$S(O)$_2$R$^6$, —S(O)$_p$R$^6$, —SO$_3$H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

U and T is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

R$^1$, R$^2$, R$^3$, R$^4$ and R$^5$ are independently selected from hydrogen, alkyl, alkenyl, alkynyl, alkoxy, acyl, acylamino, acyloxy, R$^6$, —(CR$^a$R$^b$)$_m$C(O)R$^6$, —(CR$^a$R$^b$)$_m$NR$^7$R$^8$, —(CR$^a$R$^b$)$_m$O (CR$^a$R$^b$)$_n$Si(R$^7$)$_3$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, —S(O)$_p$R$^6$, —S(O)$_2$NR$^7$R$^8$ alkylthio, or nitro;

or when R$^1$ or R$^2$ or R$^3$ or R$^4$ or R$^5$ are more than one, then any 2 R$^1$ or 2 R$^2$ or 2 R$^3$ or 2 R$^4$ or 2 R$^5$ independently is optionally, taken together form a monocyclic or a bicyclic ring system which is saturated or partially unsaturated and optionally have additional heteroatoms selected from O, N or S;

R$^6$ is selected from the group consisting of hydrogen, —(CR$^a$R$^b$)$_m$OR$^6$, halogen, haloalkyl, —(CR$^a$R$^b$)$_m$C(O)R$^6$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

R$^7$ and R$^8$ are independently selected from the group consisting of hydrogen, —(CR$^a$R$^b$)$_m$OR$^6$, haloalkyl, —(CR$^a$R$^b$)$_m$C (O)R$^6$, alkyl, alkenyl, alkynyl, aryl, arylalkyl, heteroaryl, heteroarylalkyl, cycloalkyl, cycloalkylalkyl, heterocyclyl or heterocyclylalkyl, or R$^7$ and R$^8$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_m$OR$^6$, —SR$^6$, —(CR$^a$R$^b$)$_m$NR$^7$R$^8$, oxo, alkylsulfonyl, —(CR$^a$R$^b$)$_m$COOR$^6$, —(CR$^a$R$^b$)$_m$C(O)NR$^7$R$^8$, cycloalkyl, cycloalkylalkyl, aryl, arylalkyl, heterocyclyl, heterocyclylalkyl, heteroaryl, or heteroarylalkyl;

R$^a$ and R$^b$ are independently selected from the group consisting of hydrogen, —OR$^6$, halogen, haloalkyl, perhaloalkyl and alkyl; or R$^a$ and R$^b$ taken together form a monocyclic or a bicyclic ring system which is saturated or partially unsaturated and optionally have additional heteroatoms selected from O, N or S;

m is 0-6;

n is 0-3;

p is 0, 1 or 2; and q is 1 or 2.

According to another embodiment, the present disclosure relates to compounds of formula (I) or its tautomers, polymorphs, stereoisomers, prodrugs, solvate, co-crystals or a pharmaceutically acceptable salts thereof, wherein, ring A and ring C are independently a 5-7 membered ring which is unsaturated or partially unsaturated optionally having upto three heteroatom independently selected from O, N or S;

ring B represents a 6 membered ring which is unsaturated optionally having upto three heteroatoms independently selected from O, N or S;

each X independently represents N or C(R$^1$);

Y represents —C(O);

J is absent or is selected from the group consisting of cycloalkylene, cycloalkenylene, arylene, heterocyclylene, heteroarylene, (C$_{1-6}$)alkylene, (C$_{1-6}$)alkenylene or (C$_{1-6}$) alkynylene;

K is a bond or (C$_{1-6}$)alkylene wherein optionally one or more than one methylene groups of alkylene are independently replaced by hetero atoms or groups such as —O—, —S(O)p-, —N(R$^6$)—, —C(O)—, —C(=NR')— or —C(R')=N—, wherein R' is H, alkyl, cyano, hydroxy, hydroxyalkyl, haloalkyl or perhaloalkyl;

M is selected from hydrogen, cyano, halogen, haloalkyl, perhaloalkyl, alkyl, alkenyl, alkynyl, cyanoalkyl, acyl, cyanoalkylcarbonyl, cyanoalkenylcarbonyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, thiocarbonyl, S(O)$_2$NR$^7$R$^8$, —NR$^6$S(O)$_2$R$^6$, —S(O)$_p$R$^6$, —SO$_3$H, cycloalkyl, cycloalkenyl, cycloalkylalkyl, aryl, arylalkyl, heterocyclyl, heterocyclylalkyl, heteroaryl or heteroarylalkyl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O) NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cycloalkylene, cycloalkenylene, arylene, heterocyclylene, heteroarylene, (C$_{1-6}$)alkylene, (C$_{1-6}$)alkenylene and (C$_{1-6}$)alkynylene, wherein one or more than one methylene groups of alkylene, alkenylene or alkynylene are optionally replaced by hetero atoms or groups such as —O—, —S(O)$_p$—, —N(R$^6$)—, —C(O)—C(=NR')— or —C(R')=N—, wherein R' is H, alkyl, cyano, hydroxy, hydroxyalkyl, haloalkyl or perhaloalkyl;

T is selected from hydrogen, cyano, halogen, haloalkyl, perhaloalkyl, alkyl, alkenyl, alkynyl, cyanoalkyl, acyl, cyanoalkylarbonyl, cyanoalkenylcarbonyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, thiocarbonyl, S(O)$_2$NR$^7$R$^8$, —NR$^6$S(O)$_2$R$^6$, —S(O)$_p$R$^6$ or —SO$_3$H;

R$^1$, R$^2$, R$^3$, R$^4$ and R$^5$ are independently selected from hydrogen, alkyl, alkenyl, alkynyl, alkoxy, acyl, acylamino, acyloxy, R$^6$, —(CR$^a$R$^b$)$_m$C(O)R$^6$, —(CR$^a$R$^b$)$_m$NR$^7$R$^8$, —(CR$^a$R$^b$)$_m$O(CR$^a$R$^b$)$_n$Si(R$^7$)$_3$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, —S(O)$_p$R$^6$, —S(O)$_2$NR$^7$R$^8$ alkylthio, or nitro;

or when R$^1$ or R$^2$ or R$^3$ or R$^4$ or R$^5$ are more than one, then any 2 R$^1$ or 2 R$^2$ or 2 R$^3$ or 2 R$^4$ or 2 R$^5$ independently is optionally, taken together form a monocyclic or a bicyclic ring system which is saturated or partially unsaturated and optionally have additional heteroatoms selected from O, N or S;

R$^6$ is selected from the group consisting of hydrogen, —(CR$^a$R$^b$)$_m$OR$^6$, halogen, haloalkyl, —(CR$^a$R$^b$)$_m$C(O)R$^6$, alkyl, alkenyl, alkynyl, aryl, arylalkyl, heteroaryl, heteroarylalkyl, cycloalkyl, cycloalkylalkyl, heterocyclyl or heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR$^5$, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

R$^7$ and R$^8$ are independently selected from the group consisting of hydrogen, —(CR$^a$R$^b$)$_m$OR$^6$, haloalkyl, —(CR$^a$R$^b$)$_m$C(O)R$^6$, alkyl, alkenyl, alkynyl, aryl, arylalkyl, heteroaryl, heteroarylalkyl, cycloalkyl, cycloalkylalkyl, heterocyclyl or heterocyclylalkyl, or R$^7$ and R$^8$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_m$OR$^6$, —SR$^6$, —(CR$^a$R$^b$)$_m$NR$^7$R$^8$, oxo, alkylsulfonyl, —(CR$^a$R$^b$)$_m$COOR$^6$, —(CR$^a$R$^b$)$_m$C(O)NR$^7$R$^8$, cycloalkyl, cycloalkylalkyl, aryl, arylalkyl, heterocyclyl, heterocyclylalkyl, heteroaryl, or heteroarylalkyl;

R$^a$ and R$^b$ are independently selected from the group consisting of hydrogen, —OR$^6$, halogen, haloalkyl, perhaloalkyl and alkyl; or R$^a$ and R$^b$ taken together form a monocyclic or a bicyclic ring system which is saturated or partially unsaturated and optionally have additional heteroatoms selected from O, N or S;

m is 0-6;
n is 0-3;
p is 0, 1 or 2; and
q is 1 or 2.

According to another embodiment, the present disclosure relates to compounds of formula (I) or its tautomers, polymorphs, stereoisomers, prodrugs, solvate, co-crystals or a pharmaceutically acceptable salts thereof, wherein, ring A represents a 5 membered ring which is unsaturated having upto three heteroatoms independently selected from O, N or S;

ring B represents a 6 membered ring which is unsaturated optionally having upto three heteroatoms independently selected from O, N or S;

ring C represents a 6-7 membered ring which is unsaturated or partially unsaturated optionally having upto three heteroatom independently selected from O, N or S;

each X independently represents N or C(R$^1$);

Y represents —C(O);

J is absent or is selected from the group consisting of arylene, heterocyclylene, heteroarylene, (C$_{1-6}$)alkylene, (C$_{1-6}$)alkenylene or (C$_{1-6}$)alkynylene;

K is a bond or (C$_{1-6}$)alkylene wherein optionally one or more than one methylene groups of alkylene are independently replaced by hetero atoms or groups such as —O—, —N(R$^6$)—, —C(O)—;

M is selected from hydrogen, cyano, halogen, haloalkyl, perhaloalkyl, alkyl, alkenyl, alkynyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, thiocarbonyl, —S(O)$_p$R$^6$, —SO$_3$H, cycloalkyl, aryl, arylalkyl, heterocyclyl or heteroaryl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cycloalkylene or (C$_{1-6}$)alkylene;

T is selected from hydrogen, cyano, halogen, haloalkyl, perhaloalkyl, alkyl, alkenyl, alkynyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —S(O)$_p$R$^6$ or —SO$_3$H;

R$^1$, R$^2$, R$^3$, R$^4$ and R$^5$ are independently selected from hydrogen, alkyl, alkoxy, acyl, acylamino, acyloxy, —(CR$^a$R$^b$)$_m$C(O)R$^6$, —(CR$^a$R$^b$)$_m$NR$^7$R$^8$, —(CR$^a$R$^b$)$_m$O(CR$^a$R$^b$)$_n$Si(R$^7$)$_3$, aminocarbonyl, alkoxycarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, alkylthio, aminosulfonyl, alkylsulfonyl, or nitro;

R$^6$ is selected from the group consisting of hydrogen, —(CR$^a$R$^b$)$_m$OR$^6$, halogen, haloalkyl, —(CR$^a$R$^b$)$_m$C(O)R$^6$, alkyl or cycloalkyl;

$R^7$ and $R^8$ are independently selected from the group consisting of hydrogen, $-(CR^aR^b)_mOR^6$, haloalkyl, $-(CR^aR^b)_mC(O)R^6$, alkyl, or $R^7$ and $R^8$ taken together form a monocyclic or a bicyclic ring system which is saturated or partially unsaturated and optionally have additional heteroatoms selected from O, N or S;

$R^a$ and $R^b$ are independently selected from the group consisting of hydrogen, $-OR^6$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S;

m is 0-6;

n is 0-3;

p is 0, 1 or 2; and q is 1 or 2.

According to another embodiment, the present disclosure relates to compounds of formula (I) or its tautomers, polymorphs, stereoisomers, prodrugs, solvate, co-crystals or a pharmaceutically acceptable salts thereof, wherein, ring A is selected from pyrrole, imidazole, pyrazole, oxazole, isoxazole, thiazole, isothiazole, triazole, oxadiazole, thiadiazole, dithiazole;

ring B is selected from phenyl, pyridine, pyridazine, pyrimidine or pyrazine;

ring C represents a 6-7 membered ring which is unsaturated or partially unsaturated optionally having upto three heteroatom independently selected from O, N or S;

each X independently represents N or $C(R^1)$;

Y represents $-C(O)$;

J is absent or is selected from the group consisting of arylene, heterocyclylene, heteroarylene, $(C_{1-6})$alkylene, $(C_{1-6})$alkenylene or $(C_{1-6})$alkynylene;

K is a bond or $(C_{1-6})$alkylene wherein optionally one or more than one methylene groups of alkylene are independently replaced by hetero atoms or groups such as $-O-$, $-N(R^6)-$, $-C(O)-$;

M is selected from hydrogen, cyano, halogen, haloalkyl, perhaloalkyl, alkyl, alkenyl, alkynyl, cyanoalkyl, acyl, $-(CR^aR^b)_mOR^6$, $-SR^6$, $-(CR^aR^b)_mCOOR^6$, $-(CR^aR^b)_mNR^7R^8$, $-(CR^aR^b)_mC(O)NR^7R^8$, $-(CR^aR^b)_mNR^6C(O)NR^7R^8$, thiocarbonyl, $-S(O)_pR^6$, $-SO_3H$, cycloalkyl, aryl, arylalkyl, heterocyclyl or heteroaryl;

J, K and M is optionally substituted with one or more substituents independently selected from cyano, nitro, keto, oxo, halogen, haloalkyl, perhaloalkyl, hydroxyamino, $-(CR^aR^b)_mOR^6$, $-(CR^aR^b)_mC(O)R^6$, $-OC(O)R^6$, $-SR^6$, $-(CR^aR^b)_mCOOR^6$, $-(CR^aR^b)_mNR^7R^8$, $-(CR^aR^b)_mC(O)NR^7R^8$, $-(CR^aR^b)_mNR^6C(O)NR^7R^8$, $-NR^6C(O)R^6$, thiocarbonyl, $-S(O)_2NR^7R^8$, $-NR^6S(O)_2R^6$, $-S(O)_pR^6$, $-SO_3H$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$ or $-NR^6S(O)_2R^6$;

U is a bond or is selected from the group consisting of cyclopropylene, cyclobutylene, cyclohexylene or $(C_{1-6})$alkylene;

T is selected from hydrogen, cyano, halogen, hydroxy, haloalkyl, perhaloalkyl alkyl or $-(CR^aR^b)_mOR^6$;

$R^1$, $R^2$, $R^3$, $R^4$ and $R^5$ are independently selected from hydrogen, alkyl, alkoxy, acyl, acylamino, acyloxy, $-(CR^aR^b)_mC(O)R^6$, $-(CR^aR^b)_mNR^7R^8$, $-(CR^aR^b)_mO(CR^aR^b)_nSi(R^7)_3$, aminocarbonyl, alkoxycarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy $-SO_3H$, alkylthio, aminosulfonyl, alkylsulfonyl, or nitro;

$R^6$ is selected from the group consisting of hydrogen, $-(CR^aR^b)_mOR^6$, halogen, haloalkyl, $-(CR^aR^b)_mC(O)R^6$, alkyl or cycloalkyl;

$R^7$ and $R^8$ are independently selected from the group consisting of hydrogen, $-(CR^aR^b)_mOR^6$, haloalkyl, $-(CR^aR^b)_mC(O)R^6$, alkyl;

$R^a$ and $R^b$ are independently selected from the group consisting of hydrogen, $-OR^6$, halogen, haloalkyl, perhaloalkyl and alkyl;

m is 0-6;

n is 0-3;

p is 0, 1 or 2; and q is 1 or 2.

According to another embodiment, the present disclosure relates to compounds of formula (I) or its tautomers, polymorphs, stereoisomers, prodrugs, solvate, co-crystals or a pharmaceutically acceptable salts thereof, wherein, ring A is selected from pyrrole, imidazole or pyrazole;

ring B is selected from phenyl, pyridine or pyrimidine;

ring C represents a 6-7 membered ring which is unsaturated or partially unsaturated having one, two or three heteroatoms independently selected from O, N or S;

each X independently represents N or $C(R^1)$;

Y represents $-C(O)$;

J is absent or is selected from the group consisting of arylene, heterocyclylene, heteroarylene, $(C_{1-6})$alkylene or $(C_{1-6})$alkynylene;

K is a bond or $(C_{1-6})$alkylene wherein optionally one or more than one methylene groups of alkylene are independently replaced by hetero atoms or groups such as $-O-$, $-N(R^6)-$, $-C(O)-$;

M is selected from hydrogen, cyano, halogen, haloalkyl, perhaloalkyl, alkyl, cyanoalkyl, acyl, $-(CR^aR^b)_mOR^6$, $-SR^6$, $-(CR^aR^b)_mCOOR^6$, $-(CR^aR^b)_mNR^7R^8$, $-(CR^aR^b)_mC(O)NR^7R^8$, $-SO_3H$, aryl, heterocyclyl or heteroaryl;

J, K and M is optionally substituted with one or more substituents independently selected from cyano, nitro, keto, oxo, halogen, haloalkyl, perhaloalkyl, hydroxyamino, $-(CR^aR^b)_mOR^6$, $-(CR^aR^b)_mC(O)R^6$, $-OC(O)R^6$, $-SR^6$, $-(CR^aR^b)_mCOOR^6$, $-(CR^aR^b)_mNR^7R^8$, $-(CR^aR^b)_mC(O)NR^7R^8$, $-(CR^aR^b)_mNR^6C(O)NR^7R^8$, $-NR^6C(O)R^6$, thiocarbonyl, $-S(O)_2NR^7R^8$, $-NR^6S(O)_2R^6$, $-S(O)_pR^6$, $-SO_3H$, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $-OC(O)R^6$, $-(CR^aR^b)_mC(O)NR^7R^8$, $-NR^6C(O)R^6$, $-SR^6$, $-S(O)_pR^6$, $-S(O)_2NR^7R^8$ or $-NR^6S(O)_2R^6$;

U is a bond or is selected from the group consisting of cyclopropylene, cyclobutylene, cyclohexylene or $(C_{1-6})$alkylene;

T is selected from hydrogen, cyano, halogen, hydroxy, haloalkyl, perhaloalkyl alkyl or $-(CR^aR^b)_mOR^6$;

$R^1$, $R^2$, $R^3$, $R^4$ and $R^5$ are independently selected from hydrogen, alkyl, alkoxy, acyl, acylamino, acyloxy, $-(CR^aR^b)_mC(O)R^6$, $-(CR^aR^b)_mNR^7R^8$, $-(CR^aR^b)_mO(CR^aR^b)_nSi(R^7)_3$, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, alkylthio, aminosulfonyl, alkylsulfonyl, or nitro;

R$^6$ is selected from the group consisting of hydrogen, halogen, alkyl, haloalkyl, or cycloalkyl;

R$^7$ and R$^8$ are independently selected from the group consisting of hydrogen, haloalkyl or alkyl;

R$^a$ and R$^b$ are independently selected from the group consisting of hydrogen, —OR$^6$, halogen, haloalkyl, perhaloalkyl and alkyl;

m is 0-3;

n is 0-3;

p is 0, 1 or 2; and q is 1 or 2.

According to another embodiment, the present disclosure relates to compounds of formula (I) or its tautomers, polymorphs, stereoisomers, prodrugs, solvate, co-crystals or a pharmaceutically acceptable salts thereof, wherein, ring A is selected from pyrrole, imidazole or pyrazole;

ring B is selected from phenyl, pyridine or pyrimidine;

ring C represents a 6-7 membered ring which is unsaturated or partially unsaturated having one, two or three heteroatoms independently selected from O, N or S;

each X independently represents N or C(R$^1$);

Y represents —C(O);

J is absent or is selected from the group consisting of (C$_{1-6}$) alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene or tetrahydropyridylene;

K is a bond or (C$_{1-6}$)alkylene wherein optionally one or more than one methylene groups of alkylene are independently replaced by hetero atoms or groups such as —O—, —N(R$^6$)—, —C(O)—;

M is selected from hydrogen, cyano, halogen, haloalkyl, perhaloalkyl, alkyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, thiocarbonyl, —S(O)$_p$R$^6$, —SO$_3$H, cyclopropyl, cyclobutyl, cyclopentyl, cyclohexyl, cycloheptyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl or pyrimidinyl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cyclopropylene, cyclobutylene, cyclohexylene or (C$_{1-6}$)alkylene;

T is selected from hydrogen, cyano, halogen, hydroxy, haloalkyl, perhaloalkyl alkyl or —(CR$^a$R$^b$)$_m$OR$^6$;

R$^1$, R$^2$, R$^3$, R$^4$ and R$^5$ are independently selected from hydrogen, alkyl, alkoxy, acyl, acylamino, acyloxy, —(CR$^a$R$^b$)$_m$C(O)R$^6$, —(CR$^a$R$^b$)$_m$NR$^7$R$^8$, —(CR$^a$R$^b$)$_m$O(CR$^a$R$^b$)$_n$Si(R$^7$)$_3$, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, alkylthio, aminosulfonyl, alkylsulfonyl, or nitro;

R$^6$ is selected from the group consisting of hydrogen, halogen, alkyl, haloalkyl, or cycloalkyl;

R$^7$ and R$^8$ are independently selected from the group consisting of hydrogen, haloalkyl or alkyl;

R$^a$ and R$^b$ are independently selected from the group consisting of hydrogen, —OR$^6$, halogen, haloalkyl, perhaloalkyl and alkyl;

m is 0-3;

n is 0-3;

p is 0, 1 or 2; and q is 1 or 2.

According to another embodiment, the present disclosure relates to compounds of formula (Ia) or its tautomers, polymorphs, stereoisomers, prodrugs, solvate, co-crystals or a pharmaceutically acceptable salts thereof,

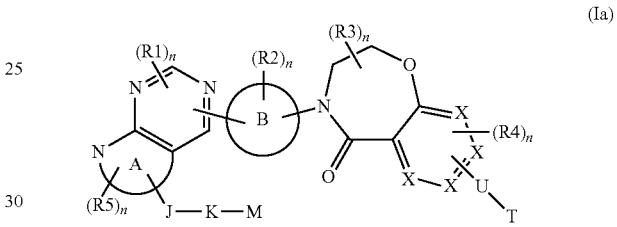

(Ia)

wherein, ring A is selected from pyrrole, imidazole, pyrazole, oxazole, isoxazole, thiazole, isothiazole, triazole, oxadiazole, thiadiazole, dithiazole;

ring B is selected from phenyl, pyridine, pyridazine, pyrimidine or pyrazine;

each X independently represents N or C(R$^1$);

J is absent or is selected from the group consisting of (C$_{1-6}$) alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene or tetrahydropyridylene;

K is a bond or (C$_{1-6}$)alkylene wherein optionally one or more than one methylene groups of alkylene are independently replaced by hetero atoms or groups such as —O—, —N(R$^6$)—, —C(O)—;

M is selected from hydrogen, cyano, halogen, haloalkyl, perhaloalkyl, alkyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, thiocarbonyl, —S(O)$_p$R$^6$, —SO$_3$H, cyclopropyl, cyclohexyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl or pyrimidinyl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cyclopropylene, cyclobutylene, cyclohexylene or (C$_{1-6}$)alkylene;

T is selected from hydrogen, cyano, halogen, haloalkyl, perhaloalkyl or alkyl —(CR$^a$R$^b$)$_m$OR$^6$;

R$^1$, R$^2$, R$^3$, R$^4$ and R$^5$ are independently selected from hydrogen, alkyl, alkoxy, acyl, acylamino, acyloxy, —(CR$^a$R$^b$)$_m$NR$^7$R$^8$, —(CR$^a$R$^b$)$_m$O(CR$^a$R$^b$)$_n$Si(R$^7$)$_3$, azido, cyano, halogen, hydroxy, hydroxyalkyl, haloalkyl, perhaloalkyl, carboxy, alkylcarboxy, carboxyalkyl, carboxyalkyloxy, —SO$_3$H, alkylthio, alkylsulfonyl, or nitro;

R$^6$ is selected from the group consisting of hydrogen, —(CR$^a$R$^b$)$_m$OR$^6$, halogen, haloalkyl, —(CR$^a$R$^b$)$_m$C(O)R$^6$ or alkyl, cycloalkyl;

R$^7$ and R$^8$ are independently selected from the group consisting of hydrogen, —(CR$^a$R$^b$)$_m$OR$^6$, haloalkyl, —(CR$^a$R$^b$)$_m$C(O)R$^6$, alkyl;

R$^a$ and R$^b$ are independently selected from the group consisting of hydrogen, —OR$^6$, halogen, haloalkyl, perhaloalkyl and alkyl;

m is 0-3;
n is 0-3;
p is 0, 1 or 2; and
q is 1 or 2.

According to another embodiment, the present disclosure relates to compounds of formula (Ib) or its tautomers, polymorphs, stereoisomers, prodrugs, solvate, co-crystals or a pharmaceutically acceptable salts thereof,

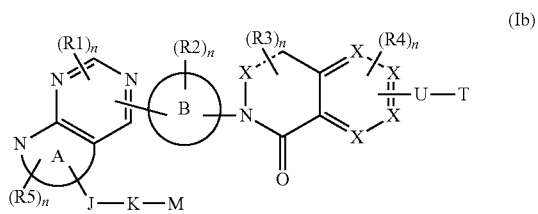

(Ib)

- - - represents a single or double bond;
ring A is selected from pyrrole, imidazole, pyrazole, oxazole, isoxazole, thiazole, isothiazole, triazole, oxadiazole, thiadiazole, dithiazole;
ring B is selected from phenyl, pyridine, pyridazine, pyrimidine or pyrazine;
each X independently represents N or C(R$^1$);
J is absent or is selected from the group consisting of arylene, heterocyclylene, heteroarylene, (C$_{1-6}$)alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene or tetrahydropyridylene;
K is a bond or (C$_{1-6}$)alkylene wherein optionally one or more than one methylene groups of alkylene are independently replaced by hetero atoms or groups such as —O—, —N(R$^6$)—, —C(O)—;
M is selected from hydrogen, cyano, halogen, haloalkyl, perhaloalkyl, alkyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O) NR$^7$R$^8$, —S(O)$_p$R$^6$, —SO$_3$H, cyclopropyl, cyclohexyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl or pyrimidinyl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cyclopropylene, cyclobutylene, cyclohexylene or (C$_{1-6}$)alkylene;

T is selected from hydrogen, cyano, halogen, haloalkyl, perhaloalkyl alkyl or —(CR$^a$R$^b$)$_m$OR$^6$;

R$^1$, R$^2$, R$^3$, R$^4$ and R$^5$ are independently selected from hydrogen, alkyl, alkoxy, acyl, acylamino, acyloxy, —(CR$^a$R$^b$)$_m$NR$^7$R$^8$, —(CR$^a$R$^b$)$_m$O(CR$^a$R$^b$)$_n$Si(R$^7$)$_3$, azido, cyano, halogen, hydroxy, hydroxyalkyl, haloalkyl, perhaloalkyl, carboxy, alkylcarboxy, carboxyalkyl, carboxyalkyloxy, —SO$_3$H, alkylthio, alkylsulfonyl, or nitro;

R$^6$ is selected from the group consisting of hydrogen, —(CR$^a$R$^b$)$_m$OR$^6$, halogen, haloalkyl, —(CR$^a$R$^b$)$_m$C(O)R$^6$ or alkyl, cycloalkyl;

R$^7$ and R$^8$ are independently selected from the group consisting of hydrogen, —(CR$^a$R$^b$)$_m$OR$^6$, haloalkyl, —(CR$^a$R$^b$)$_m$C(O)R$^6$, alkyl;

R$^a$ and R$^b$ are independently selected from the group consisting of hydrogen, —OR$^6$, halogen, haloalkyl, perhaloalkyl and alkyl;

m is 0-3;
n is 0-3;
p is 0, 1 or 2; and
q is 1 or 2.

According to another embodiment, the present disclosure relates to compounds of formula (Ia) or its tautomers, polymorphs, stereoisomers, prodrugs, solvate, co-crystals or a pharmaceutically acceptable salts thereof,

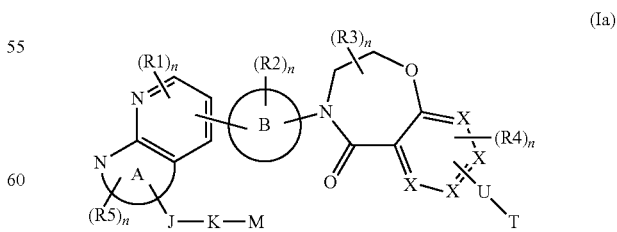

(Ia)

wherein,
ring A is selected from pyrrole, imidazole, pyrazole, oxazole, isoxazole, thiazole, isothiazole, triazole, oxadiazole, thiadiazole, dithiazole;

ring B is selected from phenyl, pyridine, pyridazine, pyrimidine or pyrazine;

each X independently represents N or C(R$^1$);

J is absent or is selected from the group consisting of (C$_{1-6}$)alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene or tetrahydropyridylene;

K is a bond or (C$_{1-6}$)alkylene wherein optionally one or more than one methylene groups of alkylene are independently replaced by hetero atoms or groups such as —O—, —N(R$^6$)—, —C(O)—;

M is selected from hydrogen, cyano, halogen, haloalkyl, perhaloalkyl, alkyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, thiocarbonyl, —S(O)$_p$R$^6$, —SO$_3$H, cyclopropyl, cyclohexyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl or pyrimidinyl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl or alkynyl, cycloalkyl, cyclkenyl, cycloalkylalkyl, aryl, heterocyclyl or heteroaryl;

wherein alkyl, alkenyl or alkynyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cyclopropylene, cyclobutylene, cyclohexylene or (C$_{1-6}$)alkylene;

T is selected from hydrogen, cyano, halogen, haloalkyl, perhaloalkyl or alkyl —(CR$^a$R$^b$)$_m$OR$^6$;

R$^1$, R$^2$, R$^3$, R$^4$ and R$^5$ are independently selected from hydrogen, alkyl, alkoxy, acyl, acylamino, acyloxy, —(CR$^a$R$^b$)$_m$NR$^7$R$^8$, —(CR$^a$R$^b$)$_m$O(CR$^a$R$^b$)$_n$Si(R$^7$)$_3$, azido, cyano, halogen, hydroxy, hydroxyalkyl, haloalkyl, perhaloalkyl, carboxy, alkylcarboxy, carboxyalkyl, carboxyalkyloxy, —SO$_3$H, alkylthio, alkylsulfonyl, or nitro;

R$^6$ is selected from the group consisting of hydrogen, —(CR$^a$R$^b$)$_m$OR$^6$, halogen, haloalkyl, —(CR$^a$R$^b$)$_m$C(O)R$^6$ or alkyl, cycloalkyl;

R$^7$ and R$^8$ are independently selected from the group consisting of hydrogen, —(CR$^a$R$^b$)$_m$OR$^6$, haloalkyl, —(CR$^a$R$^b$)$_m$C(O)R$^6$, alkyl;

R$^a$ and R$^b$ are independently selected from the group consisting of hydrogen, —OR$^6$, halogen, haloalkyl, perhaloalkyl and alkyl;

m is 0-3;

n is 0-3;

p is 0, 1 or 2; and q is 1 or 2.

According to another embodiment, the present disclosure relates to compounds of formula (Ib) or its tautomers, polymorphs, stereoisomers, prodrugs, solvate, co-crystals or a pharmaceutically acceptable salts thereof,

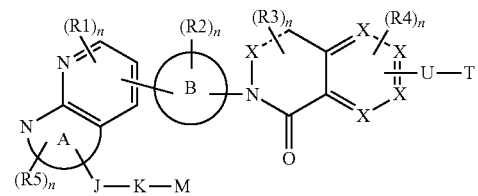

(Ib)

- - - represents a single or double bond;

ring A is selected from pyrrole, imidazole, pyrazole, oxazole, isoxazole, thiazole, isothiazole, triazole, oxadiazole, thiadiazole, dithiazole;

ring B is selected from phenyl, pyridine, pyridazine, pyrimidine or pyrazine;

each X independently represents N or C(R$^1$);

J is absent or is selected from the group consisting of arylene, heterocyclylene, heteroarylene, (C$_{1-6}$)alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene or tetrahydropyridylene;

K is a bond or (C$_{1-6}$)alkylene wherein optionally one or more than one methylene groups of alkylene are independently replaced by hetero atoms or groups such as —O—, —N(R$^6$)—, —C(O)—;

M is selected from hydrogen, cyano, halogen, haloalkyl, perhaloalkyl, alkyl, cyanoalkyl, acyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —S(O)$_p$R$^6$, —SO$_3$H, cyclopropyl, cyclohexyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl or pyrimidinyl;

J, K and M is optionally substituted with one or more substituents independently selected from cyano, nitro, keto, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O)NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl or alkynyl, cycloalkyl, cyclkenyl, cycloalkylalkyl, aryl, heterocyclyl or heteroaryl wherein alkyl, alkenyl or alkynyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ or —NR$^6$S(O)$_2$R$^6$;

U is a bond or is selected from the group consisting of cyclopropylene, cyclobutylene, cyclohexylene or (C$_{1-6}$)alkylene;

T is selected from hydrogen, cyano, halogen, haloalkyl, perhaloalkyl alkyl or —(CR$^a$R$^b$)$_m$OR$^6$;

R$^1$, R$^2$, R$^3$, R$^4$ and R$^5$ are independently selected from hydrogen, alkyl, alkoxy, acyl, acylamino, acyloxy, —(CR$^a$R$^b$)$_m$NR$^7$R$^8$, —(CR$^a$R$^b$)$_m$O(CR$^a$R$^b$)$_n$Si(R$^7$)$_3$, azido, cyano, halogen, hydroxy, hydroxyalkyl, haloalkyl, perhaloalkyl, carboxy, alkylcarboxy, carboxyalkyl, carboxyalkyloxy, —SO$_3$H, alkylthio, alkylsulfonyl, or nitro;

R$^6$ is selected from the group consisting of hydrogen, —(CR$^a$R$^b$)$_m$OR$^6$, halogen, haloalkyl, —(CR$^a$R$^b$)$_m$C(O)R$^6$ or alkyl, cycloalkyl;

$R^7$ and $R^8$ are independently selected from the group consisting of hydrogen, $-(CR^aR^b)_mOR^6$, haloalkyl, $-(CR^aR^b)_mC(O)R^6$, alkyl;

$R^a$ and $R^b$ are independently selected from the group consisting of hydrogen, $-OR^6$, halogen, haloalkyl, perhaloalkyl and alkyl;

m is 0-3;

n is 0-3;

p is 0, 1 or 2; and q is 1 or 2.

The present invention also relates to the process of preparation of compounds of formula (I), or pharmaceutically acceptable salts thereof.

The compounds of formula (I) may be prepared as outlined in Schemes below:

Scheme 1: Preparation of compounds of formula (I)

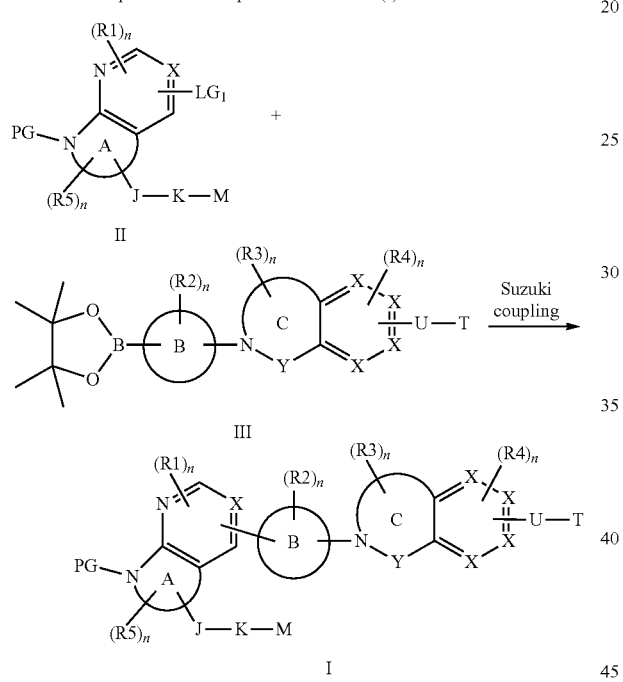

Compounds of formula (I) may be prepared from intermediates of formulae (II) and (III) using Suzuki coupling as shown in Scheme 1 wherein PG is H or a protecting group selected from Tosyl, SEM, MEM, and like, and $LG_1$ is leaving groups selected from halogens, triflate and the like. Deprotection of protecting group (PG) also leads to compounds of formula (I). Intermediates of formula (II) and (III) used herein in Scheme 1 may be prepared as outlined in Schemes 2 and 3 below:

Scheme 2: Preparation of compounds of formula (II)

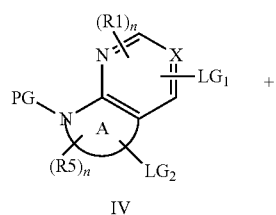

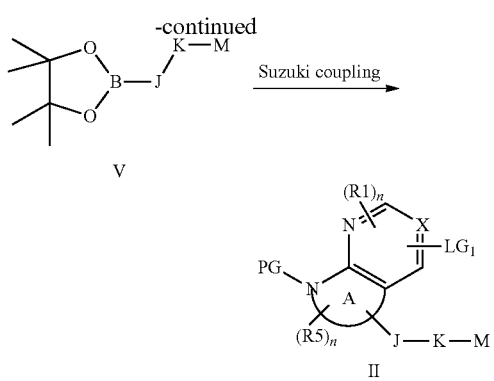

Intermediates of general formula (II) may be prepared from reactions of intermediates of general formulae (IV) and (V) using Suzuki coupling reaction as shown in Scheme 2 wherein PG is H or a protecting group selected from Tosyl, SEM, MEM, and like and $LG_1$ and $LG_2$ are leaving groups selected from halogens, triflate and the like.

Scheme 3: Preparation of compounds of formula (III)

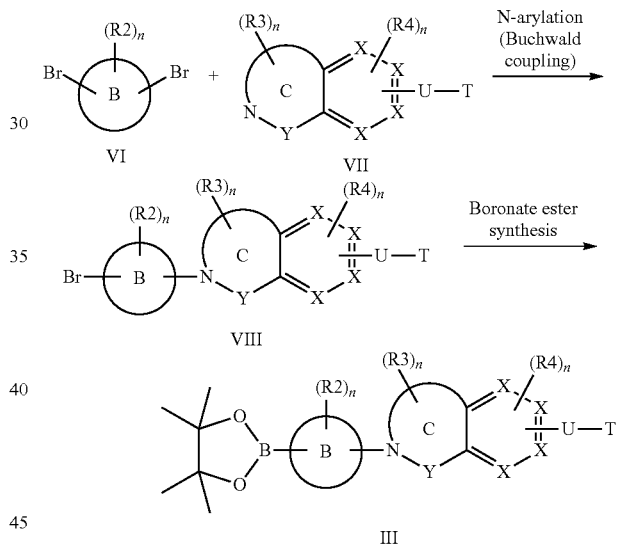

Intermediates of general formula (III) may be prepared from intermediates of general formulae (VI) and (VII) using N-arylation or Buchwald coupling conditions to furnish intermediate of general formula (VIII) which may be converted to the boronic esters of general formula (III) as shown in Scheme 3.

Scheme 4: Preparation of compounds of formula (I) wherein K is —CH2—

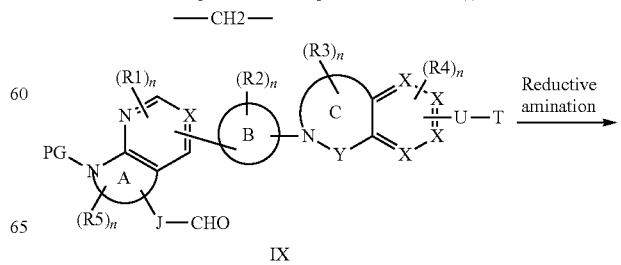

-continued

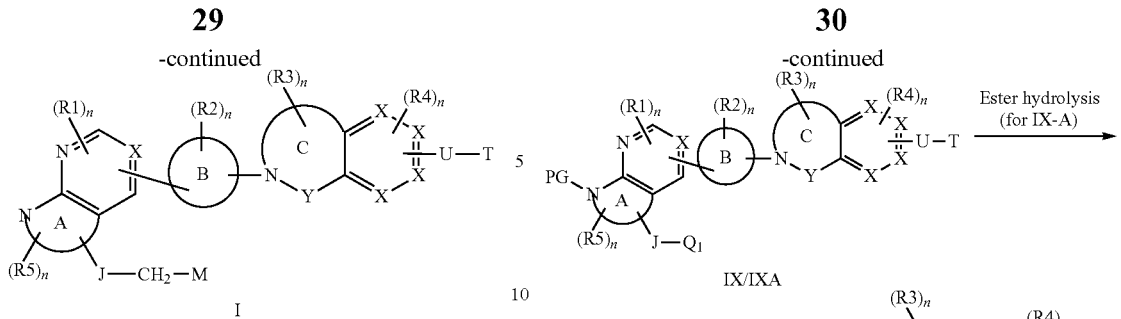

Alternatively, compounds of formula (I) may also be prepared from intermediate of formula (IX) via reductive amination as shown in Scheme 4 wherein PG is H or a protecting group selected from Tosyl, SEM, MEM, and the like. Deprotection of protecting group (PG) also leads to compounds of formula (I).

Scheme 5: Preparation of compounds of formula (I) wherein K is —CO

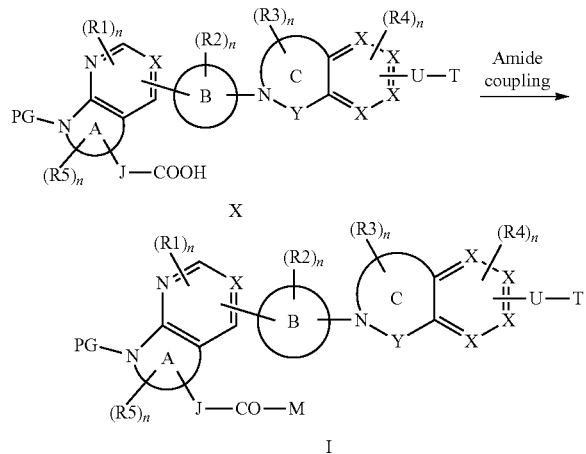

Alternatively, compounds of formula (I) may also be prepared from the corresponding intermediate of the general formula (X) using amide coupling reaction conditions as shown in Scheme 5 wherein PG is H or protecting group selected from Tosyl, SEM, MEM and the like. Deprotection of protecting group (PG) also leads to compounds of formula (I).

Scheme 6: Preparation of compounds of formula (IX) and (X)

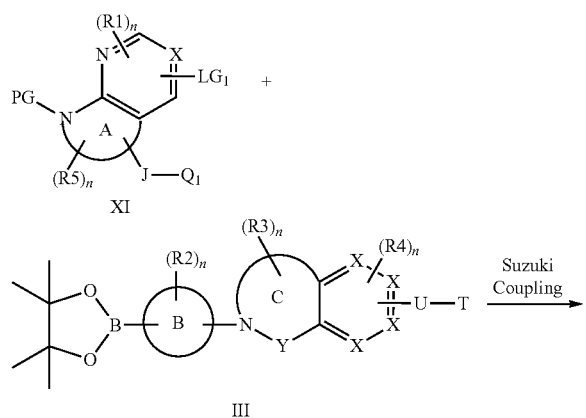

Intermediates of general formulae (IX) and (X) can be prepared from intermediates of general formulae (XI) and (III) via Suzuki coupling reaction conditions as shown in Scheme 6 wherein PG is H or protecting group selected from Tosyl, SEM, MEM; $Q_1$ is —CR(O) (Compound IX) or —$CO_2R$ (Compound IXA); R is H or lower alkyl group, $LG_1$ is leaving groups selected from halogens, triflate and the like.

Scheme 7: Preparation of compounds of formula (II)

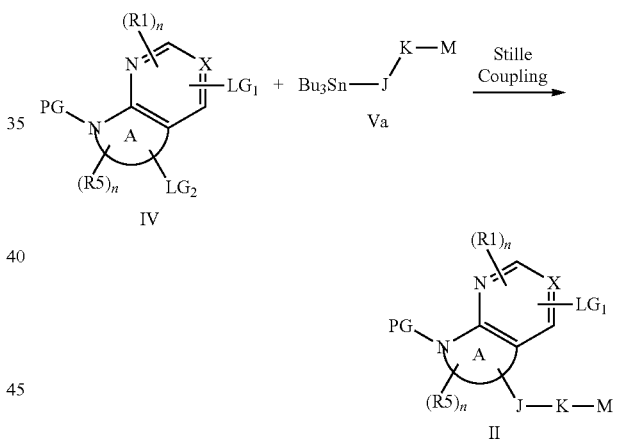

Intermediates of general formula (II) may also be prepared from reactions of intermediates of general formulae (IV) and (Va) using Stille coupling reaction as shown in Scheme 7 wherein PG is H or a protecting group selected from Tosyl, benzenesulfonyl, SEM, MEM and $LG_1$ and $LG_2$ are leaving groups selected from halogens, triflate and the like.

Suzuki coupling: Suzuki coupling is the organic reaction of an aryl- or vinyl-boronic acid with an aryl- or vinyl-halide catalyzed by a palladium(0) complex such as tetrakis(triphenylphosphine)palladium [*Chemical Reviews* 95 (7): 2457-2483].

Stille coupling: Stille coupling is the C—C bond formation reaction between an aryl- or vinyl stannanes and an aryl- or heteroaryl- or vinyl halide (or pseudo halide), which uses various Pd(0) complexes as the catalyst, e.g. tetrakis(triphenylphosphine)palladium [*J. Org. Chem.*, 2009, 74, 5599-5602].

N-arylation reaction: N-Arylation is a chemical reaction used in organic chemistry for the formation of carbon-nitrogen bonds, which may include Ullmann coupling conditions or Buchwald-Hartwig amination reaction conditions. This can be palladium-catalyzed cross-coupling of amines or amides with aryl halides in presence of ligands like Xantphos or Cu(I) catalyzed cross-coupling of amines or amides with aryl halides in presence of ligands like trans-N,N'-dimethylcyclohexane-1,2-diamine. Palladium catalysts used in this reaction may include $PdCl_2$ [P (o-tolyl) 3]$_2$, Pd (PPh$_3$)$_4$ *[Chem. Sci.* 2: 27-50; *Pure Appl. Chem.,* 71 (8): 1416-1423; *J. Am. Chem. Soc.* 2001, 123 (31), 7727-7729].

Reductive Amination: Reductive amination is a form of reaction that involves the conversion of a carbonyl group to an amine via an intermediate imine. The carbonyl group is most commonly a ketone or an aldehyde. The reaction is carried out with reducing agents that are more reactive toward protonated imines than ketones, and that are stable under moderately acidic conditions. These include sodium cyanoborohydride (NaBH$_3$CN) and sodium triacetoxyborohydride (NaBH(OCOCH$_3$)$_3$. *[Organic Reactions,* 1, 59, 2002]

Amide Coupling: Amide coupling may be carried out using any suitable amide coupling regents such as oxalyl chloride, thionyl chloride, BOP—Cl, DCC, HOBt, HOAt, HATU, EDCI, alkylchloroformate and the like in the presence of organic non-nucleophilic bases such as triethyl amine, di-isopropylethyl amine, pyridine, N-methylpyrrolidine, N,N-dimethylaminopyridine, DBU, DABCO, other hindered amines and pyridines. The amide coupling reaction may be carried out in the presence of solvents such as dichloromethane, dichloroethane, DMF, dimethylacetamide, THF, acetonitrile or mixture of them may be used at a temperature ranging from −5 to 150° C. The reaction may be carried out optionally in presence of catalytic amount of DMF. Amide coupling may also be carried out by heating ester and amine either in the absence of solvent or in presence of high boiling solvent like toluene, xylene, DMSO. Amide coupling may be carried out in presence of trialkyl aluminium (*Chem. Commun.,* 2008, 1100-1102).

Wherever desired or necessary, in any of the above mentioned processes, any of the compounds of formula (I) may be converted into a pharmaceutically acceptable salt or vice versa or converting one salt form into another pharmaceutically acceptable salt form.

According to another embodiment the present invention provides co-crystals comprising a compound of formula (I) wherein compounds of formula (I) that contain groups capable of acting as donors and/or acceptors for hydrogen bonds may be capable of forming co-crystals with suitable co-crystal formers. These co-crystals may be prepared from compounds of Formula (I) by known co-crystal forming procedures. Such procedures include grinding, heating, co-subliming, co-melting, or contacting in solution compounds of formula I with the co-crystal former under crystallization conditions and isolating co-crystals thereby formed.

According to another embodiment the present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

In another embodiment the present invention provides a compound of formula (I) or a pharmaceutically acceptable salt thereof for use as a medicament.

In another embodiment the present invention provides a compound of formula (I) or a pharmaceutically acceptable salt thereof for use in the treatment of a disease or disorder mediated by Btk.

According to another embodiment compositions can be prepared by mixing one or more compounds described herein, or pharmaceutically acceptable salts or tautomers thereof, with pharmaceutically acceptable carriers or the like, to treat or ameliorate a variety of Btk related conditions. The pharmaceutical compositions of the present disclosure can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, transmucosal administration, rectal administration, topical administration or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described above, pharmaceutically acceptable excipients and carries are generally known to those skilled in the art and are thus included in the instant invention. Such excipients and carriers are described, for example, in "Remington's Pharmaceutical Sciences" Mack Pub. Co., New Jersey (1991).

The formulations of the invention can be designed for to be short-acting, fast-releasing, long-acting, and sustained-releasing. Thus, the pharmaceutical formulations can also be formulated for controlled release or for slow release.

The pharmaceutical compositions of the present disclosure can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The pharmaceutical compositions may contain, for example, from about 0.1% by weight, to about 90% or more by weight, of the active material, depending on the method of administration. Where the compositions comprise dosage units, each unit can contain, for example, from about 0.1 to 500 mg or more of the active ingredient. The dosage as employed for adult human treatment can range, for example, from about 0.1 to 1000 mg per day, depending on the route and frequency of administration.

Specific dosages can be adjusted depending on conditions of the BTK related condition, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 1 mg/kg/day to about 500 mg/kg/day in single or in divided doses. Typically, dosages for humans can range from about 5 mg to about 100 mg per day, in a single or multiple doses.

A therapeutically effective dose or amount can vary depending upon the route of administration and dosage form. Some compositions of the instant invention is a formulation that exhibits a high therapeutic index. The therapeutic index is the dose ratio between toxic and therapeutic effects which can be expressed as the ratio between LD50 and ED50. The LD50 is the dose lethal to 50% of the population and the ED50 is the minimal efficacious dose to achieve 50% of the desired response. The LD50 and ED50 can be determined by standard pharmaceutical procedures in animal cell cultures or experimental models.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc.

Compounds of the invention may be useful in the treatment of an indication selected from: Autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjogren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including but not limited to multiple myeloma; leukemia; acute myelogenous leukemia; chronic myelogenous leukemia; lymphocytic leukemia; myeloid leukemia; non-Hodgkin lymphoma; lymphomas; polycythemia vera; chronic lymphocytic leukemia; Mantle cell lymphoma, essential thrombocythemia; myelofibrosis with myeloid metaplasia; and Waldenstroem disease.

In another embodiment, the invention provides a method of treating a disease which is treated by the modulation of Btk-comprising administration of a therapeutically acceptable amount of a compound of formula (I) or a salt thereof. In a further embodiment, the disease is selected from the aforementioned list.

The compound of the present invention may be administered either simultaneously with, or before or after, one or more other therapeutic agent. The compound of the present invention may be administered separately, by the same or different route of administration, or together in the same pharmaceutical composition as the other agents.

According to another embodiment, compounds of Formula (I) of the invention can be used alone or in combination with one or more additional therapeutic agent selected from the group consisting of a BTK inhibitors such as Ibrutinib, AVL-292, ONO-4059; B-cell depleting protein based therapeutics such as Rituxan, a CD20 antibody; calcineurin inhibitor such as cyclosporin A or FK 506; a mTOR inhibitor such as rapamycin, 40-O-(2-hydroxyethyl)-rapamycin, CCI779, ABT578, AP23573, AP23464, AP23675, AP23841, TAFA-93, biolimus-7 or biolimus-9; an ascomycin having immunosuppressive properties such as ABT-281, ASM981; corticosteroids such as cortisone, dexamethasone, methylprednisolone, prednisolone, prednisone; cyclophosphamide; azathioprene; methotrexate; leflunomide; teriflunomide; mizoribine; etanercept; infliximab; a chemotherapeutic agent such as paclitaxel, gemcitabine, cisplatine, doxorubicin, 5-fluorouracil, imatinib, dasatinib, sunitinib, gefitinib, sorafenib, erlotinib, camptothecin, topotecan, daunomycin, etoposide, taxol, vinblastine, bortezomib, carfilzomib; mycophenolic acid or salt; mycophenolate mofetil; 15-deoxyspergualine or an immunosuppressive homologue, analogue or derivative thereof; NSAIDs such as Ibuprofen, flurbiprofen, naproxen, diclofenac, misoprostol, sulindac, oxaprozin, diflunisal, piroxicam, indomethacin, etodolac, fenoprofen, ketoprofen, sodium nabumetone, sulfasalazine, tolmetin sodium, hydroxychloroquine, celecoxib, valdecoxib, lumiracoxib, etoricoxib; JAK kinase inhibitors such as Tofacitinib, LY-3009104, VX-509, GLPG-0634, ASP-015K, N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-21 1,3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550); SYK inhibitor such as fostamatinib; sphingosine-1-phosphate receptor modulators such as FTY720 (fingolimod); immunosuppressive monoclonal antibodies such as monoclonal antibodies to leukocyte receptors like MHC, CD2, CD3, CD4, CD7, CD8, CD25, CD28, CD40, CD45, CD52, CD58, CD80, CD86 or their ligands; other immunomodulatory compounds such as a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or an anti-infectious agent. Further combination partners to a compound of formula (I) may be selected from a PI3K inhibitor (e.g. pan, or alpha, beta, gamma, delta selectives), TNF inhibitors, IL1 beta inhibitors, IL17 inhibitors, and inhibitors of IL6 or IL receptor.

In one embodiment, the invention provides methods of treating or preventing a condition associated with BTK in a subject, such as a mammal, i.e., a human or non-human mammal, comprising administering an effective amount of one or more compounds described herein to the subject. Suitable non-human subjects that can be treated include domestic or wild animals, companion animals, such as dogs, cats and the like; livestock, including horses, cows and other ruminants, pigs, poultry, rabbits and the like; primates, for example monkeys, such as macaques including rhesus monkeys and cynomolgus monkeys, marmosets, tamarins and the like, apes, including chimpanzees and orangutans; and rodents, such as rats, mice, gerbils, guinea pigs and the like.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by Btk kinases. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

The invention also provides a compound of formula (I) for use in a method of treating a disease or condition mediated by Btk, wherein the compound of formula (I) is prepared for administration with another therapeutic agent. The invention also provides another therapeutic agent for use in a method of treating a disease or condition mediated by Btk, wherein the other therapeutic agent is prepared for administration with a compound of formula (I). The invention also provides a compound of formula (I) for use in a method of treating a disease or condition mediated by Btk, wherein the compound of formula (I) is administered with another therapeutic agent. The invention also provides another therapeutic agent for use in a method of treating a disease or condition mediated by Btk, wherein the other therapeutic agent is administered with a compound of formula (I).

EXAMPLES

The invention is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

Synthesis of Intermediates IV-1 to IV-5

Following intermediates were synthesized as described in the references mentioned in the following table (Table-1)

TABLE 1

| Number | Structure/IUPAC name | Reference | LCMS (M + 1)$^+$ |
|---|---|---|---|
| IV-1 | 4-chloro-6-iodo-7-(p-tolylsulfonyl)pyrrolo[2,3-d]pyrimidine | WO03000695 | 434 |
| IV-2 | 4-chloro-2-iodo-1-(p-tolylsulfonyl)pyrrolo[2,3-b]pyridine | WO2003000688 | 433 |

TABLE 1-continued

| Number | Structure/IUPAC name | Reference | LCMS (M + 1)$^+$ |
|---|---|---|---|
| IV-3 | 7-(benzenesulfonyl)-4-chloro-6-iodo-pyrrolo[2,3-d]pyrimidine | WO2010007114 | 420 |
| IV-4 | 1-(benzenesulfonyl)-4-chloro-2-iodo-pyrrolo[2,3-b]pyridine | US20070129364 | 419 |
| IV-5 | [4-chloro-1-(2-trimethylsilylethoxymethyl)pyrrolo[2,3-b]pyridin-2-yl]boronic acid | WO2010003133 | 327 |

Intermediate VII-1: 8-Cyclopropyl-3,4-Dihydro-2H-1,4-Benzoxazepin-5-One

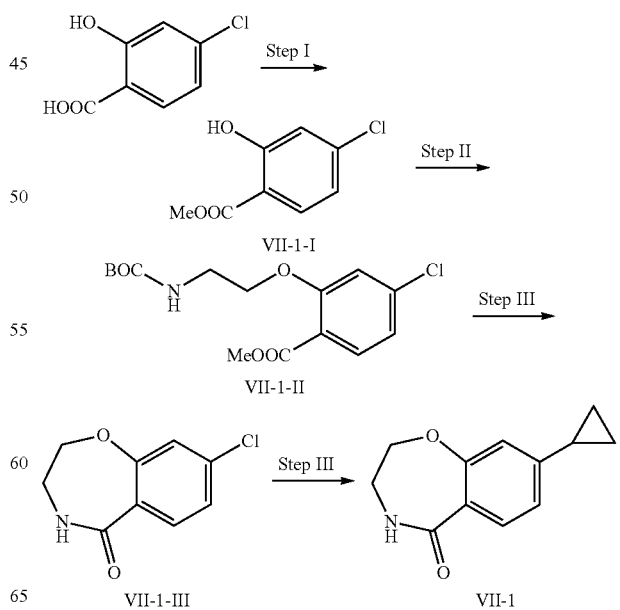

Step-I: Methyl 4-chloro-2-hydroxy-benzoate (VII-1-I)

To a solution of 4-chlorosalicylic acid (75 g, 435.6 mmol) in anhydrous DMF (871 mL) was added $Cs_2CO_3$ (70.7 g, 217.8 mmol) and MeI (27.5 mL, 439.9 mmol) sequentially. The reaction mixture was stirred at room temperature overnight. Ice cold water (3 L) was added to the reaction mixture and the precipitated solid was filtered and dried to provide VII-1-I (75 g, 92% yield).

Step-II: Methyl 2-[2-(tert-butoxycarbonylamino)ethoxy]-4-chloro-benzoate (VII-1-II)

To a solution of VII-1-I (126.8 g, 679.6 mmol) in anhydrous DMF (1 L) was added anhydrous $K_2CO_3$ (187.5 g, 1.36 mol) and stirred at room temperature for 30 min. Finally, a solution of tert-butyl N-(2-bromoethyl)carbamate (228.4 g, 1.02 mol) in THF (360 mL) was added to it and the reaction mixture was stirred at 65° C. for 16 h. The reaction mixture was, then, filtered through celite and the filtrate was concentrated under reduced pressure. Diethyl ether (1.5 L) was added to the residue and was washed with water (1 L); brine (1 L), dried over anhydrous $Na_2SO_4$, filtered and concentrated under reduced pressure to provide crude intermediate VII-1-II (242 g); which was used without further purification.

Step-III: 8-chloro-3,4-dihydro-2H-1,4-benzoxazepin-5-one (VII-1-III)

To a solution of crude VII-1-II (242 g) in $CH_2Cl_2$ (500 mL) was added TFA (250 mL, 3.68 mol) at 0° C. and the reaction mixture was stirred at room temperature for 16 h. Solvent was removed under reduced pressure and the residue was dried. To this was added toluene (500 mL) and $Et_3N$ (512 mL, 3.68 mol) and the reaction mixture was refluxed for 16 h. Finally, solvents were removed under reduced pressure and ice cold water (500 mL) was added to the residue. The precipitated solid was filtered and dried. It was, then, stirred in diethyl ether (200 mL) and filtered to provide VII-1-III (40 g, 29% yield for two steps). LCMS: m/z 198 (M+1)$^+$.

Step-IV: 8-cyclopropyl-3,4-dihydro-2H-1,4-benzoxazepin-5-one (VII-1)

Argon was purged through a suspension of VII-1-III (10 g, 50.7 mmol), cyclopropylboronic acid (13.1 g, 152 mmol), anhydrous $K_3PO_4$ (32 g, 152.3 mmol) and tricyclohexylphosphine (5.7 g, 20.3 mmol) in toluene:water (150 mL+20 mL) for 30 min, followed by addition of Pd(OAc)$_2$ (2.3 g, 10.1 mmol). The reaction mixture was then stirred at 110° C. for 16 h. After completion of reaction, the reaction mixture was filtered through celite and the residue was washed with EtOAc (50 mL×3). The combined organic layers were concentrated under reduced pressure and the residue was purified by silica gel column chromatography (25% acetone in hexane) to provide INT VII-1 (8 g, 77% yield). LCMS; m/z: 204 (M+1)$^+$. $^1$H NMR (CDCl$_3$, 400 MHz) δ 0.73-0.77 (m, 2H); 0.99-1.04 (m, 2H); 1.86-1.90 (m, 1H); 3.50 (q, J=4.8 Hz, 2H); 4.37 (two d, J=4.4 Hz, 2H); 6.80 (d, J=1.6 Hz, 1H); 6.81 (dd, J$_1$=1.2 Hz, J$_2$=8.8 Hz, 1H); 7.35 (bs, 1H); 7.89 (d, J=8.8 Hz, 1H).

Following intermediates VII-2 to VII-4 were synthesized as described in the references mentioned in the following table (Table-2)

TABLE 2

| Number | Structure/IUPAC name | Reference | LCMS (M + 1)$^+$ |
|---|---|---|---|
| VII-2 | 6-cyclopropyl-3,4-dihydro-2H-isoquinolin-1-one | WO2009098144 A1 | 188 |
| VII-3 | 6-cyclopropyl-2H-isoquinolin-1-one | WO2010/000633 A1 | 186 |
| VII-4 | 6-cyclopropyl-2H-phthalazin-1-one | WO2007002313 A2 | 187 |

Intermediate VII-5: 8-cyclopropyl-6-fluoro-3,4-dihydro-2H-1,4-benzoxazepin-5-one

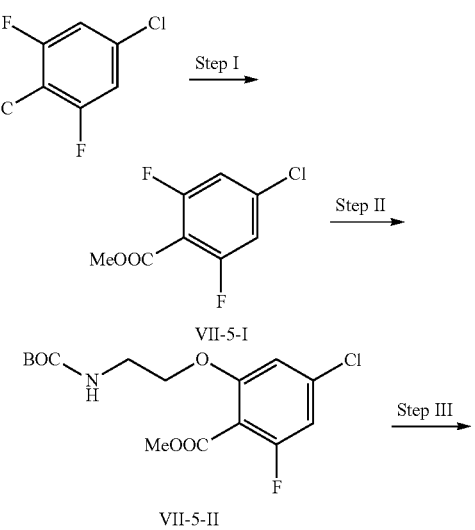

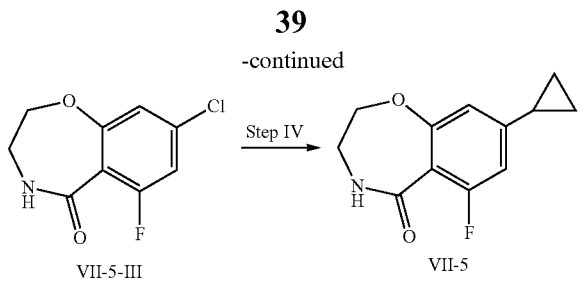

Step-I: Methyl 4-chloro-2,6-difluoro-benzoate (VII-5-I)

Intermediate VII-5-I was synthesized as described for the synthesis of VII-1-1; using 4-chloro-2,6-difluorobenzoic acid (yield: 93%).

Step-II: Methyl 2-[2-(tert-butoxycarbonylamino)ethoxy]-4-chloro-6-fluoro-benzoate (VII-5-II)

A solution of VII-5-I (5 g, 24.2 mmol) and tert-butyl N-(2-hydroxyethyl)carbamate (4.7 g, 29.0 mmol) in anhydrous THF (50 mL) was cooled to −40° C., and NaH (washed with hexane) (0.76 g, 31.5 mmol) was added to it portion wise over 30 min. The reaction mixture was warmed to −20° C. over 1 h and quenched using saturated NH$_4$Cl solution (100 mL). Extraction was carried out using EtOAc (50 mL); the combined organic layers were washed with brine (100 mL), dried over anhydrous Na$_2$SO$_4$, filtered and concentrated under reduced pressure. The residue was purified by silica gel column chromatography (12% EA in hexane) to provide VII-5-II (5.2 g, 61% yield). LCMS; m/z: 348 (M+1)$^+$.

Step-III: 8-chloro-6-fluoro-3,4-dihydro-2H-1,4-benzoxazepin-5-one (VII-5-III)

To a solution of VII-5-II (4.8 g, 13.8 mmol) in MeOH (50 mL) was added aqueous NaOH solution (2.8 g in 30 mL H$_2$O, 69.2 mmol) and the reaction mixture was stirred at 60° C. for 1 h. MeOH was removed under reduced pressure and 10% citric acid solution was added to the reaction mixture to make it acidic (pH<4). Extraction was carried out using EtOAc (50 mL×3); the combined organic layers were washed with water (100 mL), brine (100 mL), dried over anhydrous Na$_2$SO$_4$, filtered and concentrated under reduced pressure. The residue was, then, stirred in 1M HCl in dioxane (50 mL) at room temperature for 3 h. Finally, dioxane was removed under reduced pressure; the residue was washed with ether (30 mL×2) and dried. The solid obtained was, then, dissolved in DMF (30 mL), to which N-methylmorpholine (4.2 mL; 38.7 mmol) and HATU (7.4 g, 19.4 mmol) were added sequentially. The reaction mixture was stirred at room temperature for 16 h. Finally, ice-cold water was added to the reaction mixture and the resultant solid was filtered and dried to provide VII-5-III (1.8 g, 60% yield). LCMS; m/z: 216 (M+1)$^+$.

Step-IV: 8-cyclopropyl-6-fluoro-3,4-dihydro-2H-1,4-benzoxazepin-5-one (VII-5)

Intermediate VII-5 was synthesized as described for the synthesis of VII-1; using intermediate VII-5-III (yield: 80%). LCMS; m/z: 222 (M+1)$^+$. $^1$H NMR (CDCl$_3$, 400 MHz) δ 0.65-0.68 (m, 2H); 1.01-1.04 (m, 2H); 1.81-1.86 (m, 1H); 3.40 (q, J=5.6 Hz, 2H); 4.27 (t, J=5.6 Hz, 2H); 6.57 (s, 1H); 6.62 (d, J=11.2 Hz, 1H); 7.28 (bs, 1H).

Alternatively, intermediate VII-5 can also be synthesized using 4-bromo-2,6-difluorobenzoic acid as described below.

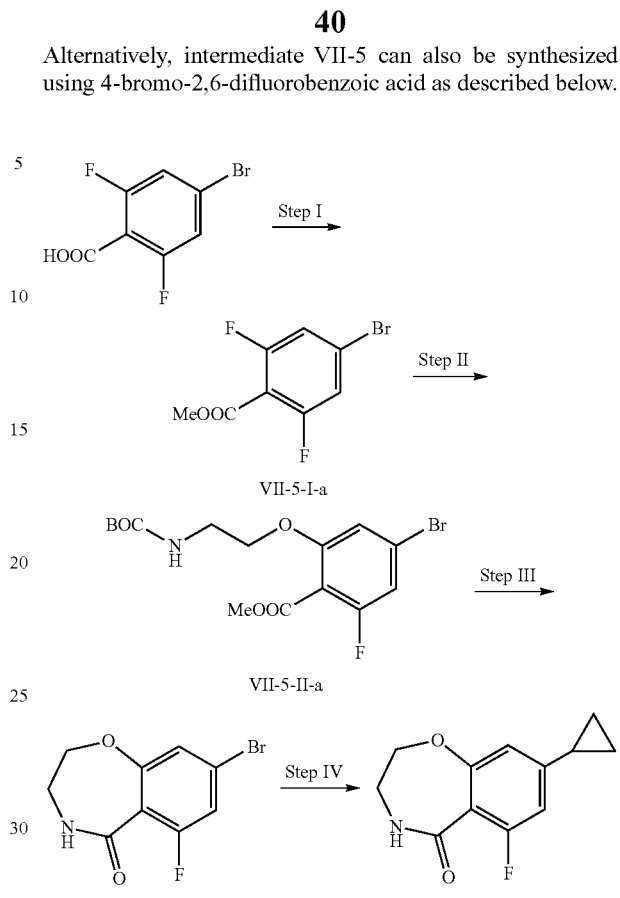

Step-I: methyl 4-bromo-2,6-difluoro-benzoate (VII-5-I-a): As described for the synthesis of VII-5-I.

Step-II: methyl 4-bromo-2-[2-(tert-butoxycarbonylamino)ethoxy]-6-fluoro-benzoate (VII-5-II-a): As described for the synthesis of VII-5-II.

Step-III: 8-bromo-6-fluoro-3,4-dihydro-2H-1,4-benzoxazepin-5-one (VII-5-III-a): As described for the synthesis of VII-5-III-a.

Step-IV: 8-cyclopropyl-6-fluoro-3,4-dihydro-2H-1,4-benzoxazepin-5-one (VII-5): As described above (VII-5-III to VII-5).

Alternate synthesis of VII-5

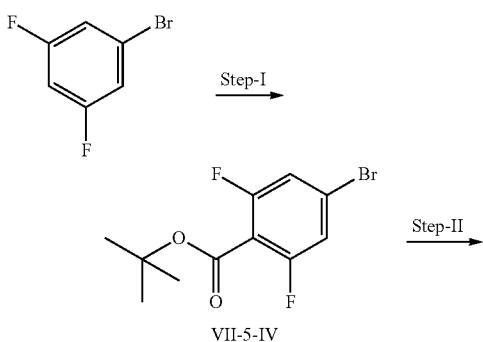

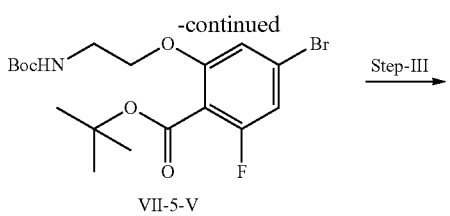

VII-5-V

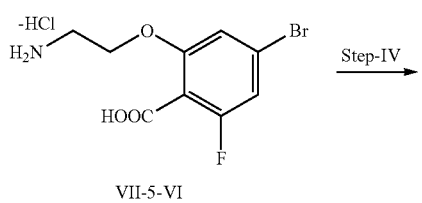

VII-5-VI

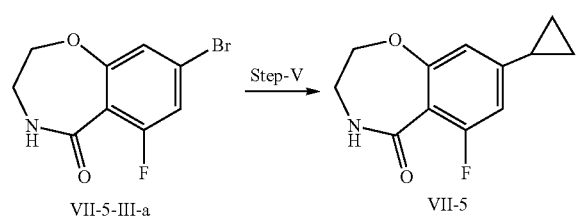

VII-5-III-a    VII-5

Step-I: tert-butyl 4-bromo-2,6-difluoro-benzoate (VII-5-IV)

To a solution of diisopropylamine (17.9 mL, 0.12 mol) in anhydrous THF at −78° C. was added n-BuLi (45.5 mL, 0.11 mol, 2.5 M in hexane) dropwise, over period of 15 min and the resulting solution was stirred at −78° C. for 30 mins. To this was added 1-bromo-3,5-difluoro benzene (20.0 g, 0.10 mol) in THF (30 mL) dropwise and it was stirred for 1 h. Finally, Boc-anhydride (26.0 mL, 0.11 mol) was added to it and the reaction mixture was slowly allowed to come to room temperature over a period of 2 h. After completion of the reaction, it was diluted with water (100 mL) and extraction was carried out using diethyl ether (300×2). The combine organic layers were washed with water (250 mL), brine (250 mL) and dried over anhydrous Na$_2$SO$_4$, filtered and concentrated under reduced pressure to provide crude VII-5-IV (26 g) as a brown liquid, which was used for next step with out any purification. $^1$H NMR (DMSO-d$_6$, 400 MHz) δ 1.42 (s, 9H), 7.63 (d, J=8.0 Hz, 2H).

Step-II: tert-butyl 4-bromo-2-[2-(tert-butoxycarbonylamino)ethoxy]-6-fluoro-benzoate (VII-5-V)

A solution of VII-5-IV (26 g, 88.7 mmol) and tert-butyl N-(2-hydroxyethyl)carbamate (15.7 g, 97.6 mmol) in anhydrous THF (400 mL) was cooled to −10° C.; and NaH (60% suspension in oil) (5.3 g, 133 mmol) was added to it portion wise over 30 min. The reaction mixture was stirred for 1 h and quenched using saturated NH$_4$Cl solution (300 mL). Extraction was carried out using EtOAc (300 mL×2); the combined organic layers were washed with brine (350 mL), dried over anhydrous Na$_2$SO$_4$, filtered and concentrated under reduced pressure to provide desired product VII-5-V (32 g) as a brown thick oil, which was used for next step with out any purification. LCMS: m/z: 278 [M-(2×BOC)]$^+$ (67% pure). $^1$H NMR (CDCl$_3$, 400 MHz) δ 1.44 (s, 9H); 1.56 (s, 9H); 3.51 (q, J=5.4 Hz, 2H); 4.07 (t, J=5.3 Hz, 2H); 5.07 (bs, 1H); 6.84 (bs, 1H); 6.93 (dd, J$_1$=1.4 Hz, J$_2$=8.1 Hz, 1H).

Step-III: 2-(2-aminoethoxy)-4-bromo-6-fluoro-benzoic acid (hydrochloride salt) (VII-5-VI)

To a solution of compound VII-5-V (32 g) in anhydrous CH$_2$Cl$_2$ (400 mL) was added a solution of 4M HCl in dioxane (55 mL); and the reaction mixture was stirred at room temperature for 16 h. Finally, solvents were removed under reduced pressure; the residue was washed with diethyl ether (50 mL×2) and dried to provide desired compound VII-5-VI (17 g) as white solid. LCMS: m/z: 278 (M+1)$^+$. $^1$H NMR (DMSO-d$_6$, 400 MHz) δ 3.10-3.16 (m, 2H); 4.33 (t, J=6.0 Hz, 2H); 7.30-7.35 (aromatics, 2H); 8.11 (bs, 3H); 13.60 (bs, 1H).

Step-IV: 8-bromo-6-fluoro-3,4-dihydro-2H-1,4-benzoxazepin-5-one (VII-5-III-a)

Intermediate VII-5-VI was subjected to intramolecular amide coupling cyclization reaction conditions as described in step-III of synthesis of VII-5-III; to provide VII-5-III-a.

Step-V

As described in step-IV for the synthesis of VII-5 (from VII-5-III).

Intermediate VII-6: 8-cyclopropyl-3,4-dihydro-2H-pyrido[2,3-f][1,4]oxazepin-5-one

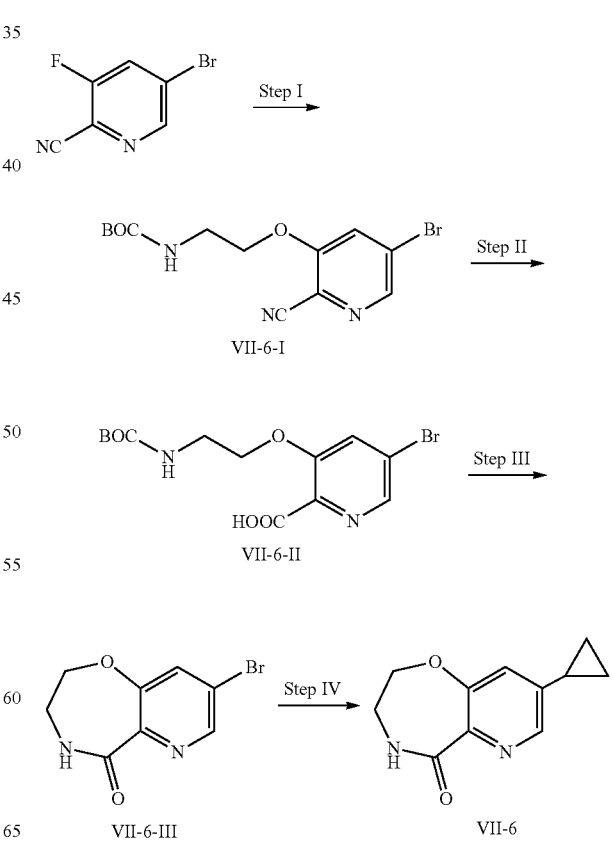

Step-I: tert-butyl N-[2-[(5-bromo-2-cyano-3-pyridyl)oxy]ethyl]carbamate (VII-6-I)

To a solution of 5-bromo-3-fluoropicolinonitrile (7.5 g, 37.7 mmol) and tert-butyl N-(2-hydroxyethyl)carbamate (7.3 g, 45.2 mmol) in anhydrous DMF (50 mL) was added anhydrous $K_2CO_3$ (10.0 g, 75.4 mmol), and the reaction mixture was stirred at 100° C. for 7 h. Ice-cold water (100 mL) was, then, added to it and the resultant solid was filtered and dried to provide VII-6-I (7.1 g, 55% yield). LCMS; m/z: 342 $(M+1)^+$.

Step-II: 5-bromo-3-[2-(tert-butoxycarbonylamino)ethoxy]pyridine-2-carboxylic acid (VII-6-II)

To a solution of VII-6-I (5 g, 20.7 mmol) in EtOH (100 mL) was added aqueous NaOH solution (4.1 g in 40 mL water, 103.7 mmol) and the reaction mixture was refluxed for 16 h. EtOH was then removed under reduced pressure and the residue was acidified using 10% citric acid solution. Extraction was carried out using EtOAc (50 mL×2); the combined organic layers were washed with brine (100 mL), dried over anhydrous $Na_2SO_4$, filtered and concentrated under reduced pressure to provide VII-6-II (3.6 g, 68% yield). LCMS; m/z: 362 $(M+1)^+$.

Step-III: 8-bromo-3,4-dihydro-2H-pyrido[2,3-f][1,4]oxazepin-5-one (VII-6-III)

HCl gas was purged to a solution of VII-6-II (3.6 g, 9.9 mmol) in MeOH (60 mL) at 0° C. for 3 h. The reaction mixture was, then, refluxed for 16 h. Solvent was removed under reduced pressure and the residue was dried. It was then refluxed in 1,4-dioxane (50 mL) and TEA (13.8 mL, 99 mmol) for 16 h. Finally, solvents were removed under reduced pressure and the residue was subjected to silica gel column chromatography (EtOAc) to provide VII-6-III (1 g, 41% yield). LCMS; m/z: 243 $(M+1)^+$; 245 $(M+3)^+$.

Step-IV: 8-cyclopropyl-3,4-dihydro-2H-pyrido[2,3-f][1,4]oxazepin-5-one (VII-6)

Intermediate VII-6 was synthesized as described for the synthesis of VII-1 using intermediate VII-6-III (yield: 80%). LCMS; m/z: 205 $(M+1)^+$. $^1H$ NMR (DMSO-$d_6$, 400 MHz) δ 0.79-0.85 (m, 2H); 1.02-1.07 (m, 2H); 1.96-2.01 (m, 1H); 3.29-3.33 (m, 2H); 4.23 (t, J=5.2 Hz, 2H); 7.10 (s, 1H); 8.24 (s, 1H); 8.41 (bs, 1H).

Intermediate VIII-1: 4-(3-bromo-2-methyl-phenyl)-8-cyclopropyl-2,3-dihydro-1,4-benzoxazepin-5-one

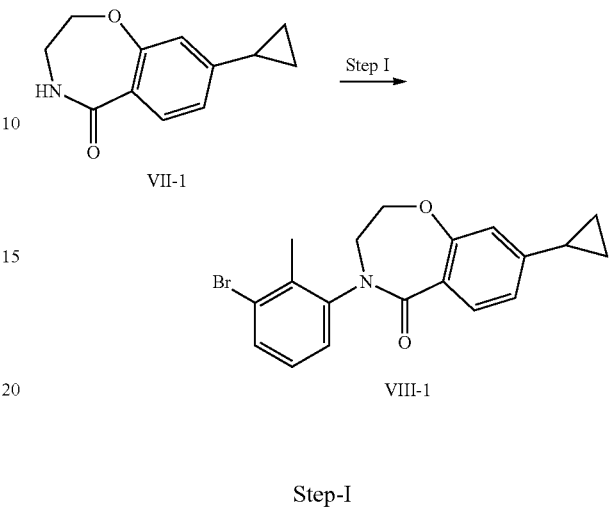

Step-I

Argon was purged through a solution of VII-1 (9 g, 44.33 mmol), 2,6-dibromo toluene (16.6 g, 66.5 mmol), N,N-dimethylcyclohexane-1,2-diamine (2.52 g, 17.7 mmol) and $K_3PO_4$ (18.8 g, 88.66 mmol) in dioxane for 30 min and then cuprous iodide (3.37 g, 3.37 mmol) was added. The resulting reaction mixture was then heated at 100° C. for 16 h. After completion of reaction (monitored by TLC), the solid was filtered off and the filtrate was diluted using EtOAc (150 mL). The organic layer was washed with water (100 mL), brine (100 mL), dried over anhydrous $Na_2SO_4$, filtered and concentrated under reduced pressure. The crude product so obtained was purified by silica gel column chromatography (using 20% EtOAc in hexane) to afford title compound VIII-1 (7 g, 44%); LCMS: m/z 372 $(M+1)^+$. $^1H$ NMR (CDCl$_3$, 400 MHz) δ 0.74-0.78 (m, 2H); 1.02-1.06 (m, 2H); 1.80-1.93 (m, 1H); 2.36 (s, 3H); 3.80-3.82 (m, 2H); 4.42-4.44 (m, 2H); 6.75 (s, 1H); 6.90 (d, J=8.0 Hz, 1H); 7.11-7.19 (aromatics, 2H); 7.55 (d, J=8.0 Hz, 1H); 7.76 (d, J=8.0 Hz, 1H).

Following three intermediates were also synthesized using similar procedure as described for the synthesis of VIII-1 from their corresponding intermediates.

TABLE 3

| No | Structure/IUPAC name | Characterization data | INT used |
|---|---|---|---|
| VIII-2 | 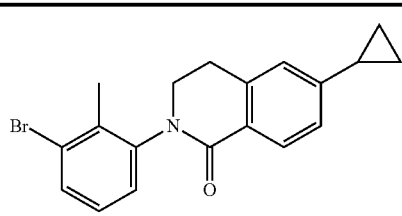<br>2-(3-bromo-2-methyl-phenyl)-6-cyclopropyl-3,4-dihydroisoquinolin-1-one | LCMS: m/z; 356 $(M + 1)^+$. $^1H$ NMR (CDCl$_3$, 400 MHz) δ 0.76-0.80 (m, 2H); 1.00-1.10 (m, 2H); 1.90-2.00 (m, 1H); 2.34 (s, 3H); 3.00-3.06 (m, 1H); 3.16-3.24 (m, 1H); 3.66-3.72 (m, 1H); 3.88-3.95 (m, 1H); 6.92 (s, 1H); 7.05 (d, J = 6.8 Hz, 1H); 7.09-7.18 (aromatics, 2H); 7.54 (d, J = 6.8 Hz, 1H); 8.01 (d, J = 8.0 Hz, 1H) | VII-2 |

TABLE 3-continued

| No | Structure/IUPAC name | Characterization data | INT used |
|---|---|---|---|
| VIII-3 | 2-(3-bromo-2-methyl-phenyl)-6-cyclopropyl-isoquinolin-1-one | LCMS: m/z; 354 (M + 1)+ | VII-3 |
| VIII-4 | 2-(3-bromo-2-methyl-phenyl)-6-cyclopropyl-phthalazin-1-one | LCMS: m/z; 355 (M + 1)+ | VII-4 |

Intermediate VIII-5: [2-bromo-6-(8-cyclopropyl-5-oxo-2,3-dihydro-1,4-benzoxazepin-4-yl)phenyl]methyl acetate

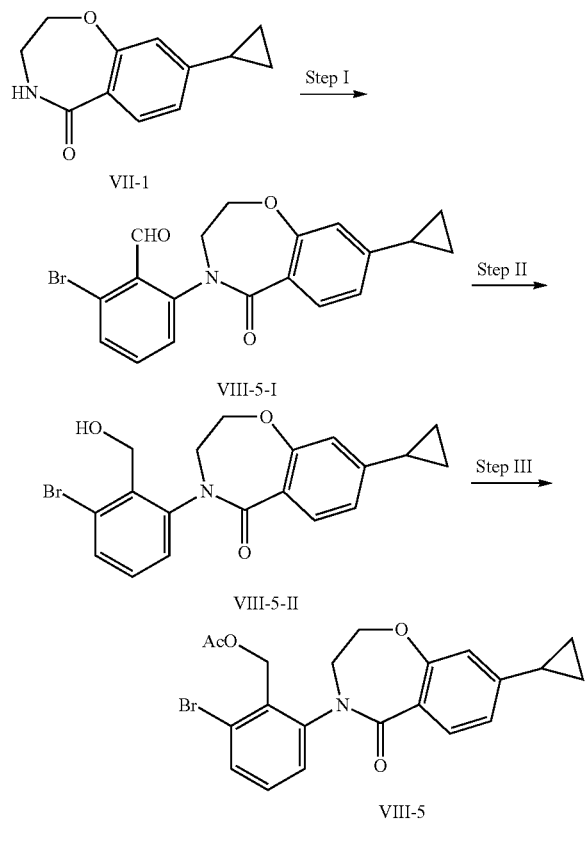

Step-I: 2-bromo-6-(8-cyclopropyl-5-oxo-2,3-dihydro-1,4-benzoxazepin-4-yl)benzaldehyde (VIII-5-I)

To a stirred solution of 8-cyclopropyl-3,4-dihydro-2H-1,4-benzoxazepin-5-one (VII-1) (2.0 g, 9.85 mmol) in 1,4-dioxane (10 ml) was added 2,6-dibromobenzaldehyde (5.14 g, 19.7 mmol), xanthphos (0.171 g, 0.29 mmol) and cesium carbonate (4.50 g, 13.79 mmol, 1.4 equiv.). The reaction mixture was purged using Argon for 45 minutes and then Pd(dba)$_2$ (0.113 g, 1.97 mmol) was added. The resulting reaction mixture was stirred at 100° C. for 18 h. Reaction mixture was cooled to room temperature and filtered through celite and washed with ethyl acetate (20 mL×2). The combined organic layers were washed with water (50 mL); brine (50 mL), dried over anhydrous Na$_2$SO$_4$, filtered and concentrated under reduced pressure to provide crude product, which was further purified using silica gel column chromatography (20-25% ethyl acetate in hexanes) to provide the title compound VIII-5-I (1.60 g, 43%). LCMS: m/z 386.0 (M+1)+.

Step-II: 4-[3-bromo-2-(hydroxymethyl)phenyl]-8-cyclopropyl-2,3-dihydro-1,4-benzoxazepin-5-one (VIII-5-II)

To a stirred solution of VIII-5-I (1.6 g, 4.14 mmol) in THF (12 mL) was added superhydride (1M solution in THF, 8.3 mL, 8.29 mmol) at 20° C. After 15 min, the reaction mixture was quenched using saturated NH$_4$Cl solution (30 mL) and extracted using EtOAc (30 mL×2). The combined organic layers were washed with brine (30 mL), dried over anhydrous Na$_2$SO$_4$, filtered and evaporated under reduced pressure to give crude product, which was further purified using silica gel column chromatography (25-30% EtOAc in hexanes) to give the title compound VIII-5-II (1.35 g, 85%). LCMS: m/z 388 (M+1)+.

Step-III: [2-bromo-6-(8-cyclopropyl-5-oxo-2,3-dihydro-1,4-benzoxazepin-4-yl)phenyl]methyl acetate (VIII-5)

To a stirred solution of VIII-5-II (1.30 g, 3.35 mmol) in CH$_2$Cl$_2$ (15 mL) was added TEA (1.0 ml, 5.02 mmol), acetic anhydride (0.62 ml, 6.71 mmol) and DMAP (50 mg, 0.35 mmol) at room temperature. After stirring for 2 h, volatiles were evaporated under reduced pressure and the residue was purified using silica gel column chromatography (15-25% ethyl acetate in hexanes) to provide title compound VIII-5 (1.37 g, 95%). LCMS: m/z 430 (M+1)$^+$. $^1$H NMR (CDCl$_3$, 400 MHz) δ 0.74-0.78 (m, 2H); 1.02-1.07 (m, 2H); 1.86-1.93 (m, 1H); 2.05 (s, 3H); 3.73-3.79 (m, 1H); 3.87-3.94 (m, 1H); 4.40-4.50 (m, 2H); 5.11 (d, J=12.0 Hz, 1H); 5.33 (d, J=12.0 Hz, 1H); 6.74 (d, J=1.6 Hz, 1H); 6.89 (dd, J$_1$=1.6 Hz, J$_2$=8.4 Hz, 1H); 7.24-7.28 (aromatics, 1H); 7.32 (t, J=8.0 Hz, 1H); 7.63 (td, J$_1$=1.2 Hz, J$_2$=8.0 Hz, 1H); 7.75 (d, J=8.0 Hz, 1H).

Intermediate VIII-6: [2-bromo-6-(6-cyclopropyl-1-oxo-2-isoquinolyl)phenyl]methyl acetate

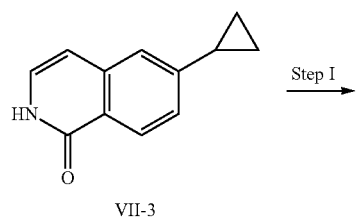

VII-3

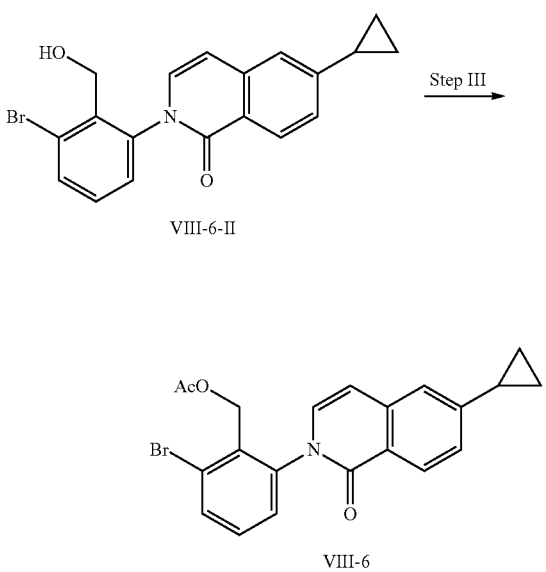

Step-I: 2-bromo-6-(6-cyclopropyl-1-oxo-2-isoquinolyl)benzaldehyde (VIII-6-I)

Intermediate VIII-6-I was synthesized as described for the synthesis of VIII-1, using VII-3 and 2,6-dibromobenzaldehyde.

Step-II and III

Intermediate VIII-6 was synthesized as described for the synthesis of VIII-5 (step-II and step-III) using VIII-6-I. LCMS: m/z 412 (M+1)$^+$. $^1$H NMR (CDCl$_3$, 400 MHz) δ 0.83-0.87 (m, 2H); 1.08-1.13 (m, 2H); 1.95 (s, 3H); 2.00-2.07 (m, 1H); 4.97 (d, J=12.4 Hz, 1H); 5.22 (d, J=12.4 Hz, 1H); 6.49 (d, J=7.2 Hz, 1H); 7.00 (d, J=7.2 Hz, 1H); 7.19-7.22 (aromatics, 2H); 7.29 (s, 1H); 7.36 (t, J=8.0 Hz, 1H); 7.72 (d, J=8.0 Hz, 1H); 8.29 (d, J=8.4 Hz, 1H).

Intermediate VIII-7 was also synthesized using similar reaction sequence and procedure as described for the synthesis of VIII-6, starting from VII-4.

TABLE 4

| No | Structure/IUPAC name | Characterization data | INT used |
|---|---|---|---|
| VIII-7 | 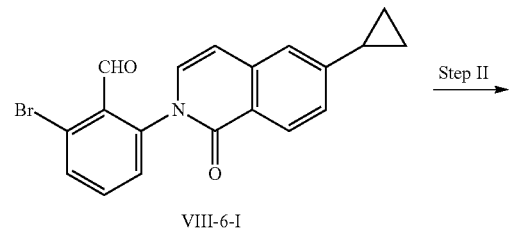<br>[2-bromo-6-(6-cyclopropyl-1-oxo-phthalazin-2-yl)phenyl]methyl acetate | LCMS: m/z; 413.2 (M + 1)$^+$. $^1$H NMR (CDCl$_3$, 400 MHz) δ 0.86-0.91 (m, 2H); 1.16-1.21 (m, 2H); 1.90 (s, 3H); 2.08-2.13 (m, 1H); 5.17 (bs, 2H); 7.35-7.40 (aromatics, 3H); 7.50 (dd, J$_1$ = 1.6 Hz, J$_2$ = 8.4 Hz, 1H); 7.73 (dd, J$_1$ = 2.4 Hz, J$_2$ = 7.2 Hz, 1H); 8.19 (s, 1H); 8.33 (d, J = 8.4 Hz, 1H). | VII-4 |

Intermediate VIII-8-a: 4-[3-bromo-2-[[tert-butyl (dimethyl)silyl]oxymethyl]phenyl]-8-cyclopropyl-2, 3-dihydro-1,4-benzoxazepin-5-one

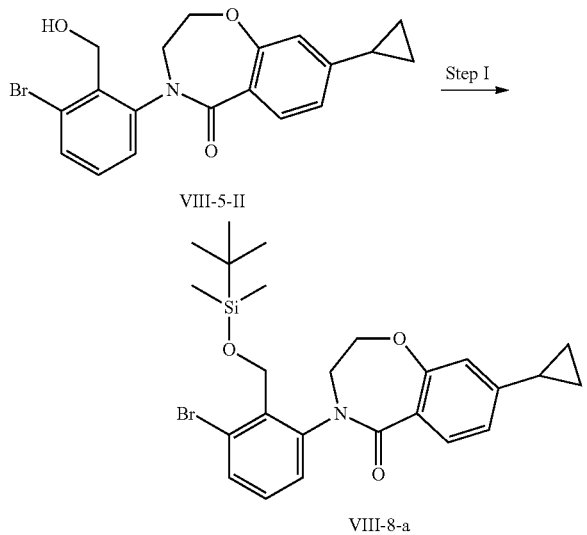

Step-I

Intermediate VIII-5-II (3.1 g, 7.98 mmol) was dissolved in anhydrous $CH_2Cl_2$ (50 mL), to which imidazole (1.36 g, 19.96 mmol) and TBDMSCl (1.56 g, 10.4 mmol) were added sequentially at 0° C. After 2 h, solvent was removed under reduced pressure and the residue was subjected to silica gel column chromatography (10% EA in hexane) to provide desired compound VIII-8-a (4 g, quantitative yield). LCMS: m/z; 502.1 $(M+1)^+$.

Following intermediates were synthesized using similar reaction sequence and procedure as described for the synthesis of intermediate VIII-5 (or VIII-8-a).

TABLE 5

| No | Structure/IUPAC name | Characterization data | INT used |
|---|---|---|---|
| VIII-8-b | 4-[3-bromo-2-[[tert-butyl(dimethyl)silyl]oxymethyl]phenyl]-8-cyclopropyl-6-fluoro-2,3-dihydro-1,4-benzoxazepin-5-one | LCMS: m/z; 520 $(M + 1)^+$ | VII-5 |
| VIII-9 | [2-bromo-6-(8-cyclopropyl-6-fluoro-5-oxo-2,3-dihydro-1,4-benzoxazepin-4-yl)phenyl]methyl acetate | LCMS: m/z; 448 $(M + 1)^+$. $^1$H NMR (DMSO-$d_6$; 400 MHz) δ 0.79-0.82 (m, 2H); 1.01-1.08 (m, 2H); 1.96-1.98 (m, 1H); 2.00 (s, 3H); 3.73-3.89 (m, 2H); 4.22-4.27 (m, 1H); 4.36-4.42 (m, 1H); 5.05 (d, J = 11.6 Hz, 1H); 5.14 (d, J = 12.0 Hz, 1H); 6.76 (s, 1H); 6.86 (dd, $J_1$ = 1.2 Hz, $J_2$ = 11.2 Hz, 1H); 7.42-7.50 (aromatics, 2H); 7.75 (dd, $J_1$ = 1.2 Hz, $J_2$ = 8.8 Hz, 1H). | VII-5 |

TABLE 5-continued

| No | Structure/IUPAC name | Characterization data | INT used |
|---|---|---|---|
| VIII-10-a | [2-bromo-6-(8-cyclopropyl-5-oxo-2,3-dihydropyrido[2,3-f][1,4]oxazepin-4-yl)phenyl]methyl acetate | LCMS: m/z; 431 (M + 1)+ | VII-6 |
| VIII-10-b | 4-[4-bromo-3-[[tert-butyl(dimethyl)silyl]oxymethyl]-2-pyridyl]-8-cyclopropyl-6-fluoro-2,3-dihydro-1,4-benzoxazepin-5-one | LCMS: m/z; 521 (M + 1)+ | VII-5 |
| VIII-11 | [2-bromo-6-(8-cyclopropyl-5-oxo-2,3-dihydro-1,4-benzoxazepin-4-yl)-4-fluoro-phenyl]methyl acetate | LCMS: m/z; 448 (M + 1)+ | VII-1 (2,6-di-bromo-4-fluorobenzaldehyde) |

Synthesis of intermediate VIII-12: [2-bromo-6-(8-cyclopropyl-6-fluoro-5-oxo-2,3-dihydro-1,4-benzoxazepin-4-yl)-4-fluoro-phenyl]methyl acetate

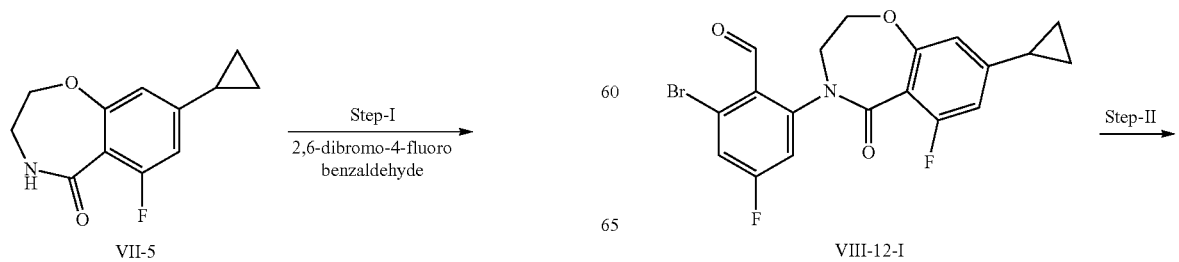

-continued

Step-II

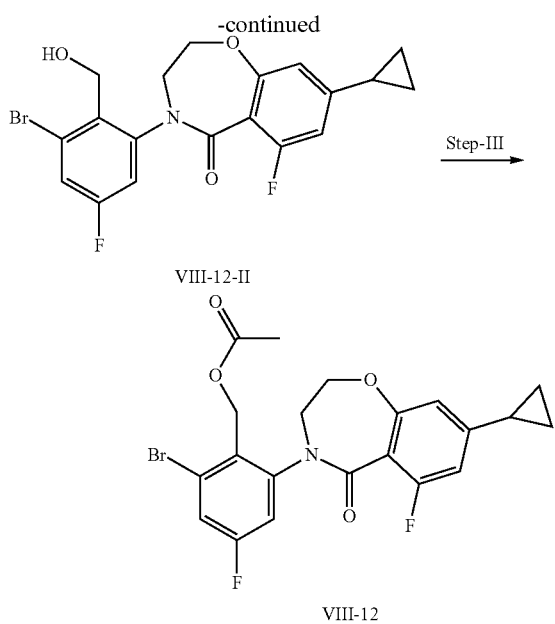

VIII-12-II

VIII-12

Step-I: 2-bromo-6-(8-cyclopropyl-6-fluoro-5-oxo-2,3-dihydro-1,4-benzoxazepin-4-yl)-4-fluoro-benzaldehyde (VIII-12-I)

To a stirred solution of VII-5 (22 g, 99.5 mmol) in 1,4-dioxane (140 ml) was added 2,6-dibromo-4-fluorobenzaldehyde (56 g, 199 mmol) and sodium carbonate (21 g, 199 mmol). The reaction mixture was purged using Argon for 30 minutes and then CuI (19 g, 99.5 mmol) was added to it. Ar purging was continued for additional 15 min and then the resulting reaction mixture was stirred at 110° C. for 24 h. It was cooled to room temperature and the solvent was removed under reduced pressure. EtOAc (220 mL) was added to the residue, stirred for 15 min and filtered through celite. The residue was washed additionally using EtOAc (150 mL×2). Finally, the combined organic layers were washed with water (250 mL); brine (250 mL), dried over anhydrous $Na_2SO_4$, filtered and concentrated under reduced pressure. The residue was then subjected to silica gel column chromatography (initially column was washed using 5-15% EtOAc in hexane, and then product was eluted using $CH_2Cl_2$) and then the solid obtained was washed using diethyl ether to provide VIII-12-I. Additional quantity of VIII-12-I was recovered by column purification of residue obtained after filtrate evaporation. Isolated yield: 25 g (60% yield). LCMS: m/z 422.0 (M+1)$^+$. $^1$H NMR (DMSO-d$_6$; 400 MHz) δ 0.77-0.81 (m, 2H); 1.01-1.05 (m, 2H); 1.96-2.02 (m, 1H); 3.91 (t, J=5.2 Hz, 2H); 4.42 (t, J=5.2 Hz, 2H); 6.76 (bs, 1H); 6.83 (dd, $J_1$=1.2 Hz, $J_2$=11.6 Hz, 1H); 7.58 (dd, $J_1$=2.4 Hz, $J_2$=9.2 Hz, 1H); 7.83 (dd, $J_1$=2.4 Hz, $J_2$=8.4 Hz, 1H); 10.0 (s, 1H).

Step-II: 4-[3-bromo-5-fluoro-2-(hydroxymethyl)phenyl]-8-cyclopropyl-6-fluoro-2,3-dihydro-1,4-benzoxazepin-5-one (VIII-12-II)

To a stirred solution of VIII-12-I (10 g, 23.7 mmol) in dry MeOH-THF (200 mL+100 mL) was added NaBH$_4$ (0.9 g, 23.7 mmol) portion wise at −20° C. The reaction was monitored by TLC (complete in 30 min). It was, then, quenched using saturated NH$_4$Cl solution (100 mL) and organic solvents were removed under reduced pressure. The aqueous layer was extracted using $CH_2Cl_2$ (100 mL×3). The combined organic layers were washed with brine (150 mL), dried over anhydrous $Na_2SO_4$, filtered and evaporated under reduced pressure to give crude product, which was further purified by silica gel column chromatography (neat $CH_2Cl_2$) (column purification done twice) to give title compound VIII-12-II (8.5 g, 85% yield). LCMS: m/z 424 (M+1)$^+$. $^1$H NMR (DMSO-d$_6$; 400 MHz) δ 0.77-0.81 (m, 2H); 1.01-1.05 (m, 2H); 1.96-2.02 (m, 1H); 3.81 (t, J=5.2 Hz, 2H); 4.42 (t, J=5.2 Hz, 2H); 4.46-4.50 (m, 2H); 5.01 (t, J=4.8 Hz, 1H); 6.76 (bs, 1H); 6.84 (dd, $J_1$=1.6 Hz, $J_2$=11.6 Hz, 1H); 7.35 (dd, $J_1$=2.8 Hz, $J_2$=9.2 Hz, 1H); 7.69 (dd, $J_1$=2.8 Hz, $J_2$=8.8 Hz, 1H).

Step-III: [2-bromo-6-(8-cyclopropyl-6-fluoro-5-oxo-2,3-dihydro-1,4-benzoxazepin-4-yl)-4-fluoro-phenyl]methyl acetate (VIII-12)

To a stirred solution of VIII-12-II (54 g, 127.4 mmol) in $CH_2Cl_2$ (540 mL) was added TEA (53 ml, 382 mmol) and DMAP (3.1 g, 25.5 mmol); and it was cooled to 0° C. Finally, acetic anhydride (24 mL, 254.7 mmol) was added to it and the reaction mixture was stirred at room temperature for 2-3 h. After completion of the reaction, the organic layer was washed with saturated NaHCO$_3$ (300 mL), brine (300 mL); dried over anhydrous $Na_2SO_4$, filtered and concentrated under reduced pressure. The residue was purified using silica gel column chromatography (initially column was washed using 10% EtOAc in hexane, then product eluted using $CH_2Cl_2$) to provide title compound VIII-12 (54 g, 94%). LCMS: m/z 466.1 (M+1)$^+$. $^1$H NMR (DMSO-d$_6$; 400 MHz) δ 0.77-0.81 (m, 2H); 1.01-1.06 (m, 2H); 1.96-2.02 (m, 1H); 2.00 (s, 3H); 3.75-3.90 (m, 2H); 4.20-4.30 (m, 1H); 4.38-4.48 (m, 1H); 4.98 (d, J=12.4 Hz, 1H); 5.11 (d, J=12.4 Hz, 1H); 6.76 (bs, 1H); 6.85 (dd, $J_1$=1.2 Hz, $J_2$=11.2 Hz, 1H); 7.46 (dd, $J_1$=2.8 Hz, $J_2$=9.2 Hz, 1H); 7.78 (dd, $J_1$=2.8 Hz, $J_2$=8.8 Hz, 1H).

Synthesis of intermediate III-1: 8-cyclopropyl-4-[2-methyl-3-(4,4,5,5-tetramethyl-1,3,2-dioxaborolan-2-yl)phenyl]-2,3-dihydro-1,4-benzoxazepin-5-one

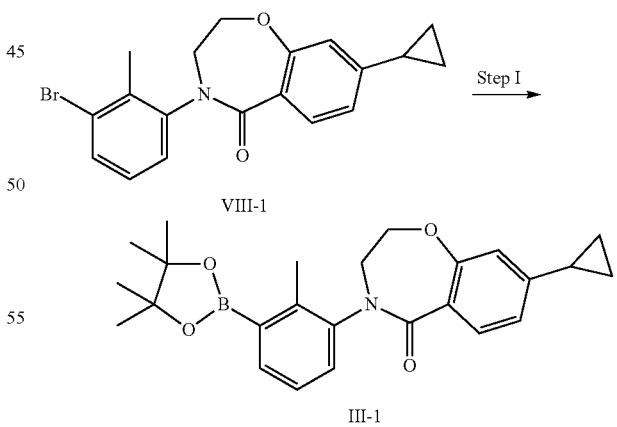

VIII-1

III-1

Step-I

A solution of VIII-1 (7 g, 18.81 mmol), bispinacolato diboron (5.7 g, 22.58 mmol) and potassium acetate (5.54 g, 56.45 mmol) in DMSO (100 mL) was purged using Argon for 30 minutes and then Pd(dppf)Cl$_2$ (0.41 g, 0.56 mmol) was added.

The resulting reaction mixture was then heated at 80° C. for 16 h. After completion of reaction (monitored by TLC), solid was filtered and the residue was washed with EtOAc (50 mL×2). The combined organic layers were washed with brine (100 mL), dried over anhydrous $Na_2SO_4$, filtered and concentrated under reduced pressure. The crude product so obtained was purified by silica gel column chromatography (50% EtOAc in hexane) to afford title compound III-1 (8 g, mixture of product along with debrominated starting material); LCMS: m/z 420.2 (M+1)+. $^1$H NMR ($CDCl_3$; 400 MHz) 0.74-0.78 (m, 2H); 1.00-1.04 (m, 2H); 1.26 (s, 12H); 1.85-1.95 (m, 1H); 2.48 (s, 3H); 3.68-3.88 (m, 2H); 4.43 (t, J=5.1 Hz, 2H); 6.74 (s, 1H); 6.89 (d, J=8.0 Hz, 1H); 7.23-7.29 (aromatics, 2H); 7.76-7.79 (aromatics, 2H).

Following intermediates were synthesized using similar procedure as described for III-1.

TABLE 6

| No | Structure/IUPAC name | Characterization data | INT used |
|---|---|---|---|
| III-2 | 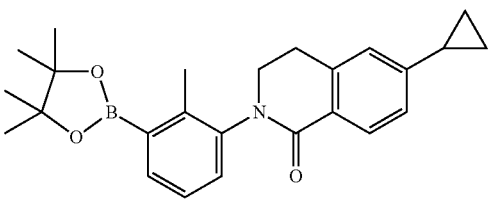 [SMILES: Cc1c(B2OC(C)(C)C(C)(C)O2)cccc1N1CCc2cc(C3CC3)ccc2C1=O]<br>6-cyclopropyl-2-[2-methyl-3-(4,4,5,5-tetramethyl-1,3,2-dioxaborolan-2-yl)phenyl]-3,4-dihydroisoquinolin-1-one | LCMS: m/z; 404.2 (M + 1)+. $^1$H NMR ($CDCl_3$; 400 MHz) δ 0.76-0.79 (m, 2H); 1.00-1.10 (m, 2H); 1.35 (s, 12H); 1.90-2.00 (m, 1H); 2.47 (s, 3H); 2.98-3.10 (m, 1H); 3.15-3.23 (m, 1H); 3.65-3.71 (m, 1H); 3.84-3.91 (m, 1H); 6.92 (s, 1H); 7.05 (d, J = 7.8 Hz, 1H); 7.23-7.29 (aromatics, 2H); 7.76 (d, J = 6.8 Hz, 1H); 8.03 (d, J = 8.1 Hz, 1H) | VIII-2 |
| III-3 | 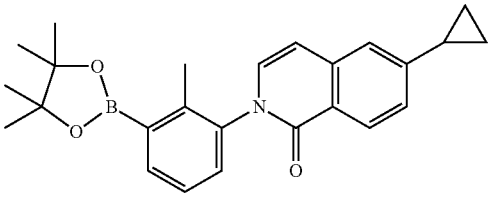 [SMILES: Cc1c(B2OC(C)(C)C(C)(C)O2)cccc1-n1ccc2cc(C3CC3)ccc2c1=O]<br>6-cyclopropyl-2-[2-methyl-3-(4,4,5,5-tetramethyl-1,3,2-dioxaborolan-2-yl)phenyl]isoquinolin-1-one | LCMS: m/z; 402.2 (M + 1)+ | VIII-3 |
| III-4 | 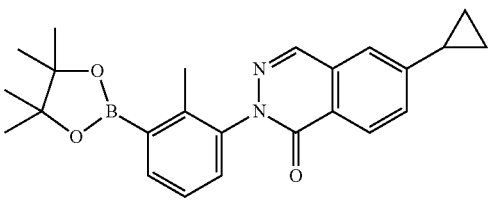 [SMILES: Cc1c(B2OC(C)(C)C(C)(C)O2)cccc1-n1ncc2cc(C3CC3)ccc2c1=O]<br>6-cyclopropyl-2-[2-methyl-3-(4,4,5,5-tetramethyl-1,3,2-dioxaborolan-2-yl)phenyl]phthalazin-1-one | LCMS: m/z; 403.2 (M + 1)+ | VIII-4 |

TABLE 6-continued

| No | Structure/IUPAC name | Characterization data | INT used |
|---|---|---|---|
| III-5 | 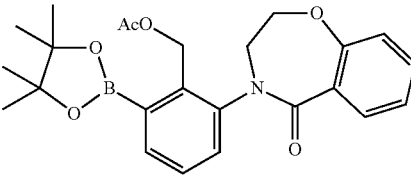<br>[2-(8-cyclopropyl-5-oxo-2,3-dihydro-1,4-benzoxazepin-4-yl)-6-(4,4,5,5-tetramethyl-1,3,2-dioxaborolan-2-yl)phenyl]methyl acetate | LCMS: m/z; 478.2 (M + 1)+. 1H NMR (CDCl3, 400 MHz) δ 0.74-0.78 (m, 2H); 1.01-1.06 (m, 2H); 1.33 (s, 12H); 1.86-1.93 (m, 1H); 2.00 (s, 3H); 3.71-3.77 (m, 1H); 3.87-3.94 (m, 1H); 4.40-4.50 (m, 2H); 5.14 (d, J = 11.6 Hz, 1H); 5.53 (d, J = 11.6 Hz, 1H); 6.73 (d, J = 1.2 Hz, 1H); 6.87 (dd, J1 = 1.2 Hz, J2 = 8.0 Hz, 1H); 7.35 (d, J = 7.6 Hz, 1H); 7.44 (t, J = 8.0 Hz, 1H); 7.76 (d, J = 8.0 Hz, 1H); 7.85 (d, J = 7.6 Hz, 1H) | VIII-5 |
| III-6 | 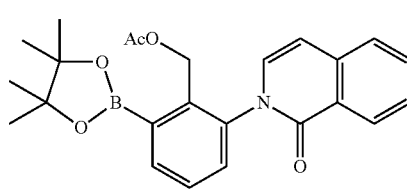<br>[2-(6-cyclopropyl-1-oxo-2-isoquinolyl)-6-(4,4,5,5-tetramethyl-1,3,2-dioxaborolan-2-yl)phenyl]methyl acetate | LCMS: m/z; 460.3 (M + 1)+. 1H NMR (CDCl3, 400 MHz) 0.83-0.88 (m, 2H); 1.08-1.13 (m, 2H); 1.34 (s, 12H); 1.90 (s, 3H); 2.00-2.06 (m, 1H); 5.02 (d, J = 12.0 Hz, 1H); 5.45 (d, J = 11.6 Hz, 1H); 6.48 (d, J = 7.6 Hz, 1H); 7.03 (d, J = 7.6 Hz, 1H); 7.18-7.22 (aromatics, 2H); 7.38 (d, J = 7.6 Hz, 1H); 7.49 (t, J = 8.0 Hz, 1H); 7.95 (d, J = 7.6 Hz, 1H); 8.31 (d, J = 8.0 Hz, 1H) | VIII-6 |
| III-7 | 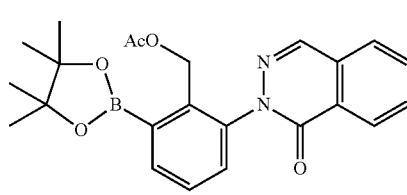<br>[2-(6-cyclopropyl-1-oxo-phthalazin-2-yl)-6-(4,4,5,5-tetramethyl-1,3,2-dioxaborolan-2-yl)phenyl]methyl acetate | LCMS: m/z; 461.4 (M + 1)+ | VIII-7 |
| III-8-a | 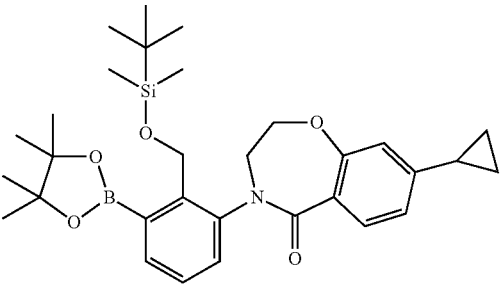 [SMILES: CC1(C)OB(c2cccc(N3CCOc4cc(C5CC5)ccc4C3=O)c2CO[Si](C)(C)C(C)(C)C)OC1(C)C]<br>4-[2-[[tert-butyl(dimethyl)silyl]oxymethyl]-3-(4,4,5,5-tetramethyl-1,3,2-dioxaborolan-2-yl)phenyl]-8-cyclopropyl-2,3-dihydro-1,4-benzoxazepin-5-one | LCMS: m/z; 550.3 (M + 1)+ | VIII-8-a |

TABLE 6-continued

| No | Structure/IUPAC name | Characterization data | INT used |
|---|---|---|---|
| III-8-b | 4-[2-[[tert-butyl(dimethyl)silyl]oxymethyl]-3-(4,4,5,5-tetramethyl-1,3,2-dioxaborolan-2-yl)phenyl]-8-cyclopropyl-6-fluoro-2,3-dihydro-1,4-benzoxazepin-5-one | LCMS: m/z; 568.3 (M + 1)$^+$ | VIII-8-b |
| III-9 | [2-(8-cyclopropyl-6-fluoro-5-oxo-2,3-dihydro-1,4-benzoxazepin-4-yl)-6-(4,4,5,5-tetramethyl-1,3,2-dioxaborolan-2-yl)phenyl]methyl acetate | LCMS: m/z; 496.3 (M + 1)$^+$. $^1$H NMR (CDCl$_3$; 400 MHz) δ 0.73-0.78 (m, 2H); 1.02-1.20 (m, 2H); 1.33 (s, 12H); 1.85-1.92 (m, 1H); 2.00 (s, 3H); 3.56-3.66 (m, 1H); 3.91-4.00 (m, 1H); 4.25-4.50 (m, 2H); 5.22 (d, J = 11.8 Hz, 1H); 5.52 (d, J = 11.9 Hz, 1H); 6.60-6.65 (aromatics, 2H); 7.39-7.42 (aromatics, 2H); 7.83-7.85 (aromatic, 1H) | VIII-9 |
| III-10-a | [2-(8-cyclopropyl-5-oxo-2,3-dihydropyrido[2,3-f][1,4]oxazepin-4-yl)-6-(4,4,5,5-tetramethyl-1,3,2-dioxaborolan-2-yl)phenyl]methyl acetate | LCMS: m/z; 479.2 (M + 1)$^+$. $^1$H NMR (DMSO-d$_6$; 400 MHz) δ 0.83-0.84 (m, 2H); 1.05-1.07 (m, 2H); 1.28 (s, 12H); 1.94 (s, 3H); 2.00-2.03 (m, 1H); 3.78-3.82 (m, 2H); 4.30-4.40 (m, 2H); 4.95 (d, J = 11.6 Hz, 1H); 5.27 (d, J = 11.6 Hz, 1H); 7.19 (s, 1H); 7.42-7.49 (aromatics, 2H); 7.76 (d, J = 6.8 Hz, 1H); 8.30 (s, 1H) | VIII-10-a |

TABLE 6-continued

| No | Structure/IUPAC name | Characterization data | INT used |
|---|---|---|---|
| III-10-b | 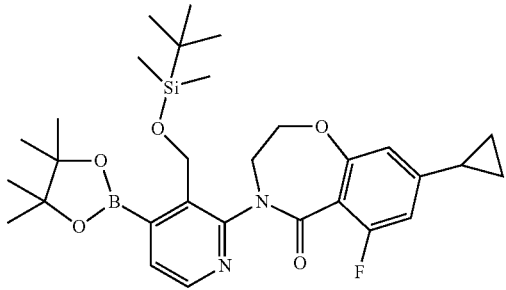 [SMILES: CC1(C)OB(c2ccnc(N3CCOc4cc(C5CC5)cc(F)c4C3=O)c2CO[Si](C)(C)C(C)(C)C)OC1(C)C]<br>4-[3-[[tert-butyl(dimethyl)silyl]oxymethyl]-4-(4,4,5,5-tetramethyl-1,3,2-dioxaborolan-2-yl)-2-pyridyl]-8-cyclopropyl-6-fluoro-2,3-dihydro-1,4-benzoxazepin-5-one | LCMS: m/z; 569.2 (M + 1)+ | VIII-10-b |
| III-11 | 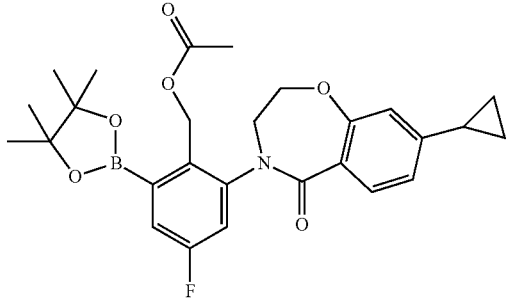 [SMILES: CC(=O)OCc1c(B2OC(C)(C)C(C)(C)O2)cc(F)cc1N1CCOc2cc(C3CC3)ccc2C1=O]<br>[2-(8-cyclopropyl-5-oxo-2,3-dihydro-1,4-benzoxazepin-4-yl)-4-fluoro-6-(4,4,5,5-tetramethyl-1,3,2-dioxaborolan-2-yl)phenyl]methyl acetate | LCMS: m/z; 496 (M + 1)+ | VIII-11 |

Intermediate III-12: [2-(8-cyclopropyl-6-fluoro-5-oxo-2,3-dihydro-1,4-benzoxazepin-4-yl)-4-fluoro-6-(4,4,5,5-tetramethyl-1,3,2-dioxaborolan-2-yl)phenyl] methyl acetate

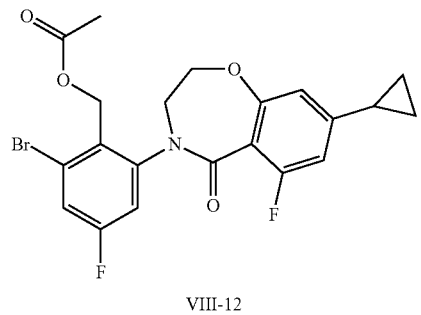

VIII-12

Step I →

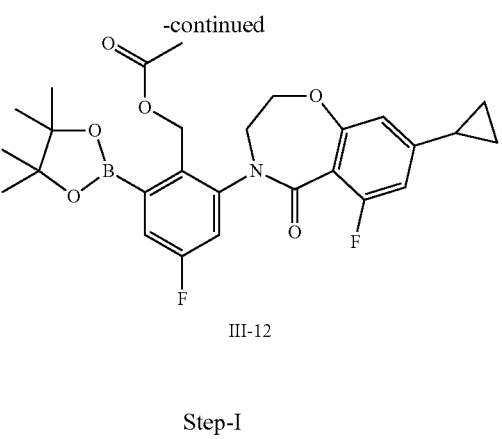

III-12

Step-I

Argon was purged through a solution of VIII-12 (15 g, 32.11 mmol), bispinacolato diboron (12.3 g, 48.2 mmol) and potassium acetate (6.3 g, 64.2 mmol) in 1,4-dioxane (300 mL), for 30 minutes and then Pd(dppf)Cl$_2$—CH$_2$Cl$_2$ (1.3 g, 1.61 mmol) was added. Purging was continued for 15 min more and then the reaction mixture was refluxed for 16 h. After completion of the reaction, dioxane was removed under reduced pressure and the residue was dissolved in EtOAc (300 mL). It was filtered through celite, which was washed with additional EtOAc (100 mL) and then the combined organic layers were washed with water (300 mL); brine (300 mL); dried over anhydrous Na$_2$SO$_4$, filtered and concentrated under reduced pressure. The residue was purified using silica gel column chromatography (5-30% EtOAc in hexane) to provide title compound III-12 (16 g, quantitative yield). LCMS: m/z 514 (M+1)$^+$ (55% boronate ester mass; 27% corresponding boronic acid, 12% des-halo byproduct)

Intermediate II-1: tert-butyl 4-[[4-[4-chloro-7-(p-tolylsulfonyl)pyrrolo[2,3-d]pyrimidin-6-yl]phenyl]methyl]piperazine-1-carboxylate

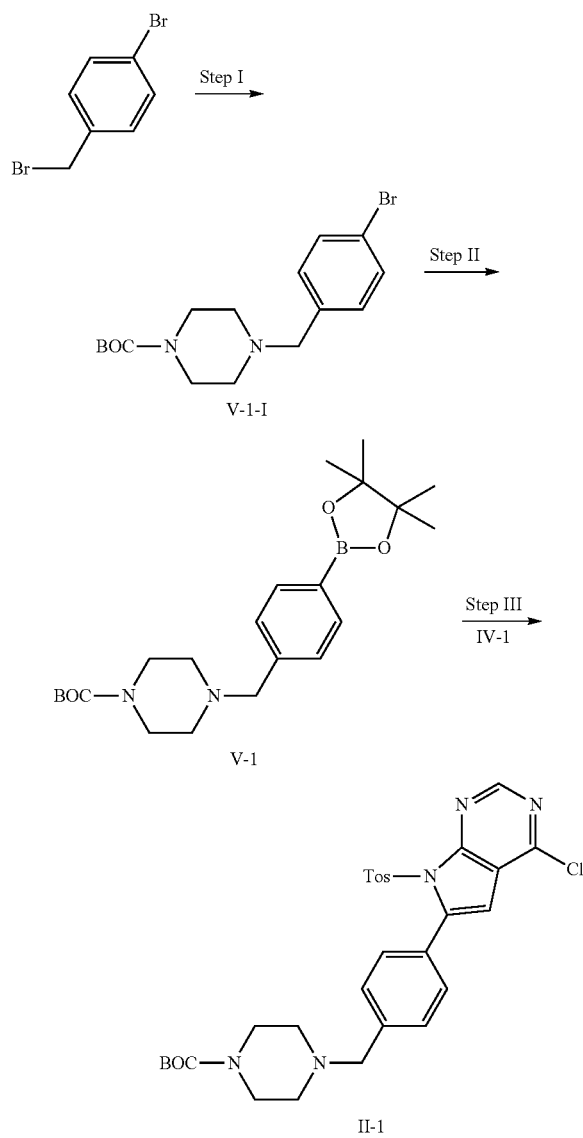

Step-I: tert-butyl 4-[(4-bromophenyl)methyl]piperazine-1-carboxylate (V-1-I)

To a mixture of 4-bromobenzyl bromide (5 g, 20 mmol) and N-Boc piperazine (4.47 g, 24 mmol) in DMF (25 mL), K$_2$CO$_3$ (5.52 g, 40 mmol) was added and the reaction mixture was stirred for 16 h at room temperature. After completion of reaction (monitored by TLC), the reaction mixture was poured into water (100 mL) and extracted with ethyl acetate (30 mL×3). The combined organic layers were washed with brine (100 mL), dried over anhydrous Na$_2$SO$_4$, filtered and concentrated under reduced pressure to give crude product, V-1-I. This compound was used for next step without purification.

Step-II: tert-butyl 4-[[4-(4,4,5,5-tetramethyl-1,3,2-dioxaborolan-2-yl)phenyl]methyl]piperazine-1-carboxylate (V-1)

A mixture of V-1-I (7.5 g, 21.1 mmol), bispinacolato diboron (8 g, 31.7 mmol) and KOAc (4.1 g, 42.2 mmol) in DMSO (50 mL) was purged using Argon for 30 min and PdCl$_2$(dppf) (0.77 g, 1.06 mmol) was added. The resulting reaction mixture was heated at 90° C. for 16 h. After completion of reaction (monitored by TLC), water (100 mL) was added to the reaction mixture and extraction was carried out using EtOAc (50 mL×3). The combined organic layers were washed with water (100 mL); brine (100 mL), dried over anhydrous Na$_2$SO$_4$, filtered and concentrated under reduced pressure. The crude product was purified by silica gel column chromatography (2-20% MeOH in CH$_2$Cl$_2$) to afford title compound V-1 (7 g, 82%). LCMS: m/z 403.3 (M+1)$^+$.

Step-III: tert-butyl 4-[[4-[4-chloro-7-(p-tolylsulfonyl)pyrrolo[2,3-d]pyrimidin-6-yl]phenyl]methyl]piperazine-1-carboxylate (II-1)

A mixture of IV-I (0.5 g, 1.15 mmol) and V-1 (0.32 g, 0.8 mmol) was dissolved in dioxane:water (4:1, 12 mL) and to this was added K$_2$CO$_3$ (0.31 g, 2.3 mmol). The reaction mixture was purged using Argon for 30 minutes followed by addition of PdCl$_2$(dppf) (0.09 g, 0.11 mmol). The resulting reaction mixture was heated at 100° C. for 4 hours. After completion of reaction (monitored by TLC), it was diluted with water (30 mL) and EtOAc (50 mL). The organic layer was separated, washed with brine (50 mL), dried over anhydrous Na$_2$SO$_4$, filtered and concentrated under reduced pressure. The crude product was purified by silica gel column chromatography (15% EtOAc in hexanes) to give title compound II-I (0.435 g, 65%); LCMS: m/z 582.2 (M+1)$^+$.

Following intermediates were synthesized from their corresponding starting materials using similar reaction sequence and procedures as described for the synthesis of II-1.

TABLE 7

| No. | Structure/IUPAC name | Characterization data |
|---|---|---|
| II-2 | tert-butyl 4-[[3-[4-chloro-7-(p-tolylsulfonyl)pyrrolo[2,3-d]pyrimidin-6-yl]phenyl]methyl]piperazine-1-carboxylate | LCMS: m/z; 582.2 (M + 1)+ |
| II-3 | 4-[[3-[4-chloro-7-(p-tolylsulfonyl)pyrrolo[2,3-d]pyrimidin-6-yl]phenyl]methyl]morpholine | LCMS: m/z; 483.1 (M + 1)+ |
| II-4 | 4-[[4-[4-chloro-7-(p-tolylsulfonyl)pyrrolo[2,3-d]pyrimidin-6-yl]phenyl]methyl]morpholine | LCMS: m/z; 483.1 (M + 1)+ |

Intermediate II-5: tert-butyl 4-[4-(4-chloro-7H-pyrrolo[2,3-d]pyrimidin-6-yl)phenyl]piperazine-1-carboxylate

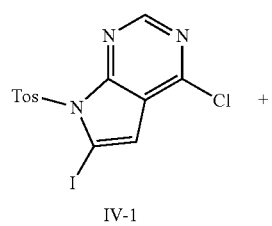

IV-1

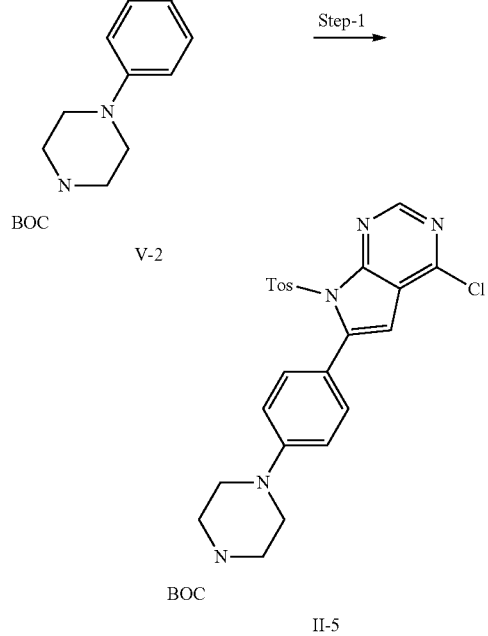

Synthesis of tert-butyl 4-[4-[4-chloro-7-(p-tolylsulfonyl)pyrrolo[2,3-d]pyrimidin-6-yl]phenyl]piperazine-1-carboxylate (Intermediate II-5)

Argon was purged through a solution of IV-1 (1.5 g, 3.46 mmol), 4-[4-(4,4,5,5-tetramethyl-[1,3,2]dioxaborolan-2-yl)-phenyl]-piperazine-1-carboxylic acid tert-butyl ester V-2 (prepared as mentioned WO2003/041649) (1.34 g, 3.46 mmol) and powdered K$_2$CO$_3$ (0.954 g, 6.92 mmol) in a mixture of dioxane (24 mL) and water (6 mL) for 15 minutes. PdCl$_2$(dppf) (0.282 g, 0.346 mmol) was added to this mixture and then stirred at 90° C. for 8 h. Solvent was removed under reduced pressure and the resultant residue was purified by silica gel column chromatography (30% EtOAc in hexane) to give the title compound II-5 (0.55 g, 30%); LCMS: m/z 568.1 (M+1)+.

Intermediate II-6: tert-butyl 4-[4-[4-chloro-7-(p-tolylsulfonyl)pyrrolo[2,3-d]pyrimidin-6-yl]pyrazol-1-yl]piperidine-1-carboxylate

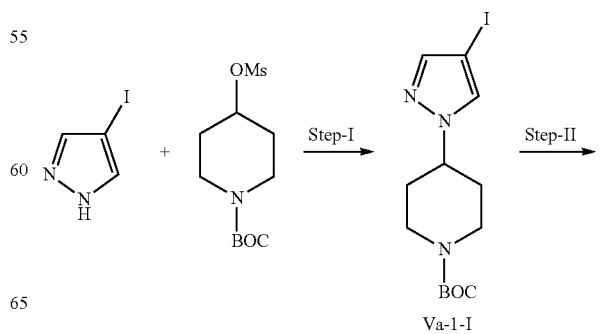

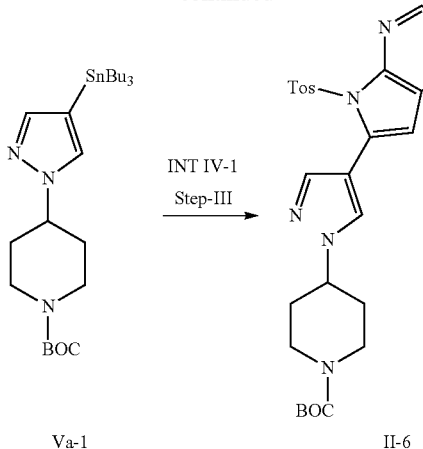

Step-I: tert-butyl 4-(4-iodopyrazol-1-yl)piperidine-1-carboxylate (Va-1-I)

NaH (60% suspension, 1.13 g, 28.4 mmol) was added portion wise to a solution of 4-iodopyrazole (5 g, 25.7 mmol) in anhydrous DMF (30 mL) at 0° C.; and it was stirred for 1 h. Finally, tert-butyl 4-mesylpiperidine-1-carboxylate (CAS: 141699-59-4) (6.5 g, 32.7 mmol) was added to the reaction mixture and it was stirred at 100° C. for 16 h. It was, then, cooled and quenched with saturated solution of NH$_4$Cl (100 mL). Extraction was carried out using EtOAc (50 mL×2); the combined organic layers were washed with water (100 mL); brine (100 mL), dried over anhydrous Na$_2$SO$_4$, filtered and concentrated under reduced pressure to provide crude product, which was further purified by silica gel column chromatography (20% EtOAc in hexanes) to give title compound Va-1-I (4 g, 41%). LCMS: m/z 378.1 (M+1)$^+$.

Step-II: tert-butyl 4-(4-tributylstannylpyrazol-1-yl)piperidine-1-carboxylate (Va-1)

n-BuLi (1.6 M in THF, 5 mL, 7.96 mmol) was added to a solution of Va-1-I (1.5 g, 3.97 mmol) in anhydrous THF (15 mL) at −78° C. and it was stirred for 1 h. Finally, n-Bu$_3$SnCl (2.2 mL, 7.96 mmol) was added to the reaction mixture at −78° C. and the reaction mixture was allowed to warm to room temperature over 2 h. Saturated NH$_4$Cl solution (30 mL) was added to the reaction mixture and extraction was carried out using EtOAc (30 mL×2). The combined organic layers were washed with water (50 mL); brine (50 mL), dried over anhydrous Na$_2$SO$_4$, filtered and concentrated under reduced pressure to provide crude product, which was further purified by silica gel column chromatography (using 10% EtOAc in hexanes) to give title compound Va-1 (0.5 g, 23%). LCMS: m/z 541.3 (M+1)$^+$.

Step-III: tert-butyl 4-[4-[4-chloro-7-(p-tolylsulfonyl)pyrrolo[2,3-d]pyrimidin-6-yl]pyrazol-1-yl]piperidine-1-carboxylate (II-6)

Argon was purged through a solution of IV-1 (0.25 g, 0.56 mmol) and Va-1 (0.47 g, 0.86 mmol) in DMF (2.5 mL) for 15 min. Finally, PdCl$_2$(PPh$_3$)$_2$ (0.02 mg, 0.03 mmol) was added to it and the reaction mixture was stirred at 100° C. for 3 h. Then, water (25 mL) was added to it and extraction was carried out using EtOAc (15 mL×2). The combined organic layers were washed with water (30 mL); brine (30 mL), dried over anhydrous Na$_2$SO$_4$, filtered and concentrated under reduced pressure to provide crude product, which was further purified by silica gel column chromatography (using 30% EtOAc in hexanes) to give title compound II-6 (0.17 g, 23%). LCMS: m/z 557.1 (M+1)$^+$. $^1$H NMR (DMSO-d$_6$; 400 MHz) δ 1.42 (s, 9H); 1.75-1.90 (m, 2H); 2.02-2.10 (m, 2H); 2.34 (s, 3H); 2.95 (bs, 2H); 4.02-4.08 (m, 2H); 4.44-4.49 (m, 1H); 6.88 (s, 1H); 7.38 (d, J=8.0 Hz, 2H); 7.71 (d, J=8.4 Hz, 2H); 7.77 (s, 1H); 8.21 (s, 1H); 8.80 (s, 1H).

Following intermediates were synthesized using similar reaction sequence and procedures as described for II-6.

TABLE 8

| No | Structure/IUPAC name | Characterization data |
|---|---|---|
| II-7 | ![structure] <br> tert-butyl 4-[4-[1-(benzenesulfonyl)-4-chloro-pyrrolo[2,3-b]pyridin-2-yl]pyrazol-1-yl]piperidine-1-carboxylate | LCMS: m/z 542.1 (M + 1)$^+$. $^1$H NMR (CDCl3; 400 MHz) δ 1.48 (s, 9H); 1.94-2.10 (m, 2H); 2.20-2.30 (m, 2H); 2.80-3.00 (m, 2H); 4.20-4.40 (m, 3H); 6.59 (s, 1H); 7.20 (d, J = 5.6 Hz, 1H); 7.38 (t, J = 8.0 Hz, 2H); 7.52 (t, J = 7.6 Hz, 1H); 7.68 (s, 1H); 7.79 (d, J = 7.6 Hz, 2H); 7.81 (s, 1H); 8.33 (d, J = 5.6 Hz, 1H). |

TABLE 8-continued

| No | Structure/IUPAC name | Characterization data |
|---|---|---|
| II-8 | 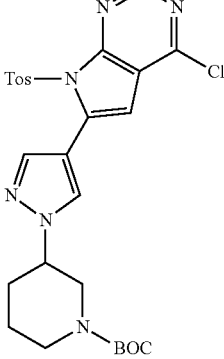<br>tert-butyl 3-[4-[4-chloro-7-(p-tolylsulfonyl)pyrrolo[2,3-d]pyrimidin-6-yl]pyrazol-1-yl]piperidine-1-carboxylate | LCMS: m/z; 557.3 (M + 1)$^+$. $^1$H NMR (DMS0-d$_6$; 400 MHz) δ 1.42 (s, 9H); 1.50-1.60 (m, 1H); 1.72-1.80 (m, 1H); 1.98-2.20 (m, 2H); 2.35 (s, 3H); 2.90-3.00 (m, 1H); 3.10-3.30 (m, 1H); 3.76-3.90 (m, 1H); 4.00-4.40 (m, 2H); 6.88 (s, 1H); 7.39 (d, J = 8.0 Hz, 2H); 7.71 (d, J = 8.0 Hz, 2H); 7.80 (s, 1H); 8.20 (s, 1H); 8.81 (s, 1H) |
| II-9 | 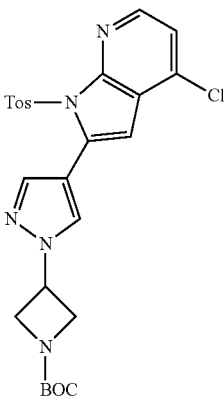<br>ten-butyl 3-[4-[4-chloro-1-(p-tolylsulfonyl)pyrrolo[2,3-b]pyridin-2-yl] pyrazol-1-yl]azetidine-1-carboxylate | LCMS: m/z; 528.3 (M + 1)$^+$. $^1$H NMR (DMSO-d$_6$; 400 MHz) 1.43 (s, 9H); 2.32 (s, 3H); 4.15-4.25 (m, 2H); 4.30-4.45 (m, 2H); 5.30-5.34 (m, 1H); 6.84 (s, 1H); 7.34 (d, J = 8.4 Hz, 2H); 7.46 (d, J = 5.2 Hz, 1H); 7.70 (d, J = 8.0 Hz, 2H); 7.93 (s, 1H); 8.31 (d, J = 5.2 Hz, 1H); 8.33 (s, 1H). |
| II-10 | 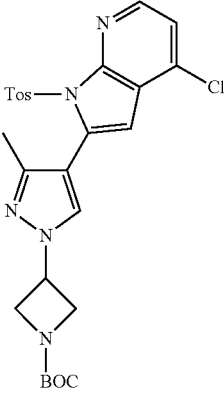<br>tert-butyl 3-[4-[4-chloro-1-(p-tolylsulfonyl)pyrrolo[2,3-b]pyridin-2-yl]-3-methyl-pyrazol-1-yl]azetidine-1-carboxylate | LCMS: m/z; 542.2 (M + 1)$^+$ |

TABLE 8-continued

| No | Structure/IUPAC name | Characterization data |
|---|---|---|
| II-11 | 4-chloro-2-[1-(oxetan-3-yl)pyrazol-4-yl]-1-(p-tolylsulfonyl)pyrrolo[2,3-b]pyridine | LCMS: m/z; 429.0 (M + 1)⁺. ¹H NMR (DMSO-d₆; 400 MHz) 2.32 (s, 3H); 4.90-5.00 (m, 4H); 5.68-5.76 (m, 1H); 6.84 (s, 1H); 7.34 (d, J = 8.4 Hz, 2H); 7.46 (d, J = 5.2 Hz, 1H); 7.71 (d, J = 8.4 Hz, 2H); 7.94 (s, 1H); 8.31 (d, J = 5.6 Hz, 1H); 8.33 (s, 1H). |

Intermediate II-12: tert-butyl 4-[4-[4-chloro-1-(p-tolylsulfonyl)pyrrolo[2,3-b]pyridin-2-yl]phenyl]-3,6-dihydro-2H-pyridine-1-carboxylate

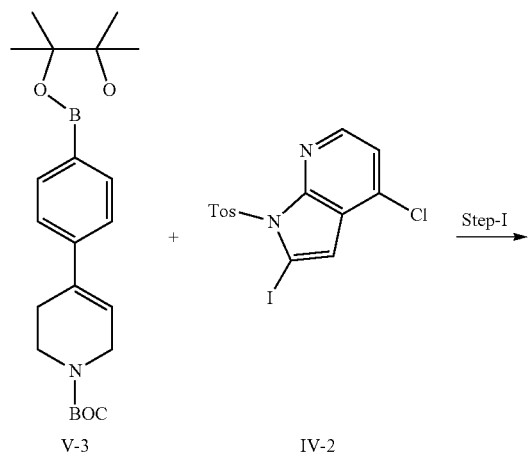

Step-I

Argon was purged through a solution of IV-2 (0.84 g, 1.95 mmol), V-3 (0.75 g, 1.95 mmol) (synthesized as described in WO2009114180) and K₂CO₃ (0.53 g, 3.9 mmol) in dioxane-water (15 mL+4 mL) for 30 min. Finally, PdCl₂(dppf)-DCM (0.158 g, 0.19 mmol) was added to the reaction mixture and Argon was again purged for 5 min. It was, then, stirred at 100° C. for 3 h. Solvents were then removed under reduced pressure and the crude product was subjected to silica gel column chromatography (50% EtOAc in hexane) to provide II-12 (0.96 g, 87% yield). LCMS: m/z; 564.1 (M+1)⁺. ¹H NMR (CDCl₃; 400 MHz) δ 1.53 (s, 9H); 2.35 (s, 3H); 2.55-2.65 (m, 2H); 3.60-3.70 (m, 2H); 4.10-4.20 (m, 2H); 6.18 (bs, 1H); 6.61 (s, 1H); 7.17-7.21 (aromatics, 3H); 7.48 (d, J=8.0 Hz, 2H); 7.53 (d, J=8.0 Hz, 2H); 7.76 (d, J=8.0 Hz, 2H); 8.35 (d, J=4.8 Hz, 1H).

Intermediate II-13: tert-butyl 4-[4-[4-chloro-7-(p-tolylsulfonyl)pyrrolo[2,3-d]pyrimidin-6-yl]phenyl]piperidine-1-carboxylate

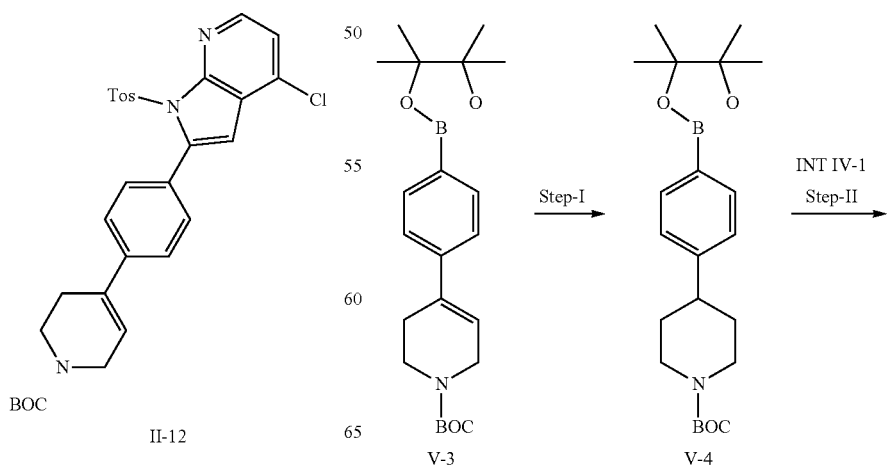

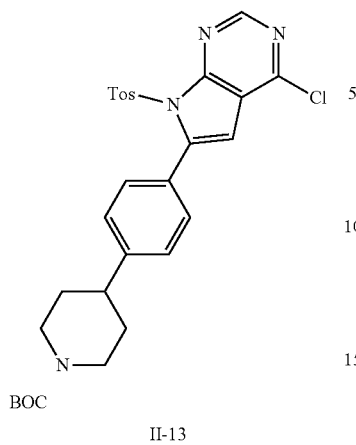

II-13

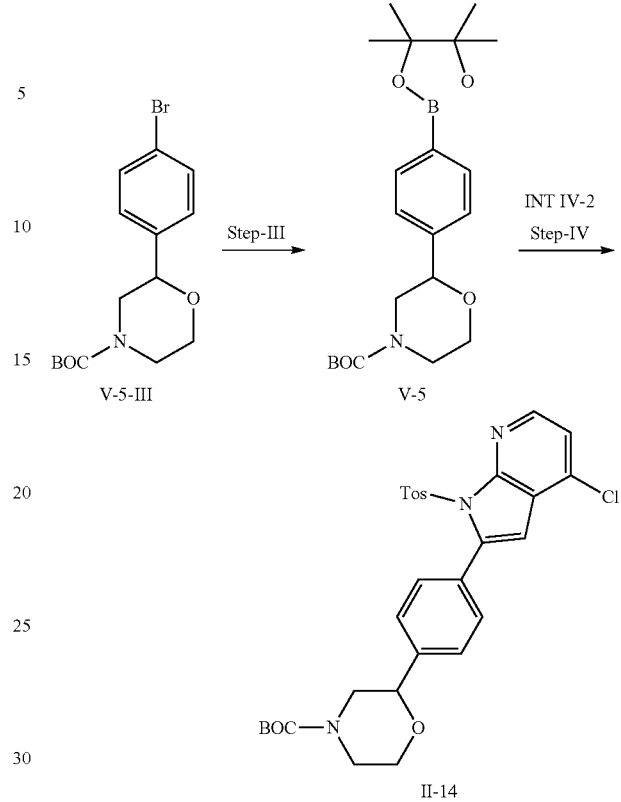

Step-I: tert-butyl 4-[4-(4,4,5,5-tetramethyl-1,3,2-dioxaborolan-2-yl)phenyl]piperidine-1-carboxylate (V-4)

To a solution of V-3 (1.4 g, 3.64 mmol) in EtOAc (15 mL) was added Pd/C (0.14 g) and the reaction mixture was stirred under $H_2$ atmosphere (balloon pressure) for 16 h. Finally, catalyst was filtered off and the filtrate was concentrated under reduced pressure to provide V-4 (1.3 g, 91% yield). LCMS: m/z; 332.1 [(M-tert-Bu)+1]$^+$.

Step-II: tert-butyl 4-[4-[4-chloro-7-(p-tolylsulfonyl)pyrrolo[2,3-d]pyrimidin-6-yl]phenyl]piperidine-1-carboxylate (II-13)

Title compound was synthesized as described for the synthesis of II-12, using intermediates V-4 and IV-1. LCMS: m/z; 567.3 (M+1)$^+$. $^1$H NMR (CDCl$_3$; 400 MHz) δ 1.24 (s, 9H); 1.64-1.74 (m, 2H); 1.88-1.96 (m, 3H); 2.34 (s, 3H); 2.72-2.92 (m, 2H); 4.20-4.40 (m, 2H); 6.58 (s, 1H); 7.25 (d, J=8.4 Hz, 2H); 7.31 (d, J=8.0 Hz, 2H); 7.45 (d, J=8.0 Hz, 2H); 7.81 (d, J=8.4 Hz, 2H); 8.82 (s, 1H).

Intermediate II-14: tert-butyl 2-[4-[4-chloro-1-(p-tolylsulfonyl)pyrrolo[2,3-b]pyridin-2-yl]phenyl]morpholine-4-carboxylate

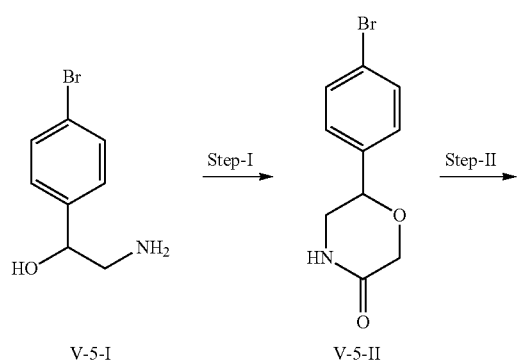

Step-I: 6-(4-bromophenyl)morpholin-3-one (V-5-II)

To a solution of V-5-I (CAS: 41147-82-4) (4.5 g, 20.0 mmol) in CH$_2$Cl$_2$ (100 mL) was added aqueous NaOH (1 g, 100 mL, 25.0 mmol) and it was cooled to 0° C. To this was added chloroacetylchloride (2.5 mL, 31.0 mmol) and the reaction mixture was stirred at room temperature for 16 h. Finally, organic layer was separated and washed with 1N HCl (50 mL), saturated NaHCO$_3$ solution (50 mL), brine (50 mL), dried over anhydrous Na$_2$SO$_4$, filtered and concentrated under reduced pressure. The residue obtained was dissolved in EtOH (50 mL), to which KOH (2.0 g, 35 mmol) in EtOH (25 mL) was added drop wise at room temperature. It was stirred for 16 h and then concentrated. Water was added to the residue and extraction was carried out using CH$_2$Cl$_2$ (50 ml×2). The combined organic layers were washed with brine (100 mL), dried over anhydrous Na$_2$SO$_4$, filtered and concentrated under reduced pressure. The residue was stirred in diethyl ether (30 mL) and filtered to provide V-5-II (1.7 g, 62% pure). LCMS: m/z; 256 (M+1)$^+$.

Step-II: tert-butyl 2-(4-bromophenyl)morpholine-4-carboxylate (V-5-III)

To a solution of V-5-II (1.7 g, 6.6 mmol) in anhydrous THF (10 mL) was added 1M BH$_3$ in THF (37.8 mL, 39 mmol) and the reaction mixture was refluxed for 16 h. It was, then, quenched using concentrated HCl (10 mL) and refluxed for 1 h. Solvents were removed under reduced pressure and 1N NaOH solution (50 mL) was added to the residue. Extraction was carried out using EtOAc (25 mL×2). The combined organic layers were washed with water (30 mL); brine (30 mL), dried over anhydrous Na$_2$SO$_4$, filtered and concentrated under reduced pressure to provide crude product, which was dissolved in CH$_2$Cl$_2$ (20 mL). To this was added TEA (1.9 mL, 14.0 mmol) and (Boc)$_2$O (1.9 g, 8.6 mmol). After stirring the reaction mixture for 16 h, the solvent was removed under reduced pressure and the residue was purified using silica gel column chromatography to provide V-5-II (1.5 g, 19% yield for two steps). LCMS: m/z; 286 [(M-tert-Bu)+1]⁺.

Step-III: tert-butyl 2-[4-(4,4,5,5-tetramethyl-1,3,2-dioxaborolan-2-yl)phenyl]morpholine-4-carboxylate (V-5)

This intermediate was synthesized as described in step-II for the synthesis of II-1 (58% yield). LCMS: m/z; 334 [(M-tert-Bu)+1]⁺.

Step-IV: tert-butyl 2-[4-[4-chloro-1-(p-tolylsulfonyl)pyrrolo[2,3-b]pyridin-2-yl]phenyl]morpholine-4-carboxylate (II-14)

As described for the synthesis of II-12 (using V-5 and IV-2, 35% yield). LCMS: m/z; 568.2 (M+1)⁺.

Intermediate II-15: tert-butyl 3-[[5-[4-chloro-1-(p-tolylsulfonyl)pyrrolo[2,3-b]pyridine-2-yl]-2-pyridyl]oxy]azetidine-1-carboxylate Step-I: tert-butyl 3-[(5-bromo-2-pyridyl)oxy]azetidine-1-carboxylate (Va-2-I)

1-Boc-3-hydroxyazetidine (4.0 g, 23 mmol) was dissolved in DMF (30 mL) and cooled to 0° C. To this was added NaH (60% suspension, 0.83 g, 34 mmol) and it was stirred for 15 min. Finally, a solution of 5-bromo-2-iodopyridine (6.5 g, 23 mmol) in DMF (20 mL) was added to it and the reaction mixture was stirred at 70° C. for 5 h. It was, then, cooled to room temperature and diluted using EtOAc (200 mL). The organic layer was washed with water (150 mL×2), brine (150 mL), dried over anhydrous Na₂SO₄, filtered and concentrated under reduced pressure. The residue obtained was purified by silica gel column chromatography (10% EtOAc in hexane) to provide Va-2-I (4.5 g, 59% yield). LCMS: m/z; 329.

Step-II and Step-III: tert-butyl 3-[(5-bromo-2-pyridyl)oxy]azetidine-1-carboxylate (Va-2) and tert-butyl 3-[[5-[4-chloro-1-(p-tolylsulfonyl)pyrrolo[2,3-b]pyridin-2-yl]-2-pyridyl]oxy]azetidine-1-carboxylate (II-15)

Similar procedures were followed for the synthesis of II-15 as described in steps-II and III for the synthesis of intermediate II-6. LCMS: m/z; 555.3 (M+1)⁺. ¹H NMR (CDCl₃; 400 MHz) δ 1.47 (s, 9H); 2.35 (s, 3H); 4.03-4.07 (m, 2H); 4.36-4.40 (m, 2H); 5.38-5.45 (m, 1H); 6.61 (s, 1H); 6.89 (d, J=8.4 Hz, 1H); 7.20 (d, J=8.4 Hz, 2H); 7.23 (d, J=5.2 Hz, 1H); 7.73 (d, J=8.4 Hz, 2H); 7.85 (dd, J₁=2.4 Hz, J₂=8.4 Hz, 1H); 8.21 (d, J=2.0 Hz, 1H); 8.37 (d, J=5.6 Hz, 1H).

Intermediate II-16: tert-butyl 4-[5-[4-chloro-1-(p-tolylsulfonyl)pyrrolo[2,3-b]pyridin-2-yl]-2-pyridyl]piperazine-1-carboxylate This intermediate was synthesized using procedure described for the synthesis of intermediate II-6 [starting from Va-3-1 (CAS: 153747-97-8) and IV-2].

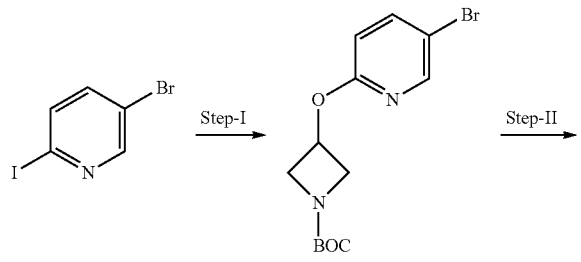

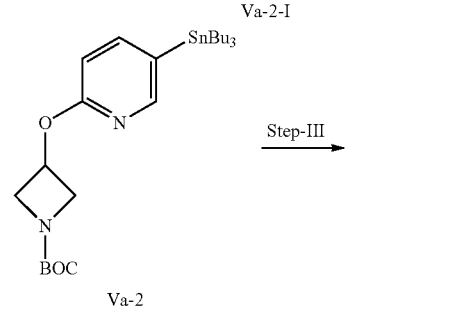

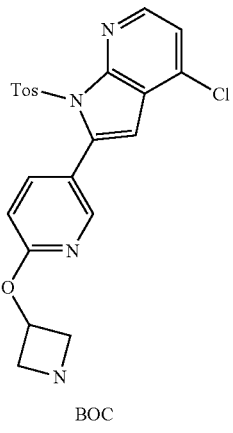

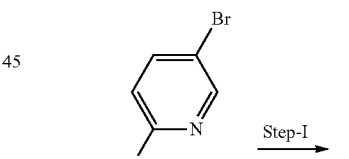

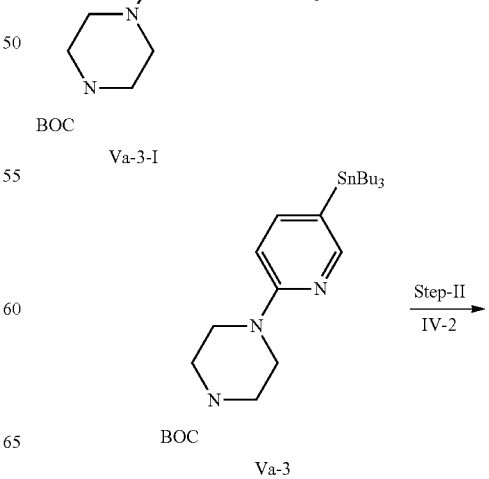

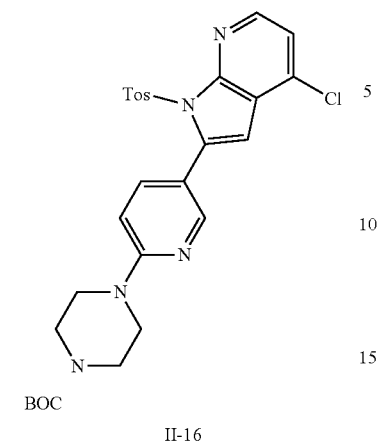

II-16

LCMS: m/z; 568.3 (M+1)+. 1H NMR (CDCl3; 400 MHz) δ 1.53 (s, 9H); 2.33 (s, 3H); 3.56-3.62 (m, 4H); 3.66-3.70 (m, 4H); 6.56 (s, 1H); 6.74 (d, J=8.8 Hz, 1H); 7.17 (d, J=8.4 Hz, 2H); 7.20 (d, J=5.2 Hz, 1H); 7.72 (d, J=8.4 Hz, 2H); 7.77 (dd, J1=2.0 Hz, J2=8.8 Hz, 1H); 8.28 (d, J=2.0 Hz, 1H); 8.34 (d, J=5.6 Hz, 1H).

Intermediate II-17: 4-chloro-2-[4-(4-fluoro-1-methyl-4-piperidyl)phenyl]-1-(p-tolyl sulfonyl)pyrrolo[2,3-b]pyridine

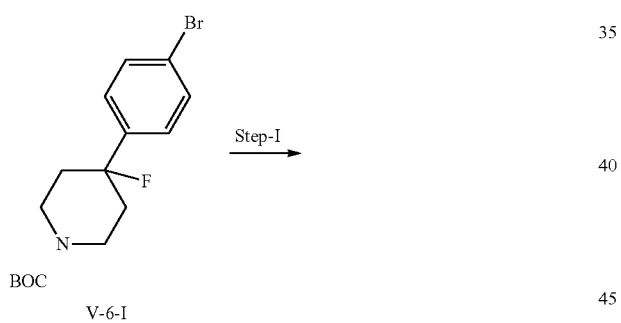

V-6-I

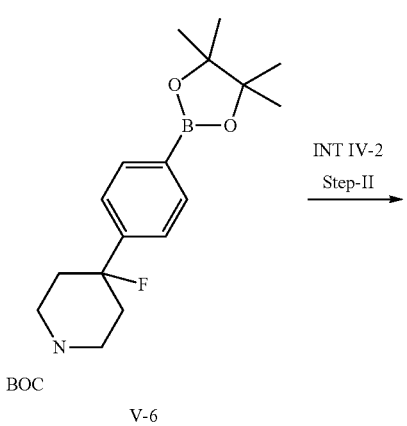

V-6

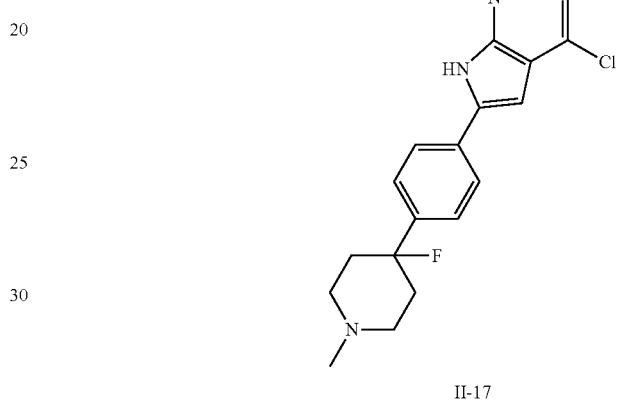

II-17-I

II-17

Step-I and Step-II: tert-butyl 4-[4-[4-chloro-1-(p-tolylsulfonyl)pyrrolo[2,3-b]pyridin-2-yl]phenyl]-4-fluoro-piperidine-1-carboxylate (II-17-I)

Intermediate II-174 was synthesized following procedure described for the synthesis of II-12, using V-6 and IV-2. Intermediate V-6 was synthesized from V-6-I (synthesized as described in WO2009151598). LCMS: m/z; 584.2 (M+1)+.

Step-III: 4-chloro-2-[4-(4-fluoro-1-methyl-4-piperidyl)phenyl]-1-(p-tolylsulfonyl)pyrrolo[2,3-b]pyridine (II-17)

4M HCl in dioxane solution (10 mL) was added to a solution of II-17-I (1.2 g, 2.05 mmol) in dioxane (4 mL) at room temperature and the reaction mixture was stirred for 16 h. Solvent was removed under reduced pressure and the residue was washed with diethyl ether (10 mL×2). Saturated NaHCO3 solution (30 mL) was then added to the residue and the resultant solid was filtered and dried to provide corresponding Boc- and tosyl-deprotected intermediate (0.6 g, 1.82 mmol), which was dissolved in MeOH (3 mL). To this was added formaline (37%, 0.7 mL, 21.8 mmol) and the reaction mixture was refluxed for 1 h. Finally, NaBH3CN (0.17 g, 2.73 mmol) was added to the reaction mixture at 0° C. and stirred for 2 h. Solvents were removed under reduced pressure and the residue was dissolved in EtOAc (50 mL). The organic layer was washed with water (30 mL), brine (30 mL), dried over anhydrous Na$_2$SO$_4$, filtered and concentrated under reduced pressure. The residue was purified using silica gel column chromatography (5% MeOH in CH$_2$Cl$_2$) to provide desired intermediate II-17 (0.32 g, 45% yield for two steps). LCMS: m/z; 344.1 (M+1)$^+$. $^1$H NMR (DMSO-d$_6$; 400 MHz) δ 1.20-1.30 (m, 2H); 1.88-1.94 (m, 2H); 2.05-2.20 (m, 2H); 2.26 (s, 3H); 2.70-2.76 (m, 2H); 7.02 (s, 1H); 7.21 (d, J=4.8 Hz, 1H); 7.53 (d, J=8.0 Hz, 2H); 8.01 (d, J=8.4 Hz, 2H); 8.18 (d, J=4.8 Hz, 1H); 12.55 (bs, 1H).

Following intermediate II-18 was also synthesized using similar reaction sequence and procedure as described for the synthesis of II-17.

TABLE 9

| Number | Structure/IUPAC name | Characterization data |
|---|---|---|
| II-18 | 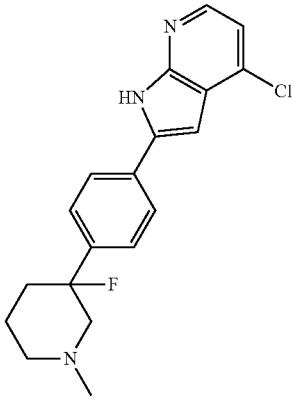 [SMILES: CN1CCCC(F)(c2ccc(-c3cc4c(Cl)ccnc4[nH]3)cc2)C1] 4-chloro-2-[4-(3-fluoro-1-methyl-3-piperidyl)phenyl]-1H-pyrrolo[2,3-b]pyridine | LCMS: m/z 344.1 (M + 1)$^+$ |

Intermediate II-19: tert-butyl 4-[4-[4-chloro-7-(p-tolylsulfonyl)pyrrolo[2,3-d]pyrimidin-6-yl]phenoxy]piperidine-1-carboxylate

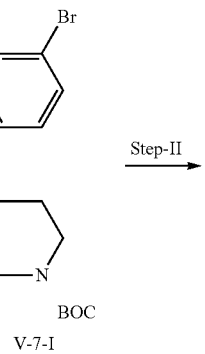

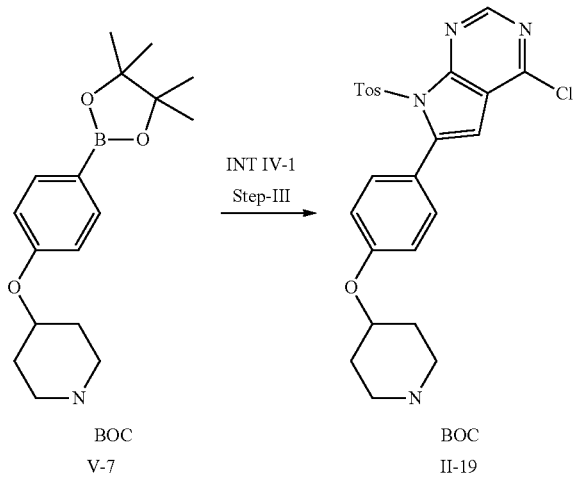

Step-I: tert-butyl 4-(4-bromophenoxy)piperidine-1-carboxylate (V-7-I)

V-7-I was synthesized as described in WO2010048149. LCMS: m/z; 356 (M+1)$^+$.

Step-II: tert-butyl 4-[4-(4,4,5,5-tetramethyl-1,3,2-dioxaborolan-2-yl)phenoxy]piperidine-1-carboxylate (V-7)

V-7 was synthesized as described in WO2008078091. LCMS: m/z; 404.2 (M+1)$^+$.

Step-III: tert-butyl 4-[4-[4-chloro-7-(p-tolylsulfonyl)pyrrolo[2,3-d]pyrimidin-6-yl]phenoxy]piperidine-1-carboxylate (II-19)

II-19 was synthesized following similar procedure as described for the synthesis of II-12, using intermediates V-7 and IV-1. LCMS: m/z; 583.3 (M+1)$^+$. $^1$H NMR (CDCl$_3$; 400 MHz) δ 1.24 (s, 9H); 1.76-2.10 (m, 4H); 2.38 (s, 3H); 3.36-3.42 (m, 2H); 3.70-3.77 (m, 2H); 4.56-4.60 (m, 1H); 6.54 (s, 1H); 6.99 (d, J=8.4 Hz, 2H); 7.24 (d, J=8.4 Hz, 2H); 7.42 (d, J=8.4 Hz, 2H); 7.79 (d, J=8.4 Hz, 2H); 8.81 (s, 1H).

Following intermediate II-20 was also synthesized using similar reaction sequence and procedures as described for II-19.

TABLE 10

| No. | Structure/IUPAC name | Characterization data |
|---|---|---|
| II-20 | 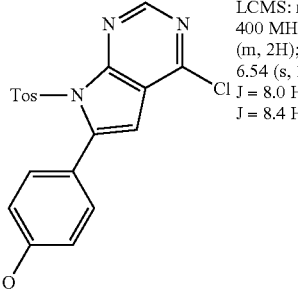<br>tert-butyl 3-[4-[4-chloro-7-(p-tolylsulfonyl)pyrrolo[2,3-d]pyrimidin-6-yl]phenoxy]azetidine-1-carboxylate | LCMS: m/z 555.2 (M + 1)+. 1H NMR (CDCl3; 400 MHz) δ 1.24 (s, 9H); 2.38 (s, 3H); 4.00-4.16 (m, 2H); 4.30-4.39 (m, 2H); 4.94-5.00 (m, 1H); 6.54 (s, 1H); 6.83 (d, J = 8.8 Hz, 2H); 7.24 (d, J = 8.0 Hz, 2H); 7.43 (d, J = 8.8 Hz, 2H); 7.79 (d, J = 8.4 Hz, 2H); 8.82 (s, 1H) |

Intermediate II-21: [4-[4-chloro-1-(2-trimethylsilylethoxymethyl)pyrrolo[2,3-b]pyridin-2-yl]phenyl]-(4-hydroxy-4-methyl-1-piperidyl)methanone

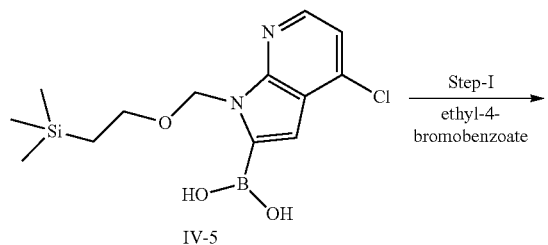

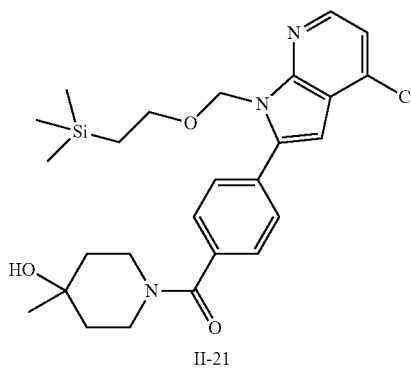

Step-I: ethyl 4-[4-chloro-1-(2-trimethylsilylethoxymethyl)pyrrolo[2,3-b]pyridin-2-yl]benzoate (II-21-I)

A solution of K2CO3 (6.7 g, 48.96 mmol) in water (10 mL) was added to a solution of IV-5 (4 g, 12.24 mmol) and ethyl-4-bromobenzoate (2.0 mL, 12.24 mmol) in 1,4-dioxane (40 mL); to which Argon was purged for 30 min. Finally, Pd(PPh3)4 (1.4 g, 1.22 mmol) was added to it and purging was continued for 10 min more. The reaction mixture was then, stirred at 90° C. for 12 h. It was, then, cooled to room temperature and diluted using EtOAc (100 mL). The organic layer was washed with brine (100 mL), dried over anhydrous Na2SO4, filtered and concentrated under reduced pressure. The residue was finally purified using silica gel column chromatography (10% EtOAc in hexane) to provide II-21-I (3.8 g, 72% yield). LCMS: m/z; 431 (M+1)+.

Step-II: [4-[4-chloro-1-(2-trimethylsilylethoxymethyl)pyrrolo[2,3-b]pyridin-2-yl]phenyl]-(4-hydroxy-4-methyl-1-piperidyl)methanone (II-21)

To a solution of II-21-I (2.0 g, 4.64 mmol) in THF (20 mL) was added aqueous NaOH (0.93 g, 23.2 mmol, 8 mL) and the reaction mixture was stirred at room temperature for 16 h. It was then acidified using 10% citric acid solution and extraction was carried out using EtOAc (30 mL×2). The combined organic layers were washed with brine (100 mL), dried over anhydrous Na2SO4, filtered and concentrated under reduced pressure to provide corresponding acid intermediate (1.3 g, 3.22 mmol), which was dissolved in DMF (15 mL). To this was added 4-methylpiperidin-4-ol (CAS: 3970-68-1) (0.97 g, 6.45 mmol), diisopropylethylamine (2.1 mL, 12.88 mmol) and HATU (1.83 g, 4.83 mmol); and the reaction mixture was stirred at room temperature for 16 h. It was, then, diluted using EtOAc (100 mL) and washed with water (100 mL×2), brine (100 mL), dried over anhydrous Na2SO4, filtered and concentrated under reduced pressure. The residue was finally purified using silica gel column chromatography (20% acetone in hexane) to provide II-21 (0.7 g, 30% yield). LCMS: m/z; 500.2 (M+1)+. 1H NMR (CDCl3, 400 MHz) δ 0.16 (s, 9H); 1.01 (t, J=8.4 Hz, 2H); 1.36 (s, 3H); 1.72-1.75 (m, 4H); 3.41-3.59 (m, 4H); 3.79 (t, J=8.4 Hz, 2H); 4.40 (bs, 1H); 5.69 (s, 2H); 6.76 (s, 1H); 7.19 (d, J=5.6 Hz, 1H); 7.56 (d, J=8.0 Hz, 2H); 7.90 (d, J=8.0 Hz, 2H); 8.26 (d, J=5.6 Hz, 1H).

Following intermediates were synthesized using similar procedure as described for the synthesis of II-21.

TABLE 11

| No. | Structure/IUPAC name | Characterization data |
|---|---|---|
| II-22a | 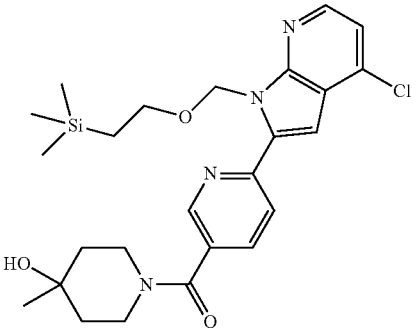 [SMILES: CC1(O)CCN(C(=O)c2ccc(-c3cc4c(Cl)ccnc4n3COCC[Si](C)(C)C)nc2)CC1]<br>[6-[4-chloro-1-(2-trimethylsilylethoxymethyl)pyrrolo[2,3-b]pyridin-2-yl]-3-pyridyl]-(4-hydroxy-4-methyl-1-piperidyl)methanone | LCMS: m/z 501.2 (M + 1)$^+$. $^1$H NMR (CDCl$_3$,400 MHz) δ 0.01 (s, 9H); 0.97 (t, J = 8.4 Hz, 2H); 1.49 (s, 3H); 1.83-2.20 (m, 4H); 3.41-3.59 (m, 4H); 3.69 (t, J = 8.4 Hz, 2H); 4.57 (bs, 1H); 6.37 (s, 2H); 7.32 (d, J = 5.2 Hz, 1H); 7.42 (s, 1H); 8.03 (dd, J = 5.6 Hz, 2.4 Hz, 1H); 8.13 (d, J = 7.6 Hz, 1H); 8.44 (d, J = 5.2 Hz, 1H); 8.99 (d, J = 2.0 Hz, 1H) |
| II-22b | 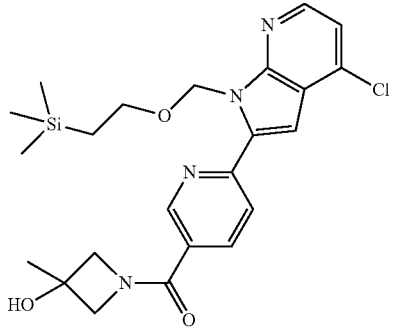 [SMILES: CC1(O)CN(C(=O)c2ccc(-c3cc4c(Cl)ccnc4n3COCC[Si](C)(C)C)nc2)C1]<br>[6-[4-chloro-1-(2-trimethylsilylethoxymethyl)pyrrolo[2,3-b]pyridin-2-yl]-3-pyridyl]-(3-hydroxy-3-methyl-azetidin-1-yl)methanone | LCMS: m/z 473.2 (M + 1)$^+$ |

Intermediate II-23: tert-butyl 4-[4-chloro-7-(p-tolyl-sulfonyl)pyrrolo[2,3-d]pyrimidin-6-yl]-3,6-dihydro-2H-pyridine-1-carboxylate

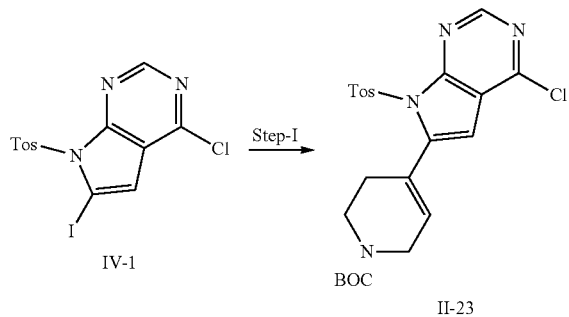

Step-I

To a mixture of IV-1 (3 gm, 6.92 mmol) and tert-butyl 4-(4,4,5,5-tetramethyl-1,3,2-dioxaborolan-2-yl)-3,6-dihydro-2H-pyridine-1-carboxylate (prepared according to the procedure mentioned in WO2010005783A1) (1.49 gm, 4.84 mmol) in dioxane (60 mL) was added a solution of K$_2$CO$_3$ (1.9 gm, 13.84 mmol) in water (12 mL); and the resulting reaction mixture was purged using Argon for 20 minutes. To the resulting solution, was added Pd(PPh$_3$)$_4$ (0.078 g, 0.06 mmol) and heated at 90-95° C. for a period of 4 hours. The reaction mixture was poured in ice cold water (100 mL) and extracted with EtOAc (3×100 mL). The combined organic layers were washed with brine solution (150 mL), dried over anhydrous Na$_2$SO$_4$, filtered and concentrated under reduced pressure to provide crude product, which was purified by silica gel column chromatography (20% EtOAc in hexanes) to give the title compound II-23 (1 g, 31.8%); LCMS: m/z 489.1 (M+1)$^+$.

Following intermediate II-24 was also synthesized following similar procedure as described for II-23.

TABLE 12

| No | Structure/IUPAC name | Characterization data |
|---|---|---|
| 11-24 | 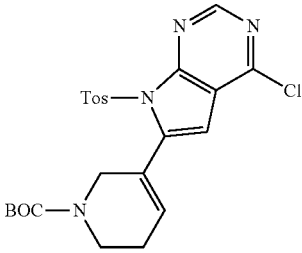<br>tert-butyl 5-[4-chloro-7-(p-tolylsulfonyl)pyrrolo[2,3-d]pyrimidin-6-yl]-3,6-dihydro-2H-pyridine-1-carboxylate | LCMS: m/z 489.1 (M + 1)⁺ |

Intermediate XI-1: 4-[4-chloro-7-(p-tolylsulfonyl)pyrrolo[2,3-d]pyrimidin-6-yl]benzaldehyde

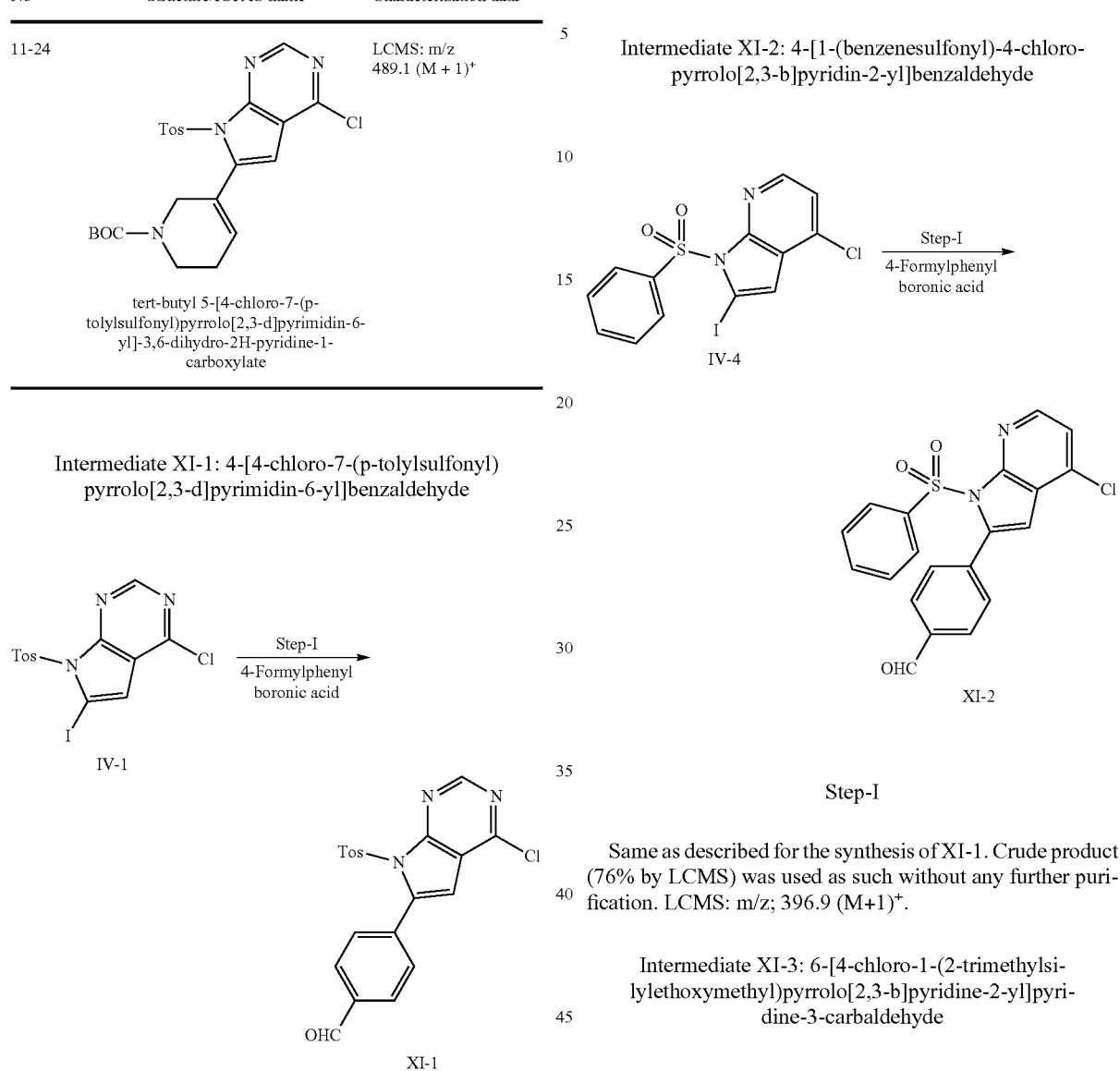

Step-I

Argon was purged through a solution of IV-1 (8.4 g, 19.39 mmol), 4-formylphenylboronic acid (2.76 g, 18.42 mmol) and $Na_2CO_3$ (5.13 g, 48.47 mmol) in acetonitrile-water (194 mL+48 mL) for 30 min. Finally, $PdCl_2(PPh_3)_2$ (1.90 g, 2.71 mmol) was added to the reaction mixture and purging was continued for 10 min more. The reaction mixture was stirred at 100° C. for 2 h. It was, then, filtered through a celite pad and the residue was washed with $CH_2Cl_2$ (300 mL×2). The combined organic layers were washed with brine (150 mL), dried over anhydrous $Na_2SO_4$, filtered and concentrated under reduced pressure. The residue was finally crystallized using EtOH (50 mL) to provide desired intermediate XI-1 (6.0 g, 75% yield). LCMS: m/z; 412.1 (M+1)⁺. ¹H NMR (DMSO-$d_6$; 400 MHz) δ 2.36 (s, 3H); 7.11 (s, 1H); 7.44 (d, J=8.1 Hz, 2H); 7.80-7.84 (aromatics, 4H); 8.05 (d, J=7.6 Hz, 2H); 8.88 (s, 1H); 10.13 (s, 1H).

Intermediate XI-2: 4-[1-(benzenesulfonyl)-4-chloro-pyrrolo[2,3-b]pyridin-2-yl]benzaldehyde

Step-I

Same as described for the synthesis of XI-1. Crude product (76% by LCMS) was used as such without any further purification. LCMS: m/z; 396.9 (M+1)⁺.

Intermediate XI-3: 6-[4-chloro-1-(2-trimethylsilylethoxymethyl)pyrrolo[2,3-b]pyridine-2-yl]pyridine-3-carbaldehyde

87

-continued

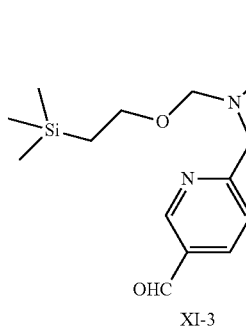

XI-3

Step-I

Argon was purged through a solution of IV-5 (1.05 g, 3.22 mmol), 6-bromo-3-pyridinecarboxaldehyde (CAS: 149806-06-4) (0.5 g, 2.7 mmol) and KF (0.47 g, 8.06 mmol) in acetonitrile: water (7 mL+3.5 mL), for 30 min. Finally, Pd(PPh$_3$)$_4$ (0.93 g, 0.81 mmol) was added to the reaction mixture and purging was continued for 10 min more. It was, then, stirred at 90° C. for 4 h. After cooling the reaction mixture, it was diluted using EtOAc (60 mL) and the organic layer was washed with water (50 mL×2), brine (50 mL), dried over anhydrous Na$_2$SO$_4$, filtered and concentrated under reduced pressure. The residue was then purified using silica gel column chromatography (12% EtOAc in hexanes) to provide XI-3 (0.56 g, 53% yield). LCMS: m/z; 388.1 (M+1)$^+$. $^1$H NMR (CDCl$_3$; 400 MHz) δ-0.16 (s, 9H); 0.82 (t, J=8.4 Hz, 2H); 3.52 (t, J=8.4 Hz, 2H); 6.29 (s, 2H); 7.18 (d, J=5.2 Hz, 1H); 7.19 (s, 1H); 8.08 (d, J=8.4 Hz, 1H); 8.26 (dd, J$_1$=2.4 Hz, J$_2$=8.4 Hz, 1H); 8.31 (d, J=5.2 Hz, 1H); 9.15 (d, J=1.2 Hz, 1H); 10.15 (s, 1H).

Following two intermediates were synthesized following similar procedures as described for the synthesis of XI-1.

TABLE 13

| No. | Structure/IUPAC name | Characterization data |
|---|---|---|
| XI-4 | ![structure]<br>4-[4-chloro-1-(p-tolylsulfonyl)pyrrolo[2,3-b]pyridin-2-yl]-2-fluoro-benzaldehyde | LCMS: m/z 429.0 (M + 1)$^+$. $^1$H NMR (CDCl$_3$; 400 MHz) δ 2.35 (s, 3H); 6.73 (s, 1H); 7.23 (d, J = 8.4 Hz, 2H); 7.26 (s, 1H); 7.42 (d, J = 10.8 Hz, 1H); 7.47 (d, J = 8.4 Hz, 1H); 7.81 (d, 7 = 8.4 Hz, 2H); 7.97 (t, J = 7.6 Hz, 1H); 8.40 (d, J = 5.2 Hz, 1H); 10.44 (s, 1H) |

TABLE 13-continued

| No. | Structure/IUPAC name | Characterization data |
|---|---|---|
| XI-5 | ![structure]<br>4-[1-(benzenesulfonyl)-4-chloro-pyrrolo[2,3-b]pyridin-2-yl]-3-fluoro-benzaldehyde | LCMS: m/z 414.9 (M + 1)$^+$. $^1$H NMR (CDCl$_3$; 400 MHz) δ 6.78 (s, 1H); 7.46 (t, J = 8.4 Hz, 3H); 7.58-7.61 (aromatic, 1H); 7.67-7.74 (aromatics, 2H); 7.82 (d, J = 7.6 Hz, 1H); 8.05 (d, J = 7.6 Hz, 2H); 8.38 (d, J = 5.2 Hz, 1H); 10.09 (s, 1H). |

Intermediate XI-6: 5-[4-chloro-1-(p-tolylsulfonyl)pyrrolo[2,3-b]pyridin-2-yl]pyridine-2-carbaldehyde

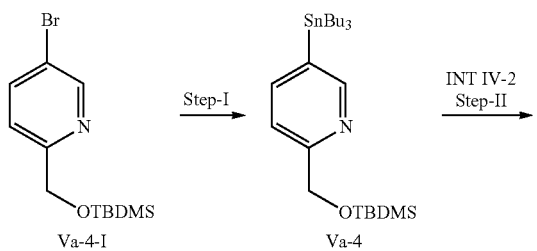

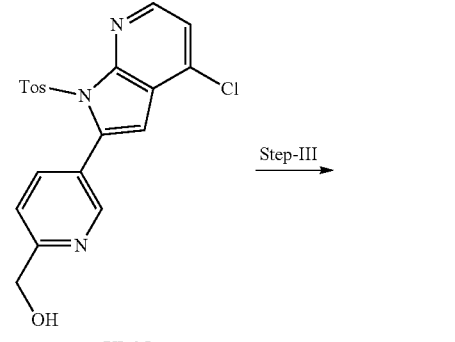

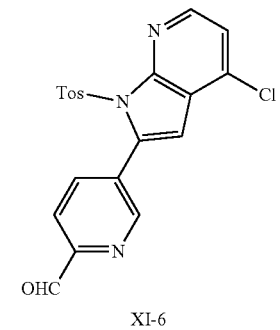

XI-6

Step-I: tert-butyl-dimethyl-[(5-tributylstannyl-2-pyridyl)methoxy]silane (Va-4)

Va-4 was synthesized following procedure described in step-II for the synthesis of II-6 using diethyl ether as the solvent and Va-4-I (synthesized according to WO2011092140) as the starting material. LCMS: m/z; 514.3 (M+1)+.

Step-II: [5-[4-chloro-1-(p-tolylsulfonyl)pyrrolo[2,3-b]pyridin-2-yl]-2-pyridyl]methanol (XI-6-I)

This intermediate was synthesized as described in step-III of the synthesis of II-6, using Va-4 and IV-2 intermediates. LCMS: m/z; 414.1 (M+1)+.

Step-III: 5-[4-chloro-1-(p-tolylsulfonyl)pyrrolo[2,3-b]pyridin-2-yl]pyridine-2-carbaldehyde (XI-6)

To a solution of XI-6-I (0.9 g, 2.17 mmol) in anhydrous $CH_2Cl_2$ (15 mL) was added Dess-Martin periodinane (1.84 g, 4.35 mmol) at 0° C. and the reaction mixture was stirred for 30 min. It was, then, diluted using $CH_2Cl_2$ (50 mL) and washed with 10% sodium thiosulphate solution (30 mL), saturated $NaHCO_3$ solution (50 mL) and brine (50 mL). Solvent was removed under reduced pressure after drying over anhydrous $Na_2SO_4$. The residue was purified by silica gel column chromatography (10% EtOAc in hexane) to provide desired intermediate XI-6 (0.64 g, 71% yield). LCMS: m/z 412.1 (M+1)+. $^1$H NMR ($CDCl_3$; 400 MHz) δ 2.35 (s, 3H); 6.78 (s, 1H); 7.23 (d, J=8.4 Hz, 2H); 7.28 (s, 1H); 7.80 (d, J=8.4 Hz, 2H); 8.41-8.44 (aromatics, 2H); 8.42 (d, J=5.2 Hz, 1H); 8.94 (s, 1H); 10.18 (s, 1H).

Intermediate XI-7: Methyl 4-(4-chloro-7H-pyrrolo[2,3-d]pyrimidin-6-yl)benzoate

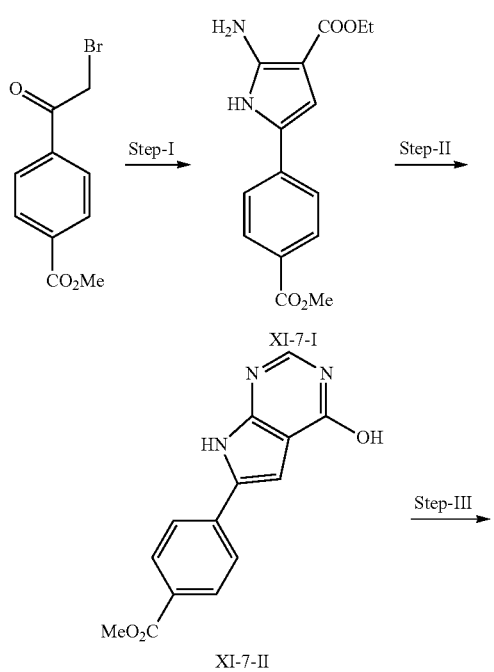

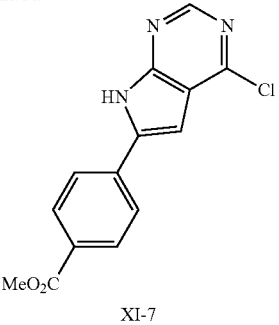

Step-I: Ethyl 2-amino-5-(4-methoxycarbonylphenyl)-1H-pyrrole-3-carboxylate (XI-7-I)

Na metal (1.96 g, 85.3 mmol) was added portion wise to ethanol (210 mL) and stirred for 30 minutes to get clear solution. To this was added ethyl 3-amino-3-imino-propanoate hydrochloride (CAS: 57508-48-2, 14.25 g, 85.6 mmol) and stirred at room temperature for additional 30 minutes. Finally, methyl 4-(2-bromoacetyl)benzoate (11 g, 42.8 mmol) was added to the reaction mixture and stirred for 16-20 h at room temperature. After completion of the reaction (as indicated by TLC and LCMS), reaction mixture was filtered through celite and the residue was washed with MeOH (50 mL×2). The combined filtrate was concentrated under reduced pressure and the residue was purified using silica gel column chromatography (40% EtOAc in hexane) to provide XI-7-I (7 g, 56.7% yield). LCMS; m/z: 289.1 (M+1)+.

Step-II: Methyl 4-(4-hydroxy-7H-pyrrolo[2,3-d]pyrimidin-6-yl)benzoate (XI-7-II)

To a mixture of formamide (10 mL), formic acid (4 mL) and DMF (2 mL), XI-7-I (7.5 g, 26 mmol) was added and the resulting reaction mixture was stirred at 150° C. for 16-20 h. After completion of the reaction (monitored by TLC and LCMS), the reaction mixture was cooled to 0° C. and 2-propanol (35 mL) was added to it. After stirring for 15 min, the residue was filtered and washed with diethyl ether (10 mL) to provide XI-7-II (6 g, 85.6% yield). LCMS; m/z: 270 (M+1)+.

Step-III: Methyl 4-(4-chloro-7H-pyrrolo[2,3-d]pyrimidin-6-yl)benzoate (XI-7)

A suspension of XI-7-II (6 g, 22.3 mmol) in excess of $POCl_3$ (100 mL) was refluxed for 16-20 h. After completion of the reaction (monitored by TLC), $POCl_3$ was removed under reduced pressure. Saturated $NaHCO_3$ (100 mL) solution was added slowly to the residue and stirred for 30 minutes. The solid was filtered and suspended in minimum quantity of MeOH (10 mL). After stirring for 30 min, it was filtered and dried to provide XI-7 (5.8 g, 90% yield). LCMS; m/z: 288 (M+1)+. $^1$H NMR ($CDCl_3$; 400 MHz) δ 3.86 (s, 3H); 7.28 (s, 1H); 8.04 (d, J=8.0 Hz, 2H); 8.16 (d, J=8.4 Hz, 2H); 8.61 (s, 1H); 13.18 (s, 1H).

Following intermediates (II-25 and II-26) were synthesized following similar sequence of reactions and procedures as described for the preparation of XI-7.

TABLE 14

| No. | Structure/IUPAC name | Characterization data |
|---|---|---|
| II-25 | 4-chloro-6-phenyl-7H-pyrrolo[2,3-d]pyrimidine | LCMS: m/z 230 (M + 1)+ |
| II-26 | 4-[4-(4-chloro-7H-pyrrolo[2,3-d]pyrimidin-6-yl)phenyl]morpholine | LCMS: m/z 315 (M + 1)+ |

Intermediate XI-8: Methyl 4-[4-chloro-2-(2,2-dimethylpropanoylamino)-7H-pyrrolo[2,3-d]pyrimidin-6-yl]benzoate

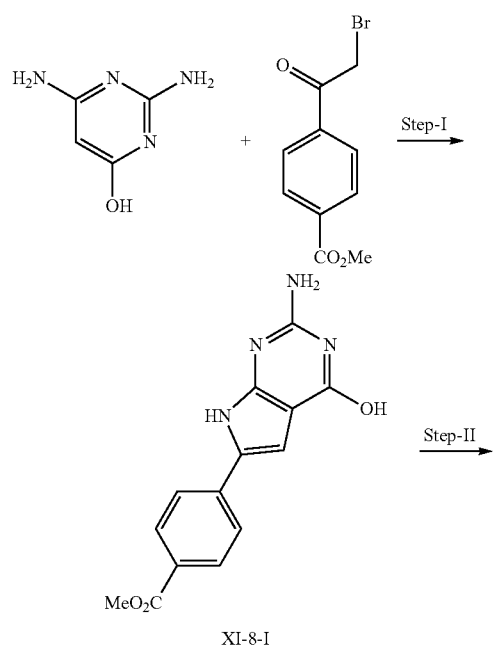

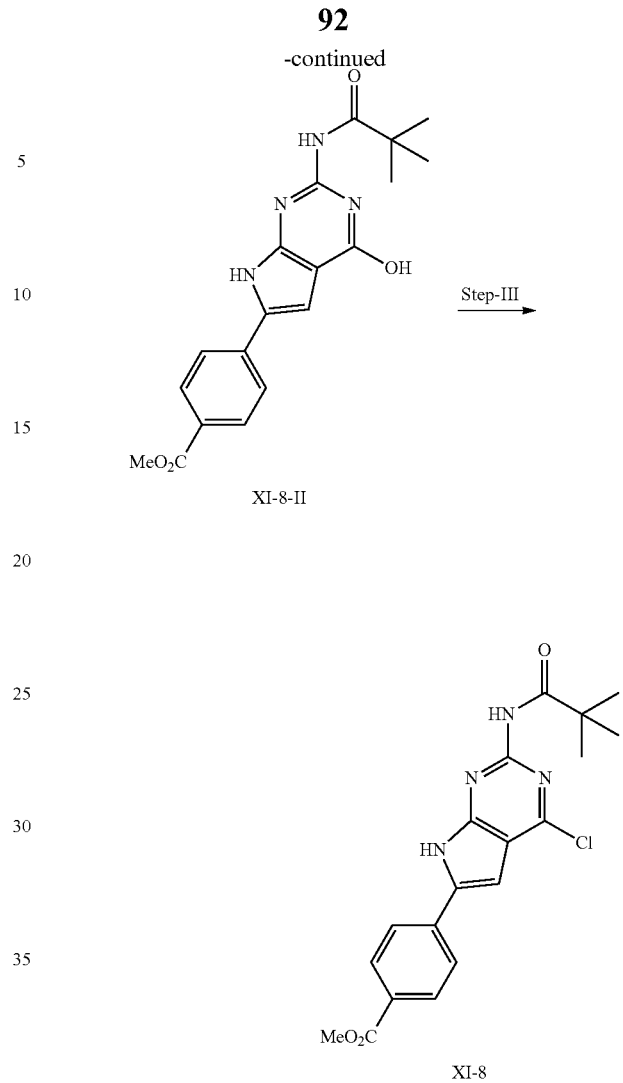

Step-I: Methyl 4-(2-amino-4-hydroxy-7H-pyrrolo[2,3-d]pyrimidin-6-yl)benzoate (XI-8-I)

A solution of 2,6-diamino-4-hydroxypyrimidine (CAS: 56-06-4, 1 g, 7.93 mmol) and sodium acetate (0.85 g, 10.32 mmol) in water (180 mL) was stirred at 100° C. for 30 minutes. Methyl 4-(2-bromoacetyl)benzoate (2.24 g, 8.72 mmol) was suspended in MeOH (25 mL) and was added slowly to the above solution. The reaction mixture was then stirred at 100° C. for 16-20 h and then cooled to room temperature. The residue was filtered and dried. It was then stirred in $CH_2Cl_2$ (10 mL) and filtered to provide XI-8-I (1.07 g, 47.5%). LCMS: m/z 285 (M+1)+.

Step-II: Methyl 4-[2-(2,2-dimethylpropanoylamino)-4-hydroxy-7H-pyrrolo[2,3-d]pyrimidin-6-yl]benzoate (XI-8-II)

A suspension of XI-8-I (2 g, 7.04 mmol) in trimethylacetic anhydride (5 mL) was refluxed for 3-5 h. After completion of the reaction (monitored by TLC), the reaction mixture was cooled to room temperature and hexane (10 mL) was added to it. The residue was filtered and washed with diethyl ether (5 mL) to provide XI-8-II (1.9 g, 73.3%). LCMS: m/z: 369.1 (M+1)+.

Step-III: Methyl 4-[4-chloro-2-(2,2-dimethylpropanoylamino)-7H-pyrrolo[2,3-d]pyrimidin-6-yl]benzoate (XI-8)

A suspension of XI-8-II (1.9 g, 5.16 mmol) in POCl₃ (2 mL) was refluxed for 3-5 h. After completion of the reaction (monitored by TLC), POCl₃ was removed under reduced pressure and saturated NaHCO₃ solution (50 mL) was added to the residue. The solid obtained was filtered and dried. It was then stirred in MeOH (5 mL) for 15 min, filtered and dried to provide XI-8 (1 g, 50%). LCMS: m/z 387.1 (M+1)⁺.

Following intermediate was prepared following similar sequence of reactions and procedures as used for the preparation of XI-8.

TABLE 15

| No. | Structure/IUPAC name | Characterization data |
|---|---|---|
| XI-9 | 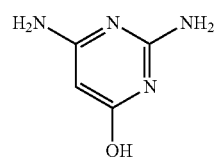<br>N-[4-chloro-6-(6-morpholino-3-pyridyl)-7H-pyrrolo[2,3-d]pyrimidin-2-yl]-2,2-dimethyl-propanamide | LCMS: m/z 415.1 (M + 1)⁺ |

Intermediate XI-10: 4-(2-amino-4-chloro-7H-pyrrolo[2,3-d]pyrimidin-6-yl)benzonitrile

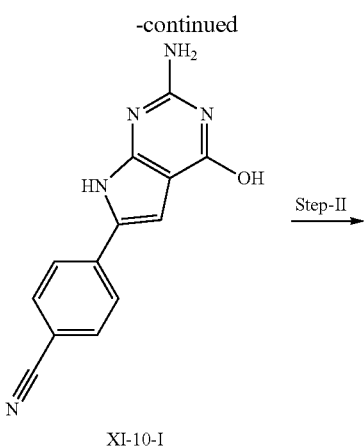

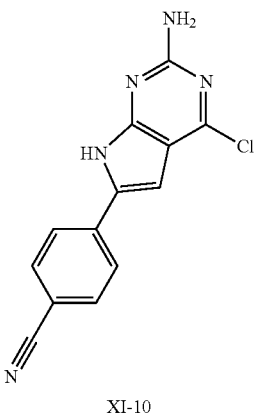

Step-I: 4-(2-amino-4-hydroxy-7H-pyrrolo[2,3-d]pyrimidin-6-yl)benzonitrile (XI-10-I)

A mixture of 2,6-diaminopyrimidin-4-ol (1 g, 7.93 mmol) and NaOAc (0.846 g, 10.31 mmol) in water (180 mL) was heated to 100° C. for 20 minutes. To this was added a suspension of 4-(2-bromoacetyl)benzonitrile (2.2 gm, 8.73 mmol) [prepared according to procedure mentioned in *J. Med. Chem.*, 2011, 54(12), 4042-4056] in MeOH (25 mL) and heated overnight at 100° C. After completion of reaction, the reaction mixture was cooled to 0° C. Resultant solid product was filtered off and dried under reduced pressure to provide title compound XI-10-I (1.2 g, 100%). LCMS: m/z 252 (M+1)⁺.

Step-II: 4-(2-amino-4-chloro-7H-pyrrolo[2,3-d]pyrimidin-6-yl)benzonitrile (XI-10)

A suspension of XI-10-I (0.5 g, 1.99 mmol) in POCl₃ (10 mL) was refluxed for 16 h. After completion of reaction, excess POCl₃ was removed under reduced pressure. The reaction mixture was cooled to 0° C. and neutralized using slow addition of saturated aqueous NaHCO₃ solution. Product was extracted with EtOAc (20 mL×2). Organic layer was washed with brine solution (50 mL), dried over anhydrous Na₂SO₄, filtered and concentrated under reduced pressure to obtain crude product, which was purified by silica gel column chromatography (40% acetone in hexanes) to provide the title compound XI-10 (0.18 g, 33%). LCMS: m/z 270 (M+1)+. $^1$H NMR (DMSO-d$_6$; 400 MHz) δ 6.78 (bs, 2H); 7.05 (s, 1H); 7.88 (d, J=8.3 Hz, 2H); 8.05 (d, J=8.3 Hz, 2H); 12.17 (bs, 1H).

Example A-1

Synthesis of 8-cyclopropyl-4-[2-methyl-3-[6-[4-(piperazin-1-ylmethyl)phenyl]-7H-pyrrolo[2,3-d]pyrimidin-4-yl]phenyl]-2,3-dihydro-1,4-benzoxazepin-5-one

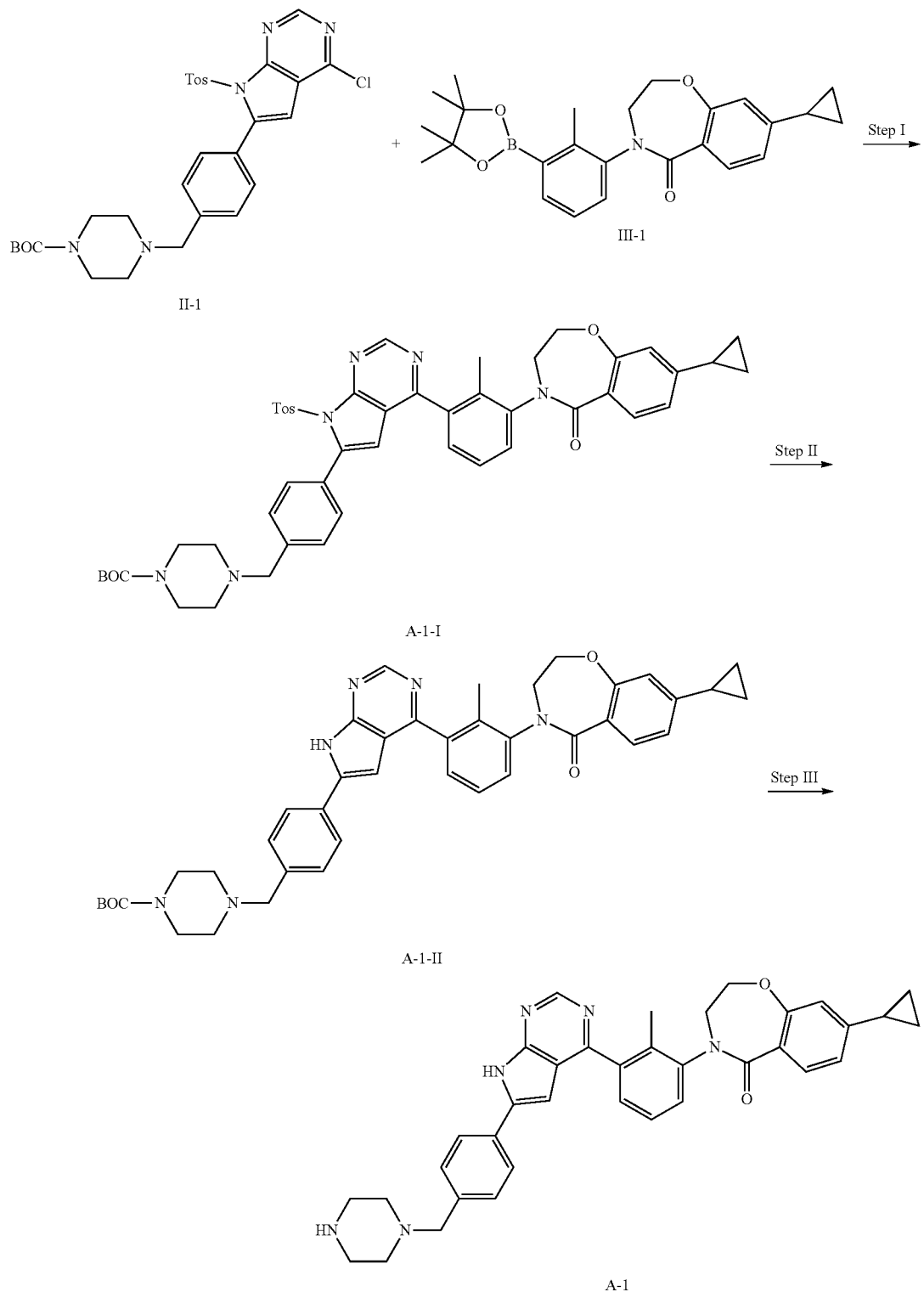

Step-I: tert-butyl 4-[[4-[4-[3-(8-cyclopropyl-5-oxo-2,3-dihydro-1,4-benzoxazepin-4-yl)-2-methyl-phenyl]-7-(p-tolylsulfonyl)pyrrolo[2,3-d]pyrimidin-6-yl]phenyl]methyl]piperazine-1-carboxylate (A-1-I)

To a solution of intermediates II-1 (0.4 g, 0.68 mmol) and III-1 (0.57 g, 1.37 mmol) in dioxane (20 mL) was added aqueous of Na$_2$CO$_3$ (0.18 g, 1.71 mmol, 4 mL). The resulting reaction mixture was purged using Argon for 30 minutes and then Pd(PPh$_3$)$_4$ (0.08 g, 0.068 mmol) was added to it. The reaction mixture was then heated at 100° C. for 6 hours. After completion of reaction (monitored by TLC), the reaction mixture was diluted with water (30 mL). Extraction was carried out using EtOAc (20 mL×2). The combined organic layers were washed with brine (50 mL), dried over anhydrous Na$_2$SO$_4$, filtered and concentrated under reduced pressure. The crude product was purified by silica gel column chromatography (60% EtOAc in hexane) to afford title compound A-1-I (0.45 g, 79%); LCMS: m/z 839.1 (M+1)$^+$.

Step-II: tert-butyl 4-[[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]phenyl]methyl]piperazine-1-carboxylate (A1-II)

To a solution of intermediate A-1-I (0.45 g, 0.53 mmol) in a mixture of THF, methanol and water (3:1:1) (5 mL) was added LiOH.H$_2$O (0.067 g, 1.60 mmol) and the reaction mixture was stirred at room temperature for 1 h. After completion of reaction, water (30 mL) was added and extraction was carried out using EtOAc (20 mL×2). The combined organic layers were washed with brine (50 mL), dried over anhydrous Na$_2$SO$_4$, filtered and concentrated under reduced pressure. The crude product (A-1-II) was used without any purification. LCMS: m/z 685.1 (M+1)$^+$.

Step-III: 8-cyclopropyl-4-[2-methyl-3-[6-[4-(piperazin-1-ylmethyl)phenyl]-7H-pyrrolo[2,3-d]pyrimidin-4-yl]phenyl]-2,3-dihydro-1,4-benzoxazepin-5-one (Example A-1)

A mixture of intermediate A-1-II (0.3 g, 0.437 mmol) and 4M HCl in dioxane (5 mL) was stirred at room temperature for 1 h. After completion of reaction (monitored by TLC), solvent was evaporated under reduced pressure and saturated NaHCO$_3$ solution (30 mL) was added to it. The precipitated solid was filtered and purified by preparative TLC (10% methanol in CH$_2$Cl$_2$) to give title compound A-1 as a yellow solid (0.045 g, 18%); LCMS: m/z 585.4 (M+1)$^+$. $^1$H NMR (400 MHz, DMSO-d$_6$) δ 0.74-0.77 (m, 2H); 0.98-1.06 (m, 2H); 1.93-2.00 (m, 1H); 2.15 (s, 3H); 2.30-2.40 (m, 4H); 2.73-2.80 (m, 4H); 3.48 (s, 2H); 3.89-3.99 (m, 2H); 4.45-4.48 (m, 2H); 6.82 (s, 2H); 6.91 (d, J=8.0 Hz, 1H); 7.39 (d, J=8.1 Hz, 2H); 7.43-7.47 (aromatics, 2H); 7.52-7.54 (aromatic, 1H); 7.62 (d, J=8.1 Hz, 1H); 7.93 (d, J=8.1 Hz, 2H); 8.84 (s, 1H); 12.80 (s, 1H).

Following compounds were synthesized following similar reaction sequence and procedures as described for the synthesis of A-1.

TABLE 16

| No | Strucure/IUPAC name | Characterization | INT used |
|---|---|---|---|
| A-2 | 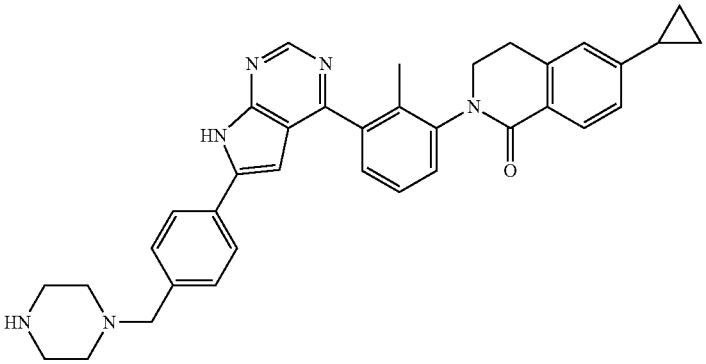 [SMILES: Cc1c(-c2ncnc3[nH]c(-c4ccc(CN5CCNCC5)cc4)cc23)cccc1N1CCc2cc(C3CC3)ccc2C1=O]<br>6-cyclopropyl-2-[2-methyl-3-[6-[4-(piperazin-1-ylmethyl)phenyl]-7H-pyrrolo[2,3-d]pyrimidin-4-yl]phenyl]-3,4-dihydroisoquinolin-1-one | LCMS: m/z 569 (M + 1)$^+$. $^1$H NMR (400 MHz, DMSO-d$_6$) δ 0.74-0.76 (m, 2H); 0.95-1.05 (m, 2H); 1.92-2.00 (m, 1H); 2.13 (s, 3H); 2.15-2.31 (m, 4H); 2.62-2.70 (m, 3H); 3.00-3.25 (m, 3H); 3.43 (s, 2H); 3.70-3.80 (m, 1H); 3.94-4.02 (m, 1H); 6.78 (s, 1H); 7.06-7.09 (aromatics, 2H); 7.30-7.55 (aromatics, 5H); 7.79 (d, J = 8.1 Hz, 1H); 7.91 (d, J = 7.8 Hz, 2H); 8.79 (s, 1H); 12.9 (bs 1H) | II-1 & III-2 |

TABLE 16-continued

| No | Strucure/IUPAC name | Characterization | INT used |
|---|---|---|---|
| A-3 | 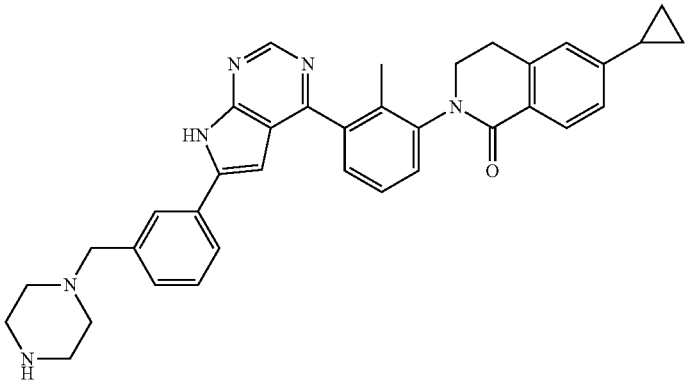 [SMILES: Cc1c(-c2ncnc3[nH]c(-c4cccc(CN5CCNCC5)c4)cc23)cccc1N1CCc2cc(C3CC3)ccc2C1=O]<br>6-cyclopropyl-2-[2-methyl-3-[6-[3-(piperazin-1-ylmethyl)phenyl]-7H-pyrrolo[2,3-d]pyrimidin-4-yl]phenyl]-3,4-dihydroisoquinolin-1-one | LCMS: m/z 569.4 (M + 1)$^+$. $^1$H NMR (400 MHz, DMSO-d$_6$) δ 0.74-0.80 (m, 2H); 0.98-1.06 (m, 2H); 1.96-2.02 (m, 1H); 2.15 (s, 3H); 2.32-2.42 (m, 4H); 2.72-2.80 (m, 4H); 3.07-3.23 (m, 3H); 3.49 (s, 2H); 3.73-3.77 (m, 1H); 3.98-4.05 (m, 1H); 6.84 (s, 1H); 7.08-7.12 (aromatics, 2H); 7.33 (d, J = 7.8 Hz, 1H ); 7.42 (d, J = 7.9 Hz, 1H); 7.45-7.52 (aromatics, 3H); 7.81 (d, J = 7.8 Hz, 1H); 7.86-7.89 (aromatics, 2H); 8.84 (s, 1H); 12.80 (bs, 1H) | II-2 & III-2 |
| A-4 | 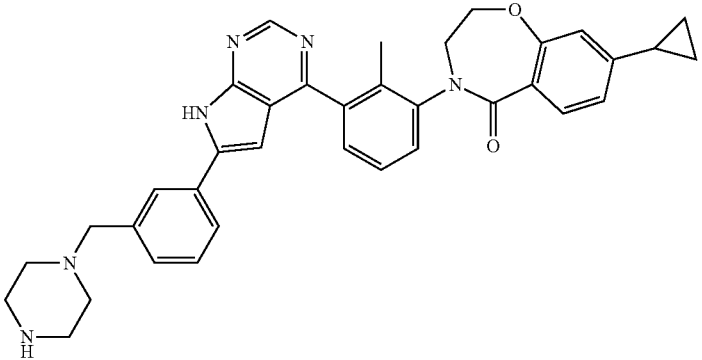 [SMILES: Cc1c(-c2ncnc3[nH]c(-c4cccc(CN5CCNCC5)c4)cc23)cccc1N1CCOc2cc(C3CC3)ccc2C1=O]<br>8-cyclopropyl-4-[2-methyl-3-[6-[3-(piperazin-1-ylmethyl)phenyl]-7H-pyrrolo[2,3-d]pyrimidin-4-yl]phenyl]-2.3-dihydro-1,4-benzoxazepin-5-one | LCMS: m/z 585.4 (M + 1)$^+$. $^1$H NMR (400 MHz, DMSO-d$_6$) δ 0.74-0.78 (m, 2H); 1.00-1.06 (m, 2H); 1.95-2.02 (m, 1H); 2.15 (s, 3H); 2.30-2.41 (m, 4H); 2.72-2.80 (m, 4H); 3.50 (s, 2H); 3.88-3.95 (m, 2H); 4.40-4.50 (m, 2H); 6.83 (d, J = 6.6 Hz, 2H); 6.92 (d, J = 8.1 Hz, 1H); 7.33 (d, J = 7.1 Hz, 1H); 7.41-7.55 (aromatics, 4H); 7.62 (d, J = 8.1 Hz, 1H); 7.85-7.89 (aromatics, 2H); 8.85 (s, 1H); 12.80 (s, 1H) | II-2 & III-1 |
| A-5 | 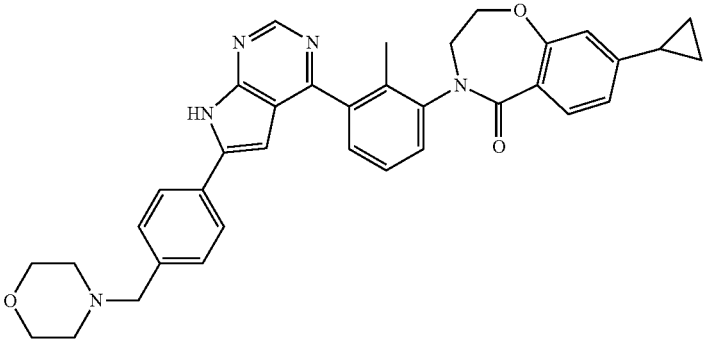 [SMILES: Cc1c(-c2ncnc3[nH]c(-c4ccc(CN5CCOCC5)cc4)cc23)cccc1N1CCOc2cc(C3CC3)ccc2C1=O]<br>8-cyclopropyl-4-[2-methyl-3-[6-[4-(morpholinomethyl)phenyl]-7H-pyrrolo[2,3-d]pyrimidin-4-yl]phenyl]-2,3-dihydro-1,4-benzoxazepin-5-one | LCMS: m/z 586.4 (M + 1)$^+$. $^1$H NMR (400 MHz, DMSO-d$_6$) δ 0.73-0.77 (m, 2H); 0.99-1.04 (m, 2H); 1.95-2.01 (m, 1H); 2.15 (s, 3H); 2.33-2.40 (m, 4H); 3.50 (s, 2H); 3.55-3.60 (m, 4H); 3.90 (t, J = 4.5 Hz, 2H); 4.45-4.49 (m, 2H); 6.82 (bs, 2H); 6.91 (d, J = 7.9 Hz, 1H); 7.40 (d, J = 8.2 Hz, 2H); 7.43-7.54 (aromatics, 3H); 7.63 (d, J = 8.2 Hz, 1H); 7.94 (d, J = 8.0 Hz, 2H); 8.84 (s, 1H); 12.73 (s, 1H) | II-4 & II-1 |

| No | Structure/IUPAC name | Characterization | INT used |
|---|---|---|---|
| A-6 | 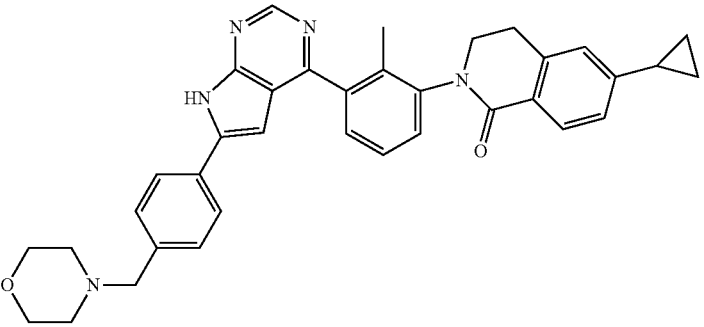 [SMILES: Cc1c(-c2ncnc3[nH]c(-c4ccc(CN5CCOCC5)cc4)cc23)cccc1N1CCc2cc(C3CC3)ccc2C1=O]<br>6-cyclopropyl-2-[2-methyl-3-[6-[4-(morpholinomethyl)phenyl]-7H-pyrrolo[2,3-d]pyrimidin-4-yl]phenyl]-3,4-dihydroisoquinolin-1-one | LCMS: m/z 570.3 (M + 1)$^+$. $^1$H NMR (400 MHz, DMSO-$d_6$) δ 0.74-0.80 (m, 2H); 1.00-1.06 (m, 2H); 1.96-2.02 (m, 1H); 2.15 (s, 3H); 2.33-2.40 (m, 4H); 3.07-3.21 (m, 2H); 3.50 (s, 2H); 3.48-3.62 (m, 4H); 3.73-7.79 (m, 1H); 3.97-4.04 (m, 1H); 6.82 (s, 1H); 7.07-7.11 (aromatics, 2H); 7.41 (d, J = 8.0 Hz, 2H); 7.44-7.46 (aromatics, 2H); 7.50-7.53 (aromatic, 1H); 7.81 (d, J = 8.0 Hz, 1H); 7.94 (d, J = 8.0 Hz, 2H); 8.83 (s, 1H); 12.73 (bs, 1H) | II-4 & III-2 |
| A-7 | 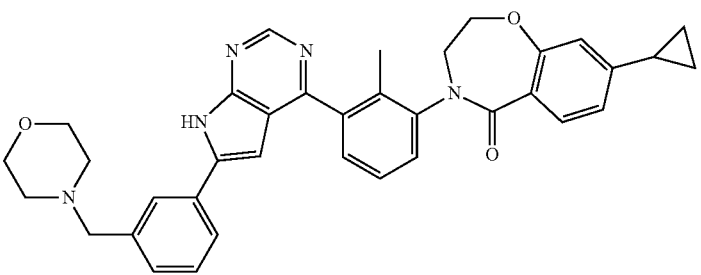 [SMILES: Cc1c(-c2ncnc3[nH]c(-c4cccc(CN5CCOCC5)c4)cc23)cccc1N1CCOc2cc(C3CC3)ccc2C1=O]<br>8-cyclopropyl-4-[2-methyl-3-[6-[3-(morpholinomethyl)phenyl]-7H-pyrrolo[2,3-d]pyrimidin-4-yl]phenyl]-2,3-dihydro-1,4-benzoxazepin-5-one | LCMS: m/z 586.3 (M + 1)$^+$. $^1$H NMR (400 MHz, DMSO-$d_6$) δ 0.74-0.78 (m, 2H); 0.98-1.06 (m, 2H); 1.94-1.99 (m, 1H); 2.15 (s, 3H); 2.32-2.40 (m, 4H); 3.52 (s, 2H); 3.56-3.60 (m, 4H); 3.88-3.96 (m, 2H); 4.45-4.49 (m, 2H); 6.82 (d, J = 5.6 Hz, 2H); 6.91 (d, J = 8.2 Hz, 1H); 7.34 (d, J = 7.4 Hz, 1H); 7.41-7.54 (aromatics, 4H); 7.63 (d, J = 8.2 Hz, 1H); 7.87 (d, J = 7.9 Hz, 1H); 7.90 (s, 1H); 8.84 (s, 1H); 12.78 (s, 1H) | II-3 & III-1 |
| A-8 | 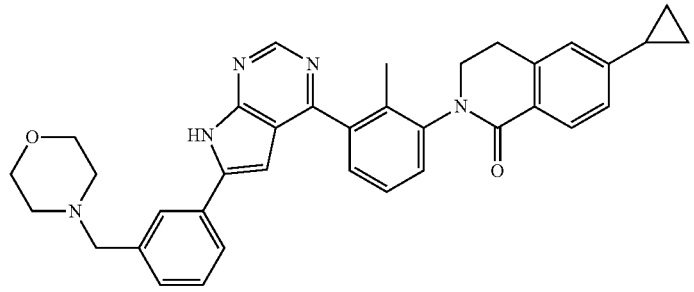 [SMILES: Cc1c(-c2ncnc3[nH]c(-c4cccc(CN5CCOCC5)c4)cc23)cccc1N1CCc2cc(C3CC3)ccc2C1=O]<br>6-cyclopropyl-2-[2-methyl-3-[6-[3-(morpholinomethyl)phenyl]-7H-pyrrolo[2,3-d]pyrimidin-4-yl]phenyl]-3,4-dihydroisoquinolin-1-one | LCMS: m/z 570.4 (M + 1)$^+$. $^1$H NMR (400 MHz. DMSO-$d_6$) δ 0.74-0.80 (m, 2H); 1.00-1.05 (m, 2H); 1.96-2.02 (m, 1H); 2.14 (s, 3H); 2.32-2.40 (m, 4H); 3.07-3.20 (m, 2H); 3.52 (s, 2H); 3.55-3.42 (m, 4H); 3.73-3.78 (m, 1H); 3.98-4.04 (m, 1H); 6.84 (d, J = 1.6 Hz, 1H); 7.07-7.11 (aromatics, 2H); 7.35 (d, J = 7.6 Hz, 1H); 7.42-7.53 (aromatics, 4H); 7.81 (d, J = 8.0 Hz, 1H); 7.87 (d, J = 8.2 Hz, 1H); 7.91 (s, 1H); 8.44 (s, 1H); 12.76 (s, 1H) | II-3 & III-2 |

Example B-1

Synthesis of 8-cyclopropyl-4-[2-(hydroxymethyl)-3-[6-[4-[(4-methyl piperazin-1-yl)methyl]phenyl]-7H-pyrrolo[2,3-d]pyrimidin-4-yl]phenyl]-2,3-dihydro-1,4-benzoxazepin-5-one

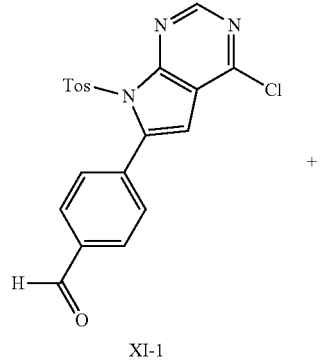

Step-I: 4-[4-[3-(8-cyclopropyl-5-oxo-2,3-dihydro-1,4-benzoxazepin-4-yl)-2-(hydroxymethyl)phenyl]-7-(p-tolylsulfonyl)pyrrolo[2,3-d]pyrimidin-6-yl]benzaldehyde (B-1-I)

Intermediate B-1-I was prepared using intermediates XI-1 and III-5 following similar procedure as described for the synthesis of A-1-I. LCMS: m/z 685.3 (M+1)$^+$.

Step-II: 8-cyclopropyl-4-[2-(hydroxymethyl)-3-[6-[4-[(4-methylpiperazin-1-yl)methyl]phenyl]-7-(p-tolylsulfonyl)pyrrolo[2,3-d]pyrimidin-4-yl]phenyl]-2,3-dihydro-1,4-benzoxazepin-5-one (B-1-II)

To a stirred solution of intermediate B-1-I (0.08 g, 0.10 mmol) in 1,2-dichloroethane (2 mL) was added N-methyl piperazine (0.016 g, 0.15 mmol), acetic acid (2 drops) and activated molecular sieves (0.1 g) at 25° C. The reaction mixture was stirred for 15 minutes at room temperature and then sodium cyanoborohydride (0.01 g, 0.16 mmol) was added to it at the same temperature. The reaction mixture was stirred for 1 h before it was evaporated to dryness and diluted with ethyl acetate (30 mL). The organic layer was washed with water (30 mL), brine (30 mL), dried over anhydrous Na$_2$SO$_4$, filtered and concentrated under reduced pressure to give crude product B-1-II (0.120 g), which was used for the next step without any purification. LCMS: m/z 769.1 (M+1)$^+$.

Step-III: 8-cyclopropyl-4-[2-(hydroxymethyl)-3-[6-[4-[(4-methylpiperazin-1-yl)methyl]phenyl]-7H-pyrrolo[2,3-d]pyrimidin-4-yl]phenyl]-2,3-dihydro-1,4-benzoxazepin-5-one (B-1)

To a stirred solution of intermediate B-1-II (0.12 g, 0.15 mmol) in 1,4-dioxane (4 mL) was added lithium hydroxide (0.032 g, 0.78 mmol). After stirring for 18 h at room temperature, volatiles were evaporated under reduced pressure. The resulting residue was dissolved in EtOAc (50 mL), and it was washed with water (50 mL), brine (50 mL), dried over anhydrous Na$_2$SO$_4$, filtered and concentrated under reduced pressure. The residue was purified by preparative HPLC to furnish title compound B-1 (0.006 g, 6%). LCMS: m/z 615.3 (M+1)$^+$.
$^1$H NMR (DMSO-d$_6$, 400 MHz) δ 0.74-0.78 (m, 2H); 1.00-1.04 (m, 2H); 1.94-2.00 (m, 1H); 2.17 (s, 3H); 2.24-2.44 (m, 8H); 3.50 (s, 2H); 3.84-4.02 (m, 2H); 4.36-4.44 (m, 2H); 4.47-4.61 (m, 2H); 5.37-5.41 (m, 1H); 6.83 (s, 1H); 6.91 (d, J=8.1 Hz, 1H); 7.04 (s, 1H); 7.41 (d, J=8.1 Hz, 2H); 7.50 (d, J=7.8 Hz, 1H); 7.63 (d, J=8.3 Hz, 2H); 7.78 (d, J=7.6 Hz, 1H); 7.96 (d, J=8.1 Hz, 2H); 8.82 (s, 1H); 12.82 (bs, 1H).

Following compounds were synthesized using similar sequence of reactions and procedures as described for the synthesis of B-1.

TABLE 17

| No | Structure/IUPAC name | Characterization | INT used |
|---|---|---|---|
| B-2 | 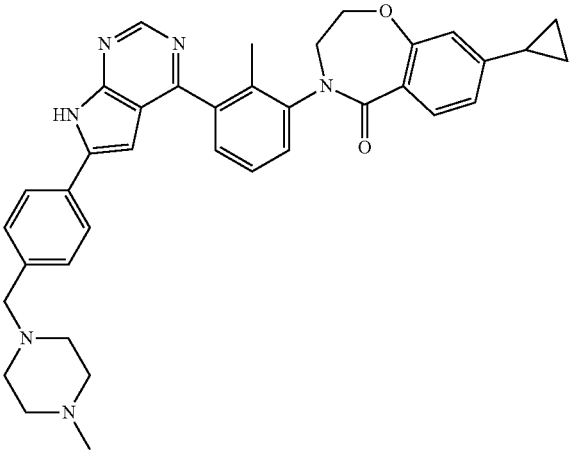 [SMILES: Cc1c(-c2ncnc3[nH]c(-c4ccc(CN5CCN(C)CC5)cc4)cc23)cccc1N1CCOc2cc(C3CC3)ccc2C1=O]<br>8-cyclopropyl-4-[2-methyl-3-[6-[4-[(4-methylpiperazin-1-yl)methyl]phenyl]-7H-pyrrolo[2,3-d]pyrimidin-4-yl]phenyl]-2,3-dihydro-1,4-benzoxazepin-5-one | LCMS: m/z 599.4 (M + 1)+. $^1$H NMR (DMSO-d$_6$, 400 MHz) δ 0.74-0.76 (m, 2H); 0.99-1.03 (m, 2H); 1.92-2.00 (m, 1H); 2.14 (s, 3H); 2.17 (s, 3H); 2.32-2.40 (m, 8H); 3.48 (s, 2H); 3.85-3.95 (m, 2H); 4.43-4.50 (m, 2H); 6.81 (s, 2H); 6.90 (d, J = 8.1 Hz, 1H); 7.37 (d, J = 7.8 Hz, 2H); 7.44-7.53 (aromatics, 3H); 7.61 (d, J = 8.0 Hz, 1H); 7.92 (d, J = 7.8 Hz, 2H); 8.83 (s, 1H); 12.78 (s, 1H) | XI-1 & III-1 |
| B-3 | 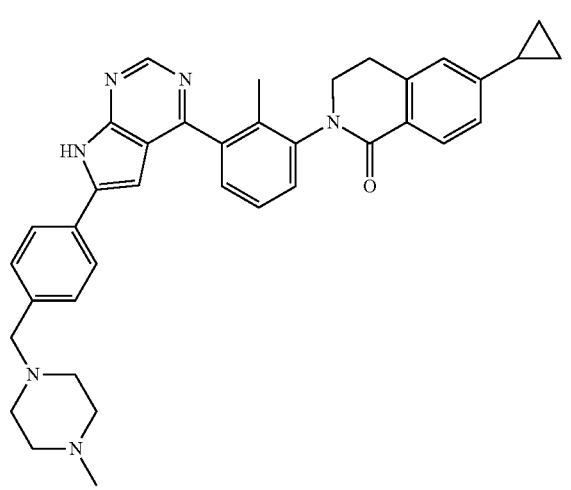 [SMILES: Cc1c(-c2ncnc3[nH]c(-c4ccc(CN5CCN(C)CC5)cc4)cc23)cccc1N1CCc2cc(C3CC3)ccc2C1=O]<br>6-cyclopropyl-2-[2-methyl-3-[6-[4-[(4-methylpiperazin-1-yl)methyl]phenyl]-7H-pyrrolo[2,3-d]pyrimidin-4-yl]phenyl]-3,4-dihydroisoquinolin-1-one | LCMS: m/z 583.4 (M + 1)+. $^1$H NMR (DMSO-d$_6$, 400 MHz) δ 0.76-0.79 (m, 2H); 1.00-1.05 (m, 2H); 1.94-2.02 (m, 1H); 2.15 (s, 3H); 2.17 (s, 3H); 2.24-2.44 (m, 8H); 3.07-3.23 (m, 2H); 3.49 (s, 2H); 3.73-3.80 (m, 1H); 3.97-4.04 (m, 1H); 6.82 (s, 1H); 7.08-7.11 (aromatics, 2H); 7.39 (d, J = 8.0 Hz, 2H); 7.45-7.53 (aromatics, 3H); 7.81 (d, J = 8.0 Hz, 1H); 7.94 (d, J = 8.0 Hz, 2H); 8.83 (s, 1H); 12.74 (s, 1H) | XI-1 & III-2 |

TABLE 17-continued

| No | Structure/IUPAC name | Characterization | INT used |
|---|---|---|---|
| B-4 | 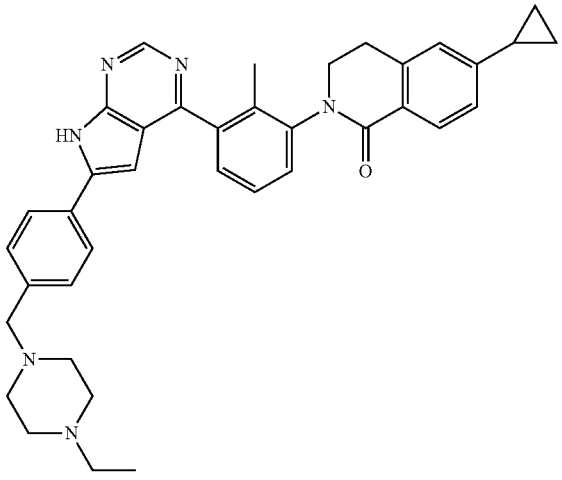 [SMILES: CCN1CCN(Cc2ccc(-c3cc4c(-c5cccc(N6CCc7cc(C8CC8)ccc7C6=O)c5C)ncnc4[nH]3)cc2)CC1]<br>6-cyclopropyl-2-[3-[6-[4-[(4-ethylpiperazin-1-yl)methyl]phenyl]-7H-pyrrolo[2,3-d]pyrimidin-4-yl]-2-methyl-phenyl]-3,4-dihydroisoquinolin-1-one | LCMS: m/z 597.4 (M + 1)+. $^1$H NMR (DMSO-$d_6$, 400 MHz) δ 0.75-0.82 (m, 2H); 0.96-1.08 (m, 5H); 1.96-2.02 (m, 1H); 2.15 (s, 3H); 2.22-2.54 (m, 10H); 3.05-3.23 (m, 2H); 3.51 (bs, 2H); 3.73-3.79 (m, 1H); 3.97-4.04 (m, 1H); 6.83 (d, J = 1.8 Hz, 1H); 7.08-7.11 (aromatics, 2H); 7.39 (d, J = 8.2 Hz, 2H); 7.45-7.53 (aromatics, 3H); 7.81 (d, J = 8.0 Hz, 1H); 7.94 (d, J = 8.2 Hz, 2H); 8.84 (s, 1H); 12.75 (bs, 1H) | XI-1 & III-2 (N-Et-piperazine for reductive amination) |
| B-5 | 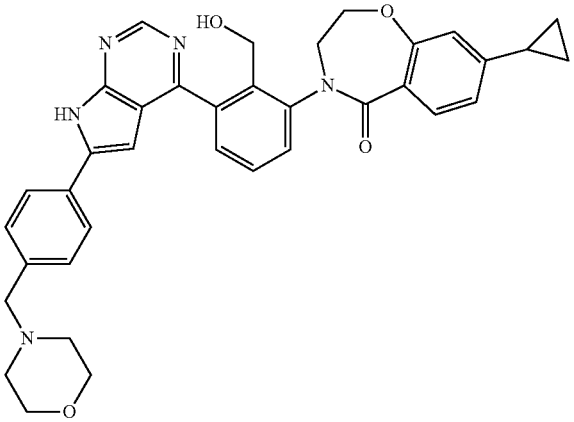 [SMILES: O=C1c2ccc(C3CC3)cc2OCCN1c1cccc(-c2ncnc3[nH]c(-c4ccc(CN5CCOCC5)cc4)cc23)c1CO]<br>8-cyclopropyl-4-[2-(hydroxymethyl)-3-[6-[4-(morpholinomethyl)phenyl]-7H-pyrrolo[2,3-d]pyrimidin-4-yl]phenyl]-2,3-dihydro-1,4-benzoxazepin-5-one | LCMS: m/z 602.4 (M + 1)+. $^1$H NMR (DMSO-$d_6$, 400 MHz) δ 0.74-0.80 (m, 2H); 1.00-1.06 (m, 2H); 1.94-2.02 (m, 1H); 2.34-2.42 (m, 4H); 3.50 (s, 2H); 3.56-3.64 (m, 4H); 3.86-3.99 (m, 2H); 4.34-4.44 (m, 2H); 4.47-4.62 (m, 2H); 5.83-5.41 (m, 1H); 6.83 (s, 1H); 6.91 (d, J = 8.3 Hz, 1H); 7.05 (s, 1H); 7.42 (d, J = 8.0 Hz, 2H); 7.50 (d, J = 7.8 Hz, 1H); 7.62 (d, J = 8.1 Hz, 2H); 7.78 (d, J = 7.6 Hz, 1H); 7.97 (d, J = 7.9 Hz, 2H); 8.86 (s, 1H); 12.86 (bs, 1H) | XI-1 & III-5 (morpholine for reductive amination) |

TABLE 17-continued

| No | Structure/IUPAC name | Characterization | INT used |
|---|---|---|---|
| B-6 | 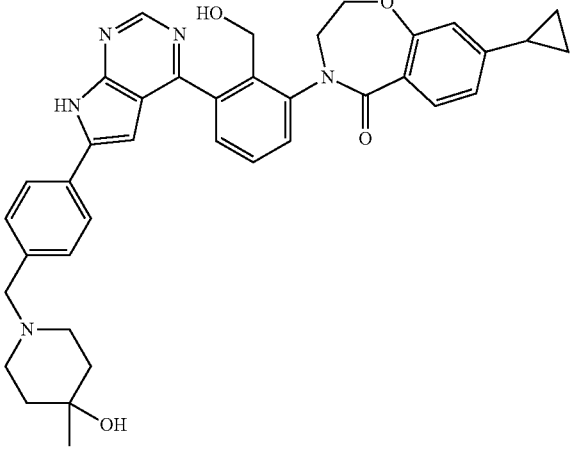<br>8-cyclopropyl-4-[2-(hydroxymethyl)-3-[6-[4-[(4-hydroxy-4-methyl-1-piperidyl)methyl]phenyl]-7H-pyrrolo[2,3-d]pyrimidin-4-yl]phenyl]-2,3-dihydro-1,4-benzoxazepin-5-one | LCMS: m/z 630.4 (M + 1)⁺. ¹H NMR (DMSO-d₆, 400 MHz) δ 0.74-0.80 (m, 2H); 0.98-1.04 (m, 2H); 1.10 (s, 3H); 1.42-1.56 (m, 4H); 1.94-1.99 (m, 1H); 2.30-2.44 (m, 4H); 3.50 (bs, 2H); 3.86-3.99 (m, 2H); 4.11 (bs, 1H); 4.39-4.44 (m, 2H); 4.47-4.51 (m, 1H); 4.57-4.61 (m, 1H); 5.39-5.42 (m, 1H); 6.83 (s, 1H); 6.91 (d, J = 8.1 Hz, 1H); 7.04 (s, 1H); 7.41 (d, J = 6.9 Hz, 2H); 7.50 (d, J = 7.8 Hz, 1H); 7.59-7.63 (aromatics, 2H); 7.78 (d, J = 7.6 Hz, 1H); 7.96 (d, J = 7.6 Hz, 2H); 8.86 (s, 1H); 12.85 (bs, 1H) | XI-1 & III-5 (4-hydroxy-4-methyl-piperidine for reductive amination) |
| B-7 | 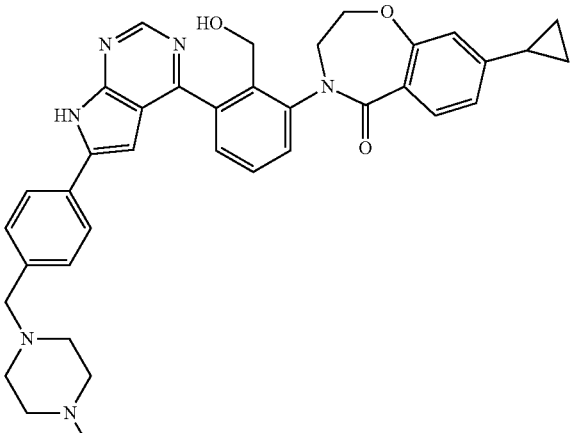<br>8-cyclopropyl-4-[3-[6-[4-[(4-ethylpiperazin-1-yl)methyl]phenyl]-7H-pyrrolo[2,3-d]pyrimidin-4-yl]-2-(hydroxymethyl)phenyl]-2,3-dihydro-1,4-benzoxazepin-5-one | LCMS: m/z 629.2 (M + 1)⁺. ¹H NMR (DMSO-d₆, 400 MHz) δ 0.74-0.78 (m, 2H); 0.96-1.06 (m, 5H); 1.94-2.01 (m, 1H); 2.20-2.50 (m, 10H); 3.50 (s, 2H); 3.85-4.02 (m, 2H); 4.36-4.44 (m, 2H); 4.48-4.64 (m, 2H); 5.38-5.41 (m, 1H); 6.83 (d, J = 1.3 Hz, 1H); 6.91 (d, J = 8.3 Hz, 1H); 7.04 (s, 1H); 7.40 (d, J = 8.1 Hz, 2H); 7.50 (d, J = 7.6 Hz, 1H); 7.59-7.63 (aromatics, 2H); 7.78 (d, J = 7.6 Hz, 1H); 7.96 (d, J = 8.1 Hz, 2H); 8.86 (s, 1H); 12.80 (bs, 1H) | XI-1 & III-5 (N-Et-piperazine for reductive amination) |

TABLE 17-continued

| No | Structure/IUPAC name | Characterization | INT used |
|---|---|---|---|
| B-8 | 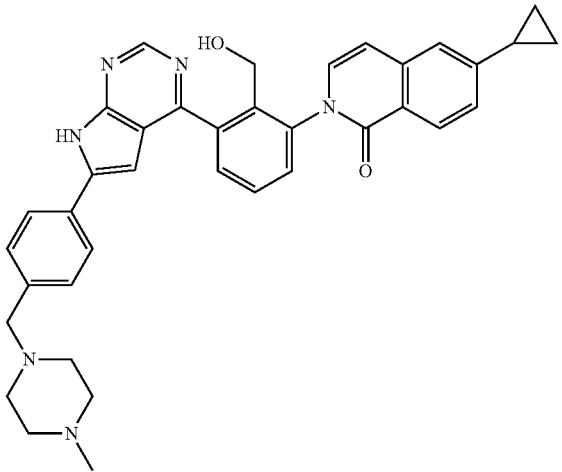 [SMILES: CN1CCN(Cc2ccc(-c3cc4c(-c5cccc(-n6ccc7cc(C8CC8)ccc7c6=O)c5CO)ncnc4[nH]3)cc2)CC1]<br>6-cyclopropyl-2-[2-(hydroxymethyl)-3-[6-[4-[(4-methylpiperazin-1-yl)methyl]phenyl]-7H-pyrrolo[2,3-d]pyrimidin-4-yl]phenyl]isoquinolin-1-one | LCMS: m/z 597.1 (M + 1)⁺. ¹H NMR (DMSO-d₆, 400 MHz) δ 0.82-0.88 (m, 2H); 1.06-1.12 (m, 2H); 2.05-2.15 (m, 1H); 2.31 (s, 3H); 2.40-2.67 (m, 8H); 3.53 (s, 2H); 4.16 (d, J = 11.9 Hz, 1H); 4.36 (d, J = 12.0 Hz, 1H); 5.25 (bs, 1H); 6.67 (d, J = 7.3 Hz, 1H); 7.07 (s, 1H); 7.28 (d, J = 8.6 Hz, 1H); 7.40-7.45 (aromatics, 4H); 7.54 (d, J = 7.6 Hz, 1H); 7.67 (t, J = 7.6 Hz, 1H); 7.87 (d, J = 7.5 Hz, 1H); 7.98 (d, J = 8.1 Hz, 2H); 8.12 (d, J = 8.3 Hz, 1H); 8.86 (s, 1H); 12.87 (s, 1H) | XI-1 & III-6 |
| B-9 | 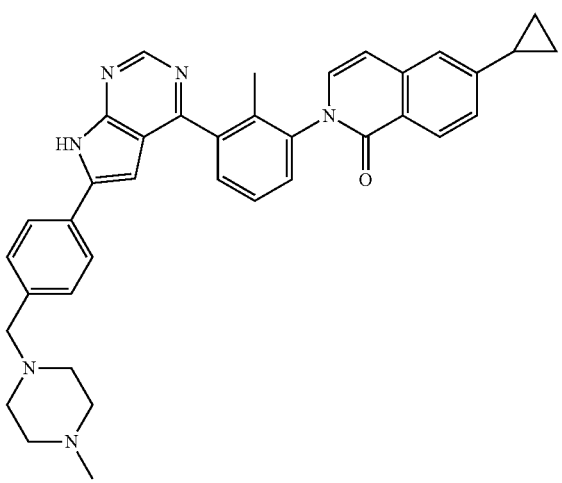 [SMILES: Cc1c(-c2ncnc3[nH]c(-c4ccc(CN5CCN(C)CC5)cc4)cc23)cccc1-n1ccc2cc(C3CC3)ccc2c1=O]<br>6-cyclopropyl-2-[2-methyl-3-[6-[4-[(4-methylpiperazin-1-yl)methyl]phenyl]-7H-pyrrolo[2,3-d]pyrimidin-4-yl]phenyl]isoquinolin-1-one | LCMS: m/z 581.1 (M + 1)⁺. ¹H NMR (DMSO-d₆, 400 MHz) δ 0.82-0.86 (m, 2H); 1.04-1.11 (m, 2H); 2.01 (s, 3H); 2.07-2.11 (m, 1H); 2.14 (s, 3H); 2.20-2.45 (m, 8H); 3.49 (s, 2H); 6.68 (d, J = 7.6 Hz, 1H); 6.87 (s, 1H); 7.27 (d, J = 8.3 Hz, 1H); 7.38-7.48 (aromatics, 5H); 7.52-7.56 (aromatic, 1H); 7.67 (d, J = 7.3 Hz, 1H); 7.94 (d, J = 8.2 Hz, 2H); 8.13 (d, J = 8.3 Hz, 1H); 8.84 (s, 1H); 12.78 (s, 1H) | XI-1 & III-3 |

TABLE 17-continued

| No | Structure/IUPAC name | Characterization | INT used |
|---|---|---|---|
| B-10 | 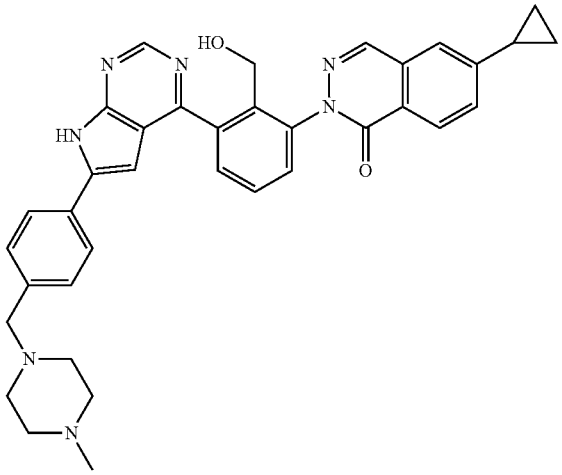<br>6-cyclopropyl-2-[2-(hydroxymethyl)-3-[6-[4-[(4-methylpiperazin-1-yl)methyl]phenyl]-7H-pyrrolo[2,3-d]pyrimidin-4-yl]phenyl]phthalazin-1-one | LCMS: m/z 598.1 (M + 1)$^+$. $^1$H NMR (DMSO-$d_6$, 400 MHz) δ 0.88-0.96 (m, 2H); 1.12-1.20 (m, 2H); 2.16-2.24 (m, 1H); 2.31-2.45 (m, 11H); 3.52-3.60 (bs, 2H); 4.26-2.40 (m, 2H); 5.10 (t, J = 6.1 Hz, 1H); 7.03 (d, J = 1.5 Hz, 1H); 7.42 (d, J = 7.9 Hz, 2H); 7.58 (d, J = 7.1 Hz, 1H); 7.63-7.67 (aromatics, 2H); 7.72 (s, 1H); 7.83 (d, J = 7.5 Hz, 1H); 7.98 (d, J = 8.2 Hz, 2H); 8.19 (d, J = 8.3 Hz, 1H); 8.49 (s, 1H); 8.85 (s, 1H); 12.82 (s, 1H) | XI-1 & III-7 |
| B-11 | 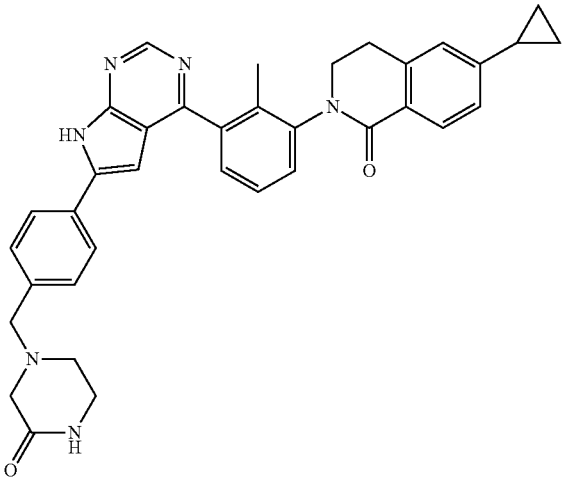 [SMILES: Cc1c(-c2ncnc3[nH]c(-c4ccc(CN5CCNC(=O)C5)cc4)cc23)cccc1N1CCc2cc(C3CC3)ccc2C1=O]<br>6-cyclopropyl-2-[2-methyl-3-[6-[4-[(3-oxopiperazin-1-yl)methyl]phenyl]-7H-pyrrolo[2,3-d]pyrimidin-4-yl]phenyl]-3,4-dihydroisoquinolin-1-one | LCMS: m/z 583.3 (M + 1)$^+$. $^1$H NMR (DMSO-$d_6$, 400 MHz) δ 0.74-0.80 (m, 2H); 1.00-1.06 (m, 2H); 1.96-2.03 (m, 1H); 2.15 (s, 3H); 2.50-2.58 (m, 2H); 2.92 (bs, 2H); 3.07-3.20 (m, 4H); 3.58 (bs, 2H); 3.73-3.80 (m, 1H); 3.97-4.03 (m, 1H); 6.84 (s, 1H); 7.08-7.11 (aromatics, 2H); 7.41-7.53 (aromatics, 4H); 7.77 (bs, 1H); 7.81 (d, J = 8.1 Hz, 1H); 7.96 (d, J = 7.8 Hz, 2H); 8.84 (s, 1H); 12.75 (bs, 1H) | XI-1 & III-2 (2-oxopiperazine for reductive amination) |

TABLE 17-continued

| No | Structure/IUPAC name | Characterization | INT used |
|---|---|---|---|
| B-12 | 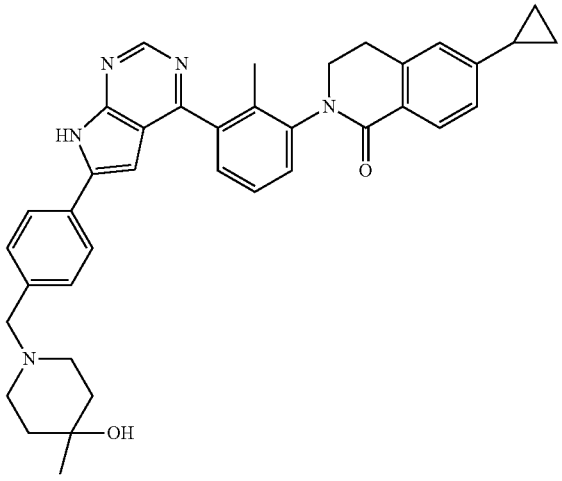 [SMILES: Cc1c(-c2ncnc3[nH]c(-c4ccc(CN5CCC(C)(O)CC5)cc4)cc23)cccc1N1CCc2cc(C3CC3)ccc2C1=O]<br>6-cyclopropyl-2-[3-[6-[4-[(4-hydroxy-4-methyl-1-piperidyl)methyl]phenyl]-7H-pyrrolo[2,3-d]pyrimidin-4-yl]-2-rnethyl-phenyl]-3,4-dihydroisoquinolin-1-one | LCMS: m/z 598.4 (M + 1)$^+$. $^1$H NMR (DMSO-d$_6$, 400 MHz) δ 0.76-0.80 (m, 2H); 1.00-1.06 (m, 2H); 1.09 (s, 3H); 1.42-1.50 (m, 4H); 1.94-2.04 (m, 3H); 2.15 (s, 3H); 2.32-2.42 (m, 4H); 3.48 (s, 2H); 3.73-3.79 (m, 1H); 3.97-4.03 (m, 1H); 4.10 (bs, 1H); 6.81 (s, 1H); 7.08-7.11 (aromatics, 2H); 7.38 (d, J = 8.1 Hz, 2H); 7.43-7.53 (aromatics, 3H); 7.81 (d, J = 7.8 Hz, 1H); 7.92 (d, J = 8.0 Hz, 2H); 8.83 (s, 1H); 12.75 (bs, 1H) | XI-1 & III-2 (4-hydroxy-4-methyl-piperidine for reductive amination) |
| B-13 | 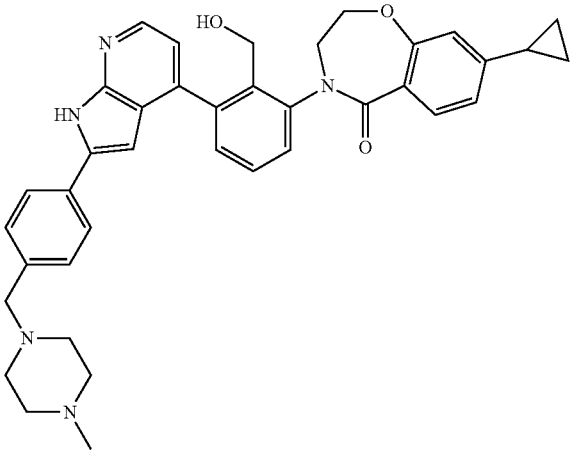<br>8-cyclopropyl-4-[2-(hydroxymethyl)-3-[2-[4-[(4-methylpiperazin-1-yl)methyl]phenyl]-1H-pyrrolo[2,3-b]pyridin-4-yl]phenyl]-2,3-dihydro-1,4-benzoxazepin-5-one | LCMS: m/z 614.2 (M + 1)$^+$. $^1$H NMR (DMSO-d$_6$, 400 MHz) δ 0.70-0.80 (m, 2H); 0.98-1.06 (m, 2H); 1.94-2.02 (m, 1H); 2.14 (s, 3H); 2.20-2.44 (m, 8H); 3.47 (bs, 2H); 3.88-3.98 (m, 2H); 4.20-4.40 (m, 2H); 4.52-4.58 (m, 2H); 4.79 (bs, 1H); 6.66 (s, 1H); 6.81 (s, 1H); 6.88 (d, J = 8.1 Hz, 1H); 7.20 (bs, 1H); 7.35 (d, J = 8.0 Hz, 2H); 7.43 (d, J = 7.5 Hz, 1H); 7.48 (d, J = 7.5 Hz, 1H); 7.57 (d, J = 7.5 Hz, 1H); 7.66 (d, J = 8.2 Hz, 1H); 7.87 (d, J = 7.9 Hz, 2H); 8.27 (d, J = 4.6 Hz, 1H); 12.27 (s, 1H) | XI-2 & III-5 |

TABLE 17-continued

| No | Structure/IUPAC name | Characterization | INT used |
|---|---|---|---|
| B-14 | 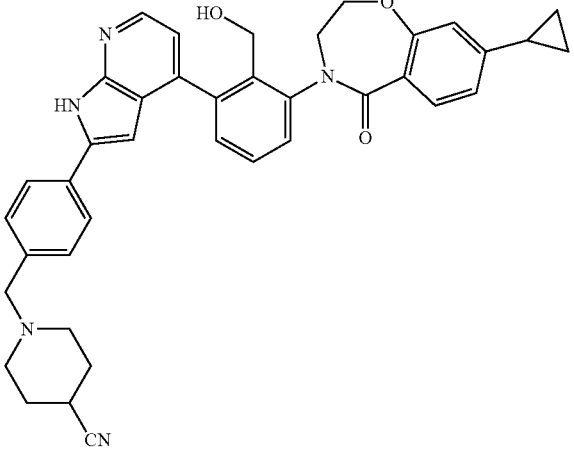<br>1-[[4-[4-[3-(8-cyclopropyl-5-oxo-2,3-dihydro-1,4-benzoxazepin-4-yl)-2-(hydroxymethyl)phenyl]-7H-pyrrolo[2,3-d]pyrimidin-6-yl]phenyl]methyl]piperidine-4-carbonitrile | LCMS: m/z 625.2 (M + 1)+. 1H NMR (DMSO-d6, 400 MHz) δ 0.74-0.78 (m, 2H); 1.00-1.05 (m, 2H); 1.67-1.74 (m, 2H); 1.82-1.90 (m, 2H); 1.94-2.01 (m, 1H); 2.24-2.34 (m, 2H); 2.42-2.57 (m, 2H); 2.84-2.92 (m, 1H); 3.51 (bs, 2H); 3.86-4.00 (m, 2H); 4.37-4.44 (m, 2H); 4.46-4.52 (m, 1H); 4.56-4.62 (m, 1H); 5.36-5.40 (m, 1H); 6.83 (d, J = 1.3 Hz, 1H); 6.91 (dd, J$_1$ = 1.3, J$_2$ = 8.2 Hz, 1H); 7.04 (d, J = 1.5 Hz, 1H); 7.40 (d, J = 8.2 Hz, 2H); 7.50 (d, J = 7.7 Hz, 1H); 7.63 (d, J = 8.2 Hz, 2H); 7.78 (d, J = 7.5 Hz, 1H); 7.96 (d, J = 8.2 Hz, 2H); 8.86 (s, 1H); 12.84 (bs, 1H) | XI-1 & III-5 (4-cyano-piperidine for reductive amination) |
| B-15 | 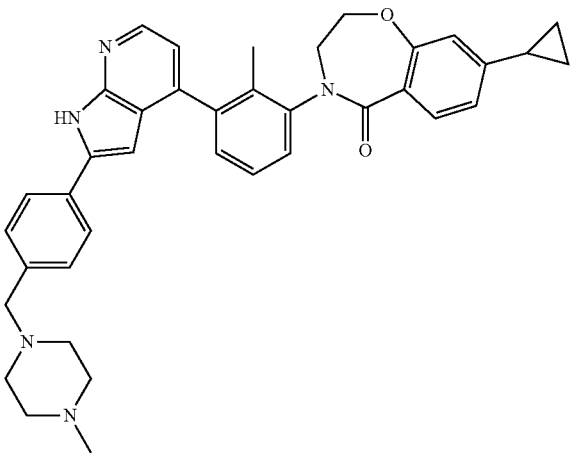 [SMILES: Cc1c(-c2ccnc3[nH]c(-c4ccc(CN5CCN(C)CC5)cc4)cc23)cccc1N1CCOc2cc(C3CC3)ccc2C1=O]<br>8-cyclopropyl-4-[2-methyl-3-[2-[4-[(4-methylpiperazin-1-yl)methyl]phenyl]-1H-pyrrolo[2,3-b]pyridin-4-yl]phenyl]-2,3-dihydro-1,4-benzoxazepin-5-one | LCMS: m/z 598.2 (M + 1)+. 1H NMR (DMSO-d6, 400 MHz) δ 0.73-0.77 (m, 2H); 0.98-1.02 (m, 2H); 1.92-2.01 (m, 1H); 2.05 (s, 3H); 2.14 (s, 3H); 2.22-2.46 (m, 8H); 3.47 (bs, 2H); 3.91 (t, J = 4.6 Hz, 2H); 4.43-4.49 (m, 2H); 6.60 (bs, 1H); 6.81 (d, J = 1.5 Hz, 1H); 6.91 (dd, J$_1$ = 1.8 Hz, J$_2$ = 8.4 Hz, 1H); 7.00 (d, J = 4.8 Hz, 1H); 7.33-7.45 (aromatics, 5H); 7.62 (d, J = 8.2 Hz, 1H); 7.87 (d, J = 8.1 Hz, 2H); 8.27 (d, J = 4.8 Hz, 1H); 12.27 (bs, 1H) | XI-2 & III-1 |

TABLE 17-continued

| No | Structure/IUPAC name | Characterization | INT used |
|---|---|---|---|
| B-16 | 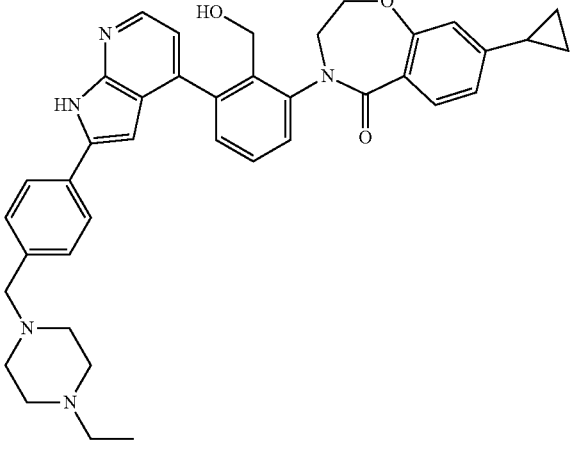<br>8-cyclopropyl-4-[3-[2-[4-[(4-ethylpiperazin-1-yl)methyl]phenyl]-1H-pyrrolo[2,3-b]pyridin-4-yl]-2-(hydroxymethyl)phenyl]-2,3-dihydro-1,4-benzoxazepin-5-one | LCMS: m/z 628.3 (M + 1)$^+$. $^1$H NMR (DMSO-d$_6$, 400 MHz) δ 0.73-0.77 (m, 2H); 0.95-1.04 (m, 5H); 1.93-2.00 (m, 1H); 2.20-2.50 (m, 10H); 3.47 (s, 2H); 3.91-3.95 (m, 2H); 4.20-4.40 (m, 2H); 4.50-4.60 (m, 2H); 4.70 (bs, 1H); 6.66 (s, 1H); 6.81 (d, J = 1.3 Hz, 1H); 6.89 (dd, J$_1$ = 1.4 Hz, J$_2$ = 8.2 Hz, 1H); 7.20 (bs, 1H); 7.35 (d, = 8.2 Hz, 2H); 7.43 (d, 7 = 7.5 Hz, 1H); 7.48 (d, J = 7.3 Hz, 1H); 7.56-7.58 (aromatics, 1H); 7.66 (d, J = 8.0 Hz, 1H); 7.87 (d, J = 8.2 Hz, 2H); 8.27 (d, J = 4.8 Hz. 1H); 12.28 (bs, 1H) | XI-2 & III-5 (N-Et-piperazine for reductive amination) |
| B-17 | 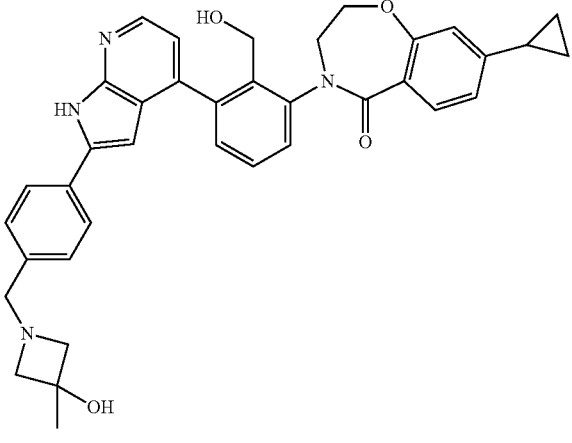 [SMILES: CC1(O)CN(Cc2ccc(-c3cc4c(-c5cccc(N6CCOc7cc(C8CC8)ccc7C6=O)c5CO)ccnc4[nH]3)cc2)C1]<br>8-cyclopropyl-4-[2-(hydroxymethyl)-3-[2-[4-[(3-hydroxy-3-methyl-azetidin-1-yl)methyl]phenyl]-1H-pyrrolo[2,3-b]pyridin-4-yl]]phenyl]-2,3-dihydro-1,4-benzoxazepin-5-one | LCMS: m/z 601.2 (M + 1)$^+$. $^1$H NMR (DMSO-d$_6$, 400 MHz) δ 0.72-0.78 (m, 2H); 1.00-1.04 (m, 2H); 1.36 (s, 3H); 1.92-2.00 (m, 1H); 2.86-2.94 (m, 2H); 3.16-3.24 (m, 2H); 3.60 (bs, 2H); 3.88-3.98 (m, 2H); 4.20-4.40 (m, 2H); 4.52-4.60 (m, 2H); 5.18 (bs, 1H); 6.65 (s, 1H); 6.81 (s, 1H); 6.88 (d, J = 8.0 Hz, 1H); 7.20 (bs, 1H); 7.32 (d, J = 8.1 Hz, 2H); 7.43 (d, J = 7.6 Hz, 1H); 7.48 (d, J = 7.4 Hz. 1H); 7.54-7.58 (m, 1H); 7.66 (d, J = 8.0 Hz, 1H); 7.85 (d, J = 8.1 Hz, 2H); 8.27 (d, J = 4.9 Hz, 1H); 12.27 (s, 1H) | XI-2 & III-5 (3-hydroxy-3-methyl-azetidine for reductive amination) |

TABLE 17-continued

| No | Structure/IUPAC name | Characterization | INT used |
|---|---|---|---|
| B-18 | 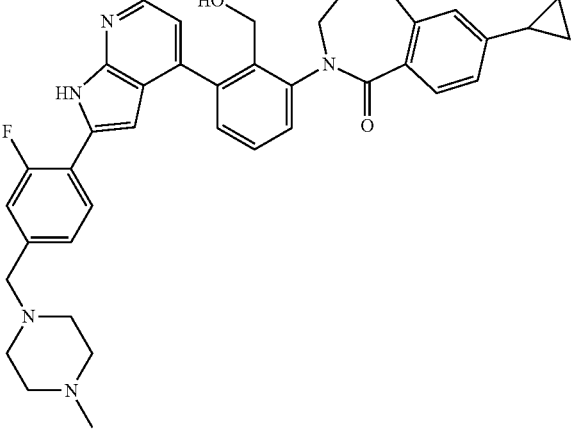<br><br>8-cyclopropyl-4-[3-[2-[2-fluoro-4-[(4-methylpiperazin-1-yl)methyl]phenyl]-1H-pyrrolo[2,3-b]pyridin-4-yl]-2-(hydroxymethyl)phenyl]-2,3-dihydro-1,4-benzoxazepin-5-one | LCMS: m/z 632.2 (M + 1)$^+$. $^1$H NMR (DMSO-d$_6$, 400 MHz) δ 0.73-0.77 (m, 2H); 0.99-1.04 (m, 2H); 1.95-1.99 (m, 1H); 2.15 (s, 3H); 2.24-2.48 (m, 8H); 3.50 (s, 2H); 3.90-3.96 (m, 2H); 4.20-4.38 (m, 2H); 4.55 (t, J = 4.6 Hz, 2H); 6.65 (s, 1H); 6.81 (d, J = 1.3 Hz, 1H); 6.89 (dd, J = 1.4 Hz, J$_2$ = 8.1 Hz, 1H); 7.20-7.25 (aromatics, 3H); 7.42-7.46 (aromatics, 2H); 7.53-7.58 (aromatic, 1H); 7.66 (d, J = 8.2 Hz, 1H); 7.96 (t, J = 7.9 Hz, 1H); 8.32 (d, J = 4.9 Hz, 1H); 12.26 (s, 1H) | XI-5 & III-5 |
| B-19 | 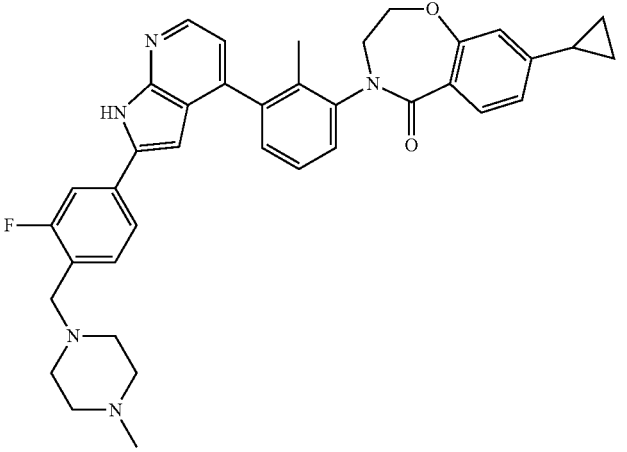 [SMILES: Cc1c(-c2ccnc3[nH]c(-c4ccc(CN5CCN(C)CC5)c(F)c4)cc23)cccc1N1CCOc2cc(C3CC3)ccc2C1=O]<br><br>8-cyclopropyl-4-[3-[2-[3-fluoro-4-[(4-methylpiperazin-1-yl)methyl]phenyl]-1H-pyrrolo[2,3-b]pyridin-4-yl]-2-methyl-phenyl]-2,3-dihydro-1,4-benzoxazepin-5-one | LCMS: m/z 616.4 (M + 1)$^+$. $^1$H NMR (DMSO-d$_6$, 400 MHz) δ 0.73-0.77 (m, 2H); 0.98-1.04 (m, 2H); 1.94-2.00 (m, 1H); 2.05 (s, 3H); 2.14 (s, 3H); 2.24-2.48 (m, 8H); 3.51 (s, 2H); 3.88-3.96 (m, 2H); 4.42-4.52 (m, 2H); 6.72 (s, 1H); 6.82 (s, 1H); 6.91 (d, J = 8.2 Hz, 1H); 7.02 (d, J = 4.6 Hz, 1H); 7.35-7.45 (aromatics, 4H); 7.62 (d, J = 8.2 Hz, 1H); 7.73-7.78 (aromatics, 2H); 8.31 (d, J = 4.8 Hz, 1H); 12.35 (s, 1H) | XI-4 & III-1 |

| No | Structure/IUPAC name | Characterization | INT used |
|---|---|---|---|
| B-20 | 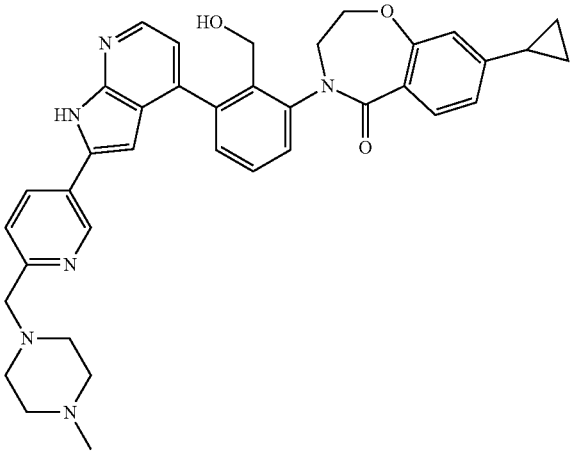 [SMILES: CN1CCN(Cc2ccc(-c3cc4c(-c5cccc(N6CCOc7cc(C8CC8)ccc7C6=O)c5CO)ccnc4[nH]3)cn2)CC1]<br>8-cyclopropyl-4-[2-(hydroxymethyl)-3-[2-[6-[(4-methylpiperazin-1-yl)methyl]-3-pyridyl]-1H-pyrrolo[2,3-b]pyridin-4-yl]phenyl]-2,3-dihydro-1,4-benzoxazepin-5-one | LCMS: m/z 615.2 (M + 1)⁺. ¹H NMR (DMSO-d₆, 400 MHz) δ 0.72-0.80 (m, 2H); 1.00-1.06 (m, 2H); 1.92-2.02 (m, 1H); 2.16 (s, 3H); 2.24-2.48 (m, 8H); 3.60 (bs, 2H); 3.90-3.98 (m, 2H); 4.18-4.40 (m, 2H); 4.54-4.60 (m, 2H); 4.83 (bs 1H); 6.81 (s, 2H); 6.89 (d, J = 7.9 Hz, 1H); 7.24 (bs, 1H); 7.43-7.48 (aromatics, 3H); 7.55-7.57 (aromatic, 1H); 7.66 (dd, J₁ = 2.0 Hz, J₂ = 8.2 Hz, 1H); 8.26-8.31 (aromatics, 2H); 9.05 (s, 1H); 12.44 (bs, 1H) | XI-6 & III-5 |
| B-21 | 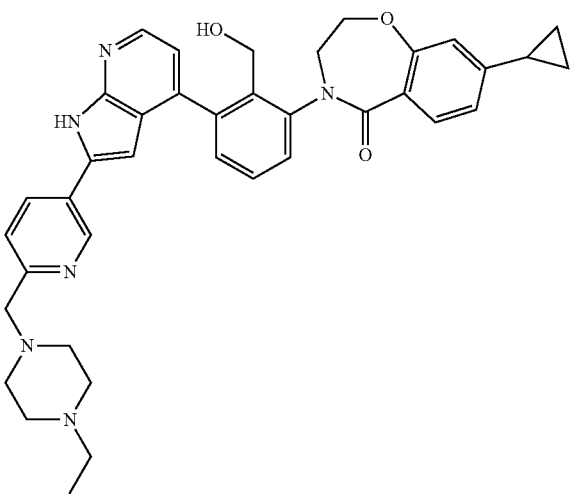 [SMILES: CCN1CCN(Cc2ccc(-c3cc4c(-c5cccc(N6CCOc7cc(C8CC8)ccc7C6=O)c5CO)ccnc4[nH]3)cn2)CC1]<br>8-cyclopropyl-4-[3-[2-[6-[(4-ethylpiperazin-1-yl)methyl]-3-pyridyl]-1H-pyrrolo[2,3-b]pyridin-4-yl]-2-(hydroxymethyl)phenyl]-2,3-dihydro-1,4-benzoxazepin-5-one | LCMS: m/z 629.2 (M + 1)⁺. ¹H NMR (DMSO-d₆, 400 MHz) δ 0.72-0.78 (m, 2H); 0.94-1.06 (m, 5H); 1.94-2.02 (m, 1H); 2.30-2.44 (m, 10H); 3.60 (s, 2H); 3.90-3.98 (m, 2H); 4.18-4.40 (m, 2H); 4.54-4.60 (m, 2H); 6.80-6.82 (aromatics, 2H); 6.89 (d, J = 8.1 Hz, 1H); 7.24 (bs, 1H); 7.43-7.58 (m, 4H); 7.66 (d, J = 8.1 Hz, 1H); 8.27 (d, J = 7.7 Hz, 1H); 8.31 (d, J = 4.8 Hz, 1H); 9.05 (s, 1H); 12.46 (bs, 1H) | XI-6 & III-5 (N-Et-piperazine for reductive amination) |

TABLE 17-continued

| No | Structure/IUPAC name | Characterization | INT used |
|---|---|---|---|
| B-22 | 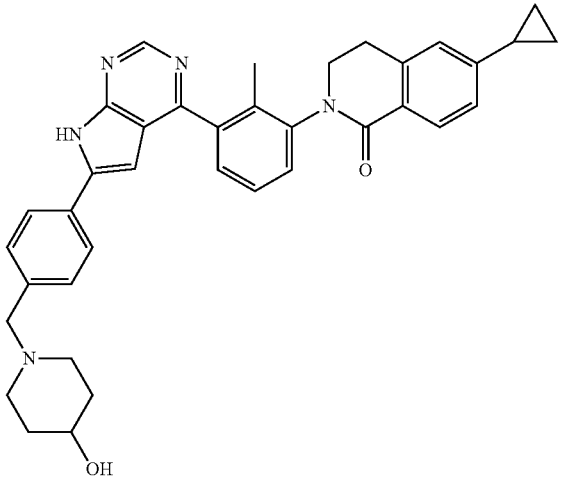 [SMILES: Cc1c(-c2ncnc3[nH]c(-c4ccc(CN5CCC(O)CC5)cc4)cc23)cccc1N1CCc2cc(C3CC3)ccc2C1=O]<br>6-cyclopropyl-2-[3-[6-[4-[(4-hydroxy-1-piperidyl)methyl]phenyl]-7H-pyrrolo[2,3-d]pyrimidin-4-yl]-2-methyl-phenyl]-3,4-dihydroisoquinolin-1-one | LCMS: m/z 584.4 (M + 1)+. $^1$H NMR (400 MHz. DMSO-$d_6$) δ 0.74-0.80 (m, 2H); 0.98-1.06 (m, 2H); 1.20-1.44 (m, 3H); 1.50-1.62 (m, 1H); 1.64-1.76 (m, 2H); 1.94-2.08 (m, 1H); 2.15 (s, 3H); 2.62-2.72 (m, 2H); 3.04-3.24 (m, 3H); 3.46 (bs, 2H); 3.72-3.80 (m, 1H); 3.96-4.04 (m, 1H); 4.54 (d, J = 3.4 Hz, 1H); 6.78 (s, 1H); 7.07-7.11 (aromatics, 2H); 7.36 (d, J = 7.9 Hz, 2H); 7.44-7.52 (aromatics, 3H); 7.81 (d, J = 7.8 Hz, 1H); 7.92 (d, J = 8.1 Hz, 2H); 8.79 (s, 1H); 12.71 (bs, 1H) | XI-1 & III-2 (4-hydroxy piperidine for reductive amination) |

Example C-1

Synthesis of 6-cyclopropyl-2-[2-(hydroxymethyl)-3-[6-[4-(4-methylpiperazin-1-yl)phenyl]-7H-pyrrolo[2,3-d]pyrimidin-4-yl]phenyl]isoquinolin-1-one

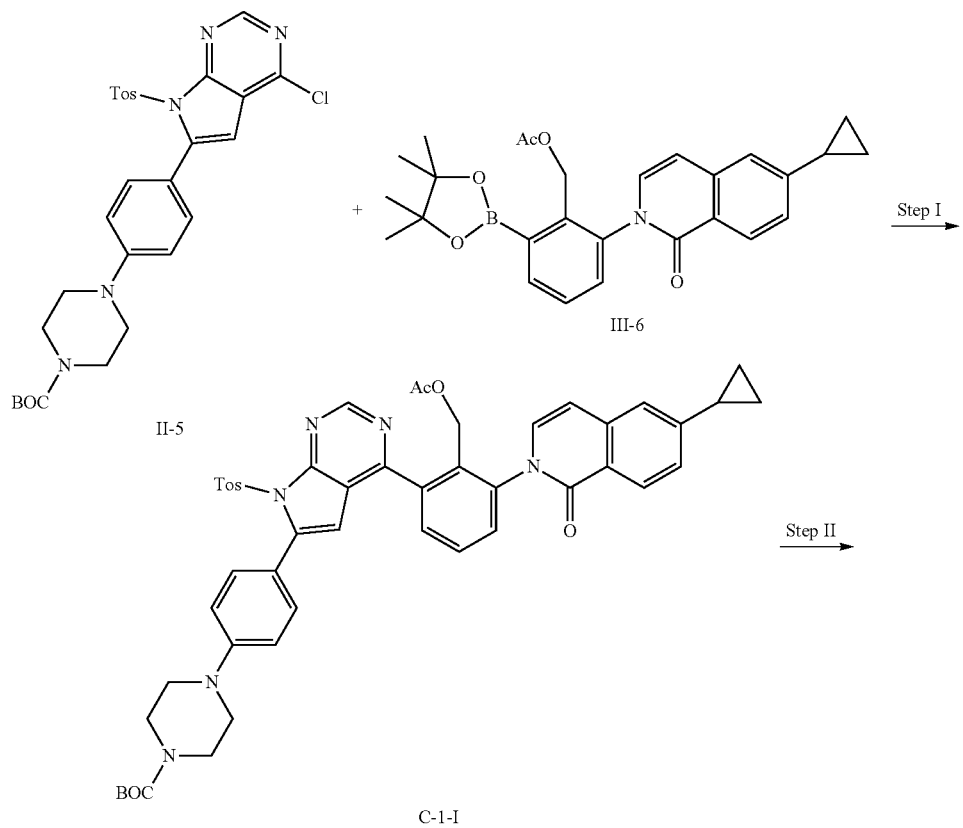

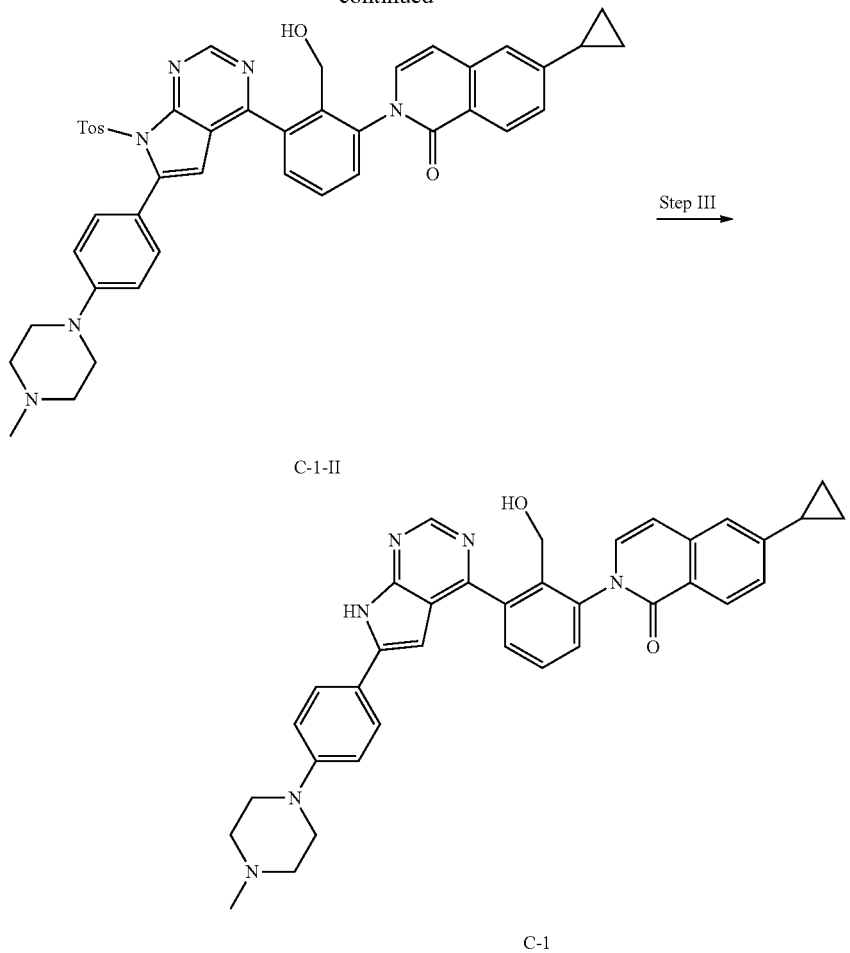

Step-I: tert-butyl 4-[4-[4-[2-(acetoxymethyl)-3-(6-cyclopropyl-1-oxo-2-isoquinolyl)phenyl]-7-(p-tolylsulfonyl)pyrrolo[2,3-d]pyrimidin-6-yl]phenyl]piperazine-1-carboxylate (C-1-I)

Intermediate C-1-I was synthesized using intermediates II-5 and III-6, following similar procedure as described for the synthesis of B-1-I. LCMS: m/z 865.3 (M+1)+.

Step-II: [2-(6-cyclopropyl-1-oxo-2-isoquinolyl)-6-[6-[4-(4-methylpiperazin-1-yl)phenyl]-7-(p-tolylsulfonyl)pyrrolo[2,3-d]pyrimidin-4-yl]phenyl]methyl acetate (C-1-II)

A solution of intermediate C-1-I (0.5 g, 0.57 mmol) in $CH_2Cl_2$ (10 mL) was treated with TFA (4 mL) at room temperature and then stirred for 30 minutes. Solvent was removed under reduced pressure and saturated $NaHCO_3$ solution (30 mL) was added to it. Extraction was carried out using $CH_2Cl_2$ (30 mL×2). The combined organic layers were successively washed with water (30 mL), brine (30 mL), dried over anhydrous $Na_2SO_4$, filtered and concentrated under reduced pressure to provide corresponding Boc-deprotected intermediate (0.1 g, 0.13 mmol), which was dissolved in MeOH (4 mL). To this was added aqueous formaldehyde (37% solution, 0.11 mL, 1.43 mmol) and glacial acetic acid (1 drop); and then the reaction mixture was stirred at 80° C. for 1 h. The mixture was slowly cooled to 0° C. and treated with $CH_2Cl_2$ (1 mL), followed by sodium cyanoborohydride (0.11 g, 1.76 mmol). Stirring was continued for additional 1 h. After confirming the completion of the reaction (by TLC), solvents were removed under reduced pressure. The residue was dissolved in $CH_2Cl_2$ (50 mL) and washed successively with water (15 mL) and brine (10 mL). The organic layer was dried over anhydrous $Na_2SO_4$, filtered and concentrated to provide the title compound C-1-II (0.115 g, 100%). LCMS: m/z 779.4 (M+1)+.

Step-III: 6-cyclopropyl-2-[2-(hydroxymethyl)-3-[6-[4-(4-methylpiperazin-1-yl)phenyl]-7H-pyrrolo[2,3-d]pyrimidin-4-yl]phenyl]isoquinolin-1-one (Example C-1)

To a solution of intermediate C-1-II (0.1 g, 0.128 mmol) in a mixture of THF (6 mL) and $H_2O$ (2 mL) was added $LiOH.H_2O$ (0.027 g, 0.64 mmol) at room temperature and the mixture was stirred at this temperature for 3 days. After confirming the completion of the reaction, solvents were removed under reduced pressure and the residue was purified using preparative TLC plate (silica gel, 8% MeOH: $CH_2Cl_2$) to afford the title compound C-1 (0.027 g, 38.5%). LCMS: m/z 583.3 (M+1)+. $^1$H NMR (DMSO-$d_6$, 400 MHz) δ 0.82-0.88 (m, 2H); 1.06-1.13 (m, 2H); 2.06-2.16 (m, 1H); 2.24 (s, 3H); 2.42-2.50 (m, 4H); 3.11-3.30 (m, 4H); 4.14 (dd, $J_1$=8.2 Hz, $J_2$=11.8 Hz, 1H); 4.33 (dd, $J_1$=4.3 Hz, $J_2$=12.0 Hz, 1H); 5.32-5.35 (m, 1H); 6.67 (d, J=7.6 Hz, 1H); 6.90 (bs, 1H); 7.03 (d, J=8.8 Hz, 2H); 7.27 (d, J=7.4 Hz, 1H); 7.40 (d, J=7.3 Hz, 1H); 7.44 (bs, 1H); 7.52 (d, J=7.6 Hz, 1H); 7.66 (t, J=7.7 Hz, 1H); 7.84-7.92 (aromatics, 3H); 8.12 (d, J=8.4 Hz, 1H); 8.80 (s, 1H); 12.68 (s, 1H).

Following examples were synthesized using similar sequence of reactions and procedures as described for the synthesis of C-1.

TABLE 18

| No | Structure/IUPAC name | Characterization | INT used |
|---|---|---|---|
| C-2 | 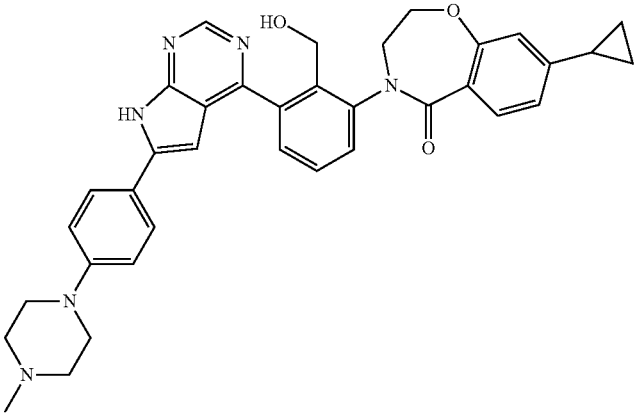 [SMILES: CN1CCN(c2ccc(-c3cc4c(-c5cccc(N6CCOc7cc(C8CC8)ccc7C6=O)c5CO)ncnc4[nH]3)cc2)CC1]<br>8-cyclopropyl-4-[2-(hydroxymethyl)-3-[6-[4-(4-methylpiperazin-1-yl)phenyl]-7H-pyrrolo[2,3-d]pyrimidin-4-yl]phenyl]-2,3-dihydro-1,4-benzoxazepin-5-one | LCMS: m/z 601.3 (M + 1)+. 1H NMR (DMSO-$d_6$, 400 MHz) 0.74-0.80 (m, 2H); 1.00-1.06 (m, 2H); 1.94-2.01 (m, 1H); 2.23 (s, 3H); 2.42-2.50 (m, 4H); 3.20-3.30 (m, 4H); 3.85-4.06 (m, 2H); 4.33-4.43 (m, 2H); 4.46-4.62 (m, 2H); 5.48 (dd, $J_1$ = 4.6 Hz, $J_2$ = 8.5 Hz, 1H); 6.83 (d, J = 1.5 Hz, 1H); 6.87 (d, J = 1.7 Hz, 1H); 6.91 (dd, $J_1$ = 1.5 Hz, $J_2$ = 8.1 Hz, 1H); 7.03 (d, J = 9.1 Hz, 2H); 7.49 (d, J = 7.8 Hz, 1H); 7.58-7.63 (aromatics, 2H); 7.79 (d, J = 7.6 Hz, 1H); 7.86 (d, J = 8.8 Hz, 2H); 8.80 (s, 1H); 12.67 (bs, 1H) | II-5 & III-5 |
| C-3 | 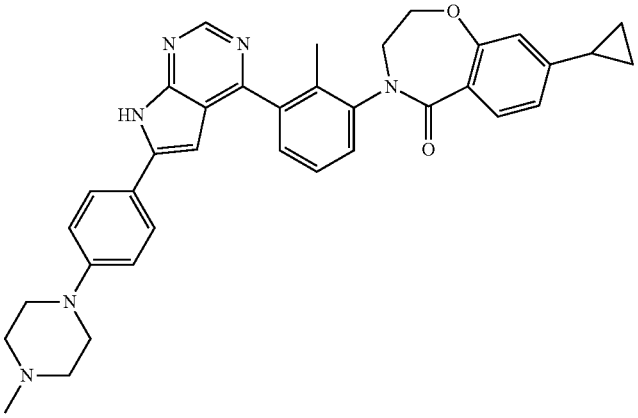 [SMILES: Cc1c(-c2ncnc3[nH]c(-c4ccc(N5CCN(C)CC5)cc4)cc23)cccc1N1CCOc2cc(C3CC3)ccc2C1=O]<br>8-cyclopropyl-4-[2-methyl-3-[6-[4-(4-methylpiperazin-1-yl)phenyl]-7H-pyrrolo[2,3-d]pyrimidin-4-yl]phenyl]-2,3-dihydro-1,4-benzoxazepin-5-one | LCMS: m/z 585.4 (M + 1)+. 1H NMR [400 MHz, $(CD_3)_2CO$] δ 0.76-0.80 (m, 2H); 1.02-1.06 (m, 2H); 1.96-1.98 (m, 1H); 2.26 (s, 3H); 2.27 (s, 3H); 2.46-2.54 (m, 4H); 3.24-3.32 (m, 4H); 3.93-4.06 (m, 2H); 4.51-4.58 (m, 2H); 6.67 (s, 1H); 6.81 (d, J = 1.6 Hz, 1H); 6.93 (dd, $J_1$ = 1.5 Hz, $J_2$ = 8.0 Hz, 1H); 7.06 (d, J = 8.7 Hz, 2H); 7.44-7.47 (aromatics, 2H); 7.55 (dd, $J_1$ = 3.6, $J_2$ = 5.5 Hz, 1H); 7.70 (d, J = 8.0 Hz, 1H); 7.85 (d, J = 9.0 Hz, 2H); 8.76 (s, 1H); 11.42 (bs, 1H) | II-5 & III-1 |
| C-4 | 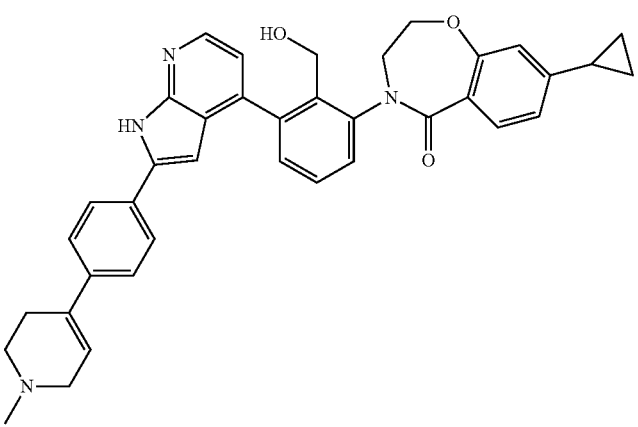 [SMILES: CN1CC=C(c2ccc(-c3cc4c(-c5cccc(N6CCOc7cc(C8CC8)ccc7C6=O)c5CO)ccnc4[nH]3)cc2)CC1]<br>8-cyclopropyl-4-[2-(hydroxymethyl)-3-[2-[4-(1-methyl-3,6-dihydro-2H-pyridin-4-yl)phenyl]-1H-pyrrolo[2,3-b]pyridin-4-yl]phenyl]-2,3-dihydro-1,4-benzoxazepin-5-one | LCMS: m/z 597.3 (M + 1)+. 1H NMR (DMSO-$d_6$, 400 MHz) δ 0.73-0.79 (m, 2H); 0.99-1.04 (m, 2H); 1.94-2.00 (m, 1H); 2.28 (s, 3H); 2.54-2.60 (m, 2H); 3.00-3.06 (m, 2H); 3.20-3.40 (m, 2H); 3.90-3.98 (m, 2H); 4.20-4.30 (m, 1H); 4.31-4.40 (m, 1H); 4.54-4.59 (m 2H); 4.76-4.88 (m, 1H); 6.26 (s, 1H); 6.69 (s, 1H); 6.81 (s, 1H); 6.88 (dd, $J_1$ = 1.2 Hz, $J_2$ = 8.1 Hz, 1H); 7.20 (bs, 1H); 7.42-7.58 (aromatics, 5H); 7.66 (d, J = 8.1 Hz, 1H); 7.89 (d, J = 8.6 Hz, 2H); 8.27 (d, J = 4.6 Hz, 1H); 12.30 (bs, 1H) | II-12 & III-5 |

TABLE 18-continued

| No | Structure/IUPAC name | Characterization | INT used |
|---|---|---|---|
| C-5 | 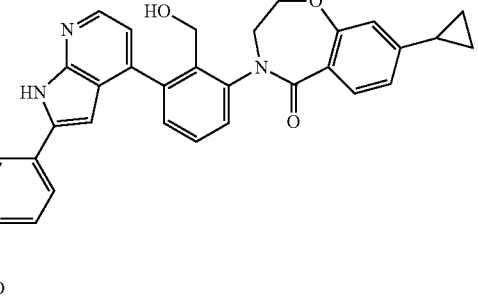<br>8-cyclopropyl-4-[2-(hydroxymethyl)-3-[2-[4-(4-methylmorpholin-2-yl)phenyl]-1H-pyrrolo[2,3-b]pyridin-4-yl]phenyl]-2,3-dihydro-1,4-benzoxazepin-5-one | LCMS: m/z 601.2 (M + 1)+. 1H NMR (DMSO-d6, 400 MHz) δ 0.73-0.77 (m, 2H); 0.99-1.04 (m, 2H); 1.86 (t, J = 10.5 Hz, 1H); 1.95-2.14 (m, 2H); 2.21 (s, 3H); 2.69 (d, J = 11.7 Hz, 1H); 2.88 (d, J = 11.3 Hz, 1H); 3.67 (td, J$_1$ = 2.0 Hz, J$_2$ = 11.4 Hz, 1H); 3.88-3.98 (m, 3H); 4.20-4.38 (m, 2H); 4.49-4.59 (m, 3H); 4.80 (bs, 1H); 6.68 (s, 1H); 6.81 (s, 1H); 6.88 (d, J = 8.2 Hz, 1H); 7.21 (bs, 1H); 7.40-7.44 (aromatics, 3H); 7.48 (d, J = 7.8 Hz, 1H); 7.54-7.58 (aromatics, 1H); 7.66 (d, J = 7.8 Hz, 1H); 7.89 (d, J = 8.2 Hz, 2H); 8.27 (d, J = 5.1 Hz, 1H); 12.30 (bs, 1H) | II-14 & III-5 |

Example D-1

8-cyclopropyl-4-[2-(hydroxymethyl)-3-[6-[1-(1-methyl-4-piperidyl)pyrazol-4-yl]-7H-pyrrolo[2,3-d]pyrimidin-4-yl]phenyl]-2,3-dihydro-1,4-benzoxazepin-5-one

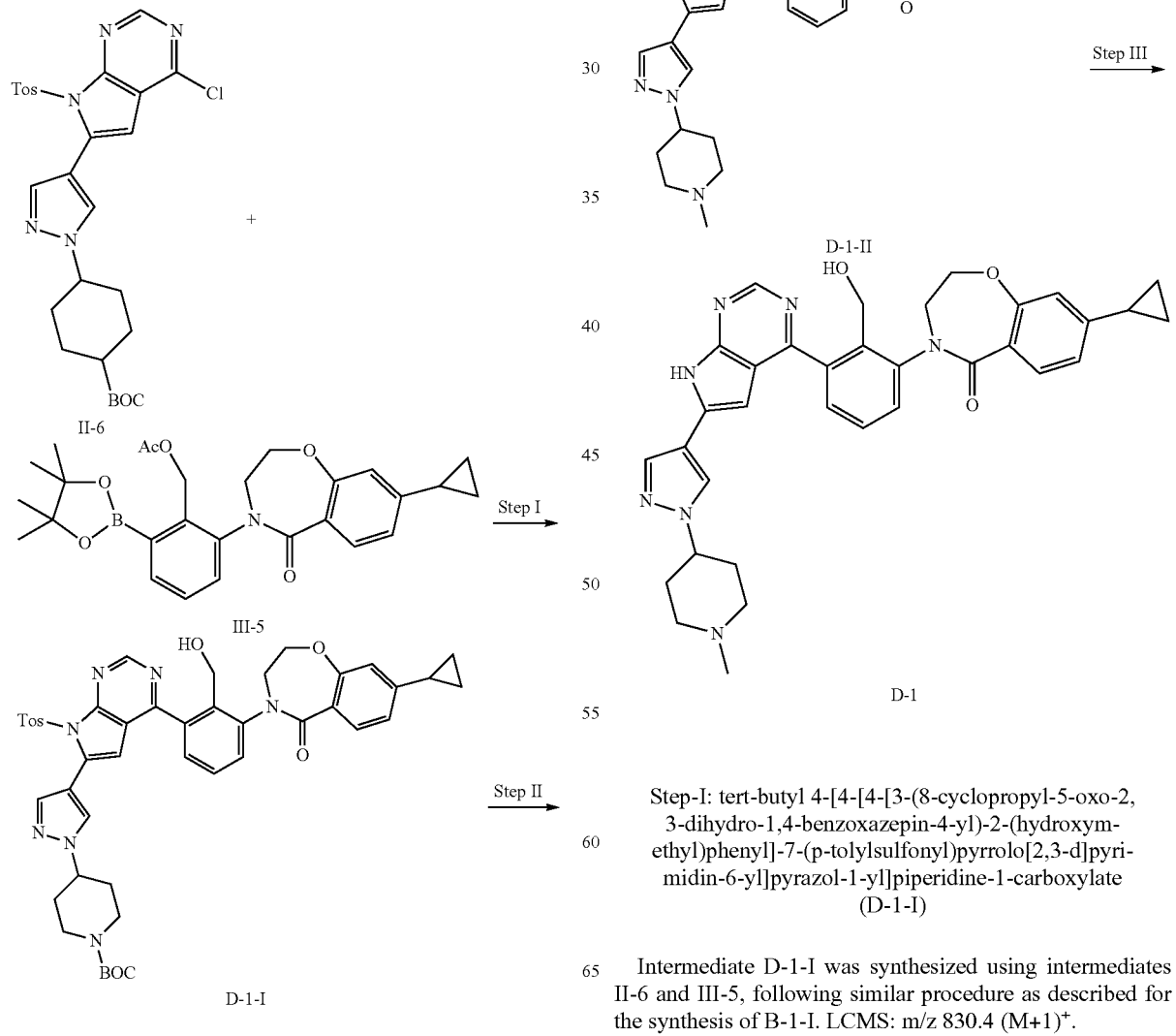

Step-I: tert-butyl 4-[4-[4-[3-(8-cyclopropyl-5-oxo-2,3-dihydro-1,4-benzoxazepin-4-yl)-2-(hydroxymethyl)phenyl]-7-(p-tolylsulfonyl)pyrrolo[2,3-d]pyrimidin-6-yl]pyrazol-1-yl]piperidine-1-carboxylate (D-1-I)

Intermediate D-1-I was synthesized using intermediates II-6 and III-5, following similar procedure as described for the synthesis of B-1-I. LCMS: m/z 830.4 (M+1)+.

Step-II: 8-cyclopropyl-4-[2-(hydroxymethyl)-3-[6-[1-(1-methyl-4-piperidyl)pyrazol-4-yl]-7-(p-tolylsulfonyl)pyrrolo[2,3-d]pyrimidin-4-yl]phenyl]-2,3-dihydro-1,4-benzoxazepin-5-one (D-1-II)

Intermediate D-1-II was synthesized from intermediate D-1-I, following similar procedure as described for the synthesis of C-1-II (step-II, example C-1). LCMS: m/z; 744.3 (M+1)⁺.

Step-III: 8-cyclopropyl-4-[2-(hydroxymethyl)-3-[6-[1-(1-methyl-4-piperidyl)pyrazol-4-yl]-7H-pyrrolo[2,3-d]pyrimidin-4-yl]phenyl]-2,3-dihydro-1,4-benzoxazepin-5-one (D-1)

Example D-1 was synthesized using similar procedure as described for the synthesis of C-1 (step-III). LCMS: m/z 590.1 (M+1)⁺. ¹H NMR (DMSO-$d_6$, 400 MHz) δ 0.72-0.78 (m, 2H); 0.98-1.04 (m, 2H); 1.90-2.00 (m, 3H); 2.03-2.09 (m, 4H); 2.22 (s, 3H); 2.80-2.90 (m, 2H); 3.82-4.00 (m, 2H); 4.10-4.20 (m, 1H); 4.33-4.39 (m, 2H); 4.42-4.58 (m, 2H); 5.42-5.45 (m, 1H); 6.75 (s, 1H); 6.82 (s, 1H); 6.91 (d, J=7.8 Hz, 1H); 6.48 (d, J=7.9 Hz, 1H); 7.58-7.63 (aromatics, 2H); 7.73 (d, J=7.6 Hz, 1H); 8.09 (s, 1H); 8.42 (s, 1H); 8.78 (s, 1H); 12.64 (s, 1H).

Following examples were synthesized using similar sequence of reactions and procedures as described for the synthesis of D-1.

TABLE 19

| No | Structure/IUPAC name | Characterization | INT used |
|---|---|---|---|
| D-2 | 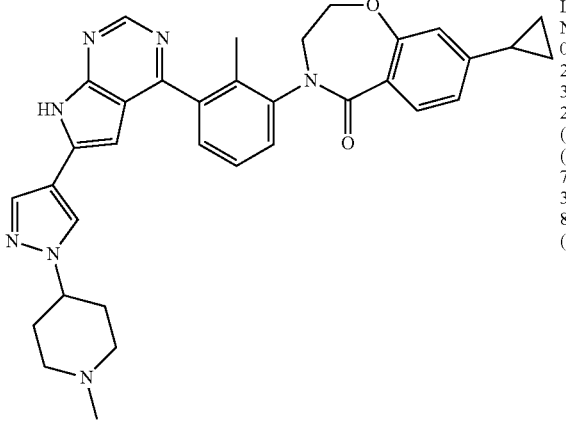<br>8-cyclopropyl-4-[2-methyl-3-[6-[1-(1-methyl-4-piperidyl)pyrazol-4-yl]-7H-pyrrolo[2,3-d]pyrimidin-4-yl]phenyl]-2,3-dihydro-1,4-benzoxazepin-5-one | LCMS: m/z 574.2 (M + 1)⁺. ¹H NMR (DMSO-$d_6$, 400 MHz) δ 0.72-0.78 (m, 2H); 0.98-1.06 (m, 2H); 1.90-2.08 (m, 7H); 2.13 (s, 3H); 2.22 (bs, 3H); 2.84-2.94 (m, 2H); 3.82-3.92 (m, 2H); 4.12-4.20 (m, 1H); 4.42-4.48 (m, 2H); 6.53 (s, 1H); 6.82 (s, 1H); 6.91 (d, J = 7.8 Hz, 1H); 7.42-7.49 (aromatics, 3H); 7.62 (d, J = 8.1 Hz, 1H); 8.06 (s, 1H); 8.38 (s, 1H); 8.76 (s, 1H); 12.51 (s, 1H) | II-6 & III-1 |
| D-3 | 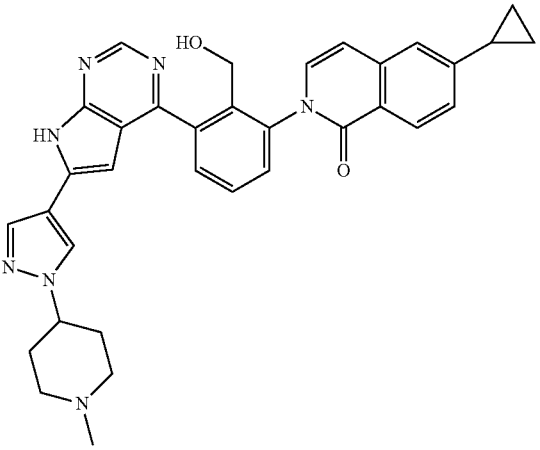 [SMILES: CN1CCC(n2cc(-c3cc4c(-c5cccc(-n6ccc7cc(C8CC8)ccc7c6=O)c5CO)ncnc4[nH]3)cn2)CC1]<br>6-cyclopropyl-2-[2-(hydroxymethyl)-3-[6-[1-(1-methyl-4-piperidyl)pyrazol-4-yl]-7H-pyrrolo[2,3-d]pyrimidin-4-yl]phenyl]isoquinolin-1-one | LCMS: m/z 572.4 (M + 1)⁺. ¹H NMR (DMSO-$d_6$, 400 MHz) δ 0.80-0.86 (m, 2H); 1.05-1.12 (m, 2H); 1.90-2.18 (m, 6H); 2.23 (s, 3H); 2.85-2.95 (m, 2H); 3.35-3.37 (m, 1H); 4.09-4.19 (m, 2H); 4.30 (dd, $J_1$ = 3.9 Hz, $J_2$ = 11.7 Hz, 1H); 5.25-5.28 (m, 1H); 6.65 (d, J = 7.3 Hz, 1H); 6.75 (d, J = 1.5 Hz, 1H); 7.26 (dd, $J_1$ = 1.2 Hz, $J_2$ = 8.3 Hz, 1H); 7.37 (d, J = 7.4 Hz, 1H); 7.43 (bs, 1H); 7.50 (d, J = 7.3 Hz, 1H); 7.64 (t, J = 7.8 Hz, 1H); 7.82 (d, J = 7.1 Hz, 1H); 8.08-8.11 (aromatics, 2H); 8.41 (s, 1H); 8.77 (s, 1H); 12.62 (bs, 1H) | II-6 & III-3 |

TABLE 19-continued

| No | Structure/IUPAC name | Characterization | INT used |
|---|---|---|---|
| D-4 | 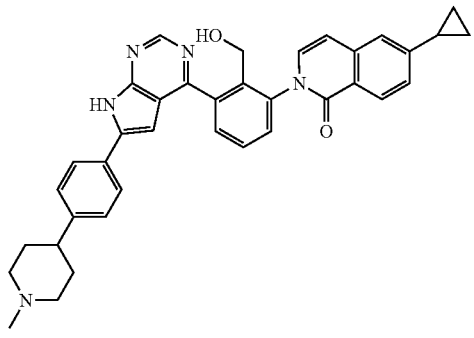 [SMILES: CN1CCC(c2ccc(-c3cc4c(-c5cccc(-n6ccc7cc(C8CC8)ccc7c6=O)c5CO)ncnc4[nH]3)cc2)CC1]<br>6-cyclopropyl-2-[2-(hydroxymethyl)-3-[6-[4-(1-methyl-4-piperidyl)phenyl]-7H-pyrrolo[2,3-d]pyrimidin-4-yl]phenyl]isoquinolin-1-one | LCMS: m/z 582.2 (M + 1)$^+$. $^1$H NMR (DMSO-$d_6$, 400 MHz) δ 0.82-0.88 (m, 2H); 1.06-1.13 (m, 2H); 1.64-1.82 (m, 4H); 2.00-2.14 (m, 3H); 2.25 (s, 3H); 2.88-2.98 (m, 2H); 3.16 (d, J = 4.9 Hz, 1H); 4.10-4.20 (m, 1H); 4.32-4.40 (m, 1H); 5.22-5.30 (m, 1H); 6.67 (d, J = 7.6 Hz, 1H); 7.04 (s, 1H); 7.27 (d, J = 8.4 Hz, 1H); 7.36-7.41 (aromatics, 3H); 7.44 (s, 1H); 7.53 (d, J = 7.8 Hz, 1H); 7.67 (t, J = 7.8 Hz, 1H); 7.87 (d, J = 7.3 Hz, 1H); 7.94 (d, J = 7.9 Hz, 2H); 8.12 (d, J = 8.3 Hz, 1H); 8.85 (s, 1H); 12.83 (bs, 1H) | II-13 & III-3 |
| D-5 | 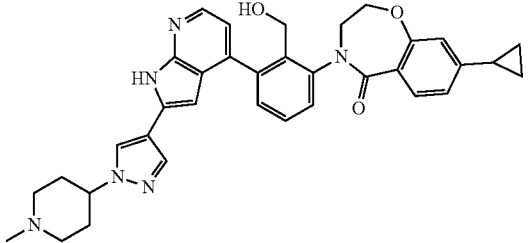 [SMILES: CN1CCC(n2cc(-c3cc4c(-c5cccc(N6CCOc7cc(C8CC8)ccc7C6=O)c5CO)ccnc4[nH]3)cn2)CC1]<br>8-cyclopropyl-4-[2-(hydroxymethyl)-3-[2-[1-(1-methyl-4-piperidyl)pyrazol-4-yl]-1H-pyrrolo[2,3-b]pyridin-4-yl]phenyl]-2,3-dihydro-1,4-benzoxazepin-5-one | LCMS: m/z 589.2 (M + 1)$^+$. $^1$H NMR (DMSO-$d_6$, 400 MHz) δ 0.72-0.78 (m, 2H); 1.00-1.04 (m, 2H); 1.90-2.10 (m, 7H); 2.21 (s, 3H); 2.86 (d, J = 11.0 Hz, 2H); 3.86-3.94 (m, 2H); 4.10-4.15 (m, 1H); 4.20-4.22 (m, 1H); 4.31-4.34 (m, 1H); 4.51-4.60 (m, 2H); 4.78 (bs, 1H); 6.38 (d, J = 1.6 Hz, 1H); 6.81 (s, 1H); 6.88 (d, J = 8.2 Hz, 1H); 7.14 (bs, 1H); 7.41 (d, J = 7.7 Hz, 1H); 7.45 (d, J = 7.1 Hz, 1H); 7.52-7.56 (aromatics, 1H); 7.66 (d, J = 8.2 Hz, 1H); 8.00 (s, 1H); 8.18 (d, J = 4.9 Hz, 1H); 8.32 (s, 1H); 12.02 (bs, 1H) | II-7 & III-5 |
| D-6 | 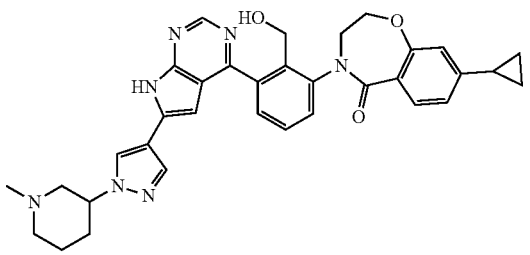 [SMILES: CN1CCCC(n2cc(-c3cc4c(-c5cccc(N6CCOc7cc(C8CC8)ccc7C6=O)c5CO)ncnc4[nH]3)cn2)C1]<br>8-cyclopropyl-4-[2-(hydroxymethyl)-3-[6-[1-(1-methyl-3-piperidyl)pyrazol-4-yl]-7H-pyrrolo[2,3-d]pyrimidin-4-yl]phenyl]-2,3-dihydro-1,4-benzoxazepin-5-one | LCMS: m/z 590.2 (M + 1)$^+$. $^1$H NMR (DMSO-$d_6$, 400 MHz) δ 0.74-0.78 (m, 2H); 1.00-1.04 (m, 2H); 1.60-1.80 (m, 4H); 1.94-2.06 (m, 3H); 2.23 (s, 3H); 2.62-2.70 (m, 1H); 2.96-3.04 (m, 1H); 3.84-3.98 (m, 2H); 4.29-4.42 (m, 3H); 4.44-4.52 (m, 1H); 4.57-4.62 (m, 1H); 5.40-5.43 (m, 1H); 6.74 (s, 1H); 6.89 (s, 1H); 6.90 (d, J = 8.0 Hz, 1H); 7.48 (d, J = 7.6 Hz, 1H); 7.58-7.74 (aromatics, 2H); 7.73 (d, J = 7.6 Hz, 1H); 8.08 (s, 1H); 8.45 (s, 1H); 8.78 (s, 1H); 12.62 (s, 1H) | II-8 & III-5 |
| D-7 | 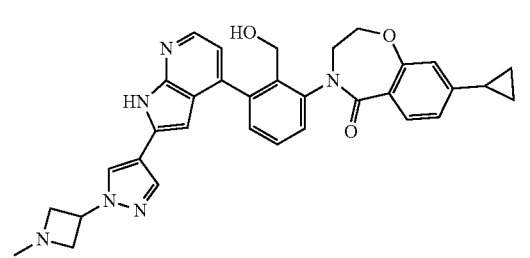 [SMILES: CN1CC(n2cc(-c3cc4c(-c5cccc(N6CCOc7cc(C8CC8)ccc7C6=O)c5CO)ccnc4[nH]3)cn2)C1]<br>8-cyclopropyl-4-[2-(hydroxymethyl)-3-[2-[1-(1-methylazetidin-3-yl)pyrazol-4-yl]-1H-pyrrolo[2,3-b]pyridin-4-yl]phenyl]-2,3-dihydro-1,4-benzoxazepin-5-one | LCMS: m/z 561.2 (M + 1)$^+$. $^1$H NMR (DMSO-$d_6$, 400 MHz) δ 0.71-0.75 (m, 2H); 0.97-1.02 (m, 2H); 1.93-1.97 (m, 1H); 2.30 (s, 3H); 3.22-3.41 (m, 2H); 3.68 (t, J = 7.3 Hz, 2H); 3.86-3.94 (m, 2H); 4.16-4.26 (m, 1H); 4.29-4.33 (m, 1H); 4.50-4.56 (m, 2H); 4.70-4.80 (m, 1H); 4.90-4.96 (m, 1H); 6.38 (d, J = 2.0 Hz, 1H); 6.79 (d, J = 1.2 Hz, 1H); 6.86 (dd, $J_1$ = 1.3 Hz, $J_2$ = 8.2 Hz, 1H); 7.14 (d, J = 4.0 Hz, 1H); 7.39 (d, J = 7.7 Hz, 1H); 7.43 (d, J = 7.1 Hz, 1H); 7.50-7.54 (m, 1H); 7.63 (d, J = 8.2 Hz, 1H); 8.03 (s, 1H); 8.17 (d, J = 5.0 Hz, 1H); 8.42 (s, 1H); 12.03 (s, 1H) | II-9 & III-5 |

| No | Structure/IUPAC name | Characterization | INT used |
|---|---|---|---|
| D-8 | 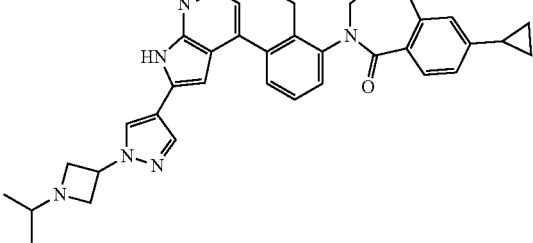<br>8-cyclopropyl-4-[2-(hydroxymethyl)-3-[2-[1-(1-isopropylazetidin-3-yl)pyrazol-4-yl]-1H-pyrrolo[2,3-b]pyridin-4-yl]phenyl]-2,3-dihydro-1,4-benzoxazepin-5-one | LCMS: m/z 589.4 (M + 1)$^+$. $^1$H NMR (DMSO-$d_6$, 400 MHz) δ 0.74-0.77 (m, 2H); 0.90 (d, J = 6.1 Hz, 6H); 0.99-1.04 (m, 2H); 1.94-2.01 (m, 1H); 3.22-3.41 (m, 2H); 3.62-3.70 (m, 2H); 3.89-3.94 (m, 2H); 4.20-4.36 (m, 2H); 4.52-4.58 (m, 2H); 4.74-4.80 (m, 1H); 4.88-4.94 (m, 1H); 6.41 (d, J = 1.7 Hz, 1H); 6.81 (d, J = 1.5 Hz, 1H); 6.88 (dd, $J_1$ = 1.6 Hz, $J_2$ = 8.3 Hz, 1H); 7.15 (d, J = 3.9 Hz, 1H); 7.41 (d, J = 7.6 Hz, 1H); 7.45 (d, J = 7.6 Hz, 1H); 7.52-7.56 (m, 1H); 7.66 (d, J = 8.3 Hz, 1H); 8.04 (s, 1H); 8.19 (d, J = 4.9 Hz, 1H); 8.44 (s, 1H); 12.04 (s, 1H) | II-9 & III-5 (acetone for reductive amination) |
| D-9 | 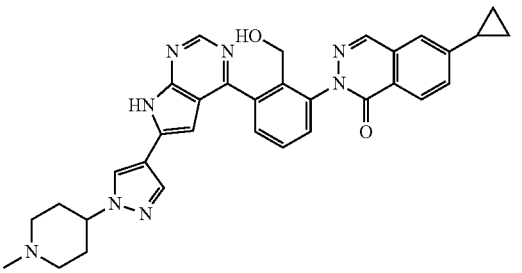 [SMILES: CN1CCC(n2cc(-c3cc4c(-c5cccc(-n6ncc7cc(C8CC8)ccc7c6=O)c5CO)ncnc4[nH]3)cn2)CC1]<br>6-cyclopropyl-2-[2-(hydroxymethyl)-3-[2-[1-(1-methyl-4-piperidyl)pyrazol-4-yl]-1H-pyrrolo[2,3-b]pyridin-4-yl]phenyl]phthalazin-1-one | LCMS: m/z 573.2 (M + 1)$^+$. $^1$H NMR (DMSO-$d_6$, 400 MHz) δ 0.88-0.92 (m, 2H); 1.13-1.18 (m, 2H); 1.91-2.24 (m, 5H); 2.25 (s, 3H); 2.84-2.94 (m, 3H); 4.12-4.26 (m, 4H); 5.15 (t, J = 6.3 Hz, 1H); 6.73 (s, 1H); 7.56 (d, J = 7.9 Hz, 1H); 7.62-7.66 (aromatics, 2H); 7.72 (s, 1H); 7.79 (d, J = 7.5 Hz, 1H); 8.09 (s, 1H); 8.19 (d, J = 8.3 Hz, 1H); 8.43 (s, 1H); 8.48 (s, 1H); 8.78 (s, 1H); 12.62 (bs, 1H) | II-6 & III-7 |
| D-10 | 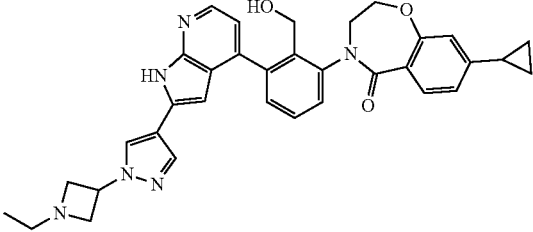 [SMILES: CCN1CC(n2cc(-c3cc4c(-c5cccc(N6CCOc7cc(C8CC8)ccc7C6=O)c5CO)ccnc4[nH]3)cn2)C1]<br>8-cyclopropyl-4-[3-[2-[1-(1-ethylazetidin-3-yl)pyrazol-4-yl]-1H-pyrrolo[2,3-b]pyridin-4-yl]-2-(hydroxymethyl)phenyl]-2,3-dihydro-1,4-benzoxazepin-5-one | LCMS: m/z 573.2 (M + 1)$^+$. $^1$H NMR (DMSO-$d_6$, 400 MHz) δ 0.74-0.76 (m, 2H); 0.92 (t, J = 7.2 Hz, 3H); 1.00-1.03 (m, 2H); 1.94-1.97 (m, 1H); 3.29-3.33 (m, 3H); 3.68 (t, J = 7.7 Hz, 2H); 3.88-3.94 (m, 2H); 4.20-4.36 (m, 2H); 4.52-4.58 (m, 2H); 4.70-5.82 (m, 1H); 4.96-5.00 (m, 1H); 6.41 (d, J = 1.7 Hz, 1H); 6.81 (d, J = 1.4 Hz, 1H); 6.88 (d, J = 8.4 Hz, 1H); 7.16 (bs, 1H); 7.41 (d, J = 7.7 Hz, 1H); 7.45 (d, J = 7.5 Hz, 1H); 7.52-7.56 (m, 1H); 7.66 (d, J = 8.2 Hz, 1H); 8.05 (s, 1H); 8.19 (d, J = 5.1 Hz, 1H); 8.44 (s, 1H); 12.03 (s, 1H) | II-9 & III-5 (acetaldehyde for reductive amination) |
| D-11 | 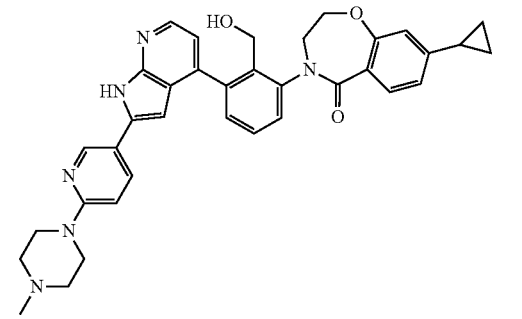 [SMILES: CN1CCN(c2ccc(-c3cc4c(-c5cccc(N6CCOc7cc(C8CC8)ccc7C6=O)c5CO)ccnc4[nH]3)cn2)CC1]<br>8-cyclopropyl-4-[2-(hydroxymethyl)-3-[2-[6-(4-methylpiperazin-1-yl)-3-pyridyl]-1H-pyrrolo[2,3-b]pyridin-4-yl]phenyl]-2,3-dihydro-1,4-benzoxazepin-5-one | LCMS: m/z 601.4 (M + 1)$^+$. $^1$H NMR (DMSO-$d_6$, 400 MHz) δ 0.73-0.77 (m, 2H); 0.99-1.04 (m, 2H); 1.95-1.99 (m, 1H); 2.22 (s, 3H); 2.38-2.41 (m, 4H); 3.50-3.60 (m, 4H); 3.87-3.98 (m, 2H); 4.21-4.28 (m, 2H); 4.32-4.36 (m, 1H); 4.52-4.57 (m, 2H); 4.72-4.84 (m, 1H); 6.55 (d, J = 1.8 Hz, 1H); 6.81 (d, J = 1.6 Hz, 1H); 6.87-6.92 (m, 2H); 7.18 (d, J = 3.7 Hz, 1H); 7.41 (d, J = 7.7 Hz, 1H); 7.48 (d, J = 6.9 Hz, 1H); 7.53-7.57 (m, 1H); 7.66 (d, J = 8.2 Hz, 1H); 8.04 (dd, $J_1$ = 2.4, $J_2$ = 9.0 Hz, 1H); 8.22 (d, J = 4.9 Hz, 1H); 8.68 (d, J = 2.5 Hz, 1H); 12.17 (bs, 1H) | II-16 & III-5 |

TABLE 19-continued

| No | Structure/IUPAC name | Characterization | INT used |
|---|---|---|---|
| D-12 | 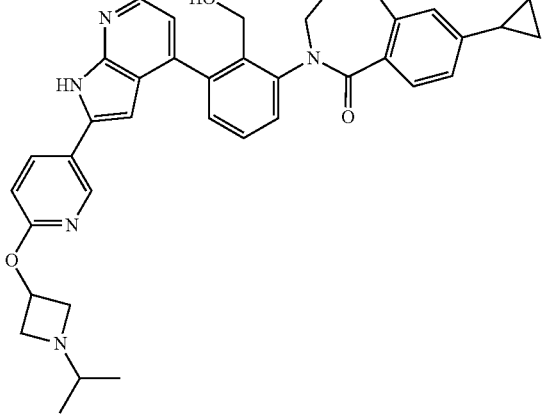<br>8-cyclopropyl-4-[2-(hydroxymethyl)-3-[2-[6-(1-isopropylazetidin-3-yl)oxy-3-pyridyl]-1H-pyrrolo[2,3-b]pyridin-4-yl]phenyl]-2,3-dihydro-1,4-benzoxazepin-5-one | LCMS: m/z 616.3 (M + 1)$^+$. $^1$H NMR (DMSO-$d_6$, 400 MHz) δ 0.72-0.78 (m, 2H); 0.88 (d, J = 5.9 Hz, 6H); 0.98-1.04 (m, 2H); 1.93-1.99 (m, 1H); 2.31-2.36 (m, 1H); 2.92-3.00 (m, 2H); 3.64-3.72 (m, 2H); 3.88-3.94 (m, 2H); 4.20-4.38 (m, 2H); 454-4.60 (m, 2H); 4.76-4.86 (m, 1H); 5.09-5.12 (m, 1H); 6.70 (s, 1H); 6.81 (s, 1H); 6.87-6.92 (aromatics, 2H); 7.22 (bs, 1H); 7.43 (d, J = 7.5 Hz, 1H); 7.48 (d, J = 7.1 Hz, 1H); 7.53-7.57 (aromatics, 1H); 7.66 (d, J = 8.1 Hz, 1H); 8.24 (dd, J$_1$ = 2.4 Hz, J$_2$ = 8.8 Hz, 1H); 8.28 (d, J = 4.9 Hz, 1H); 8.70 (d, J = 2.0 Hz, 1H); 12.30 (s, 1H) | II-15 & III-5 (acetone for reductive amination) |
| D-13 | 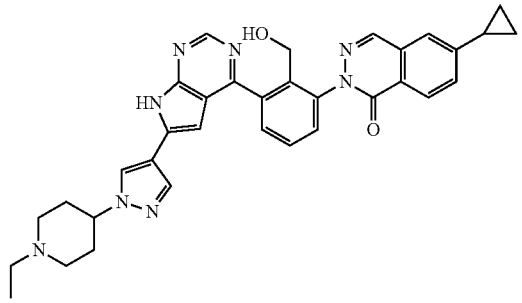 [SMILES: CCN1CCC(n2cc(-c3cc4c(-c5cccc(-n6ncc7cc(C8CC8)ccc7c6=O)c5CO)ncnc4[nH]3)cn2)CC1]<br>6-cyclopropyl-2-[3-[6-[1-(1-ethyl-4-piperidyl)pyrazol-4-yl]-7H-pyrrolo[2,3-d]pyrimidin-4-yl]-2-(hydroxymethyl)phenyl]phthalazin-1-one | LCMS: m/z 587.2 (M + 1)$^+$ | II-6 & III-7 (acetaldehyde for reductive amination) |
| D-14 | 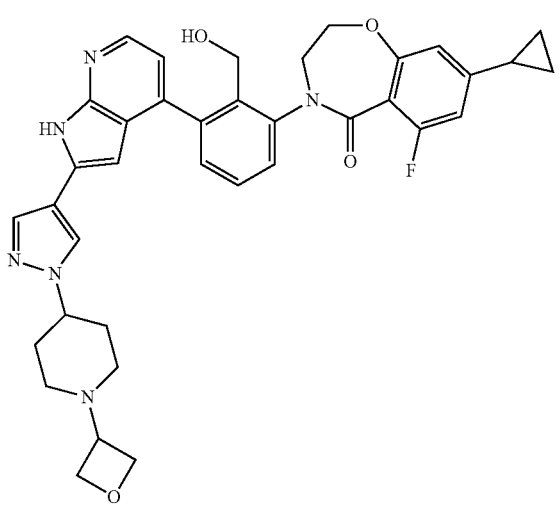 [SMILES: O=C1c2c(F)cc(C3CC3)cc2OCCN1c1cccc(-c2ccnc3[nH]c(-c4cnn(C5CCN(C6COC6)CC5)c4)cc23)c1CO]<br>8-cyclopropyl-6-fluoro-4-[2-(hydroxymethyl)-3-[2-[1-[1-(oxetan-3-yl)-4-piperidyl]pyrazol-4-yl]-1H-pyrrolo[2,3-b]pyridin-4-yl]phenyl]-2,3-dihydro-1,4-benzoxazepin-5-one | LCMS: m/z 649.3 (M + 1)$^+$. $^1$H NMR (DMSO-$d_6$, 400 MHz) δ 0.76-0.82 (m, 2H); 1.00-1.08 (m, 2H); 1.90-2.10 (m, 7H); 2.76-2.82 (m, 2H); 3.40-3.48 (m, 1H); 3.78-3.85 (m, 1H); 3.92-4.02 (m, 1H); 4.15-4.30 (m, 2H); 4.35-4.40 (m, 2H); 4.44 (t, J = 4.0 Hz, 2H); 4.50-4.58 (m, 1H); 4.54 (t, J = 6.4 Hz, 2H); 4.80 (bs, 1H); 6.37 (d, J = 2.0 Hz, 1H); 6.77 (s, 1H); 6.83 (d, J = 11.2 Hz, 1H); 7.14 (d, J = 4.4 Hz, 1H); 7.40-7.48 (aromatics, 2H); 7.54-7.58 (aromatics, 1H); 7.99 (s, 1H); 8.18 (d, J = 5.2 Hz, 1H); 8.33 (s, 1H); 12.03 (s, 1H) | II-7 & III-9; (oxetan-3-one for reductive amination) |

Example E-1

Synthesis of 8-cyclopropyl-4-[2-(hydroxymethyl)-3-[2-[3-methyl-1-(1-methylazetidin-3-yl)pyrazol-4-yl]-1H-pyrrolo[2,3-b]pyridin-4-yl]phenyl]-2,3-dihydro-1,4-benzoxazepin-5-one

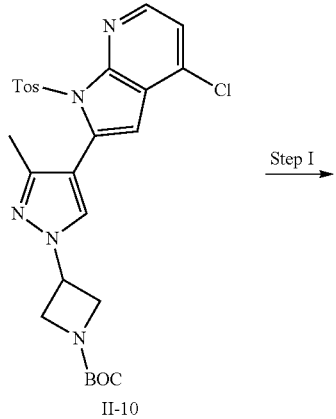

II-10

Step I →

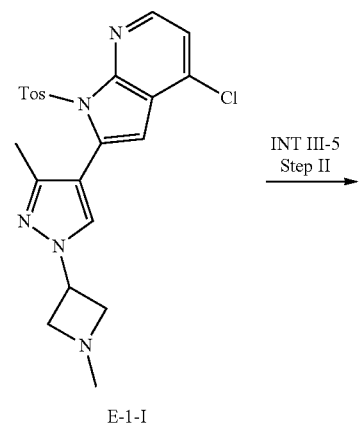

E-1-I

INT III-5
Step II →

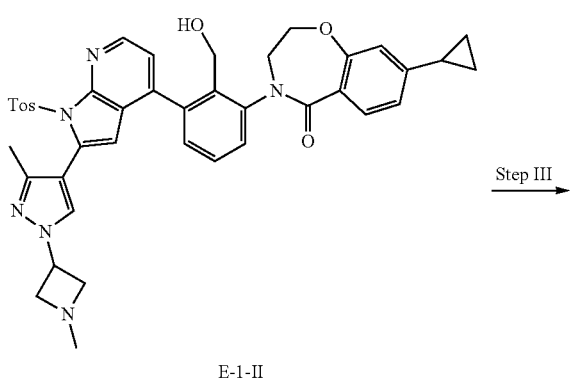

E-1-II

Step III →

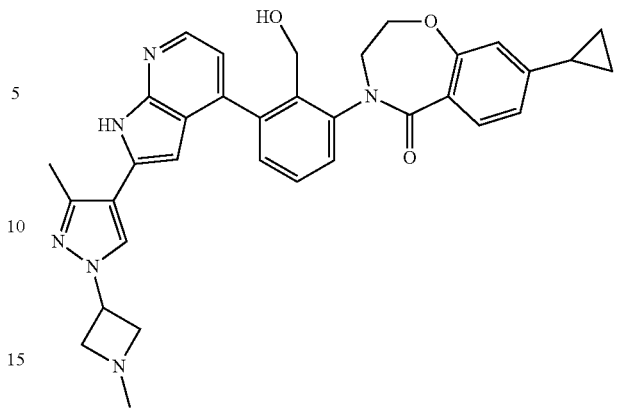

E-1

Step-I: 4-chloro-2-[3-methyl-1-(1-methylazetidin-3-yl)pyrazol-4-yl]-1-(p-tolylsulfonyl)pyrrolo[2,3-b]pyridine (E-1-I)

Intermediate E-1-I was synthesized using similar procedure as described for the synthesis of D-1-II (step-II). LCMS: m/z; 456.1 (M+1)$^+$.

Step-II: 8-cyclopropyl-4-[2-(hydroxymethyl)-3-[2-[3-methyl-1-(1-methylazetidin-3-yl)pyrazol-4-yl]-1-(p-tolylsulfonyl)pyrrolo[2,3-b]pyridin-4-yl]phenyl]-2,3-dihydro-1,4-benzoxazepin-5-one (E-1-II)

Intermediate E-1-II was synthesized using similar procedure as described for the synthesis of B-1-I. LCMS: m/z; 729.3 (M+1)$^+$.

Step-III: 8-cyclopropyl-4-[2-(hydroxymethyl)-3-[2-[3-methyl-1-(1-methylazetidin-3-yl)pyrazol-4-yl]-1H-pyrrolo[2,3-b]pyridin-4-yl]phenyl]-2,3-dihydro-1,4-benzoxazepin-5-one Example E-1 was prepared from E-1-II using similar procedure as described for the synthesis of C-1. LCMS: m/z 575.3 (M+1)$^+$. $^1$H NMR (DMSO-d$_6$, 400 MHz) δ 0.73-0.77 (m, 2H); 1.00-1.04 (m, 2H); 1.95-1.98 (m, 1H); 2.33 (s, 3H); 2.34 (s, 3H); 3.22-3.24 (m, 2H); 3.70 (t, J=7.3 Hz, 2H); 3.90-3.96 (m, 2H); 4.20-4.26 (m, 1H); 4.32-4.40 (m, 1H); 4.52-4.60 (m, 2H); 4.76-4.84 (m, 1H); 4.86-4.91 (m, 1H); 6.25 (s, 1H); 6.81 (d, J=1.5 Hz, 1H); 6.89 (dd, J$_1$=1.5 Hz, J$_2$=8.3 Hz, 1H); 7.17 (bs, 1H); 7.41 (d, J=7.8 Hz, 1H); 7.47 (d, J=6.8 Hz, 1H); 7.52-7.56 (m, 1H); 7.66 (d, J=8.1 Hz, 1H); 8.21 (d, J=4.9 Hz, 1H); 8.34 (s, 1H); 11.98 (s, 1H).

Example F-1

8-cyclopropyl-4-[2-(hydroxymethyl)-3-[2-[1-(oxetan-3-yl)pyrazol-4-yl]-1H-pyrrolo[2,3-b]pyridin-4-yl]phenyl]-2,3-dihydro-1,4-benzoxazepin-5-one

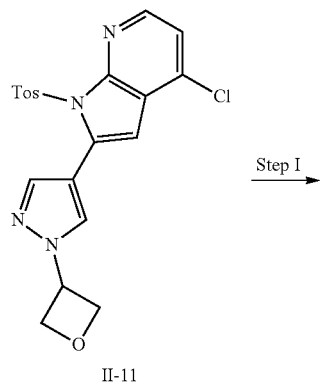

II-11

Step I →

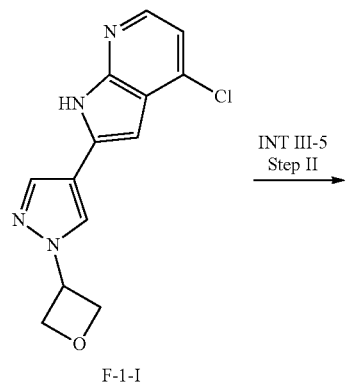

F-1-I

INT III-5
Step II →

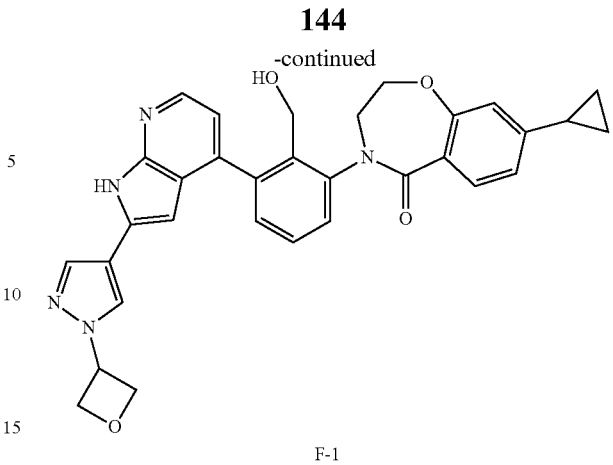

F-1

Step-I: 4-chloro-2-[1-(oxetan-3-yl)pyrazol-4-yl]-1H-pyrrolo[2,3-b]pyridine (F-1-I)

Intermediate F-1-I was synthesized using similar procedure as described in step-III of the synthesis of C-1. LCMS: m/z 275.2 (M+1)⁺.

Step-II: 8-cyclopropyl-4-[2-(hydroxymethyl)-3-[2-[1-(oxetan-3-yl)pyrazol-4-yl]-1H-pyrrolo[2,3-b]pyridin-4-yl]phenyl]-2,3-dihydro-1,4-benzoxazepin-5-one (F-1)

Example F-1 was prepared using similar procedure as described in step-I for the synthesis of B-1. LCMS: m/z 548.1 (M+1)⁺. $^1$H NMR (DMSO-$d_6$, 400 MHz) δ 0.71-0.75 (m, 2H); 0.97-1.01 (m, 2H); 1.90-1.98 (m, 1H); 3.82-3.92 (m, 2H); 4.16-4.24 (m, 1H); 4.26-4.36 (m, 1H); 4.47-4.54 (m, 2H); 4.70-4.80 (m, 1H); 4.86 (t, J=6.8 Hz, 2H); 4.92 (t, J=6.8 Hz, 2H); 5.54-5.60 (m, 1H); 6.40 (d, J=2.4 Hz, 1H); 6.78 (s, 1H); 6.86 (d, J=8.3 Hz, 1H); 7.14 (d, J=3.9 Hz, 1H); 7.38 (d, J=7.8 Hz, 1H); 7.43 (d, J=7.3 Hz, 1H); 7.50-7.54 (m, 1H); 7.63 (d, J=7.8 Hz, 1H); 8.11 (s, 1H); 8.17 (d, J=4.9 Hz, 1H); 8.40 (s, 1H); 12.03 (s, 1H).

Following example were synthesized using similar reaction sequence and procedures as described for the synthesis of F-1.

TABLE 20

| | | | |
|---|---|---|---|
| F-2 | 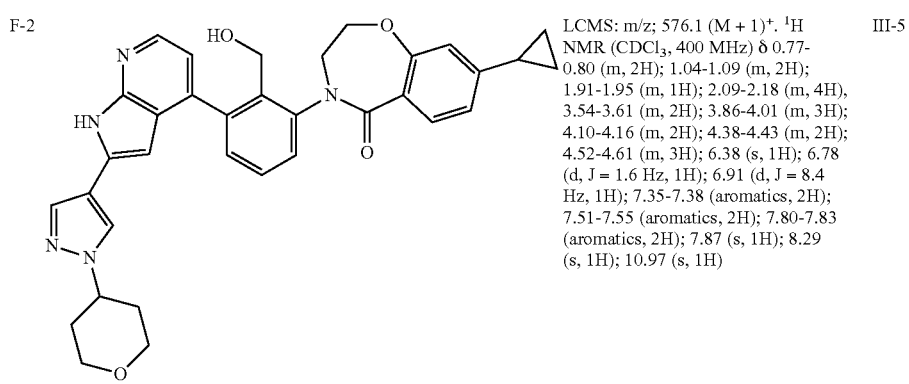 | LCMS: m/z; 576.1 (M + 1)⁺. $^1$H NMR (CDCl$_3$, 400 MHz) δ 0.77-0.80 (m, 2H); 1.04-1.09 (m, 2H); 1.91-1.95 (m, 1H); 2.09-2.18 (m, 4H), 3.54-3.61 (m, 2H); 3.86-4.01 (m, 3H); 4.10-4.16 (m, 2H); 4.38-4.43 (m, 2H); 4.52-4.61 (m, 3H); 6.38 (s, 1H); 6.78 (d, J = 1.6 Hz, 1H); 6.91 (d, J = 8.4 Hz, 1H); 7.35-7.38 (aromatics, 2H); 7.51-7.55 (aromatics, 2H); 7.80-7.83 (aromatics, 2H); 7.87 (s, 1H); 8.29 (s, 1H); 10.97 (s, 1H) | III-5 |

8-cyclopropyl-4-[2-(hydroxymethyl)-3-[2-(1-tetrahydropyran-4-ylpyrazol-4-yl)-1H-pyrrolo[2,3-b]pyridin-4-yl]phenyl]-2,3-dihydro-1,4-benzoxazepin-5-one

TABLE 20-continued

| | | | |
|---|---|---|---|
| F-3 | 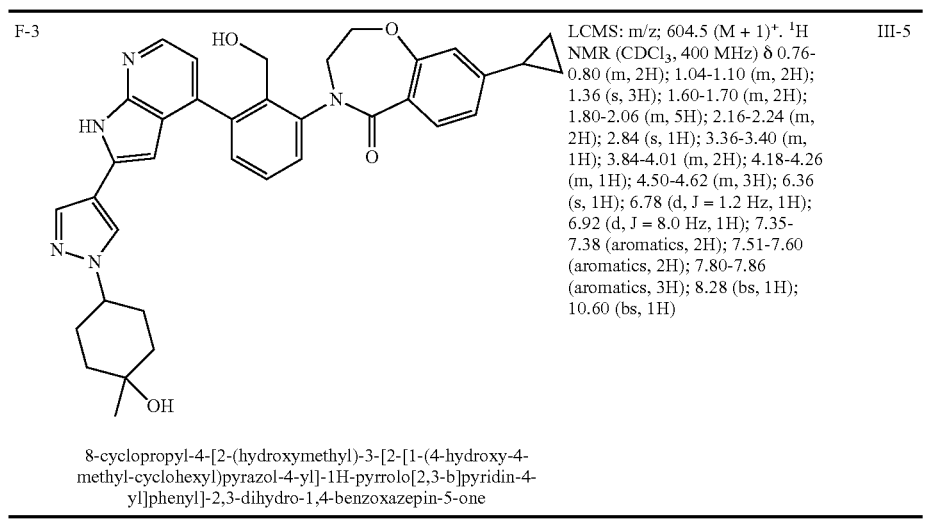<br>8-cyclopropyl-4-[2-(hydroxymethyl)-3-[2-[1-(4-hydroxy-4-methyl-cyclohexyl)pyrazol-4-yl]-1H-pyrrolo[2,3-b]pyridin-4-yl]phenyl]-2,3-dihydro-1,4-benzoxazepin-5-one | LCMS: m/z; 604.5 (M + 1)+. 1H NMR (CDCl3, 400 MHz) δ 0.76-0.80 (m, 2H); 1.04-1.10 (m, 2H); 1.36 (s, 3H); 1.60-1.70 (m, 2H); 1.80-2.06 (m, 5H); 2.16-2.24 (m, 2H); 2.84 (s, 1H); 3.36-3.40 (m, 1H); 3.84-4.01 (m, 2H); 4.18-4.26 (m, 1H); 4.50-4.62 (m, 3H); 6.36 (s, 1H); 6.78 (d, J = 1.2 Hz, 1H); 6.92 (d, J = 8.0 Hz, 1H); 7.35-7.38 (aromatics, 2H); 7.51-7.60 (aromatics, 2H); 7.80-7.86 (aromatics, 3H); 8.28 (bs, 1H); 10.60 (bs, 1H) | III-5 |

Example G-1

Synthesis of 8-cyclopropyl-4-[2-(hydroxymethyl)-3-[6-[4-[(1-methyl-4-piperidyl)oxy]phenyl]-7H-pyrrolo[2,3-d]pyrimidin-4-yl]phenyl]-2,3-dihydro-1,4-benzoxazepin-5-one

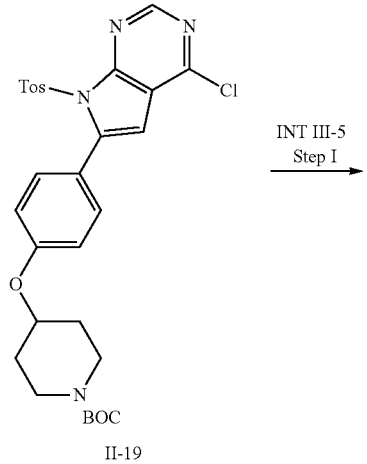

II-19

INT III-5
Step I →

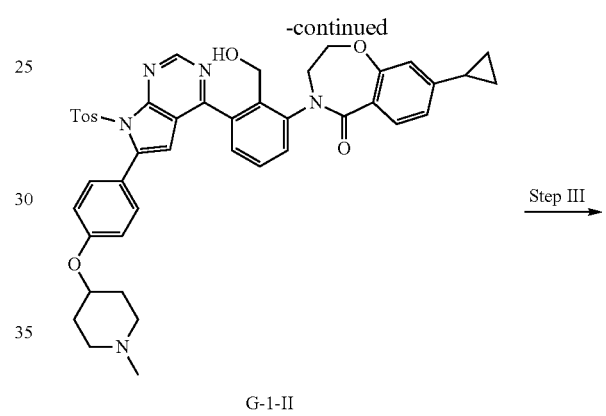

G-1-II

Step III →

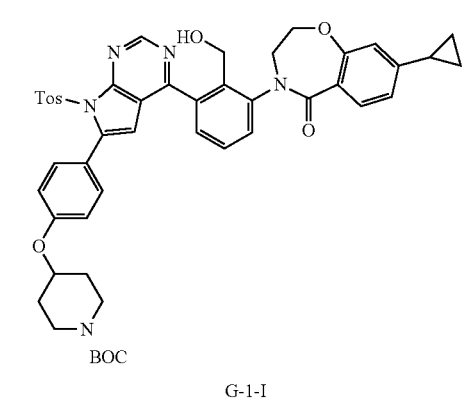

G-1-I

Step II →

G-1

Step-I: tert-butyl 4-[4-[4-[3-(8-cyclopropyl-5-oxo-2,3-dihydro-1,4-benzoxazepin-4-yl)-2-(hydroxymethyl)phenyl]-7-(p-tolylsulfonyl)pyrrolo[2,3-d]pyrimidin-6-yl]phenoxy]piperidine-1-carboxylate (G-1-I)

Intermediate G-1-I was synthesized following similar procedure as described in step-I for the synthesis of B-1. LCMS: m/z; 856 (M+1)⁺.

Step-II: 8-cyclopropyl-4-[2-(hydroxymethyl)-3-[6-[4-[(1-methyl-4-piperidyl)oxy]phenyl]-7-(p-tolylsulfonyl)pyrrolo[2,3-d]pyrimidin-4-yl]phenyl]-2,3-dihydro-1,4-benzoxazepin-5-one (G-1-II)

Intermediate G-1-II was synthesized following similar procedure as described in step-II for the synthesis of D-1-II. LCMS: m/z; 770.1 (M+1)⁺.

Step-III: 8-cyclopropyl-4-[2-(hydroxymethyl)-3-[6-[4-[(1-methyl-4-piperidyl)oxy]phenyl]-7H-pyrrolo[2,3-d]pyrimidin-4-yl]phenyl]-2,3-dihydro-1,4-benzoxazepin-5-one (G-1)

Example G-1 was prepared using similar procedure as described in step-II for the synthesis of C-1. LCMS: m/z 616.1 (M+1)⁺. ¹H NMR (DMSO-d₆, 400 MHz) δ 0.75-0.77 (m, 2H); 1.00-1.04 (m, 2H); 1.64-1.70 (m, 2H); 1.94-1.99 (m, 2H); 2.23 (s, 3H); 2.26-2.35 (m, 2H); 2.61-2.72 (m, 2H); 3.84-4.02 (m, 2H); 4.04-4.14 (m, 1H); 4.34-4.43 (m, 2H); 4.47-4.50 (m, 2H); 4.56-4.62 (m, 1H); 5.45 (two d, J=4.9 Hz, 1H); 6.83 (s, 1H); 6.89 (dd, J₁=1.7 Hz, J₂=6.5 Hz, 1H); 6.92 (d, J=1.4 Hz, 1H); 7.07 (d, J=8.8 Hz, 2H); 7.49 (d, J=8.0 Hz, 1H); 7.59-7.63 (aromatics, 2H); 7.78 (dd, J₁=1.0 Hz, J₂=7.6 Hz, 1H); 7.93 (d, J=8.8 Hz, 2H); 8.83 (s, 1H); 12.76 (s, 1H).

Example G-2 was also synthesized as described for the synthesis of G-1.

Example H-1

Synthesis of 6-cyclopropyl-2-[3-[6-[4-[1-(2-hydroxyethyl)-4-piperidyl]phenyl]-7H-pyrrolo[2,3-d]pyrimidin-4-yl]-2-methyl-phenyl]isoquinolin-1-one

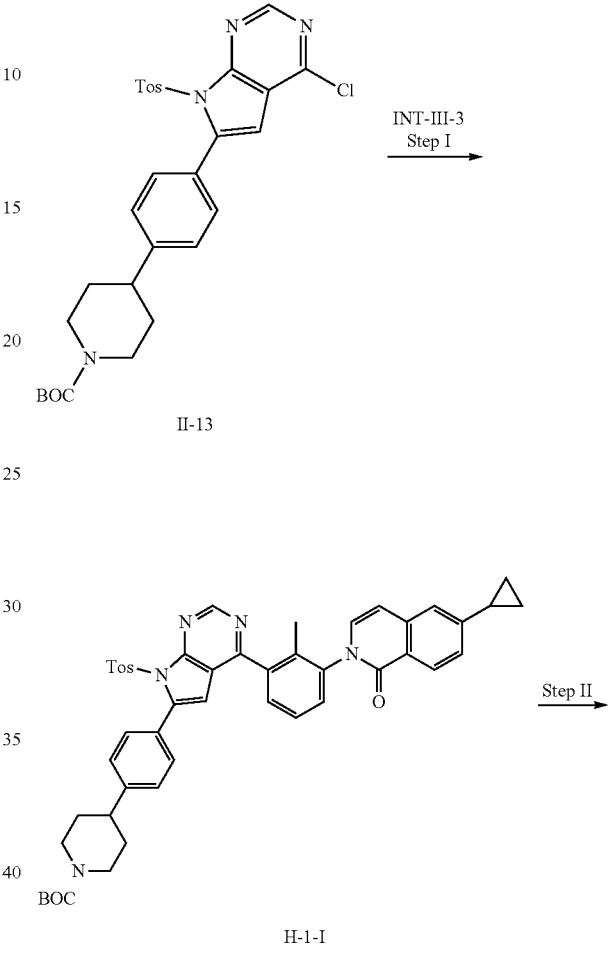

TABLE 21

| No | Structure/IUPAC name | Characterization | INT used |
|---|---|---|---|
| G-2 | 8-cyclopropyl-4-[2-(hydroxymethyl)-3-[6-[4-(1-methylazetidin-3-yl)oxyphenyl]-7H-pyrrolo[2,3-d]pyrimidin-4-yl]phenyl]-2,3-dihydro-1,4-benzoxazepin-5-one | LCMS: m/z 588.1 (M + 1)⁺. ¹H NMR (DMSO-d₆, 400 MHz) δ 0.74-0.78 (m, 2H); 1.00-1.04 (m, 2H); 1.95-2.01 (m, 1H); 2.29 (s, 3H); 2.98-3.01 (m, 2H); 3.74-3.78 (m, 2H); 3.85-3.99 (m, 2H); 4.35-4.43 (m, 2H); 4.46-4.51 (m, 1H); 4.56-4.61 (m, 1H); 4.81-4.85 (m, 1H); 5.39 and 5.41 (two d, J = 5.0 Hz, 1H); 6.82 (s, 1H); 6.89-6.95 (aromatics, 4H); 7.49 (d, J = 7.3 Hz, 1H); 7.58-7.63 (aromatics, 2H); 7.77 (d, J = 7.0 Hz, 1H); 7.93 (d, J = 8.8 Hz, 2H); 8.83 (s, 1H); 12.75 (s, 1H) | II-20 & III-5 |

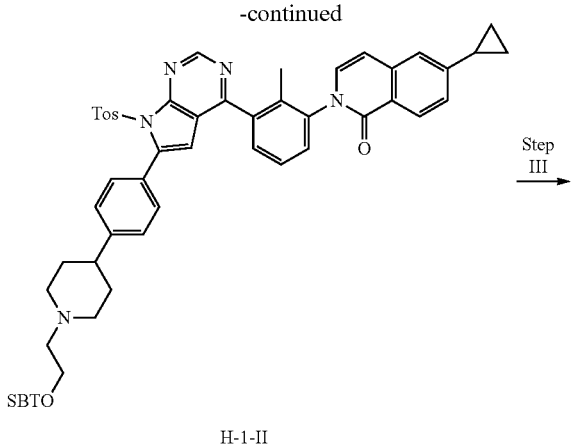

H-1-II

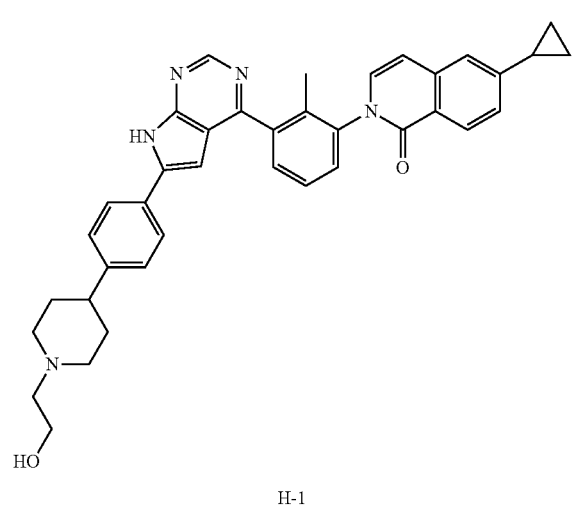

H-1

Step-I: tert-butyl 4-[4-[4-[3-(6-cyclopropyl-1-oxo-2-isoquinolyl)-2-methyl-phenyl]-7-(p-tolylsulfonyl)pyrrolo[2,3-d]pyrimidin-6-yl]phenyl]piperidine-1-carboxylate (H-1-I)

Intermediate H-1-I was synthesized following similar procedure as described in step-I of the synthesis of B-1. LCMS: m/z; 806.4 (M+1)+.

Step-II: 2-[3-[6-[4-[1-[2-[tert-butyl(dimethyl)silyl]oxyethyl]-4-piperidyl]phenyl]-7-(p-tolylsulfonyl)pyrrolo[2,3-d]pyrimidin-4-yl]-2-methyl-phenyl]-6-cyclopropyl-isoquinolin-1-one (H-1-II)

Intermediate H-1-I (0.64 g, 0.795 mmol) was dissolved in dioxane (3 mL), to which 2M HCl in ether (6 mL) was added and the reaction mixture was stirred at room temperature for 2 h. Solvents were removed under reduced pressure and saturated NaHCO$_3$ solution (30 mL) was added to the residue. Extraction was carried out using EtOAc (30 mL×2); the combined organic layers were washed with brine (50 mL), dried over anhydrous Na$_2$SO$_4$, filtered and concentrated under reduced pressure. The residue obtained (0.25 g) was dissolved in DMF (2 mL); to which anhydrous K$_2$CO$_3$ (0.073 g, 0.53 mmol) and 2-bromoethoxy-tert-butyl-dimethyl-silane (0.1 g, 0.42 mmol) were added. The reaction mixture was stirred at room temperature for 16 h. Ice cold water (30 mL) was added to it and the precipitated solid was filtered. It was finally purified using silica gel column chromatography to provide H-1-II (0.26 g, 38% yield for two steps). LCMS: m/z; 864.5 (M+1)+.

Step-III: 6-cyclopropyl-2-[3-[6-[4-[1-(2-hydroxyethyl)-4-piperidyl]phenyl]-7H-pyrrolo[2,3-d]pyrimidin-4-yl]-2-methyl-phenyl]isoquinolin-1-one Intermediate H-1-II (0.26 g, 0.30 mmol) was dissolved in THF (2 mL) and 1N HCl (2 mL) was added to it. The reaction mixture was stirred for 2 h, before volatiles were removed under reduced pressure. The residue obtained was dissolved in THF-H$_2$O (5 mL+5 mL), to which LiOH—H$_2$O (0.1 g, 2.46 mmol) was added and the reaction mixture was stirred at room temperature for 16 h. It was, then, diluted using EtOAc (30 mL) and washed with brine (30 mL). The organic layer was removed under reduced pressure and the residue obtained was purified using preparative HPLC purification to provide title compound H-1 (0.014 g, 8% yield). LCMS: m/z 596.2 (M+1)+. $^1$H NMR (DMSO-d$_6$, 400 MHz) δ 0.80-0.86 (m, 2H); 1.08-1.10 (m, 2H); 1.66-1.74 (m, 4H); 1.87-1.96 (m, 4H); 2.00-2.18 (m, 4H); 2.38-2.44 (m, 2H); 2.98 (d, J=10.3 Hz, 2H); 3.51 (t, J=6.4 Hz, 2H); 6.68 (d, J=7.3 Hz, 1H); 6.85 (s, 1H); 7.27 (d, J=7.6 Hz, 1H); 7.35 (d, J=8.1 Hz, 2H); 7.41-7.52 (aromatics, 3H); 7.56 (t, J=7.6 Hz, 1H); 7.66 (d, J=7.4 Hz, 1H); 7.91 (d, J=8.1 Hz, 2H); 8.13 (d, J=8.4 Hz, 1H); 8.84 (s, 1H).

Example I-1

Synthesis of 8-cyclopropyl-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydro-1,4-benzoxazepin-5-one

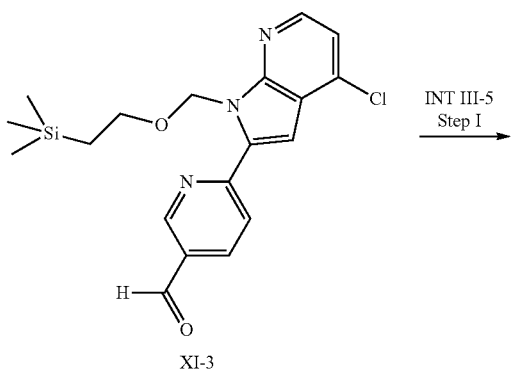

XI-3

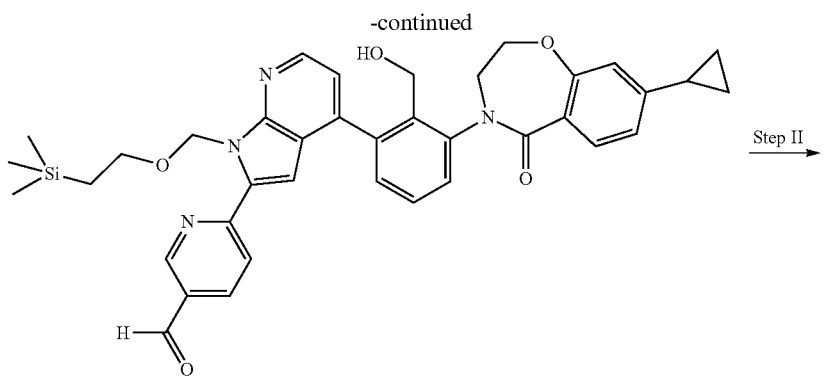

I-1-I

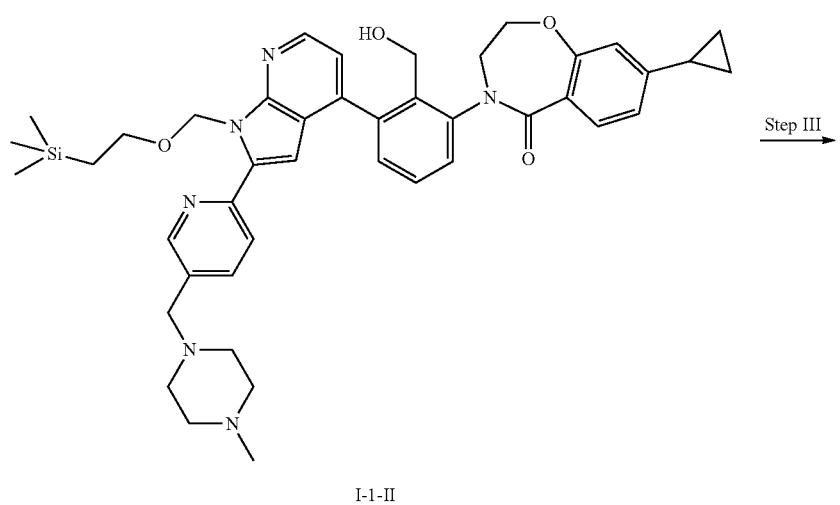

I-1-II

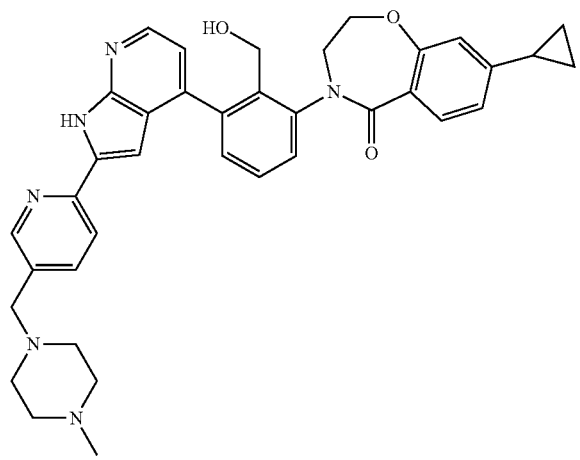

I-1

Step-I: 6-[4-[3-(8-cyclopropyl-5-oxo-2,3-dihydro-1,4-benzoxazepin-4-yl)-2-(hydroxymethyl)phenyl]-1-(2-trimethylsilylethoxymethyl)pyrrolo[2,3-b]pyridin-2-yl]pyridine-3-carbaldehyde (I-1-I)

Intermediate I-14 was synthesized using similar procedure as described in step-I for the synthesis of B-1. LCMS: m/z; 661.4 (M+1)+.

Step-II: 8-cyclopropyl-4-[2-(hydroxymethyl)-3-[2-[5-[(4-methylpiperazin-1-yl)methyl]-2-pyridyl]-1-(2-trimethylsilylethoxymethyl)pyrrolo[2,3-b]pyridin-4-yl]phenyl]-2,3-dihydro-1,4-benzoxazepin-5-one (I-1-II)

Intermediate I-1-II was synthesized following similar procedure as described in step-II of the synthesis of B-1. LCMS: m/z; 745.3 (M+1)+.

Step-III: 8-cyclopropyl-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydro-1,4-benzoxazepin-5-one (I-1)

Intermediate I-1-II (0.45 g, 0.60 mmol) was dissolved in 1M HCl in dioxane (5 mL), to which 4M aqueous HCl (20 mL) solution was added and the reaction mixture was stirred at room temperature for 48 h. Finally, solvents were removed under reduced pressure and saturated NaHCO₃ solution (30 mL) was added to the residue. Extraction was carried out using EtOAc (30 mL×2); the combined organic layers were washed with water (50 mL), brine (50 mL), dried over anhydrous Na₂SO₄, filtered and concentrated under reduced pressure. The residue was purified using preparative HPLC purification to provide title compound I-1 (0.155 g, 33% yield). LCMS: m/z 615.2 (M+1)⁺. $^1$H NMR (DMSO-$d_6$, 400 MHz) δ 0.73-0.77 (m, 2H); 1.00-1.04 (m, 2H); 1.94-1.99 (m, 1H); 2.19 (s, 3H); 2.30-2.45 (m, 8H); 3.52 (s, 2H); 3.86-3.96 (m, 2H); 4.20-4.28 (m, 1H); 4.30-4.40 (m, 1H); 4.52-4.58 (m, 2H); 4.72-4.82 (m, 1H); 6.81 (s, 1H); 6.87-6.90 (aromatics, 2H); 7.22 (bs, 1H); 7.43-7.48 (aromatics, 2H); 7.55-7.59 (m, 1H); 7.66 (d, J=8.2 Hz, 1H); 7.76 (d, J=8.1 Hz, 1H); 8.01 (d, J=8.2 Hz, 1H); 8.32 (d, J=4.6 Hz, 1H); 8.53 (s, 1H); 12.36 (bs, 1H).

Following compounds were synthesized using same sequence of reactions and procedures as described for the synthesis of I-1.

TABLE 22

| No | Structure/IUPAC name | Characterization | INT used (amine used for reductive amination) |
|---|---|---|---|
| I-2 | 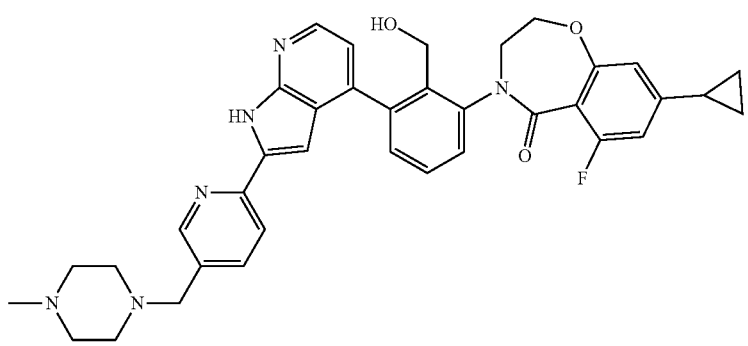<br>8-cyclopropyl-6-fluoro-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydro-1,4-benzoxazepin-5-one | LCMS: m/z 633.2 (M + 1)⁺. $^1$H NMR (DMSO-$d_6$, 400 MHz) δ 0.79-0.80 (m, 2H); 1.02-1.05 (m, 2H); 1.98-2.00 (m, 1H); 2.15 (s, 3H); 2.32-2.45 (m, 8H); 3.51 (s, 2H); 3.80-3.84 (m, 1H); 3.94-4.03 (m, 1H); 4.26 (s, 1H); 4.38-4.39 (m, 2H); 4.49-4.55 (m, 1H); 4.85 (s, 1H); 6.77 (s, 1H); 6.84 (d, J = 11.2 Hz, 1H); 6.90 (d, J = 1.2 Hz, 1H); 7.21 (bs, 1H); 7.44 (d, J = 8.0 Hz, 1H); 7.49 (d, J = 7.5 Hz, 1H); 7.56-7.60 (aromatics, 1H); 7.75 (dd, $J_1$ = 1.8 Hz, $J_2$ = 8.0 Hz, 1H); 8.01 (d, J = 8.0 Hz, 1H); 8.32 (d, J = 4.8 Hz, 1H); 8.52 (s, 1H); 12.36 (s, 1H) | XI-3 & III-9 (N-Me-piperazine) |
| I-3 | 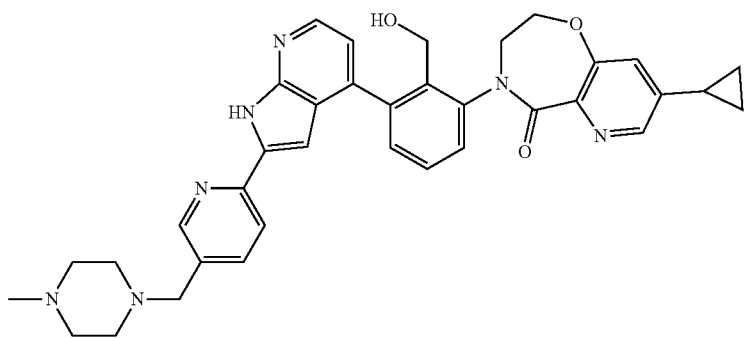 [SMILES: CN1CCN(Cc2ccc(-c3cc4c(-c5cccc(N6CCOc7cc(C8CC8)cnc7C6=O)c5CO)ccnc4[nH]3)nc2)CC1]<br>8-cyclopropyl-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydropyrido[2,3-f][1,4]oxazepin-5-one | LCMS: m/z 616.2 (M + 1)⁺. $^1$H NMR (DMSO-$d_6$, 400 MHz) δ 0.82-0.90 (m, 2H); 1.04-1.12 (m, 2H); 2.02-2.08 (m, 1H); 2.14 (s, 3H); 2.24-2.42 (m, 8H); 3.51 (bs, 2H); 3.84-4.04 (m, 2H); 4.20-4.30 (m, 1H); 4.36-4.44 (m, 1H); 4.48-4.62 (m, 2H); 4.78-4.90 (m, 1H); 6.91 (s, 1H); 7.23 (s, 2H); 7.46-7.50 (aromatics, 2H); 7.57-7.59 (aromatics, 1H); 7.76 (d, J = 7.1 Hz, 1H); 8.01 (d, J = 7.9 Hz, 1H); 8.32 (s, 2H); 8.52 (s, 1H); 12.36 (s, 1H) | XI-3 & III-10-a (N-Me-piperazine) |

TABLE 22-continued

| No | Structure/IUPAC name | Characterization | INT used (amine used for reductive amination) |
|---|---|---|---|
| I-4 | 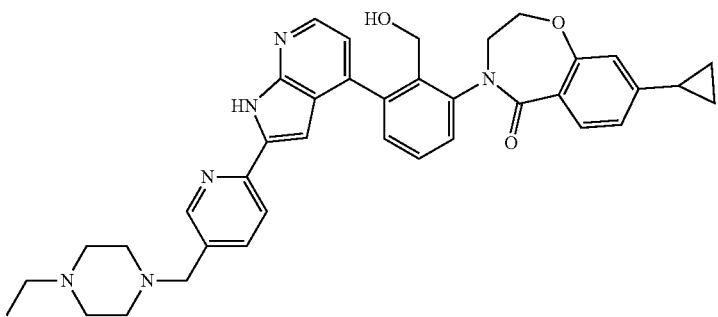 [SMILES: CCN1CCN(Cc2ccc(-c3cc4c(-c5cccc(N6CCOc7cc(C8CC8)ccc7C6=O)c5CO)ccnc4[nH]3)nc2)CC1]<br>8-cyclopropyl-4-[3-[2-[5-[(4-ethylpiperazin-1-yl)methyl]-2-pyridyl]-1H-pyrrolo[2,3-b]pyridin-4-yl]-2-(hydroxymethyl)phenyl]-2,3-dihydro-1,4-benzoxazepin-5-one | LCMS: m/z 629.2 (M + 1)$^+$. $^1$H NMR (DMSO-d$_6$, 400 MHz) δ 0.73-0.77 (m, 2H); 0.95-1.04 (m, 5H); 1.94-1.99 (m, 1H); 2.26-2.32 (m, 4H); 2.34-2.44 (m, 6H); 3.51 (bs, 2H); 3.90-3.96 (m, 2H); 4.20-4.28 (m, 1H); 4.32-4.38 (m, 1H); 4.52-4.58 (m, 2H); 4.74-4.82 (m, 1H); 6.81 (d, J = 0.8 Hz, 1H); 6.87-6.94 (aromatics, 2H); 7.21 (bs, 1H); 7.43 (d, J = 7.9 Hz, 1H); 7.47 (d, J = 7.5 Hz, 1H); 7.55-7.59 (aromatics, 1H); 7.66 (d, J = 8.4 Hz, 1H); 7.75 (d, J = 8.0 Hz, 1H); 8.01 (d, J = 7.9 Hz, 1H); 8.32 (d, J = 4.8 Hz, 1H); 8.52 (s, 1H); 12.35 (s, 1H) | XI-3 & III-5 (N-Et-piperazine) |
| I-5 | 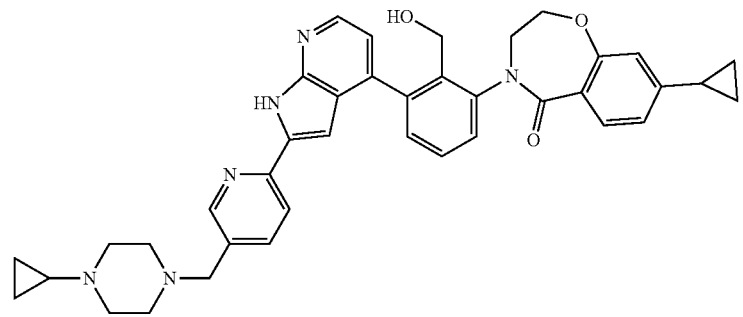 [SMILES: O=C1c2ccc(C3CC3)cc2OCCN1c1cccc(-c2ccnc3[nH]c(-c4ccc(CN5CCN(C6CC6)CC5)cn4)cc23)c1CO]<br>8-cyclopropyl-4-[3-[2-[5-[(4-cyclopropylpiperazin-1-yl)methyl]-2-pyridyl]-1H-pyrrolo[2,3-b]pyridin-4-yl]-2-(hydroxymethyl)phenyl]-2,3-dihydro-1,4-benzoxazepin-5-one | LCMS: m/z 641.2 (M + 1)$^+$. $^1$H NMR (DMSO-d$_6$, 400 MHz) δ 0.22-0.28 (m, 2H); 0.38-0.42 (m, 2H); 0.72-0.78 (m, 2H); 0.98-1.06 (m, 2H); 1.54-1.62 (m, 1H); 1.94-2.02 (m, 1H); 2.26-2.60 (m, 8H); 3.50 (bs, 2H); 3.90-3.96 (m, 2H); 4.20-4.38 (m, 2H); 4.52-4.60 (m, 2H); 4.74-4.82 (m, 1H); 6.81 (s, 1H); 6.87-6.90 (aromatics, 2H); 7.21 (bs, 1H); 7.42-7.48 (aromatics, 2H); 7.55-7.60 (aromatic, 1H); 7.67 (d, J = 8.4 Hz, 1H); 7.76 (d, J = 8.4 Hz, 1H); 8.01 (d, J = 8.4 Hz, 1H); 8.32 (d, J = 4.9 Hz, 1H); 8.52 (bs, 1H); 12.35 (bs, 1H) | XI-3 & III-5 (N-cyclopropyl-piperazine) |
| I-6 | 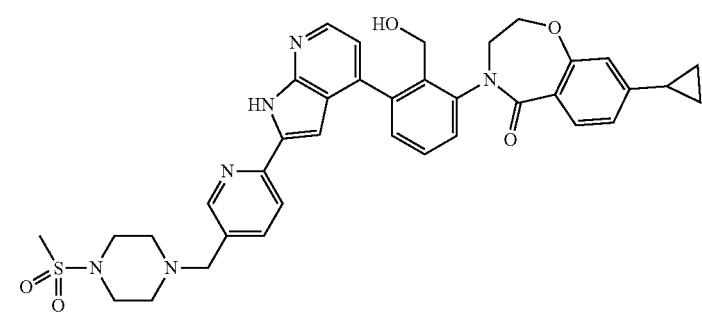 [SMILES: CS(=O)(=O)N1CCN(Cc2ccc(-c3cc4c(-c5cccc(N6CCOc7cc(C8CC8)ccc7C6=O)c5CO)ccnc4[nH]3)nc2)CC1]<br>8-cyclopropyl-4-[2-(hydroxymethyl)-3-[2-[5-[(4-methylsulfonylpiperazin-1-yl)methyl]-2-pyridyl]-1H-pyrrolo[2,3-b]pyridin-4-yl]phenyl]-2,3-dihydro-1,4-benzoxazepin-5-one | LCMS: m/z 679.1 (M + 1)$^+$. $^1$H NMR (DMSO-d$_6$, 400 MHz) δ 0.73-0.77 (m, 2H); 0.98-1.04 (m, 2H); 1.94-2.02 (m, 1H); 2.40-2.60 (m, 4H); 2.79 (s, 3H); 3.08-3.18 (m, 4H); 3.59 (bs, 2H); 3.88-3.98 (m, 2H); 4.20-4.28 (m, 1H); 4.30-4.38 (m, 1H); 4.52-4.60 (m, 2H); 4.76-4.86 (m, 1H); 6.82 (s, 1H); 6.89 (dd, J$_1$ = 1.4 Hz, J$_2$ = 8.4 Hz, 1H); 6.92 (d, J = 1.3 Hz, 1H); 7.20-7.26 (aromatics, 1H); 7.44 (d, J = 7.9 Hz, 1H); 7.48 (d, J = 7.5 Hz, 1H); 7.55-7.59 (aromatics, 1H); 7.66 (d, J = 8.4 Hz, 1H); 7.79 (dd, J$_1$ = 1.8 Hz, J$_2$ = 8.4 Hz, 1H); 8.03 (d, J = 8.0 Hz, 1H); 8.33 (d, J = 7.7 Hz, 1H); 8.55 (s, 1H); 12.40 (bs, 1H) | XI-3 & III-5 (1-methyl-sulfonyl-piperazine) |

TABLE 22-continued

| No | Structure/IUPAC name | Characterization | INT used (amine used for reductive amination) |
|---|---|---|---|
| I-7 | 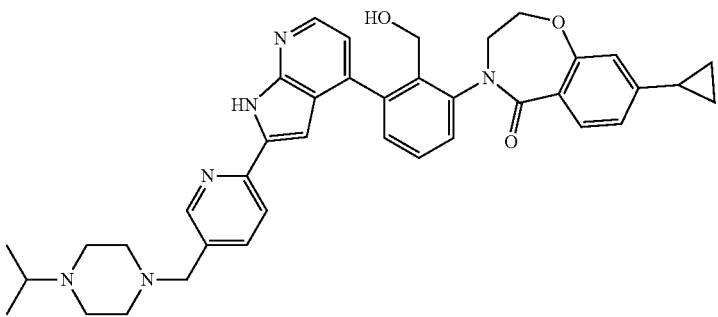<br>8-cyclopropyl-4-[2-(hydroxymethyl)-3-[2-[5-[(4-isopropylpiperazin-1-yl)methyl]-2-pyridyl]-1H-pyrrolo[2,3-b]pyridin-4-yl]phenyl]-2,3-dihydro-1,4-benzoxazepin-5-one | LCMS: m/z 643.2 (M + 1)$^+$.<br>$^1$H NMR (CDCl$_3$, 400 MHz) δ 0.76-0.80 (m, 2H); 1.02-1.12 (m, 8H); 1.92-1.98 (m, 1H); 2.50-2.80 (m, 10H); 3.55 (s, 2H); 3.90-4.00 (m, 2H); 4.30-4.40 (m, 1H); 4.48-4.64 (m, 3H); 6.78-6.81 (aromatics, 2H); 6.92 (d, J = 7.9 Hz, 1H); 7.38 (d, J = 8.8 Hz, 1H); 7.50-7.74 (aromatics, 5H); 7.82 (d, J = 8.0 Hz, 1H); 8.44 (bs, 1H); 8.55 (bs, 1H); 10.40 (bs, 1H) | XI-3 & III-5 (N-isopropyl-piperazine) |
| I-8 | 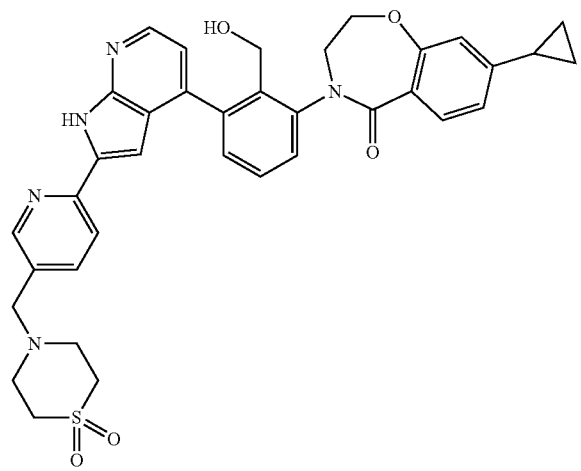 [SMILES: O=C1c2ccc(C3CC3)cc2OCCN1c1cccc(-c2ccnc3[nH]c(-c4ccc(CN5CCS(=O)(=O)CC5)cn4)cc23)c1CO]<br>8-cyclopropyl-4-[3-[2-[5-[(1,1-dioxo-1,4-thiazinan-4-yl)methyl]-2-pyridyl]-1H-pyrrolo[2,3-b]pyridin-4-yl]-2-(hydroxymethyl)phenyl]-2,3-dihydro-1,4-benzoxazepin-5-one | LCMS: m/z 650.1 (M + 1)$^+$.<br>$^1$H NMR (CDCl$_3$, 400 MHz) δ 0.76-0.81 (m, 2H); 1.04-1.09 (m, 4H); 1.90-1.97 (m, 1H); 2.63 (q, J = 7.1 Hz, 2H); 3.00-3.14 (m, 6H); 3.70 (s, 2H); 3.92-4.00 (m, 2H); 4.20-4.40 (bs, 1H); 4.50-4.62 (m, 2H); 6.79 (d, J = 1.5 Hz, 1H); 6.84 (bs, 1H); 6.93 (dd, J$_1$ = 1.5 Hz, J$_2$ = 8.1 Hz, 1H); 7.39 (d, J = 9.1 Hz, 1H); 7.55-7.59 (aromatics, 3H); 7.66-7.68 (aromatics, 1H); 7.72-7.75 (aromatics, 1H); 7.82 (d, J = 8.0 Hz, 1H); 8.44 (bs, 1H); 8.56 (bs, 1H); 10.24 (bs, 1H) | XI-3 & III-5 (1,4-thiazinane 1,1-dioxide) |
| I-9 | 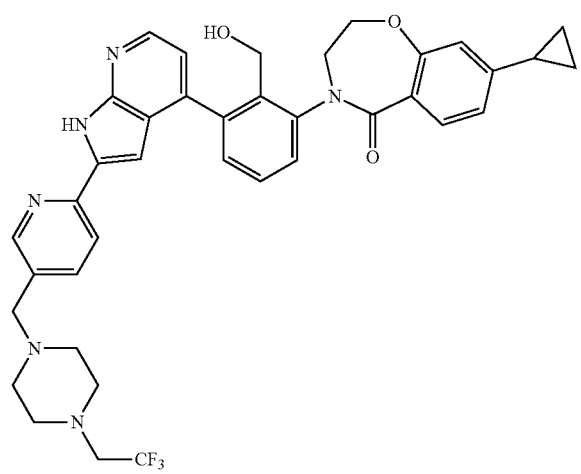 [SMILES: O=C1c2ccc(C3CC3)cc2OCCN1c1cccc(-c2ccnc3[nH]c(-c4ccc(CN5CCN(CC(F)(F)F)CC5)cn4)cc23)c1CO]<br>8-cyclopropyl-4-[2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one | LCMS: m/z 683.1 (M + 1)$^+$.<br>$^1$H NMR (CDCl$_3$, 400 MHz) δ 0.76-0.81 (m, 2H); 1.04-1.09 (m, 2H); 1.89-1.96 (m, 1H); 2.44-2.56 (m, 4H); 2.66-2.76 (m, 4H); 2.93-3.01 (m, 2H); 3.54 (s, 2H); 3.92-3.98 (m, 2H); 4.26-4.44 (bs, 1H); 4.50-4.64 (m, 3H); 6.78 (d, J = 1.2 Hz, 1H); 6.81 (bs, 1H); 6.92 (d, J = 8.1 Hz, 1H); 7.36-7.39 (aromatics, 1H); 7.52-7.72 (aromatic, 5H); 7.82 (d, J = 8.3 Hz, 1H); 8.44 (bs, 1H); 8.55 (bs, 1H); 10.40 (bs, 1H) | XI-3 & III-5 [N-(trifluoro-ethyl)piperazine] |

TABLE 22-continued

| No | Structure/IUPAC name | Characterization | INT used (amine used for reductive amination) |
|---|---|---|---|
| I-10 | 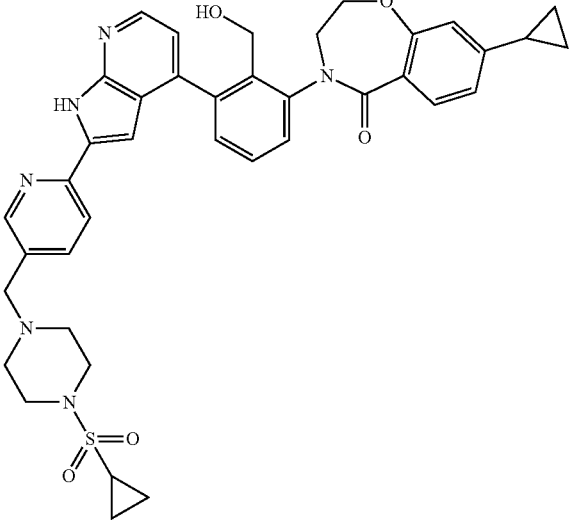<br>8-cyclopropyl-4-[3-[2-[5-[(4-cyclopropylsulfonylpiperazin-1-yl)methyl]-2-pyridyl]-1H-pyrrolo[2,3-b]pyridin-4-yl]-2-(hydroxymethyl)phenyl]-2,3-dihydro-1,4-benzoxazepin-5-one | LCMS: m/z 705.1 (M + 1)$^+$.<br>$^1$H NMR (CDCl$_3$, 400 MHz) δ 0.76-0.81 (m, 2H); 0.96-1.02 (m, 2H); 1.04-1.10 (m, 2H); 1.14-1.20 (m, 2H); 1.89-1.98 (m, 1H); 2.23-2.35 (m, 1H); 2.50-2.80 (m, 8H); 3.58 (s, 2H); 3.92-4.00 (m, 2H); 4.50-4.60 (m, 2H); 4.50-4.64 (m, 3H); 6.78 (d, J = 1.0 Hz, 1H); 6.84 (bs, 1H); 6.92 (d, J = 7.8 Hz, 1H); 7.37-7.39 (aromatics, 1H); 7.50-7.60 (aromatics, 4H); 7.65-7.73 (aromatics, 1H); 7.82 (d, J = 8.3 Hz, 1H); 8.38 (d, J = 4.4 Hz, 1H); 8.60 (bs, 1H); 11.15 (bs, 1H) | XI-3 & III-5 [1-(cyclopropylsulfonyl)piperazine] |
| I-11 | 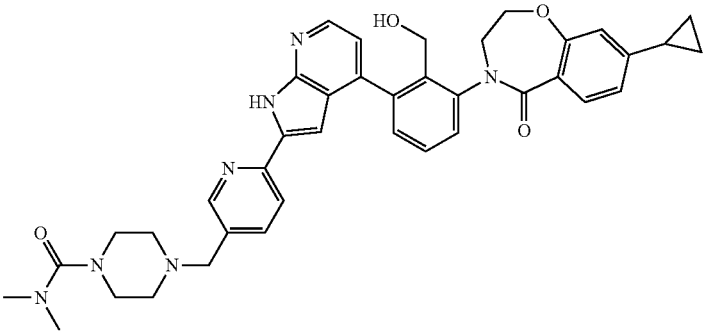 [SMILES: CN(C)C(=O)N1CCN(Cc2ccc(-c3cc4c(-c5cccc(N6CCOc7cc(C8CC8)ccc7C6=O)c5CO)ccnc4[nH]3)nc2)CC1]<br>4-[[6-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]-3-pyridyl]methyl]-N,N-dimethyl-piperazine-1-carboxamide | LCMS: m/z; 672.2 (M + 1)$^+$.<br>$^1$H NMR (CDCl$_3$, 400 MHz) δ 0.77-0.80 (m, 2H); 1.04-1.09 (m, 2H); 1.89-1.96 (m, 1H); 2.42-2.49 (m, 4H); 2.82 (s, 6H); 3.10-3.27 (m, 4H), 2.33 (s, 2H); 3.91-3.97 (m, 2H), 4.41 (bs, 1H), 4.45-4.56 (m, 4H); 6.78-6.82 (aromatics, 2H); 6.92 (d, J = 8.0 Hz, 1H); 7.37-7.39 (aromatics, 2H); 7.52-7.56 (aromatics, 2H); 7.71-7.73 (aromatics, 2H); 7.82 (d, J = 8.8 Hz, 1H); 8.46 (s, 1H); 8.55 (s, 1H); 10.24 (s, 1H) | XI-3 & III-5 [N,N-dimethylpiperazine-1-carboxamide] |

Example I-12
Synthesis of 8-cyclopropyl-4-[3-[2-[5-[(4-ethylpiperazin-1-yl)methyl]-2-pyridyl]-1H-pyrrolo[2,3-b]pyridin-4-yl]-2-(hydroxymethyl)phenyl]-6-fluoro-2,3-dihydro-1,4-benzoxazepin-5-one
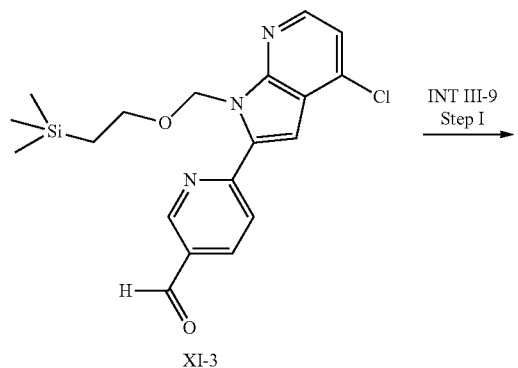
XI-3
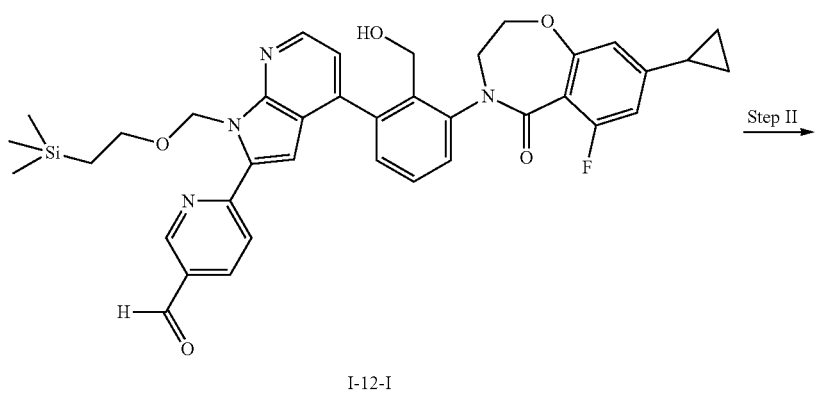
I-12-I
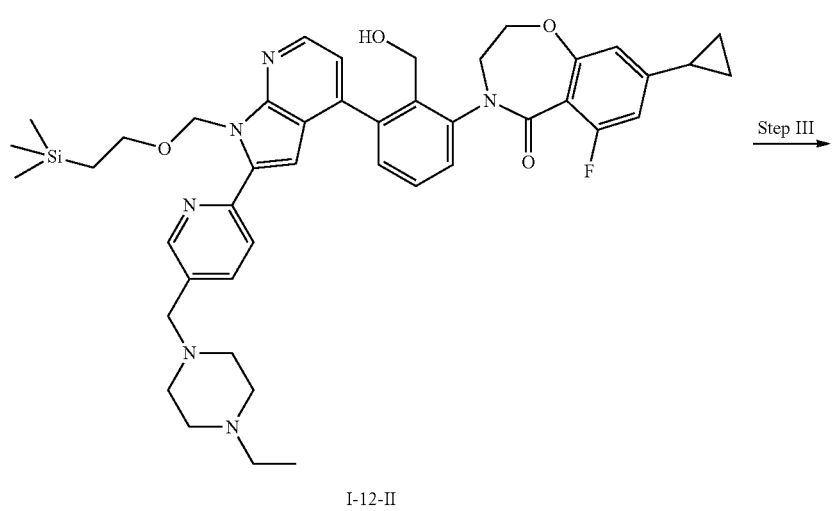
I-12-II

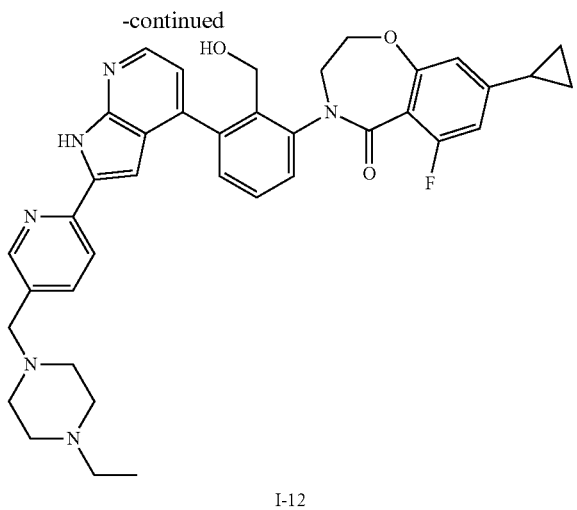

I-12

Step-I: Synthesis of 6-[4-[3-(8-cyclopropyl-6-fluoro-5-oxo-2,3-dihydro-1,4-benzoxazepin-4-yl)-2-(hydroxymethyl)phenyl]-1-(2-trimethylsilylethoxymethyl)pyrrolo[2,3-b]pyridin-2-yl]pyridine-3-carbaldehyde (I-12-I)

To a solution of XI-3 (1.5 g, 3.87 mmol) and III-9 (60% pure by HPLC) (2.8 g, 5.64 mmol) in 1,4-dioxane (60 mL) was added a solution of Na$_2$CO$_3$ (2 g, 18.9 mmol) in water (15 mL). Argon was purged through this for 20 min. Finally, Pd(PPh$_3$)$_4$ (0.223 g, 0.19 mmol) was added to it and purging was continued for 20 min more. The reaction mixture was then stirred at 90-100° C. for 16 h. Dioxane was then removed under reduced pressure and the residue was diluted using EtOAc (150 mL). The organic layers were washed with brine (100 mL); dried over anhydrous Na$_2$SO$_4$, filtered and concentrated under reduced pressure. The residue was purified using silica gel column chromatography to provide I-12-I (1.2 g, 46% yield). LCMS: 679 (M+1)$^+$ Step-II: Synthesis of 8-cyclopropyl-4-[3-[2-[5-[(4-ethylpiperazin-1-yl)methyl]-2-pyridyl]-1-(2-trimethylsilylethoxymethyl)pyrrolo[2,3-b]pyridin-4-yl]-2-(hydroxymethyl)phenyl]-6-fluoro-2,3-dihydro-1,4-benzoxazepin-5-one (I-12-II)

To a solution of I-12-I (2 g, 2.95 mmol) in CH$_2$Cl$_2$ (40 mL) was added N-Et-piperadine (4.5 mL, 35 mmol), HOAc (1 mL) and 4 A° molecular sieves. After stirring for 1 h, NaBH$_3$CN (0.186 g, 2.95 mmol) was added to it and the reaction mixture was stirred for 2-3 h. After complete consumption of SM (indicated by TLC), saturated NaHCO$_3$ solution was added to it. Extraction was carried out using CH$_2$Cl$_2$ (50 mL×2); the combined organic layers were washed with brine (70 mL); dried over anhydrous Na$_2$SO$_4$, filtered and concentrated under reduced pressure. The residue was purified using silica gel column chromatography (4-10% MeOH in CH$_2$Cl$_2$) to provide desired intermediate I-12-II (1.7 g, 74% yield). LCMS: 777.3 (M+1)$^+$.

Step-III: 8-cyclopropyl-4-[3-[2-[5-[(4-ethylpiperazin-1-yl)methyl]-2-pyridyl]-1H-pyrrolo[2,3-b]pyridin-4-yl]-2-(hydroxymethyl)phenyl]-6-fluoro-2,3-dihydro-1,4-benzoxazepin-5-one (I-12)

To a solution of I-12-II (1.8 g, 2.32 mmol) in CH$_2$Cl$_2$ (15 mL) was added TFA (7 mL, excess) and the reaction mixture was stirred at room temperature for 3-4 h. After completion of the reaction, solvents were removed under reduced pressure and saturated NaHCO$_3$ solution (50 mL) was added to the residue. Extraction was carried out using CH$_2$Cl$_2$ (50 mL×3); the combined organic layers were washed with brine (70 mL); dried over anhydrous Na$_2$SO$_4$, filtered and concentrated under reduced pressure. The residue was subjected to silica gel column chromatography followed by crystallization using acetonitrile (20 mL) to provide desired compound I-12 (1.4 g, 93% yield). LCMS: m/z 647.2 (M+1)$^+$. $^1$H NMR (DMSO-d$_6$, 400 MHz) δ 0.77-0.78 (m, 2H); 0.94-1.03 (m, 5H); 1.96-2.02 (m, 1H); 2.28-2.33 (m, 6H); 3.52 (bs, 2H); 3.76-3.85 (m, 2H); 3.93-3.99 (m, 2H); 4.20-4.26 (m, 2H); 4.31-4.41 (m, 2H); 4.46-4.52 (m, 2H); 4.82 (bs, 1H); 6.76 (s, 1H); 6.82-6.84 (aromatics, 1H); 6.88 (s, 1H); 7.20 (bs, 1H); 7.42-7.48 (aromatics, 2H); 7.59-7.61 (aromatics, 1H); 7.74 (d, J=6.8 Hz, 1H); 8.01 (d, J=8.0 Hz, 1H); 8.31 (d, J=4.8 Hz, 1H); 8.51 (s, 1H); 12.36 (s, 1H)

Following compounds were synthesized using similar sequence of reactions and procedures as described for the synthesis of I-12.

TABLE 23

| No | Structure/IUPAC name | Characterization | INT used (amine used for reductive amination) |
|---|---|---|---|
| I-13 | 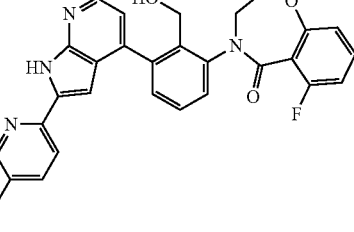<br>8-cyclopropyl-6-fluoro-4-[2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one | LCMS: m/z 675.4 (M + 1)$^+$. $^1$H NMR (DMSO-d$_6$, 400 MHz) δ 0.77-0.82 (m, 2H); 1.00-1.06 (m, 2H); 1.96-2.04 (m, 1H); 2.20-2.32 (m, 4H); 2.38-2.50 (m, 4H); 3.38 (t, J = 6.3 Hz, 1H); 3.53 (s, 2H); 3.78-4.02 (m, 2H); 4.24-4.32 (m, 1H); 4.35-4.45 (m, 4H); 4.48-4.52 (m, 3H); 4.75-4.85 (m, 1H); 6.77 (s, 1H); 6.84 (d, J = 11.2 Hz, 1H); 6.90 (d, J = 1.5 Hz, 1H); 7.21 (d, J = 3.9 Hz, 1H); 7.43-7.49 (aromatics, 2H); 7.56-7.62 (aromatics, 1H); 7.75 (dd, J$_1$ = 1.5 Hz, J$_2$ = 8.3 Hz, 1H); 8.01 (d, J = 8.4 Hz, 1H); 8.32 (d, J = 4.9 Hz, 1H); 8.52 (s, 1H); 12.38 (s, 1H) | XI-3 & III-9; [1-(oxetan-3-yl)piperazine] |
| I-14 | 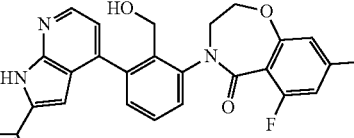<br>8-cyclopropyl-6-fluoro-4-[2-(hydroxymethyl)-3-[2-[5-[(3,4,5-trimethylpiperazin-1-yl)methyl]-2-pyridyl]-1H-pyrrolo[2,3-b]pyridin-4-yl]phenyl]-2,3-dihydro-1,4-benzoxazepin-5-one | LCMS: m/z 661.7 (M + 1)$^+$. $^1$H NMR (DMSO-d$_6$, 400 MHz) δ 0.77-0.81 (m, 2H); 0.90-1.10 (m, 8H); 1.80-2.30 (m, 6H); 2.50-2.80 (m, 4H); 3.49 (bs, 2H); 3.76-3.85 (m, 1H); 3.93-4.02 (m, 1H); 4.20-4.60 (m, 4H); 4.85 (bs, 1H); 6.77 (s, 1H); 6.83 (dd, J$_1$ = 1.2 Hz, J$_2$ = 11.2 Hz, 1H); 6.90 (d, J = 1.6 Hz, 1H); 7.21 (d, J = 4.0 Hz, 1H); 7.44-7.49 (aromatics, 2H); 7.56-7.60 (aromatics, 1H); 7.76 (d, J = 8.0 Hz, 1H); 8.02 (d, J = 8.4 Hz, 1H); 8.33 (d, J = 4.8 Hz, 1H); 8.53 (s, 1H); 12.36 (s, 1H) | XI-3 & III-9 [2,6-dimethyl-1-Methyl piperazine] |
| I-15 | 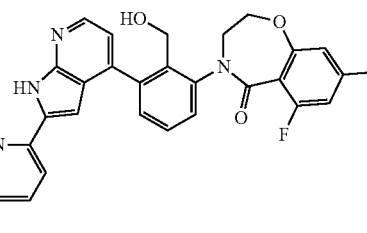<br>8-cyclopropyl-6-fluoro-4-[2-(hydroxymethyl)-3-[2-[5-[(4-methyl-3-oxo-piperazin-1-yl)methyl]-2-pyridyl]-1H-pyrrolo[2,3-b]pyridin-4-yl]phenyl]-2,3-dihydro-1,4-benzoxazepin-5-one | LCMS: m/z 647.3 (M + 1)$^+$. $^1$H NMR (DMSO-d$_6$, 400 MHz) δ 0.77-0.81 (m, 2H); 1.00-1.06 (m, 2H); 1.95-2.03 (m, 1H); 2.63-2.66 (m, 2H); 2.81 (s, 3H); 3.01 (bs, 2H); 3.24-3.27 (m, 2H); 3.60 (s, 2H); 3.80-3.88 (m, 1H); 3.92-4.03 (m, 1H); 4.20-4.60 (m, 4H); 4.80 (bs, 1H); 6.77 (s, 1H); 6.84 (d, J = 11.2 Hz, 1H); 6.91 (d, J = 2.0 Hz, 1H); 7.21 (d, J = 3.6 Hz, 1H); 7.43-7.50 (aromatics, 2H); 7.56-7.60 (aromatics, 1H); 7.80 (dd, J$_1$ = 2.0 Hz, J$_2$ = 8.4 Hz, 1H); 8.03 (d, J = 8.0 Hz, 1H); 8.33 (d, J = 4.8 Hz, 1H); 8.56 (s, 1H); 12.36 (s, 1H) | XI-3 & III-9 [1-Methyl piperazine 2-one] |

TABLE 23-continued

| No | Structure/IUPAC name | Characterization | INT used (amine used for reductive amination) |
|---|---|---|---|
| I-16 | 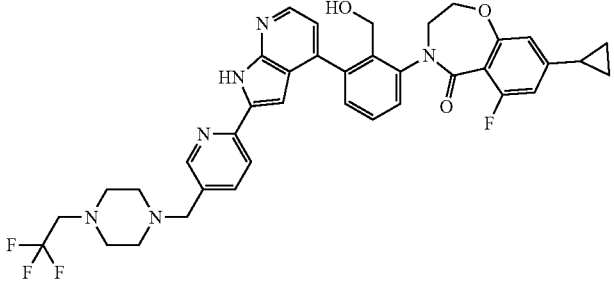 [SMILES: O=C1c2c(F)cc(C3CC3)cc2OCCN1c1cccc(-c2ccnc3[nH]c(-c4ccc(CN5CCN(CC(F)(F)F)CC5)cn4)cc23)c1CO]<br>8-cyclopropyl-6-fluoro-4-[2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one | LCMS: m/z 701.3 (M + 1)$^+$. $^1$H NMR (DMSO-d$_6$, 400 MHz) δ 0.77-0.78 (m, 2H); 0.98-1.05 (m, 2H); 1.92-2.02 (m, 1H); 2.30-2.45 (m, 4H); 2.55-2.70 (m, 4H); 3.14 (q, J = 10.4 Hz, 2H); 3.50 (s, 2H); 3.74-4.00 (m, 2H); 4.20-4.30 (m, 1H); 4.30-4.40 (m, 2H); 4.45-4.55 (m, 1H); 4.79 (bs, 1H); 6.76 (s, 1H); 6.82 (d, J = 11.2 Hz, 1H); 6.88 (s, 1H); 7.19 (d, J = 4.0 Hz, 1H); 7.40-7.50 (aromatics, 2H); 7.54-7.58 (m, 1H); 7.74 (d, J = 8.4 Hz, 1H); 8.00 (d, J = 6.8 Hz, 1H); 8.31 (d, J = 5.2 Hz, 1H); 8.50 (s, 1H); 12.36 (s, 1H) | XI-3 & III-9 [N-(trifluoroethyl)piperazine] |

Example I-17

Synthesis of 8-cyclopropyl-6-fluoro-4-[5-fluoro-2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one

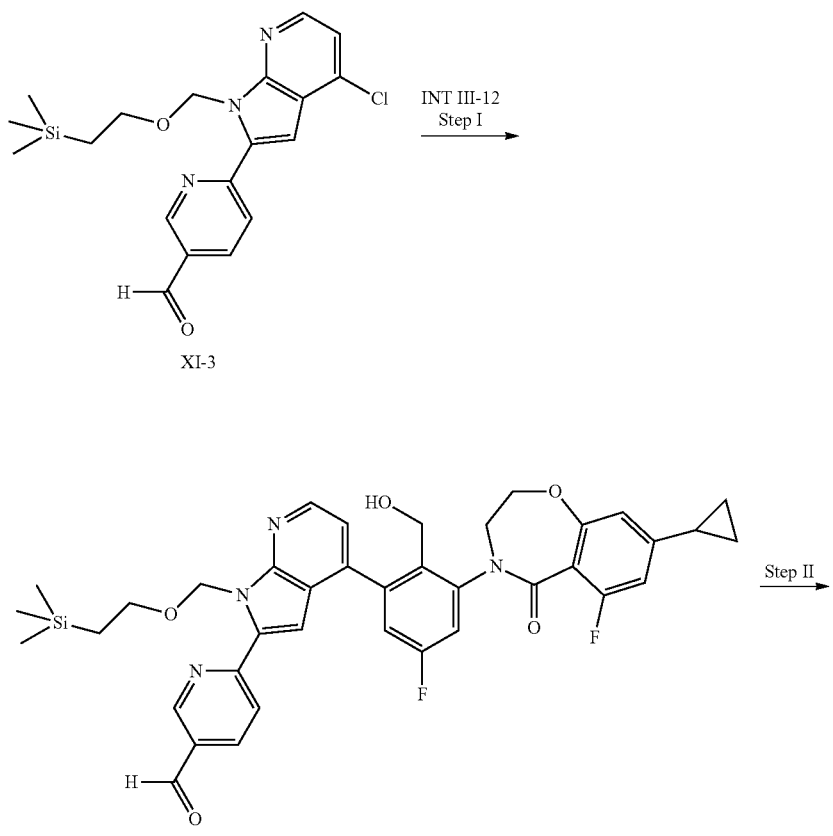

-continued

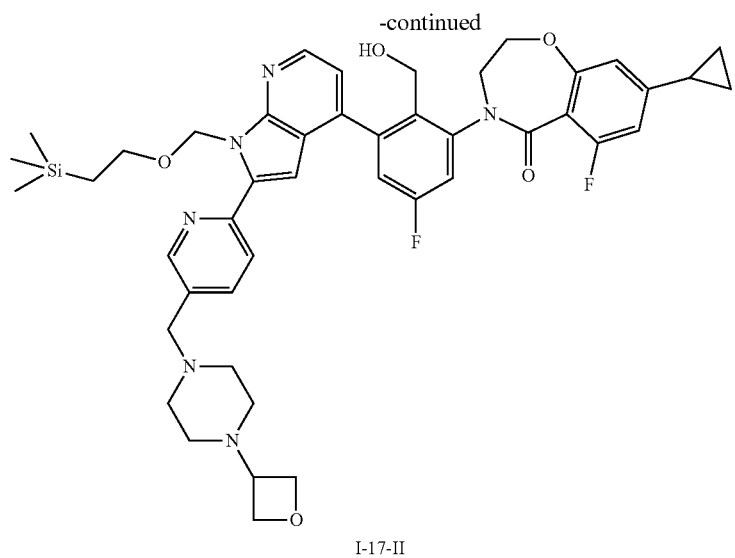

I-17-II

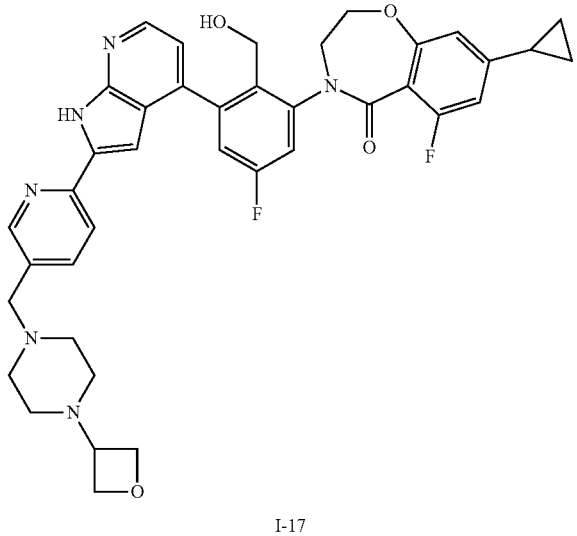

I-17

Step-I: Synthesis of 6-[4-[3-(8-cyclopropyl-6-fluoro-5-oxo-2,3-dihydro-1,4-benzoxazepin-4-yl)-5-fluoro-2-(hydroxymethyl)phenyl]-1-(2-trimethylsilylethoxymethyl)pyrrolo[2,3-b]pyridin-2-yl]pyridine-3-carbaldehyde (I-17-I)

To a solution of XI-13 (20 g, 51.67 mmol) and III-12 (80% pure by LCMS) (37.1 g, 57.74 mmol) in 1,4-dioxane (400 mL) was added a solution of $Na_2CO_3$ (5.9 g, 155 mmol) in water (80 mL). Argon was purged through this for 20 min. Finally, $Pd(PPh_3)_4$ (5.9 g, 5.16 mmol) was added to it and purging was continued for 20 min more. The reaction mixture was then stirred at 100° C. (oil-bath temperature) for 9 h. After completion of the reaction, dioxane was removed under reduced pressure and the residue was diluted using water (250 mL). Extraction was carried out using EtOAc (200 mL×3); the combined organic layers were washed with brine (300 mL); dried over anhydrous $Na_2SO_4$, filtered and concentrated under reduced pressure. The residue was purified using silica gel column chromatography to provide I-17-I (28 g, 78% yield). LCMS: m/z 697 (M+1)⁺. (60% pure, it contains TPPO as impurity).

Step-II: Synthesis of 8-cyclopropyl-6-fluoro-4-[5-fluoro-2-(hydroxymethyl)-3-[2-[5-[[4-(oxetan-3-yl)piperazin-1-yl]methyl]-2-pyridyl]-1-(2-trimethylsilylethoxymethyl)pyrrolo[2,3-b]pyridin-4-yl]phenyl]-2,3-dihydro-1,4-benzoxazepin-5-one (I-17-II)

To a solution of I-17-I (mixture of OH and OAc, ~25% OAc) (3.7 g, 5.3 mmol) in $CH_2Cl_2$ (40 mL) was added 1-(oxetan-3-yl)piperazine (7.5 g, 53 mmol) (CAS: 1254115-23-5), HOAc (5 drops) and 4 A° molecular sieves (~500 mg). After stirring for 2 h, sodium triacetoxyborohydride (2.2 g, 10.6 mmol) was added to it and the reaction mixture was stirred for 16 h. After complete consumption of starting material (indicated by TLC), saturated NaHCO$_3$ solution (60 mL) was added to it and extraction was carried out using CH$_2$Cl$_2$ (50 mL×2). The combined organic layers were washed with water (100 mL), brine (100 mL); dried over anhydrous Na$_2$SO$_4$, filtered and concentrated under reduced pressure. The residue was purified using silica gel column chromatography (2-3% MeOH in CH$_2$Cl$_2$) to provide desired intermediate I-17-II. Isolated yield: 3.3 g (mixture of OH and OAc); LCMS: m/z 823 (M+1)$^+$.

Step-III

To a solution of I-17-II (4.1 g, 4.98 mmol) in CH$_2$Cl$_2$ (40 mL) was added TFA (20 mL, excess) and the reaction mixture was stirred at room temperature for 2 h. After completion of the reaction, solvents were removed under reduced pressure and saturated NaHCO$_3$ solution (50 mL) was added to the residue (pH: ~8). Extraction was carried out using CH$_2$Cl$_2$ (70 mL×3); the combined organic layers were washed with brine (100 mL); dried over anhydrous Na$_2$SO$_4$, filtered and concentrated under reduced pressure. The residue obtained was dissolved in THF (50 mL), to which aqueous LiOH—H$_2$O (1 g, 24.9 mmol, 10 mL water) was added and it was stirred at room temperature for 6-8 h (to convert OAc to OH). It was then diluted using water (30 mL) and extraction was carried out using EtOAc (50 mL×3). The combined organic layers were washed with brine (100 mL); dried over anhydrous Na$_2$SO$_4$, filtered and concentrated under reduced pressure. The residue obtained was subjected to silica gel column chromatography (4-5% MeOH in CH$_2$Cl$_2$); followed by crystallization of the residue using acetonitrile (20 mL) to provide final product I-17 (1.3 g, 37% yield). LCMS: m/z 693.3 (M+1)$^+$. $^1$H NMR (DMSO-d$_6$, 400 MHz) δ 0.77-0.82 (m, 2H); 1.00-1.10 (m, 2H); 1.95-2.05 (m, 1H); 2.30-2.50 (m, 8H); 3.34-3.41 (m, 1H); 3.53 (s, 2H); 3.80-4.00 (m, 2H); 4.15-4.30 (m, 1H); 4.30-4.40 (m, 2H); 4.40 (t, J=6.0 Hz, 2H); 4.51 (t, J=6.0 Hz, 2H); 4.50-4.60 (m, 1H); 4.79 (bs, 1H); 6.77 (s, 1H); 6.84 (d, J=11.2 Hz, 1H); 6.93 (d, J=2.0 Hz, 1H); 7.22 (d, J=3.6 Hz, 1H); 7.34 (dd, J$_1$=2.8 Hz, J$_2$=9.2 Hz, 1H); 7.40 (dd, J$_1$=3.2 Hz, J$_2$=9.2 Hz, 1H); 7.76 (dd, J$_1$=2.0 Hz, J$_2$=8.4 Hz, 1H); 8.04 (d, J=8.0 Hz, 1H); 8.34 (d, J=4.8 Hz, 1H); 8.53 (s, 1H); 12.38 (s, 1H)

Alternate Route for the Synthesis of I-17

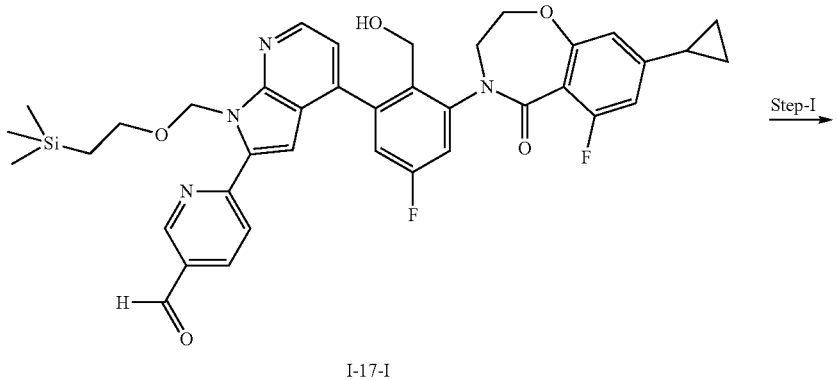

I-17-I

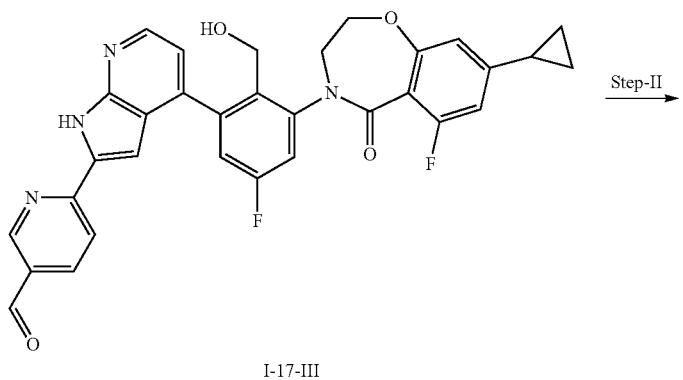

I-17-III

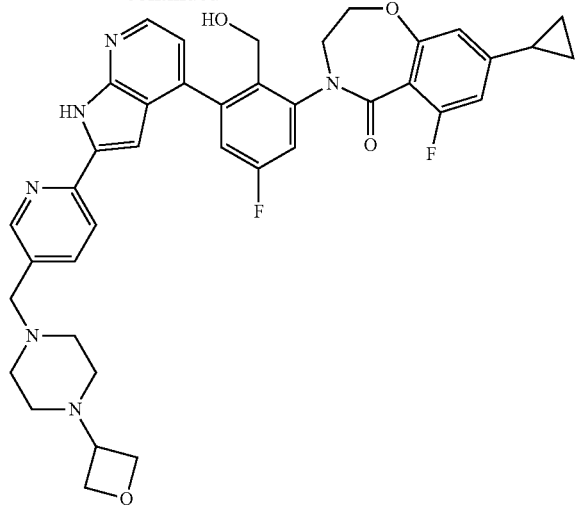

I-17

Step-I: Synthesis of 6-[4-[3-(8-cyclopropyl-6-fluoro-5-oxo-2,3-dihydro-1,4-benzoxazepin-4-yl)-5-fluoro-2-(hydroxymethyl)phenyl]-1H-pyrrolo[2,3-b]pyridin-2-yl]pyridine-3-carbaldehyde (I-17-III)

To a solution of I-17-I (60% by LCMS, TPPO as impurity) (20 g, 28.7 mmol) in anhydrous CH$_2$Cl$_2$ (200 mL) was added TFA (220 mL, excess) and it was stirred at room temperature for 3-4 h. After completion of the reaction, solvents were removed under reduced pressure (<40° C.) and saturated NaHCO$_3$ solution (~300 mL) was added to the residue (pH: ~8). Extraction was carried out using CH$_2$Cl$_2$ (200 mL×3); the combined organic layers were washed with brine (300 mL); dried over anhydrous Na$_2$SO$_4$, filtered and concentrated under reduced pressure. The residue was purified using silica gel column chromatography (2% MeOH in CH$_2$Cl$_2$) to provide I-17-III (8.5 g, 52% yield). LCMS: 567 (M+1)$^+$.

Step-II

To a solution of I-17-III (8.5 g, 15 mmol) in CH$_2$Cl$_2$ (250 mL) was added 1-(oxetan-3-yl)piperazine (10.7 g, 75 mmol), HOAc (0.84 g, 15 mmol) and 4 A° molecular sieves (~2 g). After stirring for 2 h, sodium triacetoxyborohydride (6.36 g, 30 mmol) was added to it and the reaction mixture was stirred for 3 h. After complete consumption of starting material (indicated by TLC), saturated NaHCO$_3$ solution (100 mL) was added to it and extraction was carried out using CH$_2$Cl$_2$ (100 mL×3). The combined organic layers were washed with water (150 mL), brine (150 mL); dried over anhydrous Na$_2$SO$_4$, filtered and concentrated under reduced pressure. The residue was purified using silica gel column chromatography (2-5% MeOH in CH$_2$Cl$_2$) to provide desired compound I-17 (9.1 g, 87% yield).

Following compounds were synthesized using similar sequence of reactions and procedures as described for the synthesis of I-17.

TABLE 24

| No | Structure/IUPAC name | Characterization | INT used (amine used for reductive amination) |
|---|---|---|---|
| I-18 | 8-cyclopropyl-6-fluoro-4-[5-fluoro-2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one | LCMS: m/z 719.3 (M + 1)$^+$. $^1$H NMR (DMSO-d$_6$, 400 MHz) δ 0.78-0.84 (m, 2H); 1.00-1.06 (m, 2H); 1.96-2.02 (m, 1H); 2.35-2.45 (m, 4H); 2.60-2.65 (m, 4H); 3.15 (q, J = 10.8 Hz, 2H); 3.53 (s, 2H); 3.83-4.00 (m, 2H); 4.15-4.30 (m, 1H); 4.30-4.45 (m, 2H); 4.50-4.60 (m, 1H); 4.82 (bs, 1H); 6.76 (s, 1H); 6.83 (dd, J$_1$ = 1.6 Hz, J$_2$ = 11.2 Hz, 1H); 6.93 (d, J = 2.0 Hz, 1H); 7.21 (d, J = 3.2 Hz, 1H); 7.34 (dd, J$_1$ = 2.8 Hz, J$_2$ = 9.2 Hz, 1H); 7.40 (dd, J$_1$ = 2.8 Hz, J$_2$ = 9.2 Hz, 1H); 7.77 (dd, J$_1$ = 2.4 Hz, J$_2$ = 8.0 Hz, 1H); 8.04 (d, J = 8.0 Hz, 1H); 8.34 (d, J = 4.8 Hz, 1H); 8.53 (d, J = 1.2 Hz, 1H); 12.36 (s, 1H) | XI-3 & III-12 [N-(trifluoroethyl)piperazine; CAS: 13349-90-1] |

TABLE 24-continued

| No | Structure/IUPAC name | Characterization | INT used (amine used for reductive amination) |
|---|---|---|---|
| I-19 | 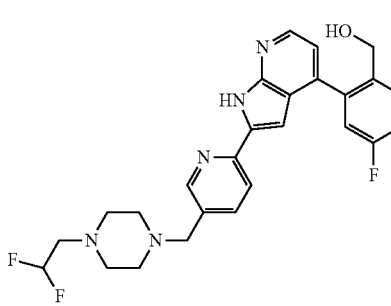<br>8-cyclopropyl-4-[3-[2-[5-[[4-(2,2-difluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one | LCMS: m/z 701.3 (M + 1)$^+$. $^1$H NMR (DMSO-d$_6$, 400 MHz) δ 0.78-0.85 (m, 2H); 1.00-1.08 (m, 2H); 1.96-2.02 (m, 1H); 2.35-2.45 (m, 4H); 2.50-2.60 (m, 4H); 2.70 (td, J$_1$ = 4.4 Hz, J$_2$ = 15.6 Hz, 2H); 3.52 (s, 2H); 3.80-4.00 (m, 2H); 4.15-4.30 (m, 1H); 4.30-4.45 (m, 2H); 4.50-4.60 (m, 1H); 4.82 (bs, 1H); 6.11 (tt, J$_1$ = 4.4 Hz, J$_2$ = 56 Hz, 1H); 6.77 (s, 1H); 6.84 (d, J = 11.2 Hz, 1H); 6.93 (d, J = 1.2 Hz, 1H); 7.21 (d, J = 4.0 Hz, 1H); 7.34 (dd, J$_1$ = 2.8 Hz, J$_2$ = 9.2 Hz, 1H); 7.40 (dd, J$_1$ = 2.8 Hz, J$_2$ = 9.2 Hz, 1H); 7.77 (dd, J$_1$ = 2.0 Hz, J$_2$ = 8.4 Hz, 1H); 8.03 (d, J = 8.4 Hz, 1H); 8.34 (d, J = 4.4 Hz, 1H); 8.53 (d, J = 1.6 Hz, 1H); 12.36 (s, 1H) | XI-3 & III-12 [N-(di-fluoro-ethyl)pipera-zine (CAS: 767609-14-3)] |
| I-20 | 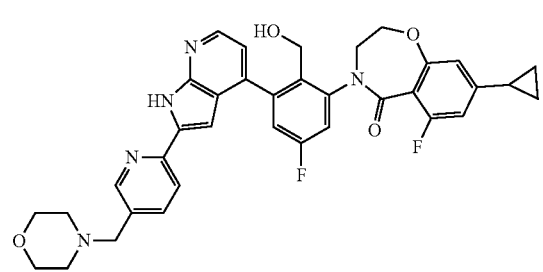 [SMILES: O=C1c2c(F)cc(C3CC3)cc2OCCN1c1cc(F)cc(-c2ccnc3[nH]c(-c4ccc(CN5CCOCC5)cn4)cc23)c1CO]<br>8-cyclopropyl-6-fluoro-4-[5-fluoro-2-(hydroxymethyl)-3-[2-[5-(morpholinomethyl)-2-pyridyl]-1H-pyrrolo[2,3-b]pyridin-4-yl]phenyl]-2,3-dihydro-1,4-benzoxazepin-5-one | LCMS: m/z 638.1 (M + 1)$^+$. $^1$H NMR (DMSO-d$_6$, 400 MHz) δ 0.78-0.82 (m, 2H); 1.00-1.06 (m, 2H); 1.96-2.04 (m, 1H); 2.30-2.44 (m, 4H); 3.53 (s, 2H); 3.56-3.60 (m, 4H); 3.80-4.00 (m, 2H); 4.15-4.28 (m, 1H); 4.30-4.45 (m, 2H); 4.50-4.60 (m, 1H); 4.82 (bs, 1H); 6.77 (s, 1H); 6.84 (dd, J$_1$ = 0.9 Hz, J$_2$ = 11.3 Hz, 1H); 6.93 (d, J = 1.5 Hz, 1H); 7.20-7.24 (aromatics, 1H); 7.34 (dd, J$_1$ = 3.0 Hz, J$_2$ = 9.3 Hz, 1H); 7.40 (dd, J$_1$ = 2.5 Hz, J$_2$ = 9.3 Hz, 1H); 7.79 (dd, J$_1$ = 1.9 Hz, J$_2$ = 7.8 Hz, 1H); 8.04 (d, J = 8.3 Hz, 1H); 8.34 (d, J = 4.9 Hz, 1H); 8.55 (d, J = 1.5 Hz, 1H); 12.40 (s, 1H) | XI-3 & III-12 [morph-oline] |

Example J-1

Synthesis of 8-cyclopropyl-4-[3-[2-[4-(4-fluoro-1-methyl-4-piperidyl)phenyl]-1H-pyrrolo[2,3-b]pyridin-4-yl]-2-(hydroxymethyl)phenyl]-2,3-dihydro-1,4-benzoxazepin-5-one

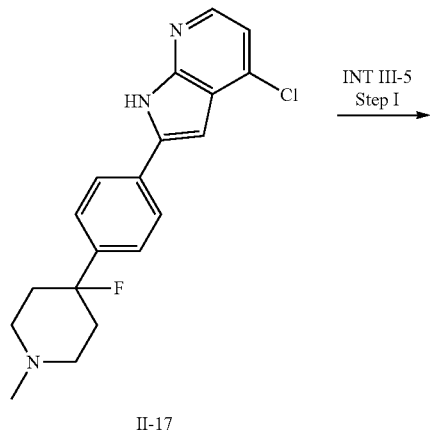

Step-I: Synthesis of 8-cyclopropyl-4-[3-[2-[4-(4-fluoro-1-methyl-4-piperidyl)phenyl]-1H-pyrrolo[2,3-b]pyridin-4-yl]-2-(hydroxymethyl)phenyl]-2,3-dihydro-1,4-benzoxazepin-5-one (J-1)

Example J-1 was prepared using similar procedure as described in step-I for the synthesis of B-1. LCMS: m/z 617.2 (M+1)$^+$. $^1$H NMR (DMSO-$d_6$, 400 MHz) δ 0.72-0.77 (m, 2H); 0.96-1.02 (m, 2H); 1.87-2.00 (m, 6H); 2.06-2.27 (m, 4H); 2.66-2.76 (m, 2H); 3.88-4.00 (m, 2H); 4.20-4.28 (m, 1H); 4.30-4.38 (m, 1H); 4.50-4.60 (m, 2H); 4.72-4.84 (m, 1H); 6.70 (s, 1H); 6.81 (s, 1H); 6.88 (d, J=8.3 Hz, 1H); 7.20 (bs, 1H); 7.43 (d, J=7.9 Hz, 1H); 7.49 (d, J=7.5 Hz, 3H); 7.54-7.58 (aromatics, 1H); 7.66 (d, J=8.4 Hz, 1H); 7.93 (d, J=8.0 Hz, 2H); 8.28 (d, J=4.4 Hz, 1H); 12.33 (s, 1H).

Following example J-2 was also synthesized using same reaction sequence and procedure as described for the synthesis of J-1.

TABLE 25

| No | Structure/IUPAC name | Characterization | INT used |
|---|---|---|---|
| J-2 | 8-cyclopropyl-4-[3-[2-[4-(3-fluoro-1-methyl-3-piperidyl)phenyl]-1H-pyrrolo[2,3-b]pyridin-4-yl]-2-(hydroxymethyl)phenyl]-2,3-dihydro-1,4-benzoxazepin-5-one | LCMS: m/z 617.2 (M + 1)$^+$. $^1$H NMR (DMSO-$d_6$, 400 MHz) δ 0.70-0.76 (m, 2H); 0.96-1.02 (m, 2H); 1.50-1.58 (m, 1H); 1.80-1.98 (m, 4H); 2.04-2.09 (m, 1H); 2.18 (s, 3H); 2.29-2.40 (m, 1H); 2.66-2.81 (m, 2H); 3.86-3.94 (m, 2H); 4.16-4.36 (m, 2H); 4.48-4.58 (m, 2H); 4.70-4.80 (m, 1H); 6.69 (s, 1H); 6.79 (s, 1H); 6.86 (d, J = 7.9 Hz, 1H); 7.19 (bs, 1H); 7.41 (d, J = 8.0 Hz, 1H); 7.46 (d, J = 7.5 Hz, 1H); 7.50-7.54 (aromatics, 3H); 7.64 (d, J = 7.9 Hz, 1H); 7.92 (d, J = 8.0 Hz, 2H); 8.26 (d, J = 4.8 Hz, 1H); 12.32 (s, 1H) | II-18 & III-5 |

Example K-1

8-cyclopropyl-4-[2-methyl-3-[6-[4-(4-methylpiperazine-1-carbonyl)phenyl]-7H-pyrrolo[2,3-d]pyrimidin-4-yl]phenyl]-2,3-dihydro-1,4-benzoxazepin-5-one

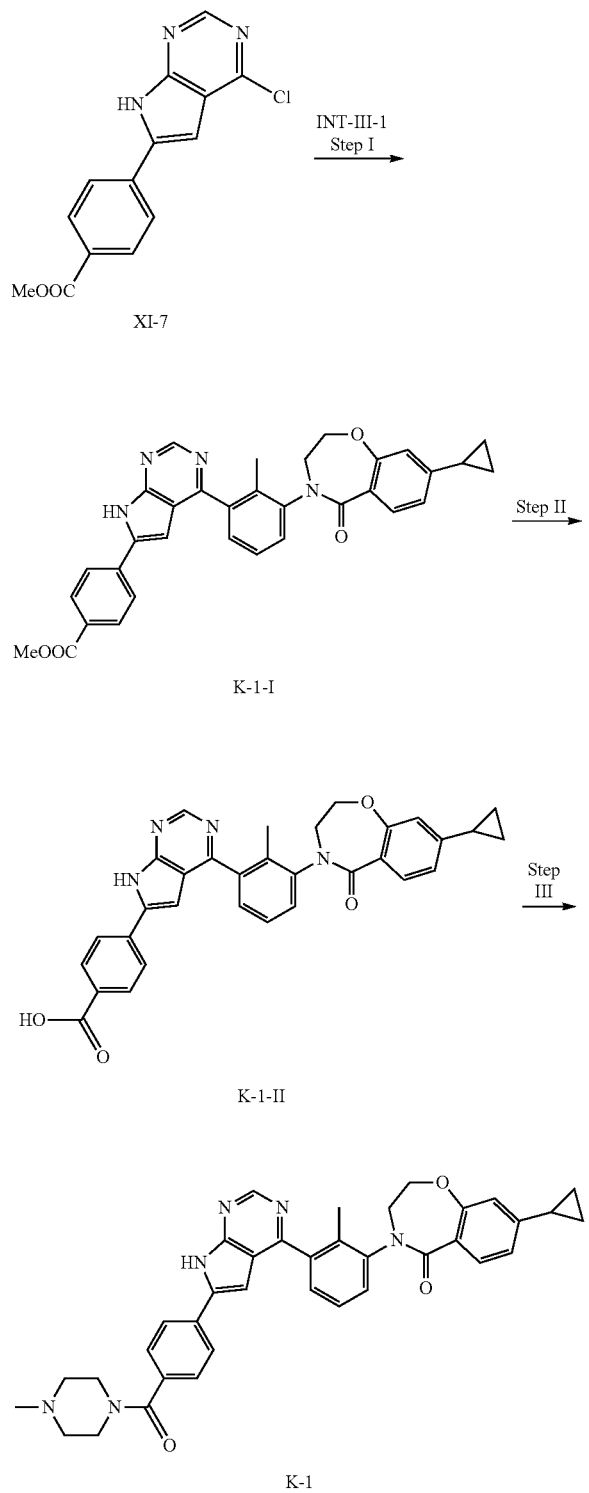

Step-I: Methyl 4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoate (K-1-I)

Intermediate K-1-I was prepared from intermediates XI-7 and III-1, following similar procedure as described in step-I of the synthesis of B-1. LCMS: m/z 545.3 (M+1)$^+$.

Step-II: 4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoic acid (K-1-II)

To a solution of intermediate K-1-I (2 g, 3.67 mmol) in MeOH (20 mL) was added aqueous sodium hydroxide (0.44 g, 11.02 mmol, 10 mL) and the resulting reaction mixture was heated to reflux for 6-8 h. After completion of the reaction (monitored by TLC), solvent was evaporated under vacuum and the residue was then acidified with aqueous 10% citric acid solution. The solid so obtained was filtered and dried under vacuum to afford title compound K-1-II (1.9 g, 98%). LCMS: m/z 531.3 (M+1)$^+$.

Step-III: 8-cyclopropyl-4-[2-methyl-3-[6-[4-(4-methylpiperazine-1-carbonyl)phenyl]-7H-pyrrolo[2,3-d]pyrimidin-4-yl]phenyl]-2,3-dihydro-1,4-benzoxazepin-5-one To a mixture of intermediate K-1-II (0.1 g, 0.188 mmol), N-methyl piperazine (0.09 g, 0.943 mmol) and benzotriazol-1-yl-oxytripyrrolidinophosphonium hexafluorophosphate (0.15 g, 0.283 mmol) in DMF (3 mL) was added N,N-diisopropylethylamine (0.12 g, 0.943 mmol). The resulting reaction mixture was then stirred at room temperature for overnight. After completion of reaction (monitored by TLC), the reaction mixture was poured over ice cold water (15 mL). The resulting precipitate was filtered and dried under vacuum. Crude solid so obtained was purified by preparative TLC (7% MeOH in CH$_2$Cl$_2$) to afford title compound K-1 (0.055 g, 48%). LCMS: m/z 613.1 (M+1)$^+$. $^1$H NMR (DMSO-d$_6$, 400 MHz) δ 0.73-0.78 (m, 2H); 0.81-0.87 (m, 2H); 0.99-1.03 (m, 2H); 1.94-2.02 (m, 1H); 2.16 (s, 3H); 2.19 (s, 3H); 2.21-2.41 (m, 4H); 3.62 (bs, 2H); 3.88-3.94 (m, 2H); 4.44-4.50 (m, 2H); 6.82 (d, J=1.4 Hz, 1H); 6.92 (dd, J$_1$=1.2 Hz, J$_2$=8.0 Hz, 1H); 6.95 (d, J=1.5 Hz, 1H); 7.44-7.50 (aromatics, 4H); 7.55 (dd, J$_1$=2.0 Hz, J$_2$=6.6 Hz, 1H); 7.63 (d, J=8.1 Hz, 1H); 8.05 (d, J=8.3 Hz, 2H); 8.87 (s, 1H); 12.85 (s, 1H).

Following compounds were synthesized using the similar sequence of reactions and procedures as used for the synthesis of K-1.

TABLE 26

| No | Structure/IUPAC name | Characterization | INT used (amine used for reductive amination) |
|---|---|---|---|
| K-2 | 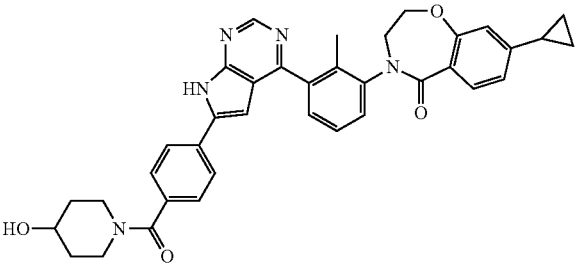 [SMILES: Cc1c(-c2ncnc3[nH]c(-c4ccc(C(=O)N5CCC(O)CC5)cc4)cc23)cccc1N1CCOc2cc(C3CC3)ccc2C1=O]<br>8-cyclopropyl-4-[3-[6-[4-(4-hydroxypiperidine-1-carbonyl)phenyl]-7H-pyrrolo[2,3-d]pyrimidin-4-yl]-2-methyl-phenyl]-2,3-dihydro-1,4-benzoxazepin-5-one | LCMS: m/z 614.4 (M + 1)$^+$. $^1$H NMR (DMSO-d$_6$, 400 MHz) δ 0.70-0.76 (m, 2H); 0.96-1.04 (m, 2H); 1.35-1.45 (m, 2H); 1.64-1.84 (m, 2H); 1.92-1.98 (m, 1H); 2.14 (s, 3H); 3.14-3.24 (m, 3H); 3.62-3.72 (m, 1H); 3.84-3.92 (m, 2H); 3.97-4.03 (m, 1H); 4.40-4.50 (m, 2H); 4.79 (d, J = 3.6 Hz, 1H); 6.80 (s, 1H); 6.88-6.92 (aromatics, 2H); 7.44-7.46 (aromatics, 4H); 7.51-7.53 (aromatic, 1H); 7.61 (d, J = 8.0 Hz, 1H); 8.02 (d, J = 8.1 Hz, 2H); 8.85 (s, 1H); 12.82 (s, 1H) | XI-7 & III-1 (4-hydroxy-piperidine) |
| K-3 | 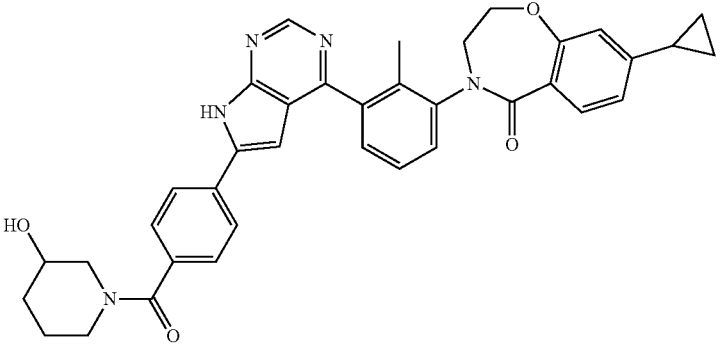 [SMILES: Cc1c(-c2ncnc3[nH]c(-c4ccc(C(=O)N5CCCC(O)C5)cc4)cc23)cccc1N1CCOc2cc(C3CC3)ccc2C1=O]<br>8-cyclopropyl-4-[3-[6-[4-(4-(3-hydroxypiperidine-1-carbonyl)phenyl]-7H-pyrrolo[2,3-d]pyrimidin-4-yl]-2-methyl-phenyl]-2,3-dihydro-1,4-benzoxazepin-5-one | LCMS: m/z 614.4 (M + 1)$^+$. $^1$H NMR (DMSO-d$_6$, 400 MHz) δ 0.73-0.78 (m, 2H); 0.98-1.04 (m, 2H); 1.20-1.28 (m, 2H); 1.36-1.50 (m, 2H); 1.72-1.92 (m, 2H); 1.94-2.04 (m, 1H); 2.16 (s, 3H); 2.96-3.10 (m, 1H); 3.45-3.60 (m, 2H); 3.74-3.84 (m, 1H); 3.86-3.96 (m, 2H); 4.42-4.54 (m, 2H); 6.82 (s, 1H); 6.91-6.95 (aromatics, 2H); 7.46-7.49 (aromatics, 3H); 7.55 (dd, J$_1$ = 2.0 Hz, J$_2$ = 6.8 Hz, 2H); 7.62 (d, J = 8.1 Hz, 1H); 8.05 (d, J = 7.9 Hz, 2H); 8.87 (s, 1H); 12.85 (s, 1H) | XI-7 & III-1 (3-hydroxy-piperidine) |
| K-4 | 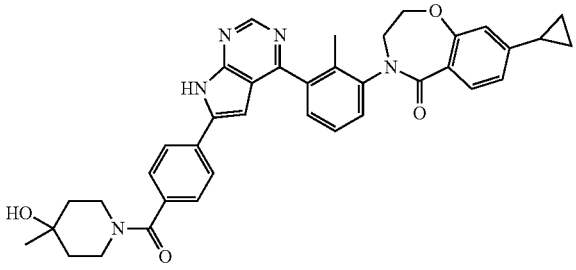 [SMILES: Cc1c(-c2ncnc3[nH]c(-c4ccc(C(=O)N5CCC(C)(O)CC5)cc4)cc23)cccc1N1CCOc2cc(C3CC3)ccc2C1=O]<br>8-cyclopropyl-4-[3-[6-[4-(4-hydroxy-4-methyl-piperidine-1-carbonyl)phenyl]-7H-pyrrolo[2,3-d]pyrimidin-4-yl]-2-methyl-phenyl]-2,3-dihydro-1,4-benzoxazepin-5-one | LCMS: m/z 628.2 (M + 1)$^+$. $^1$H NMR (DMSO-d$_6$, 400 MHz) δ 0.72-0.80 (m, 2H); 0.98-1.04 (m, 2H); 1.15 (s, 3H); 1.40-1.60 (m, 4H); 1.95-2.02 (m, 1H); 2.16 (s, 3H); 3.16-3.39 (m, 4H); 3.84-3.92 (m, 2H); 4.04-4.14 (bs, 1H); 4.40-4.52 (m, 2H); 6.82 (s, 1H); 6.90-6.94 (aromatics, 2H); 7.46-7.49 (aromatics, 3H); 7.54 (d, J = 7.8 Hz, 2H); 7.62 (d, J = 8.1 Hz, 1H); 8.03 (d, J = 8.0 Hz, 2H); 8.87 (s, 1H); 12.83 (s, 1H) | XI-7 & III-1 (4-hydroxy-4-methyl-piperidine) |

TABLE 26-continued

| No | Structure/IUPAC name | Characterization | INT used (amine used for reductive amination) |
|---|---|---|---|
| K-5 | 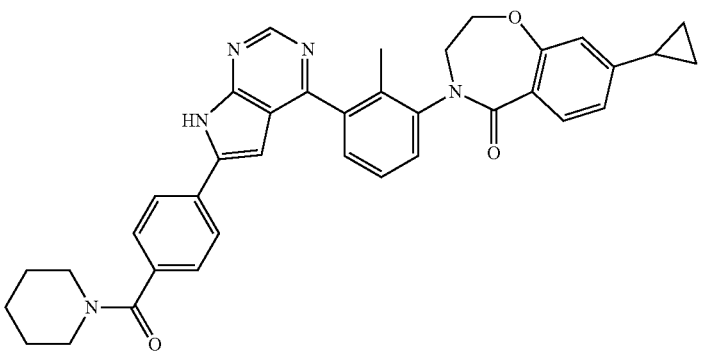 [SMILES: Cc1c(-c2ncnc3[nH]c(-c4ccc(C(=O)N5CCCCC5)cc4)cc23)cccc1N1CCOc2cc(C3CC3)ccc2C1=O]<br>8-cyclopropyl-4-[2-methyl-3-[6-[4-(piperidine-1-carbonyl)phenyl]-7H-pyrrolo[2,3-d]pyrimidin-4-yl]phenyl]-2,3-dihydro-1,4-benzoxazepin-5-one | LCMS: m/z 598.1 (M + 1)+. $^1$H NMR (DMSO-$d_6$, 400 MHz) δ 0.72-0.80 (m, 2H); 0.98-1.06 (m, 2H); 1.42-1.64 (m, 5H); 1.70-1.76 (m, 2H); 1.94-2.02 (m, 1H); 2.16 (s, 3H); 2.99-3.01 (m, 2H); 3.56-3.64 (m, 1H); 3.88-3.96 (m, 2H); 4.42-4.52 (m, 2H); 6.82 (s, 1H); 6.90-6.94 (aromatics, 2H); 7.46-7.49 (aromatics, 4H); 7.54 (d, J = 6.1, 1H); 7.62 (d, J = 8.1 Hz, 1H); 8.04 (d, J = 8.1 Hz, 2H); 8.87 (s, 1H); 12.84 (s, 1H) | XI-7 & III-1 (piperidine) |
| K-6 | 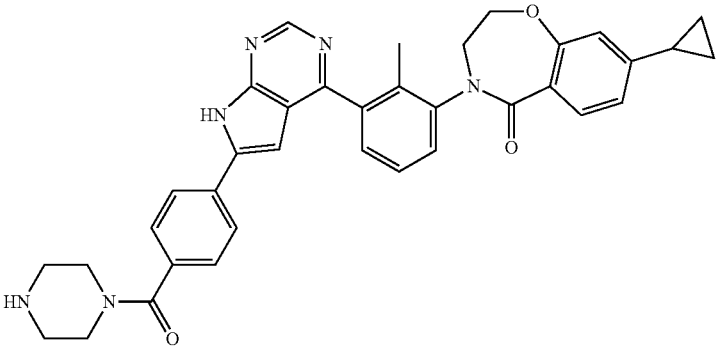 [SMILES: Cc1c(-c2ncnc3[nH]c(-c4ccc(C(=O)N5CCNCC5)cc4)cc23)cccc1N1CCOc2cc(C3CC3)ccc2C1=O]<br>8-cyclopropyl-4-[2-methyl-3-[6-[4-(piperazine-1-carbonyl)phenyl]-7H-pyrrolo[2,3-d]pyrimidin-4-yl]phenyl]-2,3-dihydro-1,4-benzoxazepin-5-one | LCMS: m/z 599.1 (M + 1)+. $^1$H NMR (DMSO-$d_6$, 400 MHz) δ 0.72-0.79 (m, 2H); 0.98-1.06 (m, 2H); 1.94-2.00 (m, 1H); 2.16 (s, 3H); 2.60-2.80 (m, 4H); 3.20-3.30 (m, 2H); 3.50-3.60 (m, 2H); 3.86-3.94 (m, 2H); 4.40-4.54 (m, 2H); 6.82 (d, J = 1.2 Hz, 1H); 6.90-6.94 (aromatics, 2H); 7.46-7.49 (aromatics, 4H); 7.54 (dd, $J_1$ = 2.0, $J_2$ = 6.6 Hz, 1H); 7.62 (d, J = 8.0 Hz, 1H); 8.04 (d, J = 8.1 Hz, 2H); 8.87 (s, 1H); 12.84 (s, 1H) | XI-7 & III-1 (piperazine) |
| K-7 | 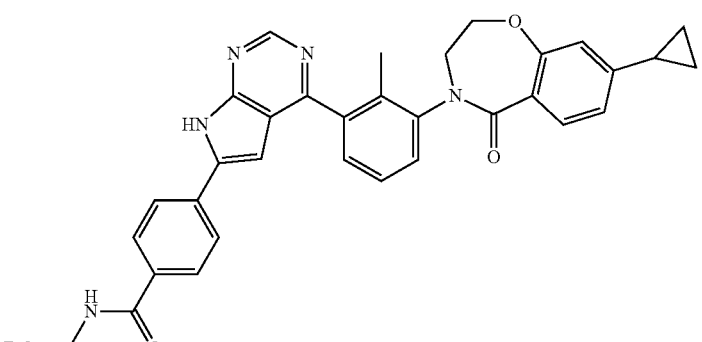<br>4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]-N-(2,2,2-trifluoroethyl)benzamide | LCMS: m/z 612.1 (M + 1)+. $^1$H NMR (DMSO-$d_6$, 400 MHz) δ 0.75-0.77 (m, 2H); 0.99-1.04 (m, 2H); 1.95-2.00 (m, 1H); 2.16 (s, 3H); 3.90-3.92 (m, 2H); 4.07-4.16 (m, 2H); 4.45-4.51 (m, 2H); 6.82 (s, 1H); 6.92 (dd, $J_1$ = 1.4 Hz, $J_2$ = 8.3 Hz, 1H); 7.03 (s, 1H); 7.45-7.50 (aromatics, 2H); 7.56 (dd, $J_1$ = 1.9 Hz, $J_2$ = 6.6 Hz, 1H); 7.63 (d, J = 8.1 Hz, 1H); 7.99 (d, J = 8.3 Hz, 2H); 8.13 (d, J = 8.4 Hz, 2H); 8.88 (s, 1H); 9.17 (t, J = 6.2 Hz, 1H); 12.89 (s, 1H) | XI-7 & III-1 (2,2,2-trifluoroethylamine) |

TABLE 26-continued

| No | Structure/IUPAC name | Characterization | INT used (amine used for reductive amination) |
|---|---|---|---|
| K-8 | 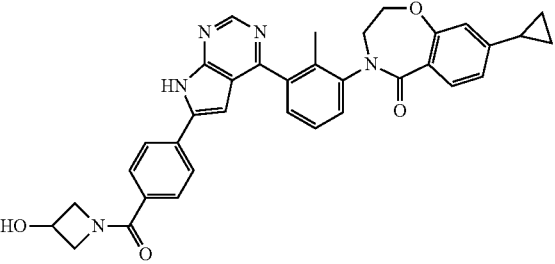 [SMILES: Cc1c(-c2ncnc3[nH]c(-c4ccc(C(=O)N5CC(O)C5)cc4)cc23)cccc1N1CCOc2cc(C3CC3)ccc2C1=O]<br>8-cyclopropyl-4-[3-[6-[4-(3-hydroxyazetidine-1-carbonyl)phenyl]-7H-pyrrolo[2,3-d]pyrimidin-4-yl]-2-methyl-phenyl]-2,3-dihydro-1,4-benzoxazepin-5-one | LCMS: m/z 586.4 (M + 1)⁺. ¹H NMR (DMSO-d₆, 400 MHz) δ 0.74-0.78 (m, 2H); 1.00-1.06 (m, 2H); 1.96-2.02 (m, 1H); 2.16 (s, 3H); 3.76-3.85 (m, 1H); 3.88-3.98 (m, 2H); 4.05-4.13 (m, 1H); 4.22-4.32 (m, 1H); 4.42-4.56 (m, 4H); 5.77 (d, J = 5.9 Hz, 1H); 6.82 (s, 1H); 6.92 (dd, J₁ = 1.7 Hz, J₂ = 8.3 Hz, 1H); 6.98 (d, J = 1.7 Hz, 1H); 7.45-7.50 (aromatics, 2H); 7.55 (dd, J₁ = 2.2 Hz, J₂ = 6.6 Hz, 1H); 7.62 (d, J = 8.1 Hz, 1H); 7.70 (d, J = 8.6 Hz, 2H); 8.06 (d, J = 8.3 Hz, 2H); 8.87 (s, 1H); 12.87 (s, 1H) | XI-7 & III-1 (3-hydroxy-azetidine) |
| K-9 | 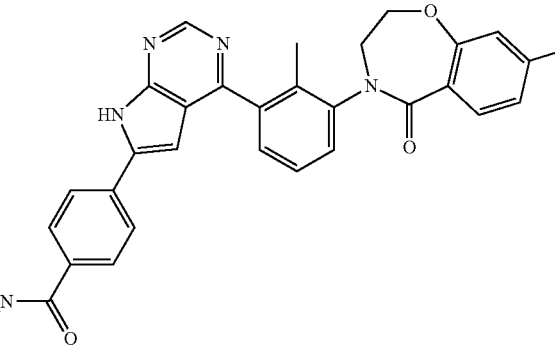<br>8-cyclopropyl-4-[2-methyl-3-[6-[4-(pyrrolidine-1-carbonyl)phenyl]-7H-pyrrolo[2,3-d]pyrimidin-4-yl]phenyl]-2,3-dihydro-1,4-benzoxazepin-5-one | LCMS: m/z 584.1 (M + 1)⁺. ¹H NMR (DMSO-d₆, 400 MHz) δ 0.73-0.77 (m, 2H); 0.99-1.04 (m, 2H); 1.80-1.89 (m, 4H); 1.95-1.99 (m, 1H); 2.16 (s, 3H); 3.41-3.52 (m, 4H); 3.89-3.92 (m, 2H); 4.45-4.49 (m, 2H); 6.82 (s, 1H); 6.91 (d, J = 8.0 Hz, 1H); 6.95 (s, 1H); 7.44-7.49 (aromatics, 2H); 7.54 (dd, J = 1.9 Hz, J = 6.9 Hz, 1H); 7.60-7.63 (aromatics, 3H); 8.03 (d, J = 8.3 Hz, 2H); 8.87 (s, 1H); 12.84 (s, 1H) | XI-7 & III-1 (pyrroli-dine) |
| K-10 | 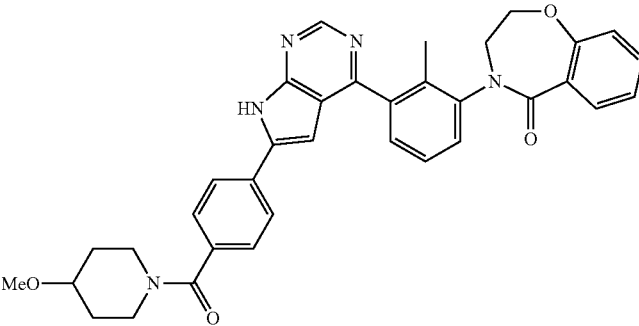<br>8-cyclopropyl-4-[3-[6-[4-(4-methoxypiperidine-1-carbonyl)phenyl]-7H-pyrrolo[2,3-d]pyrimidin-4-yl]-2-methyl-phenyl]-2,3-dihydro-1,4-benzoxazepin-5-one | LCMS: m/z 628.1 (M + 1)⁺. ¹H NMR (DMSO-d₆, 400 MHz) δ 0.73-0.78 (m, 2H); 0.99-1.04 (m, 2H); 1.38-1.54 (m, 2H); 1.77-1.93 (m, 2H); 1.95-2.02 (m, 1H); 2.16 (s, 3H); 3.26 (s, 3H); 3.26-3.46 (m, 4H); 3.88-3.98 (m, 3H); 4.45-4.49 (m, 2H); 6.82 (d, J = 1.4 Hz, 1H); 6.91 (dd, J₁ = 1.4 Hz, J₂ = 8.1 Hz, 1H); 6.95 (d, J = 2.0 Hz, 1H); 7.46-7.49 (aromatics, 3H); 7.54 (dd, J₁ = 2.2 Hz, J₂ = 6.8 Hz, 1H); 7.63 (d, J = 8.0 Hz, 2H); 8.04 (d, J = 8.3 Hz, 2H); 8.87 (s, 1H); 12.84 (s, 1H) | XI-7 & III-1 (4-methoxy-piperidine) |

TABLE 26-continued

| No | Structure/IUPAC name | Characterization | INT used (amine used for reductive amination) |
|---|---|---|---|
| K-11 | 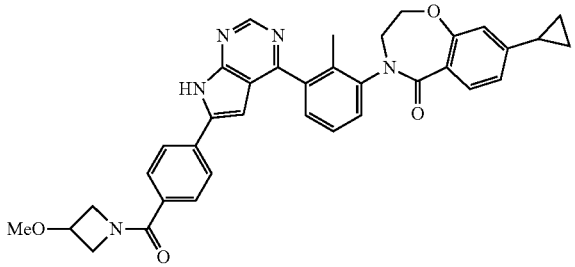 [SMILES: COC1CN(C(=O)c2ccc(-c3cc4c(-c5cccc(N6CCOc7cc(C8CC8)ccc7C6=O)c5C)ncnc4[nH]3)cc2)C1]<br>8-cyclopropyl-4-[3-[6-[4-(3-methoxyazetidine-1-carbonyl)phenyl]-7H-pyrrolo[2,3-d]pyrimidin-4-yl]-2-methyl-phenyl]-2,3-dihydro-1,4-benzoxazepin-5-one | LCMS: m/z 600.1 (M + 1)$^+$. $^1$H NMR (DMSO-$d_6$, 400 MHz) δ 0.74-0.78 (m, 2H); 0.99-1.04 (m, 2H); 1.95-1.99 (m, 1H); 2.16 (s, 3H); 3.22 (s, 3H); 3.80-3.92 (m, 3H); 4.15-4.30 (m, 3H); 4.45-4.50 (m, 3H); 6.82 (d, J = 1.4 Hz, 1H); 6.91 (dd, $J_1$ = 1.5 Hz, $J_2$ = 8.1 Hz, 1H); 6.98 (s, 1H); 7.44-7.50 (aromatics, 2H); 7.55 (dd, $J_1$ = 2.2 Hz, $J_2$ = 6.6 Hz, 1H); 7.63 (d, J = 8.1 Hz, 1H); 7.72 (d, J = 8.3 Hz, 2H); 8.07 (d, J = 8.3 Hz, 2H); 8.88 (s, 1H); 12.88 (s, 1H) | XI-7 & III-1 (3-methoxy-azetidine) |
| K-12 | 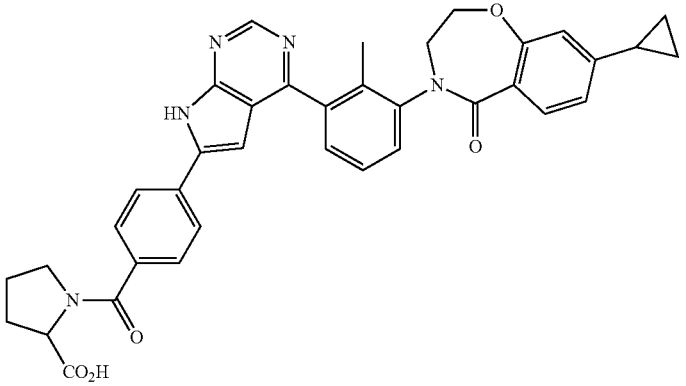 [SMILES: Cc1c(-c2ncnc3[nH]c(-c4ccc(C(=O)N5CCCC5C(=O)O)cc4)cc23)cccc1N1CCOc2cc(C3CC3)ccc2C1=O]<br>1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]pyrrolidine-2-carboxylic acid | LCMS: m/z 628.1 (M + 1)$^+$. $^1$H NMR (DMSO-$d_6$, 400 MHz) δ 0.72-0.76 (m, 2H); 0.97-1.02 (m, 2H); 1.80-1.90 (m, 4H); 1.92-2.00 (m, 1H); 2.14 (s, 3H); 3.50-3.60 (m, 2H); 3.86-3.92 (m, 2H); 4.38-4.41 (m, 1H); 4.41-4.47 (m, 2H); 6.81 (s, 1H); 6.90 (d, J = 8.1 Hz, 1H); 6.95 (bs, 1H); 7.44-7.48 (aromatics, 2H); 7.53 (d, J = 6.8 Hz, 1H); 7.61 (d, J = 8.0 Hz, 2H); 7.99 (d, J = 8.0 Hz, 1H); 8.05 (d, J = 8.3 Hz, 2H); 8.85 (s, 1H); 12.56 (bs, 1H); 12.85 (s, 1H) | XI-7 & III-1 (proline-methyl ester) |
| K-13 | 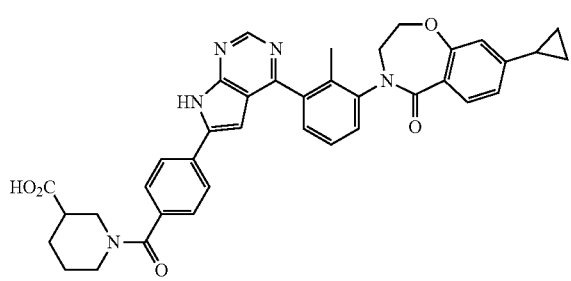 [SMILES: Cc1c(-c2ncnc3[nH]c(-c4ccc(C(=O)N5CCCC(C(=O)O)C5)cc4)cc23)cccc1N1CCOc2cc(C3CC3)ccc2C1=O]<br>1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]piperidine-3-carboxylic acid | LCMS: m/z 642.1 (M + 1)$^+$. $^1$H NMR (DMSO-$d_6$, 400 MHz) δ 0.72-0.79 (m, 2H); 0.98-1.04 (m, 2H); 1.40-1.55 (m, 2H); 1.56-1.76 (m, 3H); 1.94-2.04 (m, 2H); 2.16 (s, 3H); 2.94-3.10 (m, 2H); 3.60-3.72 (m, 0.5H); 3.86-3.96 (m, 2H); 4.06-4.16 (m, 0.5H); 4.40-4.49 (m, 2H); 6.82 (s, 1H); 6.91 (d, J = 8.4 Hz, 1H); 6.95 (s, 1H); 7.44-7.50 (aromatics, 4H); 7.54 (d, J = 6.6 Hz, 1H); 7.63 (d, J = 8.0 Hz, 1H); 8.05 (d, J = 8.1 Hz, 2H); 8.87 (s, 1H); 12.50 (bs, 1H); 12.84 (s, 1H) | XI-7 & III-1 (methyl piperidine-3-carboxy-late) |

TABLE 26-continued

| No | Structure/IUPAC name | Characterization | INT used (amine used for reductive amination) |
|---|---|---|---|
| K-14 | 1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]piperidine-4-carboxylic acid | LCMS: m/z 642.1 (M + 1)$^+$. $^1$H NMR (DMSO-$d_6$, 400 MHz) δ 0.72-0.79 (m, 2H); 0.98-1.04 (m, 2H); 1.44-1.56 (m, 2H); 1.70-1.89 (m, 2H); 1.94-2.00 (m, 1H); 2.16 (s, 3H); 2.90-3.20 (m, 3H); 3.50-3.64 (m, 1H); 3.86-3.96 (m, 2H); 4.22-4.36 (m, 1H); 4.44-4.49 (m, 2H); 6.82 (s, 1H); 6.91 (d, J = 8.0 Hz, 1H); 6.94 (s, 1H); 7.44-7.50 (aromatics, 4H); 7.54 (d, J = 6.6 Hz, 1H); 7.62 (d, J = 8.4 Hz, 1H); 8.04 (d, J = 8.1 Hz, 2H); 8.86 (s, 1H); 12.84 (s, 1H) | XI-7 & III-1 (methyl piperidine-4-carboxylate) |
| K-15 | 6-cyclopropyl-2-[2-methyl-3-[6-[4-(morpholine-4-carbonyl)phenyl]-7H-pyrrolo[2,3-d]pyrimidin-4-yl]phenyl]-3,4-dihydroisoquinolin-1-one | LCMS: m/z 584.4 (M + 1)$^+$. $^1$H NMR (DMSO-$d_6$, 400 MHz) δ 0.72-0.80 (m, 2H); 1.02-1.08 (m, 2H); 1.70-1.78 (m, 2H); 1.95-2.02 (m, 1H); 2.16 (s, 3H); 2.95-3.20 (m, 4H); 3.52-3.70 (m, 4H); 3.70-3.86 (m, 1H); 3.95-4.05 (m, 1H); 6.95 (s, 1H); 7.08-7.11 (aromatics, 2H); 7.47-7.52 (aromatics, 5H); 7.81 (d, J = 7.8 Hz, 1H); 8.07 (d, J = 8.1 Hz, 2H); 8.87 (s, 1H); 12.82 (s, 1H) | XI-7 & III-2 (morpholine) |
| K-16 | 6-cyclopropyl-2-[3-[6-[4-(4-hydroxypiperidine-1-carbonyl)phenyl]-7H-pyrrolo[2,3-d]pyrimidin-4-yl]-2-methyl-phenyl]-3,4-dihydroisoquinolin-1-one | LCMS: m/z 598.3 (M + 1)$^+$. $^1$H NMR (DMSO-$d_6$, 400 MHz) δ 0.74-0.82 (m, 2H); 1.00-1.04 (m, 2H); 1.32-1.44 (m, 2H); 1.64-1.84 (m, 2H); 1.94-2.04 (m, 1H); 2.16 (s, 3H); 3.07-3.24 (m, 3H); 3.48-3.54 (m, 2H); 3.74-3.80 (m, 2H); 3.98-4.08 (m, 2H); 4.81 (d, J = 3.6 Hz, 1H); 6.94 (s, 1H); 7.08-7.11 (aromatics, 2H); 7.46-7.56 (aromatics, 5H); 7.81 (d, J = 7.8 Hz, 1H); 8.05 (d, J = 8.1 Hz, 2H); 8.86 (s, 1H); 12.83 (s, 1H) | XI-7 & III-2 (4-hydroxy-piperidine) |

TABLE 26-continued

| No | Structure/IUPAC name | Characterization | INT used (amine used for reductive amination) |
|---|---|---|---|
| K-17 | 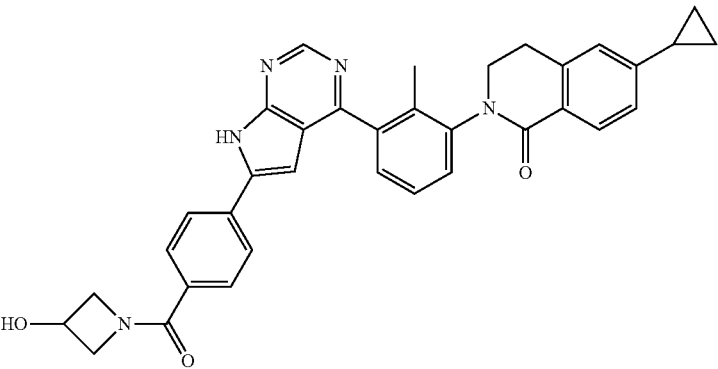 [SMILES: Cc1c(-c2ncnc3[nH]c(-c4ccc(C(=O)N5CC(O)C5)cc4)cc23)cccc1N1CCc2cc(C3CC3)ccc2C1=O]<br>6-cyclopropyl-2-[3-[6-[4-(3-hydroxyazetidine-1-carbonyl)phenyl]-7H-pyrrolo[2,3-d]pyrimidin-4-yl]-2-methyl-phenyl]-3,4-dihydroisoquinolin-1-one | LCMS: m/z 570.3 (M + 1)+. $^1$H NMR (DMSO-$d_6$, 400 MHz) δ 0.74-0.80 (m, 2H); 1.00-1.06 (m, 2H); 1.96-2.02 (m, 1H); 2.16 (s, 3H); 3.07-3.22 (m, 2H); 3.75-3.84 (m, 2H); 3.98-4.14 (m, 2H); 4.22-4.30 (m, 1H); 4.46-4.54 (m, 2H); 5.76-5.78 (m, 1H); 6.98 (d, J = 1.7 Hz, 1H); 7.08-7.11 (aromatics, 2H); 7.43-7.54 (aromatics, 3H); 7.68-7.72 (aromatics, 2H); 7.81 (d, J = 7.8 Hz, 1H); 8.07 (d, J = 8.3 Hz, 2H); 8.87 (s, 1H); 12.82 (s, 1H) | XI-7 & III-2 (3-hydroxy-azetidine) |
| K-18 | 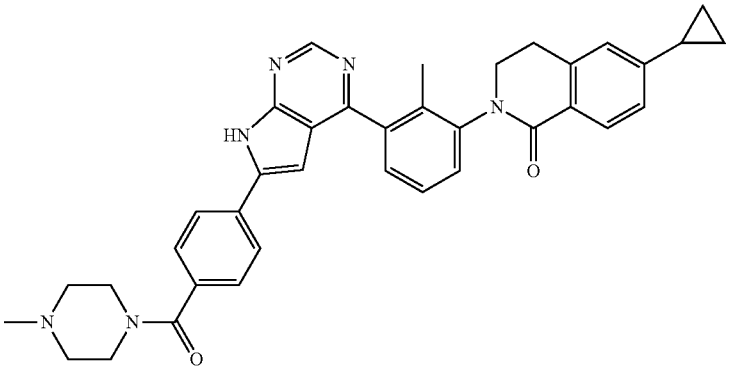 [SMILES: Cc1c(-c2ncnc3[nH]c(-c4ccc(C(=O)N5CCN(C)CC5)cc4)cc23)cccc1N1CCc2cc(C3CC3)ccc2C1=O]<br>6-cyclopropyl-2-[2-methyl-3-[6-[4-(4-methylpiperazine-1-carbonyl)phenyl]-7H-pyrrolo[2,3-d]pyrimidin-4-yl]phenyl]-3,4-dihydroisoquinolin-1-one | LCMS: m/z 597.3 (M + 1)+. $^1$H NMR (DMSO-$d_6$, 400 MHz) δ 0.74-0.80 (m, 2H); 1.00-1.06 (m, 2H); 1.96-2.02 (m, 1H); 2.16 (s, 3H); 2.21 (s, 3H); 2.26-2.46 (m, 6H); 3.06-3.22 (m, 2H); 3.56-3.68 (m, 2H); 3.72-3.80 (m, 1H); 3.96-4.02 (m, 1H); 6.96 (d, J = 1.7 Hz, 1H); 7.08-7.11 (aromatics, 2H); 7.45-7.54 (aromatics, 5H); 7.81 (d, J = 8.1 Hz, 1H); 8.06 (d, J = 8.3 Hz, 2H); 8.87 (s, 1H); 12.86 (bs, 1H) | XI-7 & III-2 (N-Methyl-piper-azine) |
| K-19 | 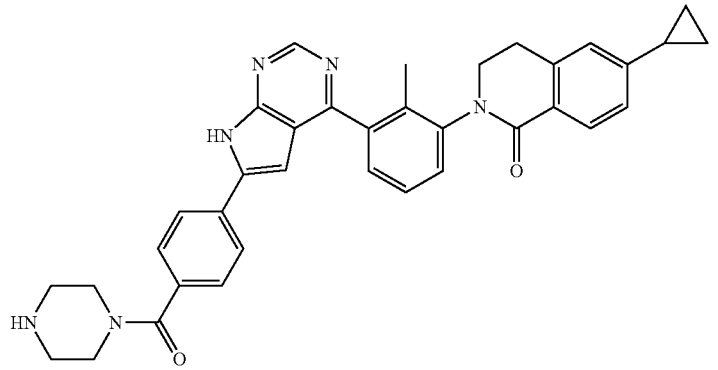 [SMILES: Cc1c(-c2ncnc3[nH]c(-c4ccc(C(=O)N5CCNCC5)cc4)cc23)cccc1N1CCc2cc(C3CC3)ccc2C1=O]<br>6-cyclopropyl-2-[2-methyl-3-[6-[4-(piperazine-1-carbonyl)phenyl]-7H-pyrrolo[2,3-d]pyrimidin-4-yl]phenyl]-3,4-dihydroisoquinolin-1-one | LCMS: m/z 583.4 (M + 1)+. $^1$H NMR (DMSO-$d_6$, 400 MHz) δ 0.74-0.80 (m, 2H); 0.98-1.03 (m, 2H); 1.96-2.04 (m, 1H); 2.16 (s, 3H); 2.60-2.80 (m, 4H); 3.07-3.19 (m, 4H); 3.48-3.68 (m, 2H); 3.70-3.80 (m, 1H); 3.95-4.10 (m, 1H); 6.93 (s, 1H); 7.07-7.11 (aromatics, 2H); 7.46-7.52 (aromatics, 5H); 7.81 (d, J = 7.8 Hz, 1H); 8.05 (d, J = 7.4 Hz, 2H); 8.85 (s, 1H); 12.83 (bs, 1H) | XI-7 & III-2 (piper-azine) |

TABLE 26-continued

| No | Structure/IUPAC name | Characterization | INT used (amine used for reductive amination) |
|---|---|---|---|
| K-20 | 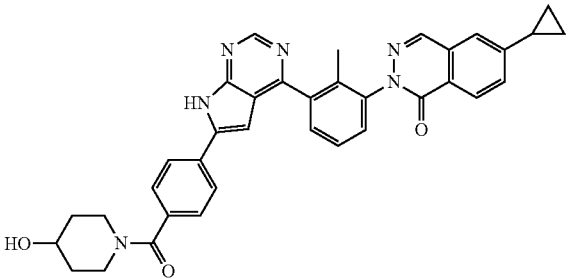 [SMILES: Cc1c(-c2ncnc3[nH]c(-c4ccc(C(=O)N5CCC(O)CC5)cc4)cc23)cccc1-n1ncc2cc(C3CC3)ccc2c1=O]<br>6-cyclopropyl-2-[3-[6-[4-(4-hydroxypiperidine-1-carbonyl)phenyl]-7H-pyrrolo[2,3-d]pyrimidin-4-yl]-2-methyl-phenyl]phthalazin-1-one | LCMS: m/z 597.1 (M + 1)$^+$.<br>$^1$H NMR (400 MHz, DMSO-d$_6$) δ 0.86-0.92 (m, 2H); 1.12-1.20 (m, 2H); 1.27-1.48 (m, 2H); 1.66-1.87 (m, 2H); 2.03 (s, 3H); 2.16-2.27 (m, 1H); 3.12-3.28 (m, 2H); 3.46-3.60 (m, 1H); 3.70-3.80 (m, 1H); 3.94-4.08 (m, 1H); 4.80 (d, J = 3.9 Hz, 1H); 6.96 (s, 1H); 7.47 (d, J = 8.3 Hz, 2H); 7.52-7.55 (aromatics, 2H); 7.64-7.69 (aromatics, 2H); 7.72 (s, 1H); 8.06 (d, J = 8.6 Hz, 2H); 8.21 (d, J = 8.4 Hz, 1H); 8.50 (s, 1H); 8.87 (s, 1H); 12.82 (s, 1H) | XI-7 & III-4 (4-hydroxy-piperi-dine) |
| K-21 | 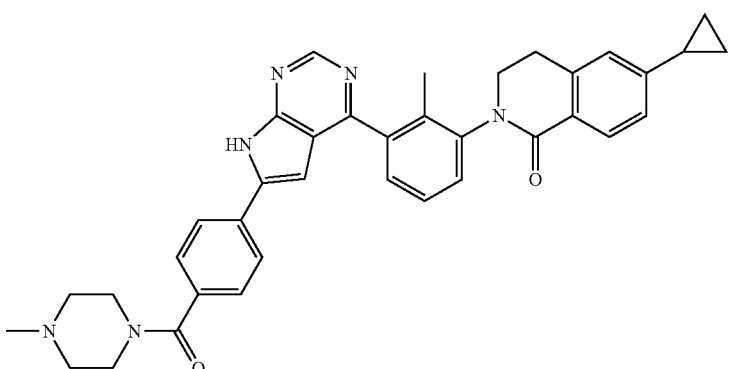<br>6-cyclopropyl-2-[2-methyl-3-[6-[4-(4-methylpiperazine-1-carbonyl)phenyl]-7H-pyrrolo[2,3-d]pyrimidin-4-yl]phenyl]-3,4-dihydroisoquinolin-1-one (hydrochloride salt) | LCMS: m/z 597 (M + 1)$^+$.<br>$^1$H NMR (DMSO-d$_6$,, 400 MHz) δ 0.72-0.78 (m, 2H); 0.98-1.06 (m, 2H); 1.94-2.02 (m, 1H); 2.16 (s, 3H); 2.76 (d, J = 4.2 Hz, 3H); 3.00-3.24 (m, 4H); 3.30-3.50 (m, 4H); 3.72-3.78 (m, 2H); 3.97-4.04 (m, 2H); 7.07-7.16 (aromatics, 3H); 7.49-7.59 (aromatics, 5H); 7.79 (d, J = 7.8 Hz, 1H); 8.14 (d, J = 8.0 Hz, 2H); 9.04 (s, 1H); 10.95 (bs, 1H); 13.49 (bs, 1H) | XI-7 & III-2 (N-Me-piper-azine) |
| K-22 | 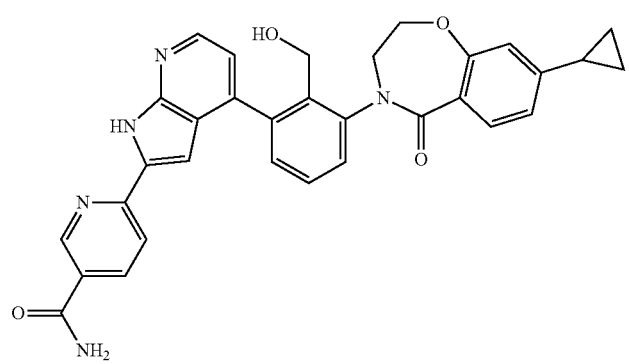 [SMILES: NC(=O)c1ccc(-c2cc3c(-c4cccc(N5CCOc6cc(C7CC7)ccc6C5=O)c4CO)ccnc3[nH]2)nc1]<br>6-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]pyridine-3-carboxamide | LCMS: m/z 546.4 (M + 1)$^+$.<br>$^1$H NMR (DMSO-d$_6$, 400 MHz) δ 0.74-0.78 (m, 2H); 0.99-1.04 (m, 2H); 1.23 (m, 2H); 1.94-1.99 (m, 1H); 3.93-9.38 (m, 1H); 4.20-4.36 (m, 3H); 4.54-4.59 (m, 2H); 6.81 (d, J = 1.2 Hz, 1H); 6.88-6.90 (aromatics, 2H); 7.05 (s, 1H); 7.25 (aromatics, 1H); 7.47.49 (aromatics, 2H); 7.56-7.60 (aromatics, 1H); 7.66 (d, J = 8.4 Hz, 1H); 8.14 (d, J = 8.4 Hz, 1H); 8.27-8.29 (aromatics, 1H); 8.37 (d, J = 5.4 Hz, 1H); 12.48 (bs, 1H) | XI-7 & III-8-a |

Example L-1

Synthesis of 8-cyclopropyl-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one

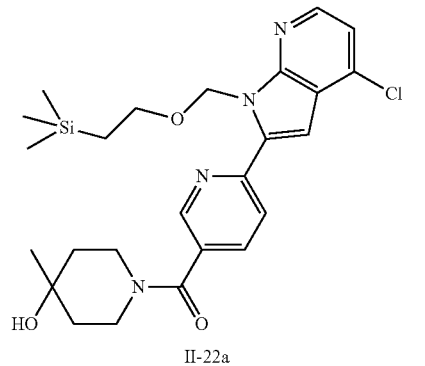

II-22a

INT III-8a
Step I

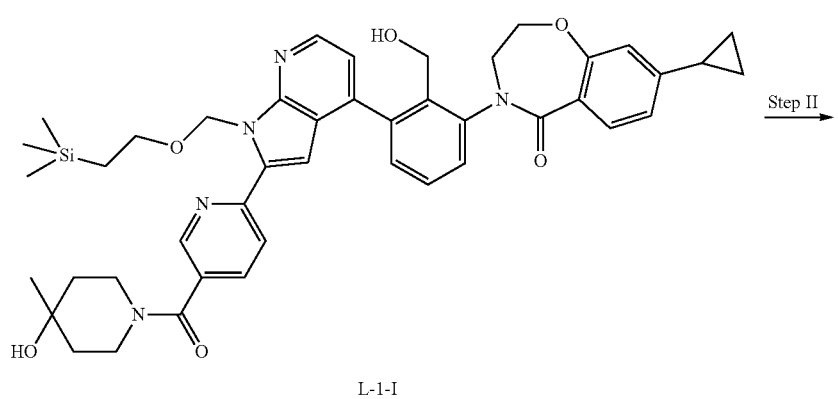

L-1-I

Step II

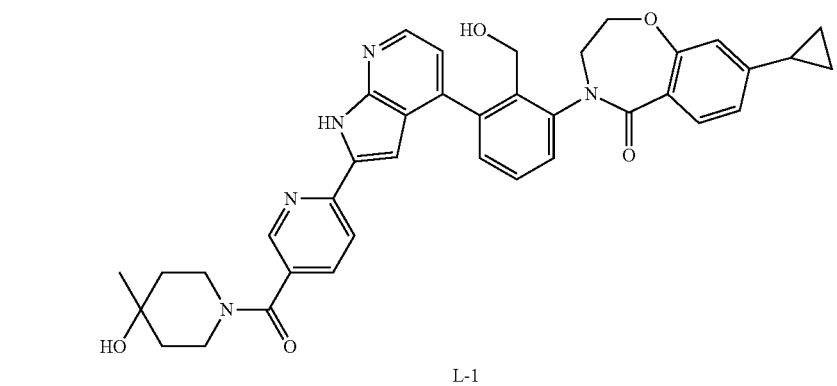

L-1

Step-I: 8-cyclopropyl-4-[2-(hydroxymethyl)-3-[2-[5-(4-hydroxy-4-methyl-piperidine-1-carbonyl)-2-pyridyl]-1-(2-trimethylsilylethoxymethyl)pyrrolo[2,3-b]pyridin-4-yl]phenyl]-2,3-dihydro-1,4-benzoxazepin-5-one (L-1-I)

Intermediate L-1-I was synthesized using intermediates II-22a and III-8-a following similar procedure as described in step-I for the synthesis of B-1. LCMS: m/z; 774.3 (M+1)⁺.

Step-II: 8-cyclopropyl-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one (L-1)

Intermediate L-1-I (0.16 g, 0.206 mmol) was dissolved in CH$_2$Cl$_2$ (10 mL) and cooled to 0° C. To this was added TFA (2 mL, excess) and it was stirred for 6 h. After completion of the reaction, solvent was removed under reduced pressure and saturated NaHCO$_3$ solution (30 mL) was added to the residue. Extraction was carried out using EtOAc (20 mL×2); the combined organic layers were washed with water (30 mL), brine (30 mL), dried over anhydrous Na$_2$SO$_4$, filtered and concentrated under reduce pressure. The residue obtained was purified using silica gel column chromatography (3% MeOH in CH$_2$Cl$_2$) to provide the title compound L-1 (0.05 g, 37% yield). LCMS: m/z 644.5 (M+1)⁺. ¹H NMR (DMSO-d$_6$, 400

MHz) δ 0.74-0.77 (m, 2H); 0.99-1.04 (m, 2H); 1.16 (s, 3H); 1.44-1.56 (m, 4H); 1.95-1.99 (m, 1H); 3.37-3.42 (m, 2H); 3.90-3.95 (m, 2H); 4.08-4.12 (m, 1H); 4.22-4.28 (m, 1H); 4.32-4.38 (m, 1H); 4.45 (s, 1H); 4.52-4.58 (m, 2H); 4.80 (bs, 1H); 6.81 (s, 1H); 6.89 (dd, J$_1$=1.3 Hz, J$_2$=7.9 Hz, 1H); 7.01 (d, J=1.8 Hz, 1H); 7.24 (d, J=3.9 Hz, 1H); 7.43-7.48 (aromatics, 2H); 7.55-7.59 (aromatics, 1H); 7.66 (d, J=8.4 Hz, 1H); 7.89 (dd, J$_1$=1.8 Hz, J$_2$=8.0 Hz, 1H); 8.11 (d, J=7.9 Hz, 1H); 8.36 (d, J=4.9 Hz, 1H); 8.63 (d, J=1.3 Hz, 1H); 12.47 (s, 1H).

Following compounds were synthesized following similar reaction sequence and procedure as described for the synthesis of L-1.

TABLE 27

| No | Structure/IUPAC name | Characterization | INT used |
|---|---|---|---|
| L-2 | 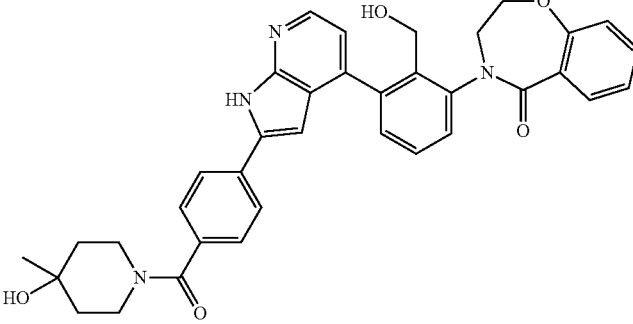<br>8-cyclopropyl-4-[2-(hydroxymethyl)-3-[2-[4-(4-hydroxy-4-methyl-piperidine-1-carbonyl)phenyl]-1H-pyrrolo[2,3-b]pyridin-4-yl]phenyl]-2,3-dihydro-1,4-benzoxazepin-5-one | LCMS: m/z 643.2 (M + 1)$^+$. $^1$H NMR (400 MHz, DMSO-d$_6$) δ 0.73-0.77 (m, 2H); 0.99-1.04 (m, 2H); 1.14 (s, 3H); 1.38-1.56 (m, 4H); 1.95-1.99 (m, 1H); 3.16-3.26 (m, 2H); 3.88-3.98 (m, 2H); 4.02-4.12 (m, 1H); 4.20-4.28 (m, 1H); 4.30-4.38 (m, 1H); 4.45 (s, 1H); 4.54-4.58 (m, 2H); 4.83 (bs, 1H); 6.78 (bs, 1H); 6.81 (d, J = 1.3 Hz, 1H); 6.89 (dd, J$_1$ = 1.3 Hz, J$_2$ = 8.3 Hz, 1H); 7.23 (bs, 1H); 7.42-7.49 (aromatics, 3H); 7.49 (d, J = 7.5 Hz, 1H); 7.54-7.58 (aromatics, 1H); 7.66 (d, J = 8.4 Hz, 1H); 7.98 (d, J = 8.4 Hz, 2H); 8.31 (d, J = 4.8 Hz, 1H); 12.41 (bs, 1H) | II-21 & III-8-a |
| L-3 | 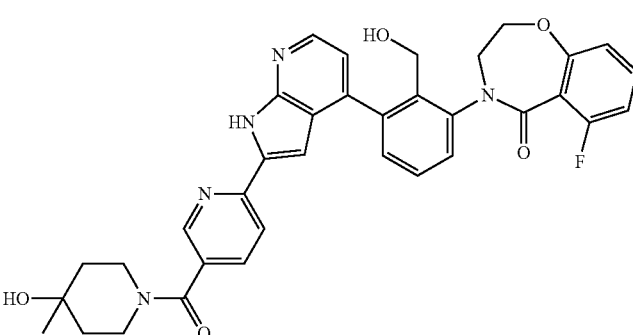<br>8-cyclopropyl-6-fluoro-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one | LCMS: m/z 662.2 (M + 1)$^+$. $^1$H NMR (CDCl$_3$, 400 MHz,) δ 0.75-0.79 (m, 2H); 1.06-1.15 (m, 2H); 1.32 (s, 3H); 1.58-1.79 (m, 4H); 1.95-1.99 (m, 1H); 3.32-3.55 (m, 4H); 3.31-3.99 (m, 2H); 4.31-4.49 (m, 4H); 4.64 (bs, 1H); 6.66-6.71 (aromatics, 2H); 6.89 (s, 1H); 7.37-7.43 (aromatics, 2H); 7.56-7.59 (aromatics, 2H); 7.79 (s, 2H); 8.46 (s, 1H); 8.67 (s, 1H); 10.88 (s, 1H) | II-22a & III-9 |

TABLE 27-continued

| No | Structure/IUPAC name | Characterization | INT used |
|---|---|---|---|
| L-4 | 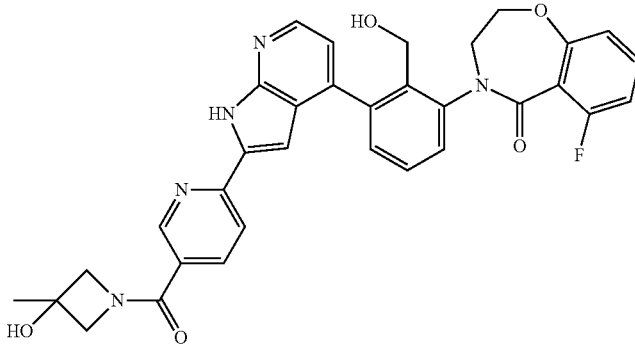<br>8-cyclopropyl-6-fluoro-4-[2-(hydroxymethyl)-3-[2-[5-(3-hydroxy-3-methyl-azetidine-1-carbonyl)-2-pyridyl]-1H-pyrrolo[2,3-b]pyridin-4-yl]phenyl]-2,3-dihydro-1,4-benzoxazepin-5-one | LCMS: m/z 634.4 (M + 1)+. 1H NMR (CDCl3, 400 MHz,) δ 0.78-0.84 (m, 2H); 1.02-1.08 (m, 2H); 1.40 (s, 3H); 1.96-2.04 (m, 1H); 3.78-3.84 (m, 1H); 3.90-4.00 (m, 3H); 4.16-4.30 (m, 3H); 4.36-4.46 (m, 2H); 4.48-4.56 (m, 1H); 4.80-4.90 (m, 1H); 6.78 (s, 1H); 6.84 (d, J = 11.5 Hz, 1H); 7.04 (bs, 1H); 7.22-7.26 (aromatics, 1H); 7.44-7.52 (aromatics, 2H); 7.58-7.62 (aromatics, 1H); 8.06-8.14 (aromatics, 2H); 8.37 (d, J = 4.9 Hz, 1H); 8.84 (s, 1H); 12.55 (bs, 1H) | II-22b & III-9 |

Example M-1

8-cyclopropyl-4-[2-methyl-3-(6-phenyl-7H-pyrrolo[2,3-d]pyrimidin-4-yl)phenyl]-2,3-dihydro-1,4-benzoxazepin-5-one

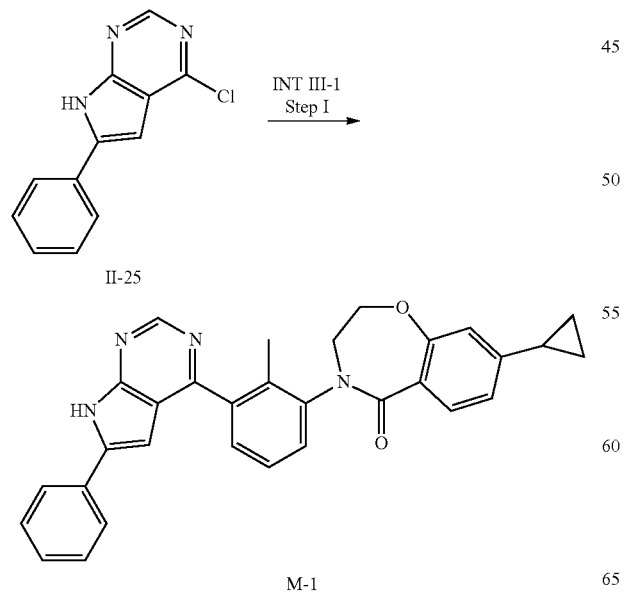

Step-I

Example M-1 was synthesized using intermediates II-25 and III-1 following similar procedure as described in step-I for the synthesis of B-1. LCMS: m/z 487.2 (M+1)+. 1H NMR (DMSO-d6, 400 MHz) δ 0.70-0.80 (m, 2H); 0.95-1.05 (m, 2H); 1.91-2.04 (m, 1H); 2.16 (s, 3H); 3.83-4.00 (m, 2H); 4.38-4.55 (m, 2H); 6.79-6.88 (aromatics, 2H); 6.91 (d, J=7.9 Hz, 1H); 7.34-7.58 (aromatics, 6H); 7.63 (d, J=7.6 Hz, 1H); 7.99 (d, J=7.1 Hz, 2H); 8.85 (s, 1H); 12.77 (s, 1H).

Following examples were synthesized using similar sequence of reactions and procedures as described for the synthesis of example M-1.

TABLE 28

| No | Structure/IUPAC name | Characterization | INT used |
|---|---|---|---|
| M-2 | 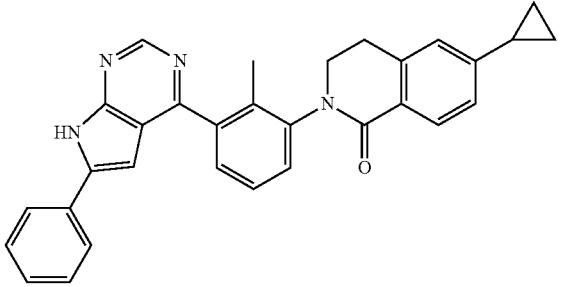 [SMILES: Cc1c(-c2ncnc3[nH]c(-c4ccccc4)cc23)cccc1N1CCc2cc(C3CC3)ccc2C1=O]<br>6-cyclopropyl-2-[2-methyl-3-(6-phenyl-7H-pyrrolo[2,3-d]pyrimidin-4-yl)phenyl]-3,4-dihydroisoquinolin-1-one | LCMS: m/z 471.2 (M + 1)$^+$. $^1$H NMR (DMSO-d$_6$, 400 MHz) δ 0.72-0.80 (m, 2H); 1.00-1.06 (m, 2H); 1.96-2.02 (m, 1H); 2.15 (s, 3H); 3.06-3.20 (m, 2H); 3.72-3.80 (m, 1H); 3.95-4.08 (m, 1H); 6.86 (s, 1H); 7.04-7.12 (aromatics, 2H); 7.36-7.56 (aromatics, 6H); 7.81 (d, J = 7.9 Hz, 1H); 7.99 (d, J = 7.4 Hz, 2H); 8.85 (s, 1H); 12.77 (s, 1H) | II-25 & III-2 |
| M-3 | 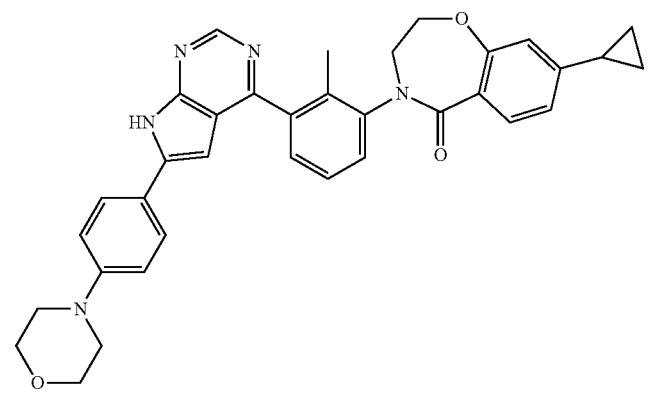 [SMILES: Cc1c(-c2ncnc3[nH]c(-c4ccc(N5CCOCC5)cc4)cc23)cccc1N1CCOc2cc(C3CC3)ccc2C1=O]<br>8-cyclopropyl-4-[2-methyl-3-[6-(4-morpholinophenyl)-7H-pyrrolo[2,3-d]pyrimidin-4-yl]phenyl]-2,3-dihydro-1,4-benzoxazepin-5-one | LCMS: m/z 572.3 (M + 1)$^+$. $^1$H NMR (DMSO-d$_6$, 400 MHz) δ 0.73-0.77 (m, 2H); 0.99-1.04 (m, 2H); 1.95-2.01 (m, 1H); 2.15 (s, 3H); 3.15-3.21 (m, 4H); 3.70-3.80 (m, 4H); 3.88-3.95 (m, 2H); 4.44-4.49 (m, 2H); 6.66 (s, 1H); 6.82 (s, 1H); 6.91 (d, J = 8.1 Hz, 1H); 7.03 (d, J = 8.8 Hz, 2H); 7.44-7.53 (aromatic, 3H); 7.63 (d, J = 8.1 Hz, 1H); 7.84 (d, J = 8.8 Hz, 2H); 8.78 (s, 1H); 12.56 (s, 1H) | II-26 & III-1 |

Example N-1
Synthesis of 4-[3-[2-amino-6-[4-[(4-methylpiperazin-1-yl)methyl]phenyl]-7H-pyrrolo[2,3-d]pyrimidin-4-yl]-2-methyl-phenyl]-8-cyclopropyl-2,3-dihydro-1,4-benzoxazepin-5-one
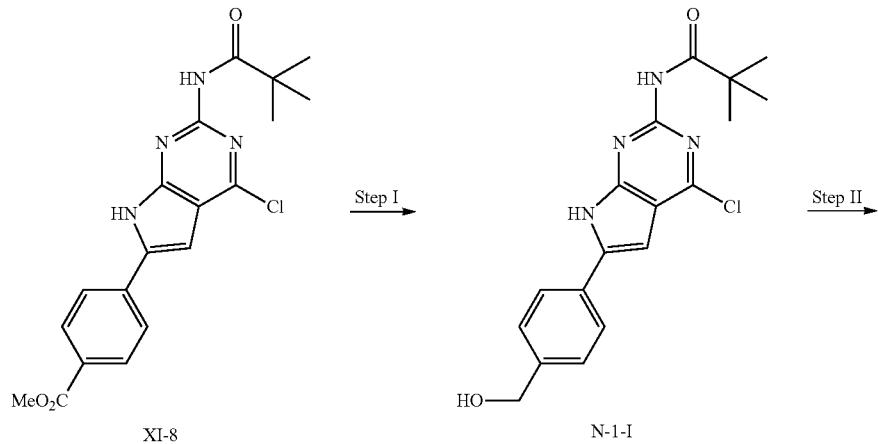
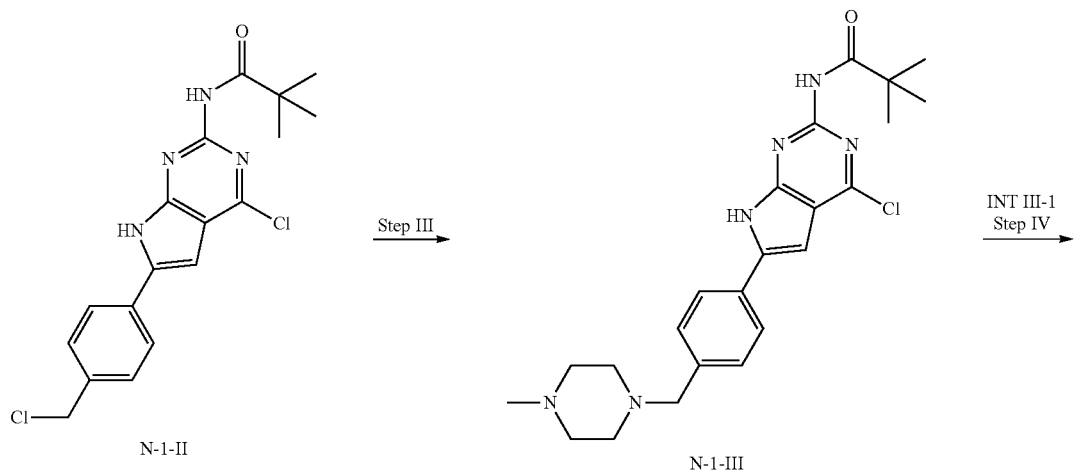
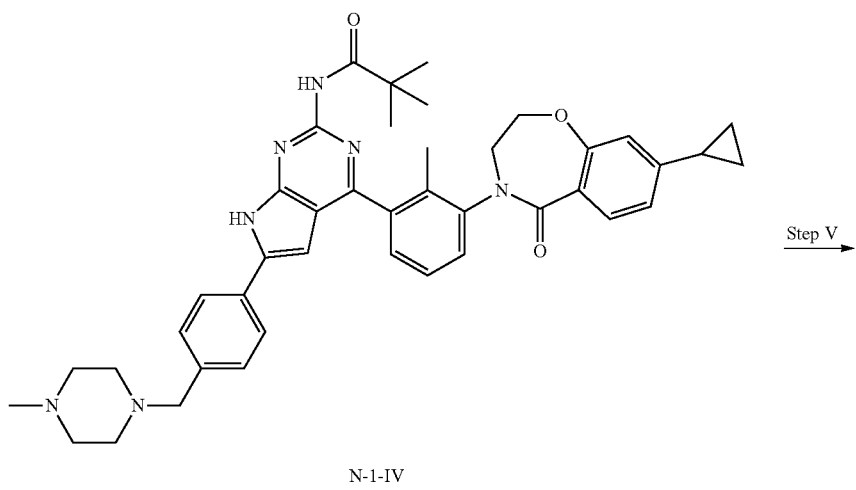

-continued

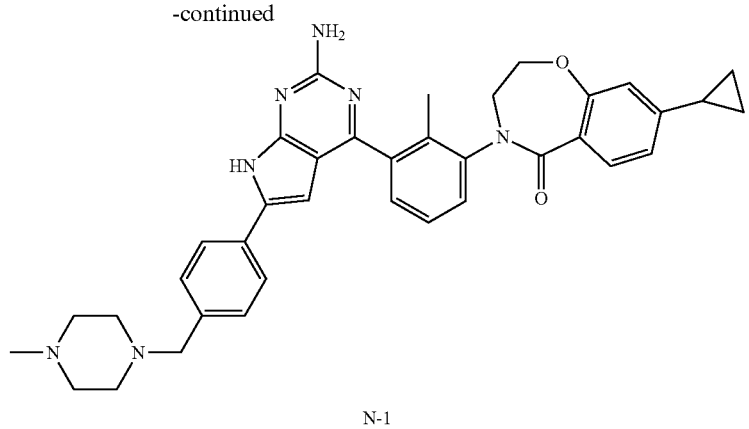

N-1

Step-I: N-[4-chloro-6-[4-(hydroxymethyl)phenyl]-7H-pyrrolo[2,3-d]pyrimidin-2-yl]-2,2-dimethyl-propanamide (N-1-I)

A solution of XI-8 (2.2 g, 5.69 mmol) in dry THF was cooled to −78° C. and DIBAL (1M solution in toluene) (28.4 mL, 28.45 mmol) was added drop wise. The resulting reaction mixture was stirred at −78° C. for 1 hour and slowly allowed to warm to 0° C. over a period of 2-3 hours. Then the reaction was quenched by slow addition of saturated $NH_4Cl$ solution (50 mL) followed by addition of 1N HCl (10 mL). Extraction was carried out using EtOAc (30 mL×3). The combined organic layers were washed with brine (60 mL), dried over anhydrous $Na_2SO_4$, filtered and concentrated under reduced pressure to get crude product which was crystallized using diethyl ether to provide title compound N-1-I (1.1 g, 55%). LCMS: m/z; 359 (M+1)$^+$.

Step-II: N-[4-chloro-6-[4-(chloromethyl)phenyl]-7H-pyrrolo[2,3-d]pyrimidin-2-yl]-2,2-dimethyl-propanamide (N-1-II)

To a solution of intermediate N-1-I (1.1 gm, 3.06 mmol) in toluene (30 mL) was added thionyl chloride (4.4 mL, 61.31 mmol) at 0° C. and the resulting reaction mixture was stirred at room temperature for 1 hour. After completion of reaction, it was concentrated under reduced pressure to dryness. The residue was cooled to 0° C. and neutralized using saturated $NaHCO_3$ solution. The resulting precipitate was filtered, washed with hexane and dried under vacuum to provide intermediate N-1-II (1.1 g, 95%). LCMS: m/z 377 (M+1)$^+$.

Step-III: N-[4-chloro-6-[4-[(4-methylpiperazin-1-yl)methyl]phenyl]-7H-pyrrolo[2,3-d]pyrimidin-2-yl]-2,2-dimethyl-propanamide (N-1-III)

To a mixture of intermediate N-1-II (1.1 g, 2.91 mmol) and powdered $K_2CO_3$ (0.603 g, 4.37 mmol) in dry DMF was added N-methylpiperazine (0.48 mL, 4.37 mmol); and the reaction mixture was stirred overnight at room temperature under $N_2$ atmosphere. Reaction mixture was poured on ice cold water (50 mL) and the resulting precipitate was filtered off. The filtrate was saturated with aqueous NaCl and extracted with EtOAc (50 mL). Organic layer was washed with brine (50 mL), dried over anhydrous $Na_2SO_4$, filtered and concentrated to get crude product, which was purified by silica gel column chromatography to give title product N-1-III (0.470 g, 39%). LCMS: m/z 441 (M+1)$^+$.

Step-IV: N-[4-[3-(8-cyclopropyl-5-oxo-2,3-dihydro-1,4-benzoxazepin-4-yl)-2-methyl-phenyl]-6-[4-[(4-methylpiperazin-1-yl)methyl]phenyl]-7H-pyrrolo[2,3-d]pyrimidin-2-yl]-2,2-dimethyl-propanamide (N-1-IV)

To a mixture of intermediates N-1-III (0.3 g, 0.68 mmol) and III-1 (0.34 g, 0.81 mmol) in dioxane (20 mL) was added a solution of $Na_2CO_3$ (0.18 g, 1.70 mmol) in water (4 mL); and the resulting reaction mixture was purged using Argon for 20 minutes at room temperature. To the resulting solution was added Pd(PPh$_3$)$_4$ (0.078 g, 0.06 mmol) and heated at 95° C. for 10 h. After completion of the reaction (monitored by TLC), it was concentrated under reduced pressure to give the crude product, which was purified by silica gel column chromatography (1% triethylamine and 2% MeOH in $CH_2Cl_2$) as eluent to give the title compound N-1-IV (0.1 g, 21%). LCMS: m/z 698 (M+1)$^+$.

Step V: 4-[3-[2-amino-6-[4-[(4-methylpiperazin-1-yl)methyl]phenyl]-7H-pyrrolo[2,3-d]pyrimidin-4-yl]-2-methyl-phenyl]-8-cyclopropyl-2,3-dihydro-1,4-benzoxazepin-5-one (Example N-1)

To a solution of intermediate N-1-IV (0.1 g, 0.14 mmol) in MeOH (5 mL) was added sodium hydroxide (0.057 g, 1.43 mmol) in water (2.5 mL); and heated to 80° C. overnight. After completion of reaction (monitored by TLC), the reaction mixture was concentrated under reduced pressure to give the crude product, which was purified by preparative TLC (10% MeOH in $CH_2Cl_2$) to provide title compound N-1 (0.022 g, 27%) as a yellow solid. LCMS: m/z 614.4 (M+1)$^+$. $^1$H NMR (DMSO-d$_6$, 400 MHz) δ 0.68-0.74 (m, 2H); 0.96-1.01 (m, 2H); 1.90-1.99 (m, 1H); 2.11 (bs, 6H); 2.24-2.38 (m, 6H); 2.60-2.66 (m, 2H); 3.41 (bs, 2H); 3.81-3.88 (m, 2H); 4.36-4.48 (m, 2H); 6.22 (bs, 2H); 6.45 (d, J=1.9 Hz, 1H); 6.78 (s, 1H); 6.88 (d, J=8.2 Hz, 1H); 7.26 (d, J=8.0 Hz, 2H); 7.31-7.42 (aromatics, 3H); 7.59 (d, J=8.2 Hz, 1H); 7.72 (d, J=8.2 Hz, 2H); 11.7 (s, 1H).

Following example was synthesized following similar sequence of procedures as described for the synthesis of N-1.

TABLE 29

| No | Structure/IUPAC name | Characterization | INT used |
|----|----------------------|------------------|----------|
| N-2 | 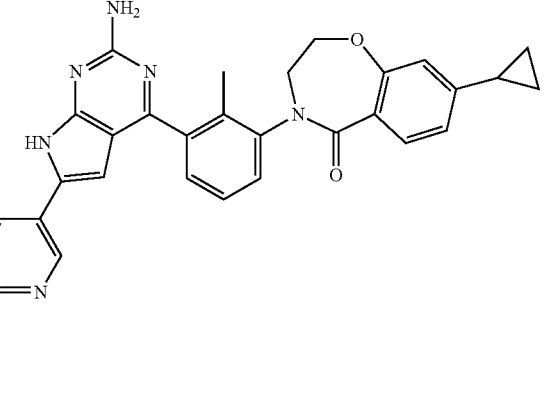

4-[3-[2-amino-6-(6-morpholino-3-pyridyl)-7H-pyrrolo[2,3-d]pyrimidin-4-yl]-2-methyl-phenyl]-8-cyclopropyl-2,3-dihydro-1,4-benzoxazepin-5-one | LCMS: m/z 588.1 (M + 1)$^+$. $^1$H NMR (DMSO-d$_6$, 400 MHz) δ 0.70-0.76 (m, 2H); 0.96-1.04 (m, 2H); 1.90-2.00 (m, 1H); 2.12 (s, 3H); 3.40-3.50 (m, 4H); 3.62-3.72 (m, 4H); 3.80-3.90 (m, 2H); 4.38-4.50 (m, 2H); 6.17 (bs, 2H); 6.37 (s, 1H); 6.79 (s, 1H); 6.86 (d, J = 9.3 Hz, 1H); 6.89 (d, J = 8.3 Hz, 1H); 7.32-7.42 (aromatics, 3H); 7.60 (d, J = 8.1 Hz, 1H); 7.96 (d, J = 9.1 Hz, 1H); 8.58 (s, 1H); 11.68 (s, 1H) | XI-9 & III-1 |

Example O-1

4-[3-[2-amino-6-[4-(morpholine-4-carbonyl)phenyl]-7H-pyrrolo[2,3-d]pyrimidin-4-yl]-2-methyl-phenyl]-8-cyclopropyl-2,3-dihydro-1,4-benzoxazepin-5-one

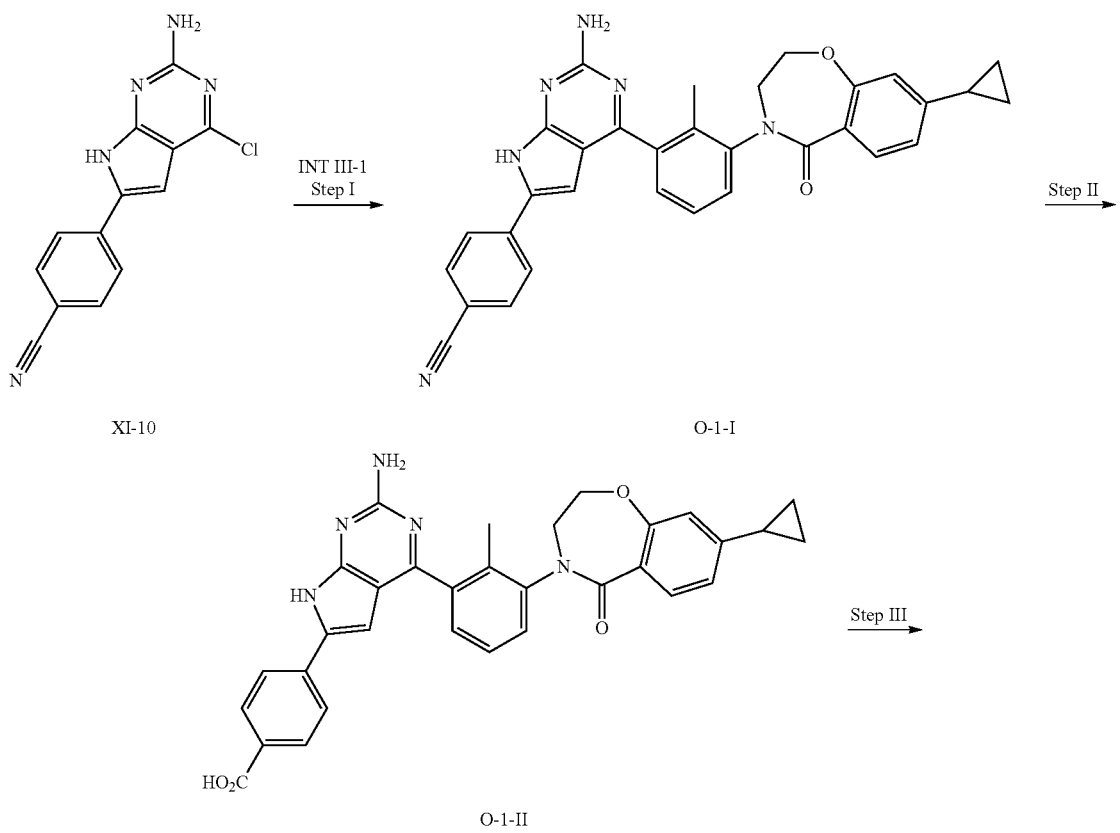

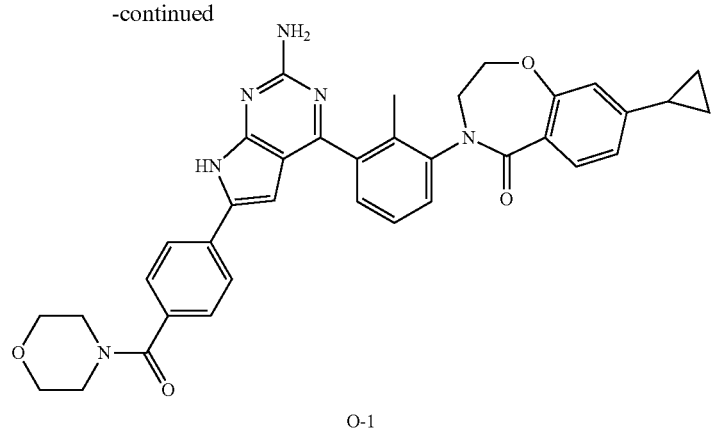

O-1

Step-I: 4-[2-amino-4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzonitrile (O-1-I)

Intermediate O-1-I was synthesized using intermediates XI-10 and III-1, following similar procedure as described for the synthesis of N-1-IV (example N-1). LCMS: m/z 527 (M+1)$^+$.

Step-II: 4-[2-amino-4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoic acid (O-1-II)

To a stirred suspension of intermediate O-1-I (0.15 g, 0.28 mmol) in methanol (3 mL) was added a solution of NaOH (0.113 g, 2.84 mmol) in water (1 mL) and the resulting reaction mixture was refluxed overnight. Solvent was removed under reduced pressure and the reaction mixture was acidified using aqueous 10% citric acid solution. The resulting precipitate was filtered, washed with water and dried under vacuum to provide target compound O-1-II (0.12 g, 77%). LCMS: m/z 546 (M+1)$^+$.

Step-III: 4-[3-[2-amino-6-[4-(morpholine-4-carbonyl)phenyl]-7H-pyrrolo[2,3-d]pyrimidin-4-yl]-2-methyl-phenyl]-8-cyclopropyl-2,3-dihydro-1,4-benzoxazepin-5-one (O-1)

To a solution of intermediate O-1-II (0.12 g, 0.22 mmol) and morpholine (0.09 mL, 1.1 mmol) in dry DMF (1 mL) was added benzotriazol-1-yl-oxytripyrrolidino-phosphonium hexafluorophosphate (0.17 g, 0.33 mmol); and the reaction mixture was stirred overnight at room temperature. The reaction mixture was, then, slowly poured to ice cold water (10 mL) and the resulting solid precipitate was filtered. It was dissolved in CH$_2$Cl$_2$ (30 mL), dried over anhydrous Na$_2$SO$_4$, filtered and concentrated under reduced pressure to provide title compound O-1 (0.015 g, 11%). LCMS: m/z 615.3 (M$^+$+1). $^1$H NMR (DMSO-d$_6$, 400 MHz) δ 0.70-0.78 (m, 2H); 0.98-1.11 (m, 2H); 1.92-2.02 (m, 1H); 2.08 (s, 3H); 2.12-2.30 (m, 4H); 3.50-3.68 (m, 4H); 3.82-3.95 (m, 2H); 4.40-4.50 (m, 2H); 6.31 (bs, 2H); 6.61 (s, 1H); 6.82 (s, 1H); 6.91 (d, J=7.8 Hz, 1H); 7.35-7.48 (aromatics, 5H); 7.62 (d, J=8.0 Hz, 1H); 7.88 (d, J=7.8 Hz, 2H); 11.86 (s, 1H).

Example P-1

Synthesis of 8-cyclopropyl-4-[3-[6-[1-(3-hydroxypropyl)-3,6-dihydro-2H-pyridin-4-yl]-7H-pyrrolo[2,3-d]pyrimidin-4-yl]-2-methyl-phenyl]-2,3-dihydro-1,4-benzoxazepin-5-one

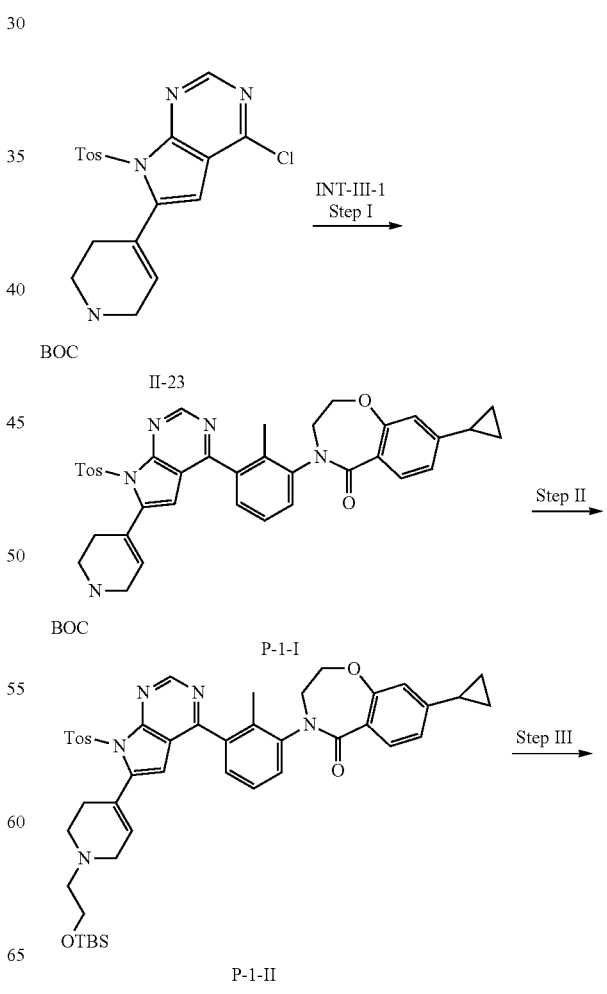

-continued

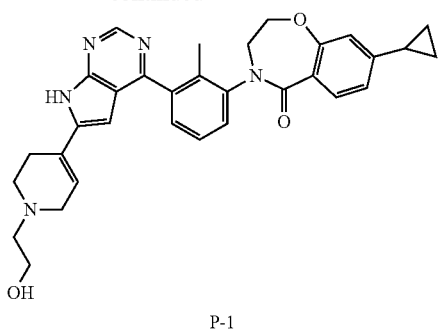

P-1

Step-I: tert-butyl 4-[4-[3-(8-cyclopropyl-5-oxo-2,3-dihydro-1,4-benzoxazepin-4-yl)-2-methyl-phenyl]-7-(p-tolylsulfonyl)pyrrolo[2,3-d]pyrimidin-6-yl]-3,6-dihydro-2H-pyridine-1-carboxylate (P-1-I)

Intermediate P-1-I was synthesized using intermediates II-23 and III-1, following similar procedure as described in step-I for the synthesis of B-1. LCMS: m/z; 746.3 (M+1)$^+$.

Step-II: 4-[3-[6-[1-[3-[tert-butyl(dimethyl)silyl]oxypropyl]-3,6-dihydro-2H-pyridin-4-yl]-7-(p-tolylsulfonyl)pyrrolo[2,3-d]pyrimidin-4-yl]-2-methyl-phenyl]-8-cyclopropyl-2,3-dihydro-1,4-benzoxazepin-5-one (P-1-II)

Intermediate P-1-II was synthesized from intermediate P-1-I following similar procedure as described in step-II for the synthesis of H-1-II (example H-1). LCMS: m/z; 704.4 (M-TBS)$^+$.

Step-III: 8-cyclopropyl-4-[3-[6-[1-(3-hydroxypropyl)-3,6-dihydro-2H-pyridin-4-yl]-7H-pyrrolo[2,3-d]pyrimidin-4-yl]-2-methyl-phenyl]-2,3-dihydro-1,4-benzoxazepin-5-one (P-1)

Example P-1 was synthesized using similar procedure as described in step-III for the synthesis of example H-1. LCMS: m/z 550.3 (M+1)$^+$. $^1$H NMR (DMSO-d$_6$, 400 MHz): δ 0.70-0.78 (m, 2H); 0.96-1.02 (m, 2H); 1.56-1.66 (m, 2H); 1.90-2.00 (m, 1H); 2.09 (s, 3H); 2.38-3.47 (m, 4H); 2.54-2.63 (m, 2H); 3.06-3.14 (m, 2H); 3.42 (t, J=6.2 Hz, 2H); 3.84-3.91 (m, 2H); 4.36-4.46 (m, 2H); 6.26 (s, 1H); 6.54 (s, 1H); 6.79 (s, 1H); 6.89 (d, J=8.0 Hz, 1H); 7.40-7.46 (aromatics, 3H); 7.59 (d, J=8.1 Hz, 1H); 8.77 (s, 1H); 12.30 (bs, 1H).

Following example was synthesized using similar procedure described for the synthesis of P-1.

TABLE 30

| No | Structure/IUPAC name | Characterization | INT used |
|---|---|---|---|
| P-2 | ![structure] 8-cyclopropyl-4-[3-[6-[1-(2-hydroxyethyl)-3,6-dihydro-2H-pyridin-4-yl]-7H-pyrrolo[2,3-d]pyrimidin-4-yl]-2-methyl-phenyl]-2,3-dihydro-1,4-benzoxazepin-5-one | LCMS: m/z 536.3 (M + 1)$^+$. $^1$H NMR (DMSO-d$_6$, 400 MHz), δ 0.74-0.78 (m, 2H); 0.98-1.04 (m, 2H); 1.92-2.02 (m, 1H); 2.12 (s, 3H); 2.63-2.70 (m, 2H); 3.15-3.25 (m, 2H); 3.50-3.60 (m, 3H); 3.85-3.92 (m, 3H); 4.40-4.70 (m, 4H); 6.28 (s, 1H); 6.55 (s, 1H); 6.82 (s, 1H); 6.92 (d, J = 8.3 Hz, 1H); 7.40-7.52 (aromatics, 3H); 7.61 (d, J = 8.1 Hz, 1H); 8.79 (s, 1H); 12.35 (bs, 1H) | II-23 & III-1 |

Example P-3

Synthesis of 8-cyclopropyl-4-[3-[6-[1-(3-hydroxypropyl)-4-piperidyl]-7H-pyrrolo[2,3-d]pyrimidin-4-yl]-2-methyl-phenyl]-2,3-dihydro-1,4-benzoxazepin-5-one

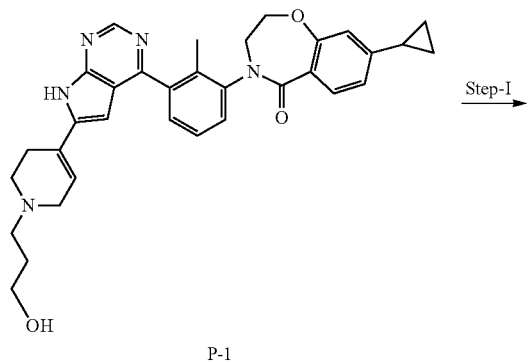

P-1

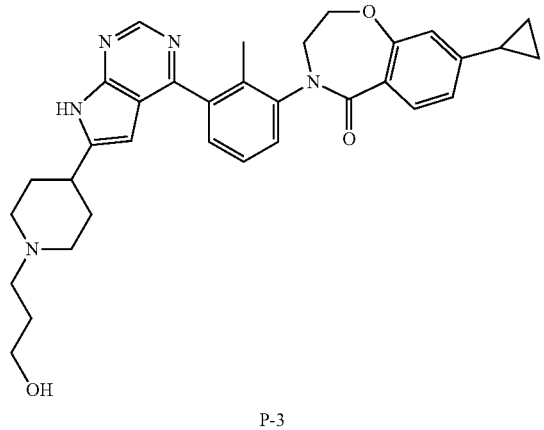

P-3

Step-I

To a solution of P-1 (0.085 g, 0.15 mmol) in MeOH (15 mL) was added 10% Pd/C (10 mg) and the resulting reaction mixture was stirred under $H_2$ atmosphere for 16 h. After completion of reaction (monitored by TLC), reaction mixture was filtered through celite and washed with excess 10% MeOH in $CH_2Cl_2$. Filtrate was concentrated under reduced pressure and the residue was washed using diethyl ether to provide title product P-3 (0.018 g, 21%). LCMS: m/z; 552.3 $(M^++1)$. $^1$H NMR (DMSO-$d_6$, 400 MHz) 0.70-0.80 (m, 2H); 0.98-1.08 (m, 2H); 1.58-1.82 (m, 6H); 1.93-2.08 (m, 2H); 2.10 (s, 3H); 2.72-2.78 (m, 2H); 2.90-3.20 (m, 2H); 3.44 (t, J=6.2 Hz, 3H); 3.85-3.95 (m, 3H); 4.40-4.51 (m, 2H); 6.08 (s, 1H); 6.82 (s, 1H); 6.92 (d, J=8.1 Hz, 1H); 7.38-7.50 (aromatics, 3H); 7.62 (d, J=8.0 Hz, 1H); 8.76 (s, 1H); 12.20 (bs, 1H).

Example P-4

Synthesis of 8-cyclopropyl-4-[2-methyl-3-[6-(1,2,3,6-tetrahydropyridin-5-yl)-7H-pyrrolo[2,3-d]pyrimidin-4-yl]phenyl]-2,3-dihydro-1,4-benzoxazepin-5-one

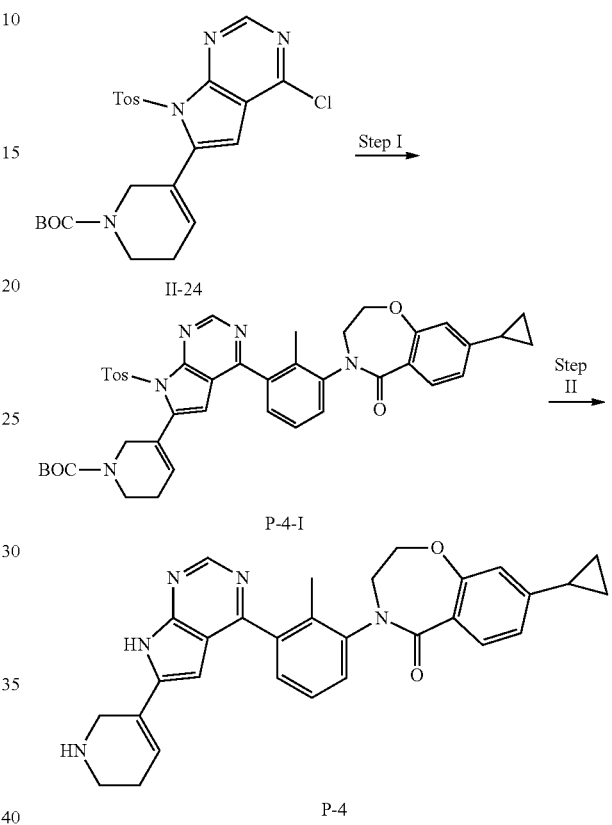

Step-I tert-butyl 5-[4-[3-(8-cyclopropyl-5-oxo-2,3-dihydro-1,4-benzoxazepin-4-yl)-2-methyl-phenyl]-7-(p-tolylsulfonyl)pyrrolo[2,3-d]pyrimidin-6-yl]-3,6-dihydro-2H-pyridine-1-carboxylate (P-4-I)

Intermediate P-4-I was synthesized using intermediates II-24 and III-1, following similar procedure as described in step-I of synthesis of P-1. LCMS: m/z; 746 $(M+1)^+$.

Step-II: 8-cyclopropyl-4-[2-methyl-3-[6-(1,2,3,6-tetrahydropyridin-5-yl)-7H-pyrrolo[2,3-d]pyrimidin-4-yl]phenyl]-2,3-dihydro-1,4-benzoxazepin-5-one (P-4)

Example P-4 was synthesized using similar procedure as described for Boc-deprotection (in step-II) and tosyl-deprotection (in step-III) of the synthesis of P-1. LCMS: m/z; 492.3 $(M+1)^+$. $^1$H NMR (DMSO-$d_6$, 400 MHz) 0.73-0.78 (m, 2H); 0.98-1.06 (m, 2H); 1.95-2.10 (m, 1H); 2.11 (s, 3H); 2.20-2.30 (m, 2H); 2.85-2.92 (m, 2H); 3.60-3.65 (m, 2H); 3.85-3.95 (m, 2H); 4.40-4.52 (m, 2H); 6.25 (s, 1H); 6.65-6.70 (aromatics, 1H); 6.82 (d, J=1.4 Hz, 1H); 6.91 (d, J=8.1 Hz, 1H); 7.40-7.50 (aromatics, 3H); 7.62 (d, J=7.9 Hz, 1H); 8.79 (s, 1H); 12.35 (s, 1H).

Example P-5

4-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]-N,N-dimethyl-3,6-dihydro-2H-pyridine-1-carboxamide

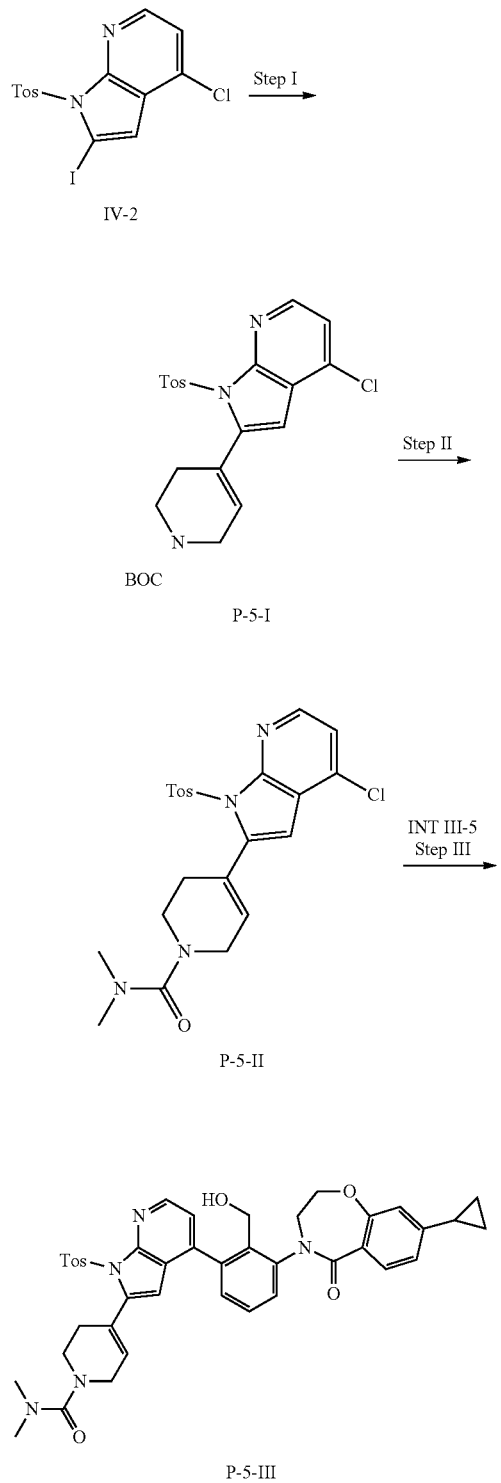

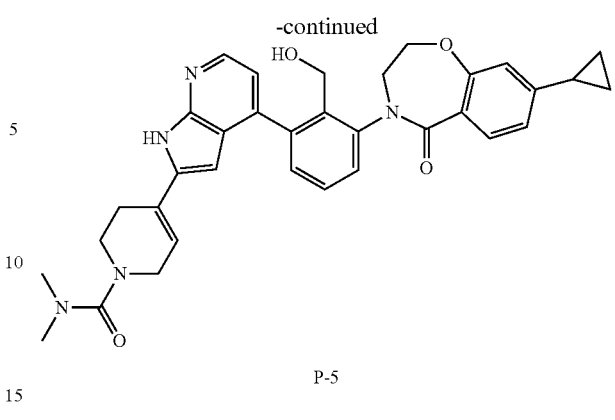

Step-I: tert-butyl 4-[4-chloro-1-(p-tolylsulfonyl)pyrrolo[2,3-b]pyridin-2-yl]-3,6-dihydro-2H-pyridine-1-carboxylate (P-5-I)

Intermediate P-5-I was synthesized following the procedure as described for the synthesis of intermediate II-23. LCMS: m/z; 488.3 $(M+1)^+$.

Step-II: 4-[4-chloro-1-(p-tolylsulfonyl)pyrrolo[2,3-b]pyridin-2-yl]-N,N-dimethyl-3,6-dihydro-2H-pyridine-1-carboxamide (P-5-II)

Intermediate P-5-I (2 g, 6.94 mmol) was dissolved in $CH_2Cl_2$ (20 mL), to which trifluoroacetic acid (10 mL, excess) was added at 0° C. and the reaction mixture was stirred at room temperature for 2 h. Solvents were removed under reduced pressure and saturated $NaHCO_3$ solution (50 mL) was added to it. Extraction was carried out using EtOAc (30 mL×2); the combined organic layers were washed with water (60 mL), brine (60 mL), dried over anhydrous $Na_2SO_4$, filtered and concentrated under reduced pressure to provide corresponding Boc-deprotected intermediate (1.6 g). It (0.5 g, 1.28 mmol) was dissolved in $CH_2Cl_2$ (10 mL) and cooled to 0° C. To this was added pyridine (1.0 mL, 12.8 mmol) and 4-nitrophenylchloroformate (1.29 g, 6.44 mmol) sequentially. The reaction mixture was stirred at room temperature for 3 h before solvent was removed under reduced pressure. To the residue obtained was added DMF (10 mL) and cooled to 0° C. To this reaction mixture, TEA (1.6 mL, 12.8 mmol) and dimethylaminehydrochloride (0.525 g, 6.44 mmol) were added and it was stirred at room temperature for 16 h. It was then diluted using water (30 mL) and extraction was carried out using EtOAc (20 mL×3). The combined organic layers were washed with brine (50 mL), dried over anhydrous $Na_2SO_4$, filtered and concentrated under reduced pressure. The residue was purified using silica gel column chromatography (25% acetone in hexane) to provide the title compound P-5-II (0.25 g, 53% yield). LCMS: m/z; 459.2 $(M+1)^+$.

Step-III: 4-[4-[3-(8-cyclopropyl-5-oxo-2,3-dihydro-1,4-benzoxazepin-4-yl)-2-(hydroxymethyl)phenyl]-1-(p-tolylsulfonyl)pyrrolo[2,3-b]pyridin-2-yl]-N,N-dimethyl-3,6-dihydro-2H-pyridine-1-carboxamide (P-5-III)

Intermediate P-5-III was synthesized using intermediates P-5-II and III-5, following similar procedure as described in step-II of the synthesis of B-1-I. LCMS: m/z; 732.4 $(M+1)^+$.

Step-IV: 4-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]-N,N-dimethyl-3,6-dihydro-2H-pyridine-1-carboxamide (P-5)

Intermediate P-5-III (0.15 g, 0.19 mmol) was dissolved in acetone (5 mL); to which aqueous NaOH (0.038 g, 0.96 mmol, 2 mL) was added and the reaction mixture was stirred at 70° C. for 16 h. Finally, acetone was removed under reduced pressure and water was added to the residue. Extraction was carried out using EtOAc (10 mL×3). The combined organic layers were washed with brine (30 mL), dried over anhydrous $Na_2SO_4$, filtered and concentrated under reduced pressure. The residue was purified using preparative TLC (S % MeOH in $CH_2Cl_2$) to provide the title compound P-5 (0.02 g, 17% yield). LCMS: m/z; 578.1 (M+1)+. 1H NMR (DMSO-d6, 400 MHz) δ 0.76-0.80 (m, 2H); 1.04-1.09 (m, 2H); 1.89-1.97 (m, 1H); 2.56-2.68 (m, 2H); 2.87 (bs, 6H); 3.44-3.52 (m, 2H); 3.92-3.98 (m, 2H); 4.02-4.08 (m, 2H), 4.24-4.34 (m, 1H); 4.50-4.60 (m, 3H); 6.28 (s, 1H); 6.32 (s, 1H); 6.78 (s, 1H); 6.92 (d, J=8.0 Hz, 1H); 7.36 (d, J=8.8 Hz, 1H); 7.48-7.58 (aromatics, 3H); 7.82 (d, J=8.0 Hz, 1H); 8.31 (d, J=4.7 Hz, 1H); 10.97 (bs, 1H).

Example P-6

4-[3-(8-cyclopropyl-5-oxo-2,3-dihydro-1,4-benzoxazepin-4-yl)phenyl]-2-[4-[(4-methylpiperazin-1-yl)methyl]phenyl]-1H-pyrrolo[2,3-b]pyridine-5-carbonitrile

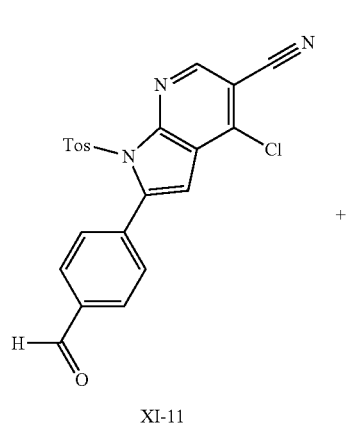

XI-11

+

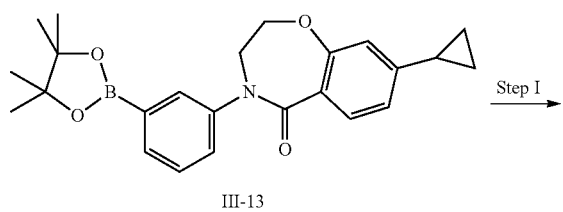

III-13

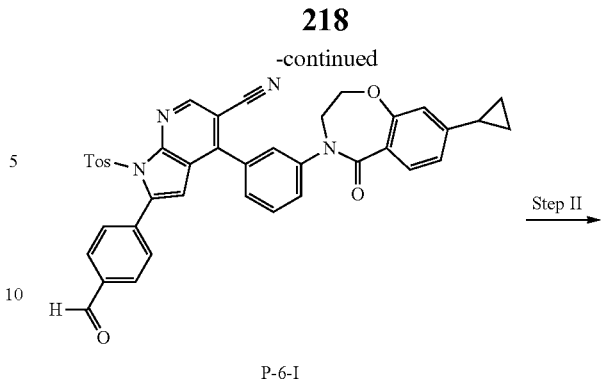

P-6-I

Step II

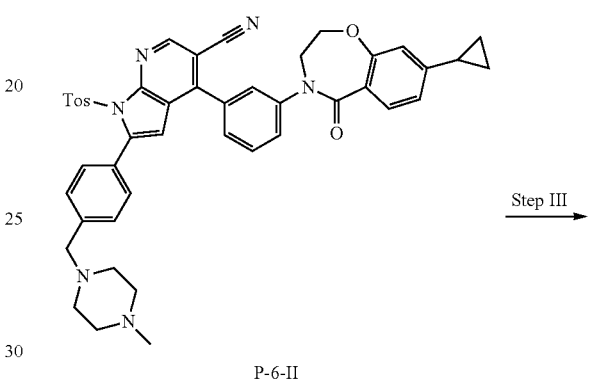

P-6-II

Step III

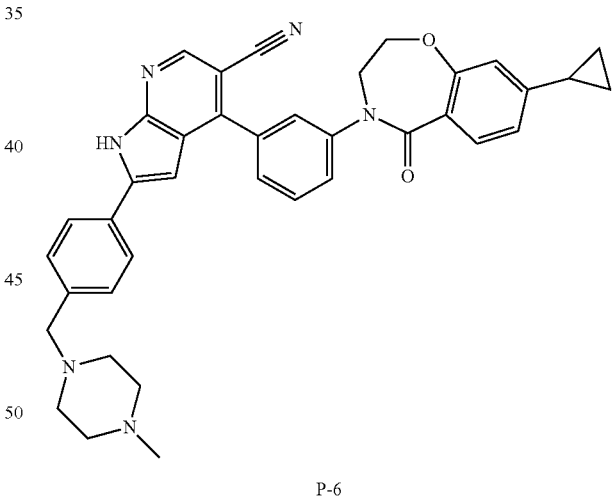

P-6

Examples P-6 was synthesized following similar sequence of reactions and procedures as described for the synthesis of example B-1, starting from intermediates XI-11 and III-13. LCMS: m/z; 609.2 (M+1)+. 1H NMR (DMSO-d6, 400 MHz) δ 0.73-0.79 (m, 2H); 0.99-1.06 (m, 2H); 1.91-2.02 (m, 1H); 2.16 (s, 3H); 2.25-2.45 (m, 8H); 3.49 (s, 2H); 4.00-4.08 (m, 2H), 4.48-4.55 (m, 2H); 6.81 (s, 1H); 6.92 (d, J=7.9 Hz, 1H); 7.09 (s, 1H); 7.40 (d, J=7.3 Hz, 2H); 7.61-7.71 (aromatics, 4H); 7.82 (s, 1H); 7.94 (d, J=7.0 Hz, 2H); 8.70 (d, J=1.7 Hz, 1H); 12.93 (bs, 1H).

Example P-7

6-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]pyridine-3-carboxylic acid thesis of L-1. Ester hydrolysis was done under alkaline hydrolysis conditions. LCMS: m/z; 547.1 (M+1)$^+$. $^1$H NMR (DMSO-d$_6$, 400 MHz) δ 0.74-0.78 (m, 2H); 0.99-1.04 (m, 2H); 1.93-2.00 (m, 1H); 3.88-3.98 (m, 2H); 4.20-4.30 (m, 1H); 4.32-4.38 (m, 1H); 4.52-4.60 (m, 2H); 4.70-4.82 (m,

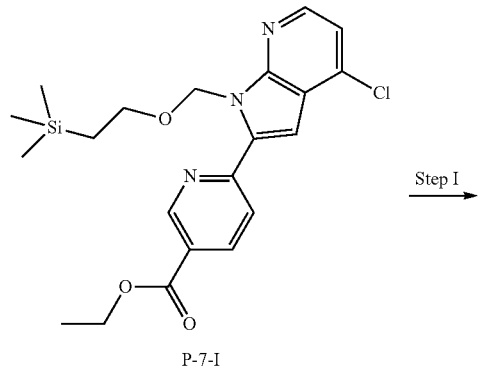

P-7-I

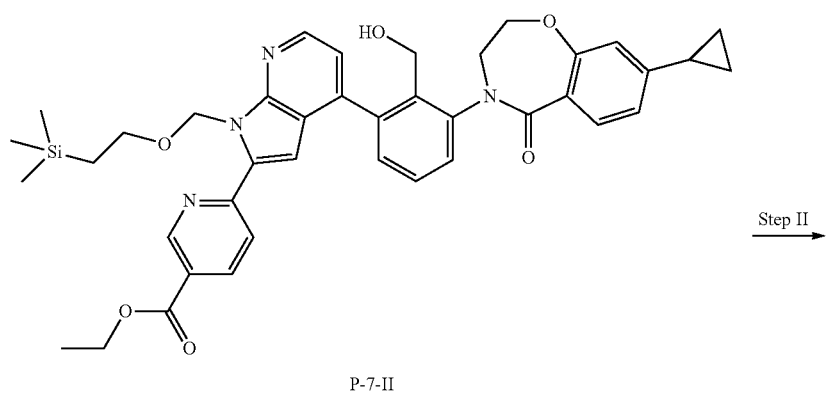

P-7-II

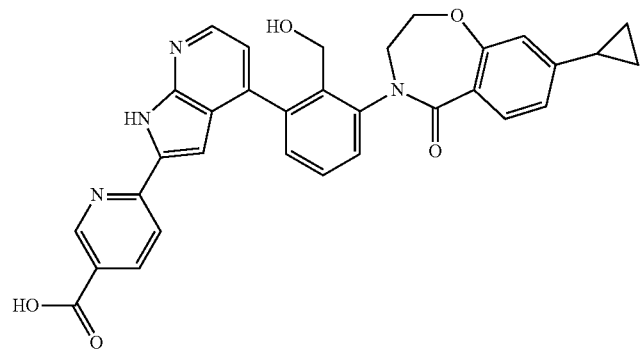

P-7

Example P-7 was synthesized following above reaction sequence and using similar procedure described for the synthesis 1H); 6.81 (s, 1H); 6.87-6.90 (aromatics, 2H); 7.20 (bs, 1H); 7.44 (d, J=7.8 Hz, 2H); 7.48 (d, J=7.3 Hz, 1H); 7.55-7.59

(aromatics, 1H); 7.67 (d, J=8.3 Hz, 1H); 7.93 (d, J=7.8 Hz, 1H); 8.12 (dd, J1=1.9 Hz, J2=7.8 Hz, 1H); 8.31 (d, J=4.9 Hz, 1H); 12.38 (bs, 1H).

Example P-8

8-cyclopropyl-4-[3-[2-[4-(1,2-dihydroxyethyl)phenyl]-1H-pyrrolo[2,3-b]pyridin-4-yl]-2-(hydroxymethyl)phenyl]-2,3-dihydro-1,4-benzoxazepin-5-one

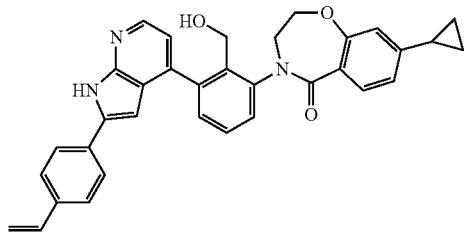

P-8-I

P-8

Step-I

Intermediate P-8-I was synthesized following procedure described for the synthesis of G-1 (step-I and step-III). P-8-I (0.05 g, 0.095 mmol) was dissolved in THF-water (4 mL+1 mL), to which N-methylmorpholine-N-oxide (0.017 g, 0.142 mmol) and $OsO_4$ (0.003 g, 0.0095 mmol) were added sequentially. The reaction mixture was stirred for 16 h at room temperature before it was diluted using EtOAc (30 mL). The organic layer was washed with water (30 mL), brine (30 mL), dried over anhydrous $Na_2SO_4$, filtered and concentrated under reduced pressure. The residue obtained was purified using preparative TLC (5% MeOH in $CH_2Cl_2$) to provide title compound P-8 (0.01 g, 18% yield). LCMS: m/z; 562.2 (M+1)+. 1H NMR (CD3OD, 400 MHz) δ 0.74-0.80 (m, 2H); 1.02-1.10 (m, 2H); 1.92-2.00 (m, 1H); 3.54-3.68 (m, 3H); 3.96-4.06 (m, 2H); 4.50-4.56 (m, 1H); 4.58-4.64 (m, 2H); 4.70-4.74 (m, 1H); 6.69 (s, 1H); 6.82 (s, 1H); 6.94 (d, J=8.0 Hz, 1H); 7.22 (d, J=4.8 Hz, 1H); 7.46 (d, J=7.9 Hz, 2H); 7.51 (d, J=7.5 Hz, 2H); 7.58-7.62 (aromatics, 1H); 7.70 (d, J=8.0 Hz, 1H); 7.82 (d, J=8.0 Hz, 2H); 8.24 (d, J=3.9 Hz, 1H).

Example P-9

8-cyclopropyl-4-[2-(hydroxymethyl)-3-[2-[1-(1-isopropylazetidin-3-yl)imidazol-4-yl]-1H-pyrrolo[2,3-b]pyridin-4-yl]phenyl]-2,3-dihydro-1,4-benzoxazepin-5-one

P-9-I

P-9

Step-I

Intermediate P-9-I was synthesized following similar reaction sequence and procedures described for the synthesis of D-1. LCMS: m/z; 801.4 (M+1)+. Example P-9 was synthesized following similar procedure described for the synthesis of D-1 (step-II and III) using intermediate P-9-I (acetone was used for reductive amination step). LCMS: m/z 589.2 (M+1)+. 1H NMR (DMSO-d6, 400 MHz) δ 0.74-0.77 (m, 2H); 0.91 (d, J=6.3 Hz, 6H); 0.99-1.04 (m, 2H); 1.93-2.00 (m, 1H); 3.22 (t, J=6.8 Hz, 2H); 3.63-3.70 (m, 2H); 3.86-3.96 (m, 2H); 4.20-4.38 (m, 2H); 4.52-4.58 (m, 2H); 4.74-4.80 (m, 1H); 4.82-4.88 (m, 1H); 6.41 (d, J=1.5 Hz, 1H); 6.81 (d, J=1.5 Hz, 1H); 6.88 (d, J=7.8 Hz, 1H); 7.15 (d, J=3.9 Hz, 1H); 7.41 (d, J=7.8 Hz, 1H); 7.44 (d, J=7.3 Hz, 1H); 7.53-7.57 (m, 1H); 7.67 (d, J=7.8 Hz, 1H); 7.85 (s, 1H); 8.05 (s, 1H); 8.19 (d, J=4.9 Hz, 1H); 12.00 (bs, 1H).

Example P-10

4-[4-[2-(hydroxymethyl)-3-[8-(1-hydroxy-1-methyl-ethyl)-5-oxo-2,3-dihydro-1,4-benzoxazepin-4-yl]phenyl]-1H-pyrrolo[2,3-b]pyridin-2-yl]-N,N-dimethyl-3,6-dihydro-2H-pyridine-1-carboxamide

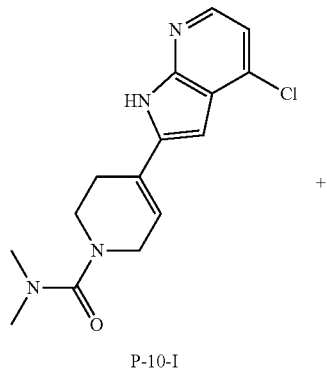

P-10-I

+

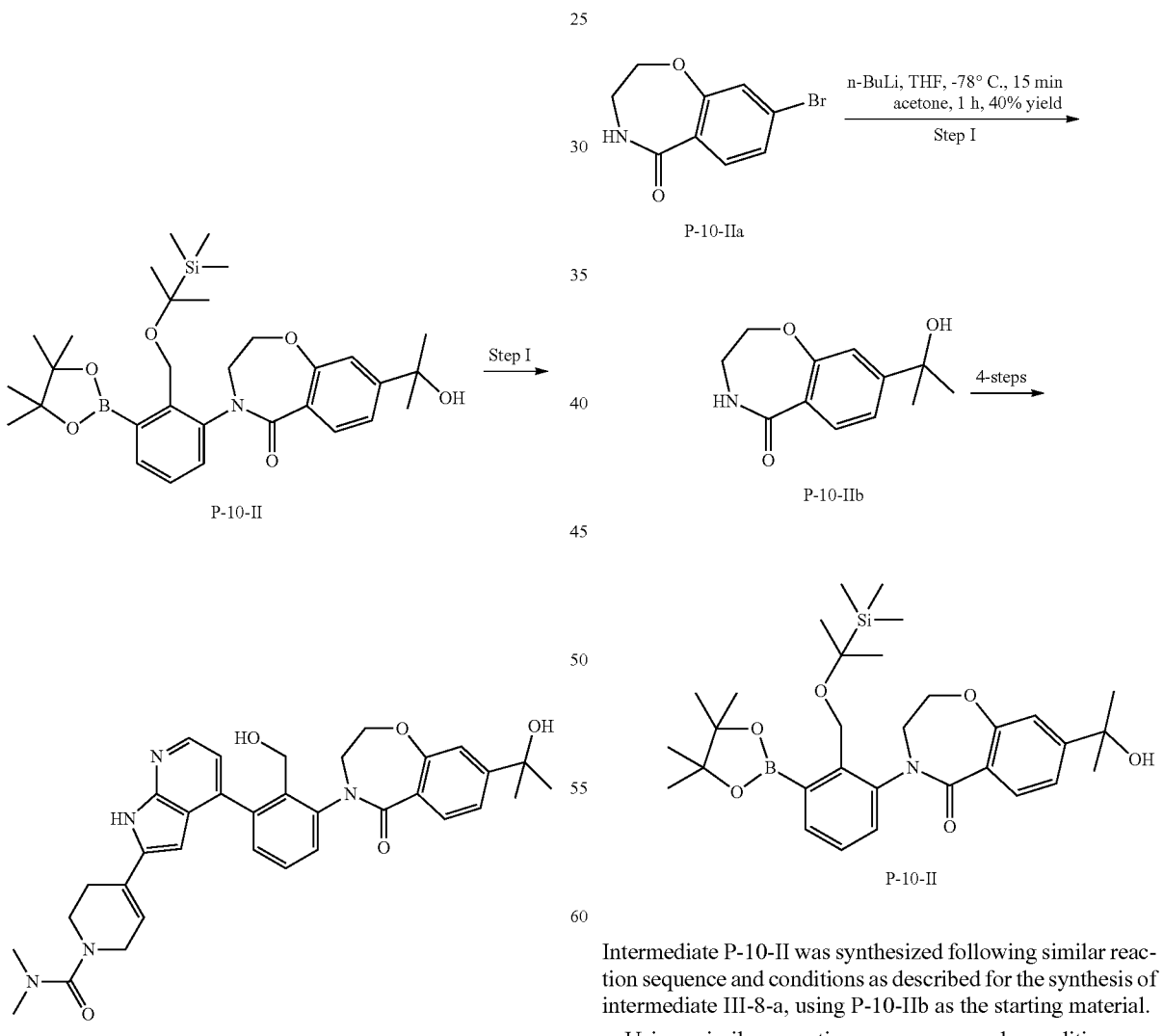

Step-I

To a solution of intermediate P-10-I (0.18 g, 0.59 mmol) and intermediate P-10-II (0.34 g, 0.59 mmol) in 1-propanol (8 mL) was added aqueous $Na_2CO_3$ solution (0.06 g, 1.18 mmol, 0.6 mL) and Argon was purged through it for 15 min. Finally, $PdCl_2(PPh_3)_2$ (0.033 g, 0.047 mmol) was added to it and Argon purging was continued for 10 min more. Finally, the reaction mixture was stirred at 90° C. for 16 h. After completion of the reaction, solvents were removed under reduced pressure and the residue was purified using silica gel column chromatography first and then preparative TLC (5% MeOH in $CH_2Cl_2$) to provide the title compound P-10 (60 mg, 17% yield). LCMS: m/z; 596.2 (M+1)$^+$. $^1$H NMR (DMSO-$d_6$, 400 MHz) δ 1.40 (s, 6H); 2.73 (s, 6H); 3.20-3.40 (m, 4H); 3.80-3.96 (m, 4H); 4.10-4.35 (m, 2H); 4.50-4.60 (m, 2H); 4.70-4.80 (m, 1H); 5.25 (s, 1H); 6.21 (s, 1H); 6.49 (s, 1H); 7.10-7.18 (aromatics, 2H); 7.24 (dd, $J_1$=1.5 Hz, $J_2$=8.3 Hz, 1H); 7.38-7.46 (aromatics, 2H); 7.50-7.54 (aromatic, 1H); 7.70 (d, J=8.3 Hz, 1H); 8.22 (d, J=4.9 Hz, 1H); 11.91 (bs, 1H).

Intermediate P-10-II can be synthesized using following sequence of reactions and conditions.

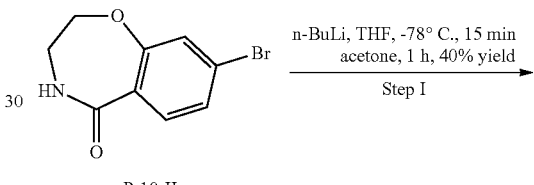

P-10-IIa

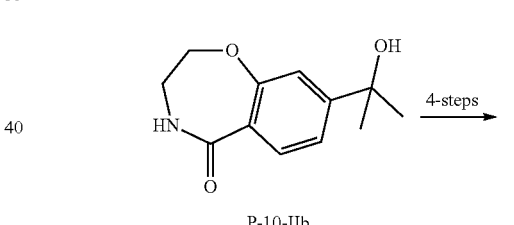

P-10-IIb

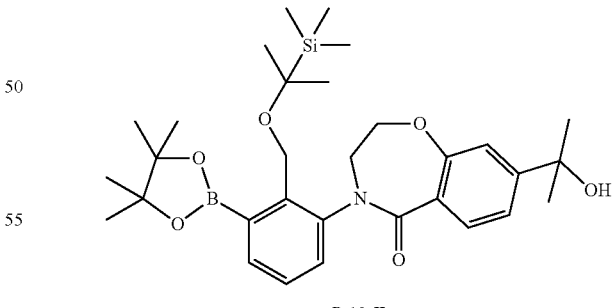

P-10-II

Intermediate P-10-II was synthesized following similar reaction sequence and conditions as described for the synthesis of intermediate III-8-a, using P-10-IIb as the starting material.

Using similar reaction sequence and conditions as described for the synthesis of P-10, following compounds were also synthesized.

225
226

TABLE 31

| No | Structure/IUPAC name | Characterization | INT used |
|---|---|---|---|
| P-11 | 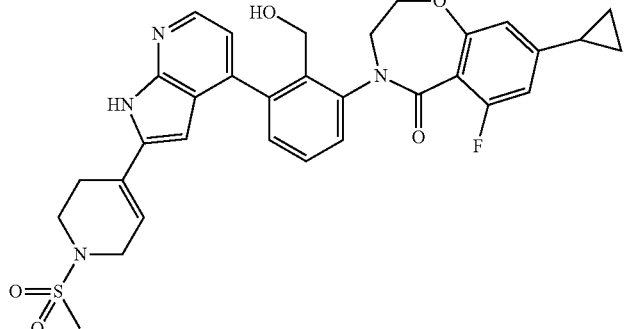<br>8-cyclopropyl-6-fluoro-4-[2-(hydroxymethyl)-3-[2-(1-methylsulfonyl-3,6-dihydro-2H-pyridin-4-yl)-1H-pyrrolo[2,3-b]pyridin-4-yl]phenyl]-2,3-dihydro-1,4-benzoxazepin-5-one | LCMS: m/z 603.1 (M + 1)⁺.<br>¹H NMR (DMSO-d₆, 400 MHz) δ 0.76-0.84 (m, 2H); 1.03-1.05 (m, 2H); 1.98-2.02 (m, 1H), 2.57-2.62 (m, 2H); 2.94 (s, 3H); 3.34-3.36 (m, 2H); 3.79-4.00 (m, 4H); 4.18-4.24 (m, 1H); 4.32-4.39 (m, 2H); 4.48-4.51 (m, 1H); 4.82 (bs, 1H); 6.26 (s, 1H); 6.55 (s, 1H); 6.78 (s, 1H); 6.84 (d, J = 8.0 Hz, 1H); 7.71 (s, 1H); 7.43 (t, J = 8.8 Hz, 2H); 7.53-7.57 (aromatics, 1H); 8.26 (d, J = 5.2 Hz, 1H); 11.99 (s, 1H) | III-9 |
| P-12 | 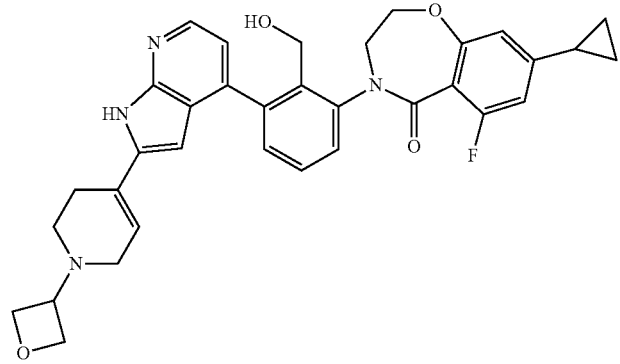 [SMILES: O=C1c2c(F)cc(C3CC3)cc2OCCN1c1cccc(-c2ccnc3[nH]c(C4=CCN(C5COC5)CC4)cc23)c1CO]<br>8-cyclopropyl-6-fluoro-4-[2-(hydroxymethyl)-3-[2-[1-(oxetan-3-yl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z 581.3 (M + 1)⁺.<br>¹H NMR (DMSO-d₆, 400 MHz) δ 0.74-0.84 (m, 2H); 0.98-1.08 (m, 2H); 1.96-2.06 (m, 1H); 2.40-2.48 (m, 4H); 2.98-3.06 (m, 2H); 3.50-3.58 (m, 1H); 3.76-3.84 (m, 1H); 3.90-4.00 (m, 1H); 4.16-4.28 (m, 1H); 4.34-4.44 (m, 2H); 4.46-4.62 (m, 5H); 4.76-4.90 (m, 1H); 6.18 (s, 1H); 6.50 (s, 1H); 6.77 (s, 1H); 6.84 (d, J = 11.0 Hz, 1H); 7.15 (bs, 1H); 7.36-7.58 (aromatics, 3H); 8.23 (d, J = 4.4 Hz, 1H); 11.89 (bs, 1H) | III-9 |

TABLE 31-continued

| No | Structure/IUPAC name | Characterization | INT used |
|---|---|---|---|
| P-13 | 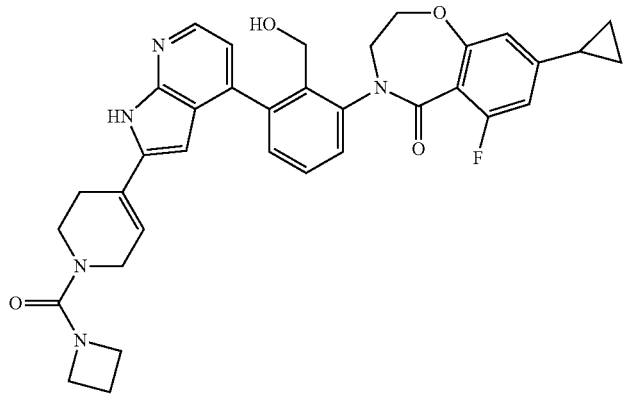 [SMILES: O=C(N1CC=C(c2cc3c(-c4cccc(N5CCOc6cc(C7CC7)cc(F)c6C5=O)c4CO)ccnc3[nH]2)CC1)N1CCC1]<br><br>4-[3-[2-[1-(azetidine-1-carbonyl)-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one | LCMS: m/z 608.1 (M + 1)$^+$.<br>$^1$H NMR (DMSO-d$_6$, 400 MHz) δ 0.76-0.84 (m, 2H); 1.01-1.09 (m, 2H); 1.94-2.04 (m, 1H); 2.10-2.19 (m, 2H); 2.38-2.45 (m, 2H); 3.34-3.43 (m, 2H); 3.76-3.84 (m, 1H); 3.89-3.95 (m, 7H); 4.16-4.27 (m, 1H); 4.32-4.42 (m, 2H); 4.47-4.56 (m, 1H); 4.71-4.92 (m, 1H); 6.22 (s, 1H); 6.49 (bs, 1H); 6.77 (s, 1H); 6.84 (d, J = 11.2 Hz, 1H); 7.15 (bs, 1H); 7.40-7.45 (aromatics, 2H); 7.55 (app. t, J = 7.7 Hz, 1H); 8.24 (d, J = 4.9 Hz, 1H); 11.94 (bs, 1H) | III-9 |
| P-14 | 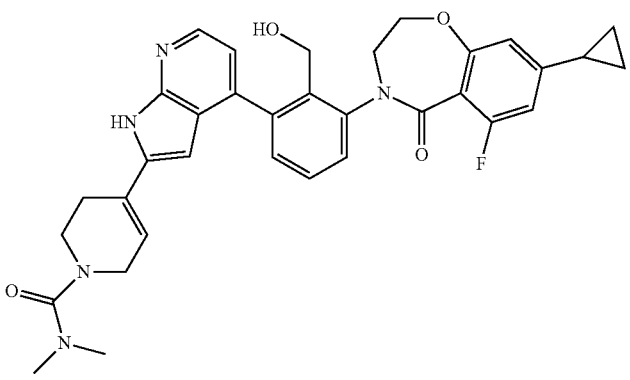 [SMILES: CN(C)C(=O)N1CC=C(c2cc3c(-c4cccc(N5CCOc6cc(C7CC7)cc(F)c6C5=O)c4CO)ccnc3[nH]2)CC1]<br><br>4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-N,N-dimethyl-3,6-dihydro-2H-pyridine-1-carboxamide | LCMS: m/z 596.2 (M + 1)$^+$.<br>$^1$H NMR (400 MHz; CDCl$_3$): δ 0.76-0.84 (m, 2H); 1.01-1.09 (m, 2H); 1.84-1.95 (m, 1H); 2.54-2.68 (m, 2H); 2.87 (s, 6H); 3.40-3.54 (m, 2H); 3.90-3.99 (m, 2H); 4.01-4.10 (m, 2H); 4.24-4.50 (m, 3H); 4.55-4.72 (m, 1H); 6.28 (bs, 1H); 6.34 (s, 1H); 6.66 (s, 1H); 6.69 (d, J = 10.6 Hz, 1H); 7.40 (d, J = 8.9 Hz, 1H); 7.44-7.62 (aromatics, 3H); 8.30 (d, J = 4.4 Hz, 1H); 11.19 (bs, 1H) | III-9 |

TABLE 31-continued

| No | Structure/IUPAC name | Characterization | INT used |
|---|---|---|---|
| P-15 | 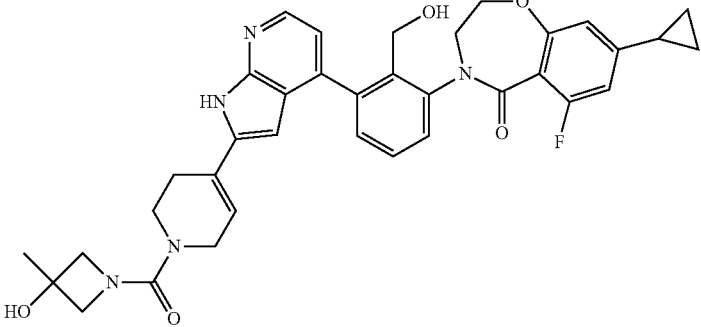<br>8-cyclopropyl-6-fluoro-4-[2-(hydroxymethyl)-3-[2-[1-(3-hydroxy-3-methyl-azetidine-1-carbonyl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z 638.2 (M + 1)$^+$.<br>$^1$H NMR (DMSO-d$_6$, 400 MHz) δ 0.76-0.82 (m, 2H); 1.01-1.06 (m, 2H); 1.35 (s, 3H); 1.94-2.04 (m, 1H); 2.38-2.46 (m, 2H); 3.37-3.42 (m, 2H); 3.70-3.84 (m, 5H); 3.92-3.98 (m, 3H); 4.16-4.26 (m, 1H); 4.34-4.42 (m, 2H); 4.46-4.56 (m, 1H); 4.74-4.86 (m, 1H); 5.46 (s, 1H); 6.22 (s, 1H); 6.49 (bs, 1H); 6.77 (s, 1H); 6.84 (d, J = 11.2 Hz, 1H); 7.15 (bs, 1H); 7.40-7.45 (aromatics, 2H); 7.52-7.56 (aromatics, 1H); 8.24 (d, J = 4.8 Hz, 1H); 11.93 (bs, 1H) | III-9 |
| P-16 | 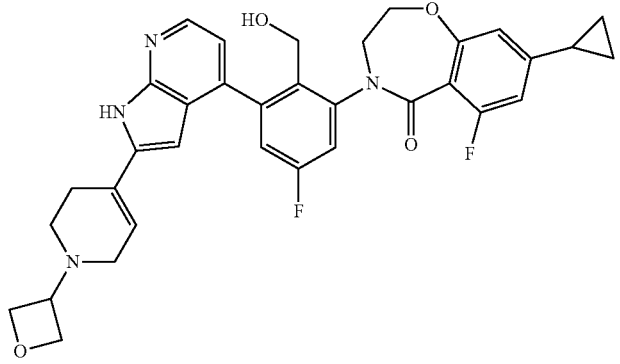 [SMILES: O=C1c2c(F)cc(C3CC3)cc2OCCN1c1cc(F)cc(-c2ccnc3[nH]c(C4=CCN(C5COC5)CC4)cc23)c1CO]<br>8-cyclopropyl-6-fluoro-4-[5-fluoro-2-(hydroxymethyl)-3-[2-[1-(oxetan-3-yl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z 599.2 (M + 1)$^+$.<br>$^1$H NMR (DMSO-d$_6$, 400 MHz) δ 0.77-0.82 (m, 2H); 1.00-1.09 (m, 2H); 1.96-2.06 (m, 1H); 2.45-2.50 (m, 4H); 3.03 (bs, 2H); 3.50-3.60 (m, 1H); 3.70-4.00 (m, 2H); 4.10-4.40 (m, 3H); 4.51 (t, J = 6.4 Hz, 2H); 4.57 (t, J = 6.4 Hz, 2H); 4.50-4.60 (m, 1H); 4.76-4.90 (m, 1H); 6.21 (s, 1H); 6.48-6.54 (aromatics, 1H); 6.77 (s, 1H); 6.83 (d, J = 11.2 Hz, 1H); 7.12-7.18 (aromatics, 1H); 7.29 (dd, J$_1$ = 2.8 Hz, J$_2$ = 8.8 Hz, 1H); 7.36 (dd, J$_1$ = 2.8 Hz, J$_2$ = 9.2 Hz, 1H); 8.24 (d, J = 5.2 Hz, 1H); 11.90 (bs, 1H) | III-12 |
| P-17 | 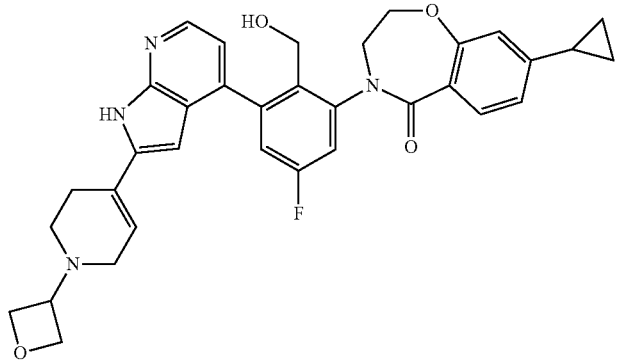 [SMILES: O=C1c2ccc(C3CC3)cc2OCCN1c1cc(F)cc(-c2ccnc3[nH]c(C4=CCN(C5COC5)CC4)cc23)c1CO]<br>8-cyclopropyl-4-[5-fluoro-2-(hydroxymethyl)-3-[2-[1-(oxetan-3-yl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z 581.2 (M + 1)$^+$.<br>$^1$H NMR (DMSO-d$_6$, 400 MHz) δ 0.70-0.80 (m, 2H); 0.98-1.05 (m, 2H); 1.92-2.02 (m, 1H); 2.45-2.50 (m, 4H); 3.03 (bs, 2H); 3.50-3.60 (m, 1H); 3.88-4.00 (m, 2H); 4.10-4.35 (m, 2H); 4.40-4.65 (m, 6H); 4.70-4.80 (m, 1H); 6.21 (s, 1H); 6.51 (bs, 1H); 6.80 (s, 1H); 6.87 (d, J = 8.0 Hz, 1H); 7.12-7.18 (aromatics, 1H); 7.26 (d, J = 8.0 Hz, 1H); 7.38 (d, J = 8.8 Hz, 1H); 7.68 (d, J = 8.4 Hz, 1H); 8.20-8.24 (aromatics, 1H); 11.90 (bs, 1H) | III-11 |

TABLE 31-continued

| No | Structure/IUPAC name | Characterization | INT used |
|---|---|---|---|
| P-18 | 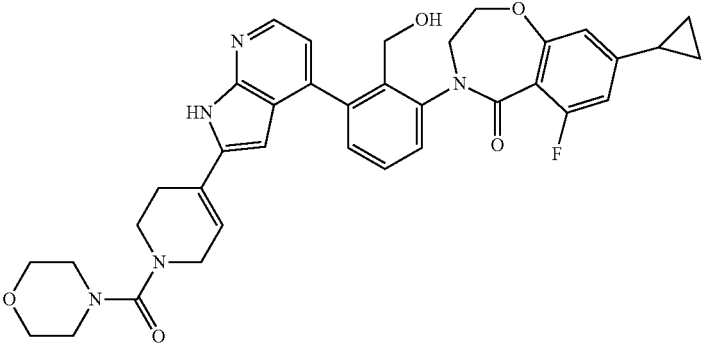 [SMILES: O=C(N1CC=C(c2cc3c(-c4cccc(N5CCOc6cc(C7CC7)cc(F)c6C5=O)c4CO)ccnc3[nH]2)CC1)N1CCOCC1]<br><br>8-cyclopropyl-6-fluoro-4-[2-(hydroxymethyl)-3-[2-[1-(morpholine-4-carbonyl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z; 638.2 (M + 1)⁺. $^1$H NMR (DMSO-$d_6$, 400 MHz) δ 0.78-0.82 (m, 2H); 0.96-1.02 (m, 4H); 1.96-2.08 (m, 1H); 3.10-3.18 (m, 4H); 3.34-3.40 (m, 2H); 3.56-3.62 (m, 4H); 3.90-4.00 (m, 4H); 4.18-4.26 (m, 1H); 4.34-4.42 (m, 2H); 4.48-4.54 (m, 1H); 4.75-4.88 (m, 1H); 6.22 (s, 1H); 6.50 (bs, 1H); 6.77 (s, 1H); 6.84 (d, J = 11.4 Hz, 1H); 7.10-7.20 (aromatics, 1H); 7.40-7.46 (aromatics, 2H); 7.54 (app. t, J = 8.0 Hz, 1H); 8.24 (d, J = 4.8 Hz, 1H); 11.95 (bs, 1H) | III-8-b |
| P-19 | 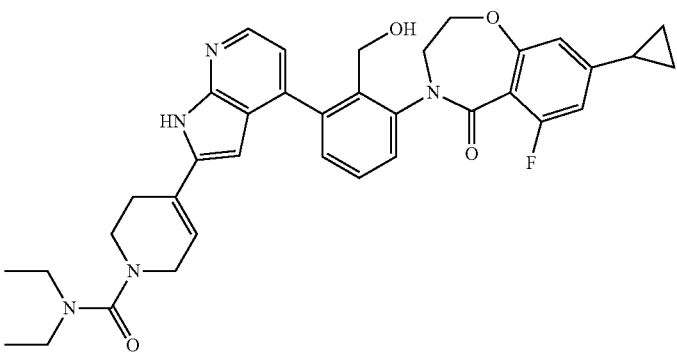 [SMILES: CCN(CC)C(=O)N1CC=C(c2cc3c(-c4cccc(N5CCOc6cc(C7CC7)cc(F)c6C5=O)c4CO)ccnc3[nH]2)CC1]<br><br>4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-N,N-diethyl-3,6-dihydro-2H-pyridine-1-carboxamide | LCMS: m/z; 624.3 (M + 1)⁺. $^1$H NMR (CD$_3$OD, 400 MHz) δ 0.78-0.82 (m, 2H); 1.06-1.2 (m, 8H); 1.96-2.06 (m, 1H); 2.56-2.62 (m, 2H); 2.86 (q, J = 7.1 Hz, 3H); 3.25 (q, J = 7.1 Hz, 3H); 3.45 (t, J = 5.8 Hz, 2H); 3.87-4.07 (m, 3H); 4.44-4.60 (m, 3H); 6.31 (s, 1H); 6.39 (bs, 1H); 6.73 (s, 1H); 6.79 (d, J = 11.1 Hz, 1H); 7.17 (d, J = 4.8 Hz, 1H); 7.45-7.50 (aromatics, 2H); 7.54-7.60 (aromatics,1H); 8.21 (d, J = 5.3 Hz, 1H) | III-8-b |
| P-20 | 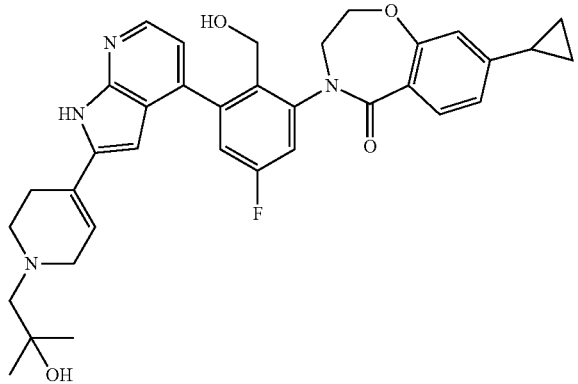 [SMILES: CC(C)(O)CN1CC=C(c2cc3c(-c4cc(F)cc(N5CCOc6cc(C7CC7)ccc6C5=O)c4CO)ccnc3[nH]2)CC1]<br><br>8-cyclopropyl-4-[5-fluoro-2-(hydroxymethyl)-3-[2-[1-(2-hydroxy-2-methyl-propyl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z 597.3 (M + 1)⁺.<br>$^1$H NMR (DMSO-$d_6$, 400 MHz) δ 0.70-0.77 (m, 2H); 0.99-1.03 (m, 2H); 1.10 (s, 6H); 1.92-2.00 (m, 1H); 2.30 (bs, 2H); 2.40-2.50 (m, 2H); 2.74 (t, J = 5.6 Hz, 2H); 3.26 (bs, 2H); 3.92 (t, J = 4.4 Hz, 2H); 4.10-4.30 (m, 3H); 4.50-4.60 (m, 2H); 4.70-4.80 (m, 1H); 6.19 (s, 1H); 6.46-6.50 (aromatics, 1H); 6.80 (d, J = 1.6 Hz, 1H); 6.88 (dd, J$_1$ = 1.2 Hz, J$_2$ = 8.4 Hz, 1H); 7.12-7.18 (aromatics, 1H); 7.26 (dd, J$_1$ 2.8 Hz, J$_2$ = 8.8 Hz, 1H); 7.38 (dd, J$_1$ = 2.8 Hz, J$_2$ = 8.8 Hz, 1H); 7.68 (d, J = 8.4 Hz, 1H); 8.23 (d, J = 4.8 Hz 1H); 11.82 (bs, 1H) | III-11 |

TABLE 31-continued

| No | Structure/IUPAC name | Characterization | INT used |
|---|---|---|---|
| P-21 | 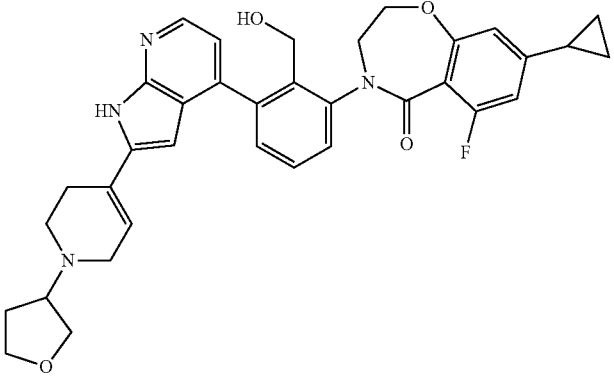 [SMILES: O=C1c2c(F)cc(C3CC3)cc2OCCN1c1cccc(-c2ccnc3[nH]c(C4=CCN(C5CCOC5)CC4)cc23)c1CO]<br>8-cyclopropyl-6-fluoro-4-[2-(hydroxymethyl)-3-[2-(1-tetrahydrofuran-3-yl-3,6-dihydro-2H-pyridin-4-yl)-1H-pyrrolo[2,3-b]pyridin-4-yl]phenyl]-2,3-dihydro-1,4-benzoxazepin-5-one | LCMS: m/z 595.2 (M + 1)$^+$.<br>$^1$H NMR (DMSO-d$_6$, 400 MHz) δ 0.75-0.88 (m, 2H); 1.00-1.08 (m, 2H); 1.74-1.84 (m, 1H); 1.96-2.06 (m, 2H); 2.40-2.48 (m, 2H); 2.55-2.70 (m, 2H); 2.95-3.20 (m, 3H); 3.50-3.58 (m, 1H); 3.64-3.68 (m, 1H); 3.76-3.85 (m, 3H); 3.90-4.00 (m, 1H); 4.18-4.28 (m, 1H); 4.34-4.42 (m, 2H); 4.45-4.55 (m, 1H); 4.76-4.90 (m, 1H); 6.16 (s, 1H); 6.44-6.50 (aromatics, 1H); 6.77 (s, 1H); 6.84 (d, J = 11.2 Hz, 1H); 7.14 (d, J = 5.2 Hz, 1H); 7.38-7.46 (aromatics, 2H); 7.52-7.58 (aromatics, 1H); 8.23 (d, J = 4.8 Hz, 1H); 11.82 (bs, 1H) | III-9 |
| P-22 | 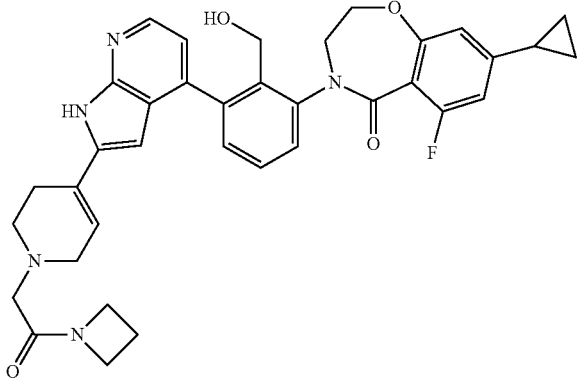 [SMILES: O=C(CN1CC=C(c2cc3c(-c4cccc(N5CCOc6cc(C7CC7)cc(F)c6C5=O)c4CO)ccnc3[nH]2)CC1)N1CCC1]<br>4-[3-[2-[1-[2-(azetidin-1-yl)-2-oxo-ethyl]-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one | LCMS: m/z 622.3 (M + 1)$^+$.<br>$^1$H NMR (DMSO-d$_6$, 400 MHz) δ 0.75-0.80 (m, 2H); 0.99-1.10 (m, 2H); 1.94-2.04 (m, 1H); 2.14-2.22 (m, 2H); 2.40-2.46 (m, 2H); 2.60-2.70 (m, 2H); 3.06 (s, 2H); 3.15-3.22 (m, 2H); 3.78-4.05 (m, 4H); 4.14-4.30 (m, 3H); 4.35-4.42 (m, 2H); 4.48-4.58 (m, 1H); 4.75-4.85 (m, 1H); 6.17 (s, 1H); 6.47 (bs, 1H); 6.77 (s, 1H); 6.83 (dd, J$_1$ = 1.2 Hz, J$_2$ = 10.8 Hz, 1H); 7.10-7.18 (aromatics, 1H); 7.38-7.46 (aromatics, 2H); 7.52-7.58 (aromatics, 1H); 8.23 (d, J = 4.9 Hz 1H); 11.82 (bs, 1H) | III-9 |

TABLE 31-continued

| No | Structure/IUPAC name | Characterization | INT used |
|---|---|---|---|
| P-23 | 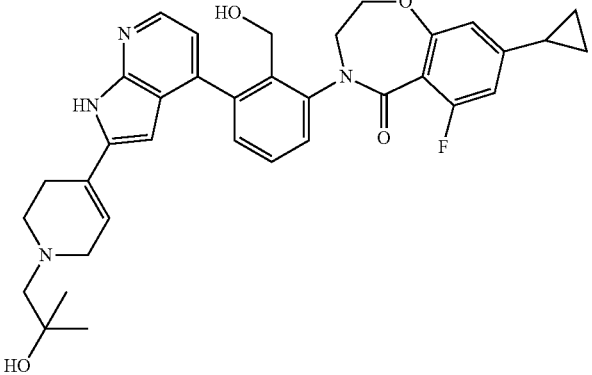<br>8-cyclopropyl-6-fluoro-4-[2-(hydroxymethyl)-3-[2-[1-(2-hydroxy-2-methyl-propyl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z 597.3 (M + 1)$^+$.<br>$^1$H NMR (DMSO-$d_6$, 400 MHz) δ 0.75-0.80 (m, 2H); 0.99-1.04 (m, 2H); 1.10 (s, 6H); 1.94-2.04 (m, 1H); 2.28-2.34 (m, 2H); 2.40-2.46 (m, 2H); 2.70-2.80 (m, 2H); 3.20-3.26 (m, 2H); 3.78-3.88 (m, 1H); 3.90-4.00 (m, 1H); 4.10-4.30 (m, 2H); 4.35-4.45 (m, 2H); 4.48-4.58 (m, 1H); 4.70-4.90 (m, 1H); 6.16 (s, 1H); 6.47 (s, 1H); 6.77 (s, 1H); 6.83 (d, J = 10.8 Hz, 1H); 7.10-7.18 (aromatics, 1H); 7.38-7.46 (aromatics, 2H); 7.52-7.58 (aromatics, 1H); 8.23 (d, J = 4.8 Hz 1H); 11.82 (bs, 1H) | III-9 |
| P-24 | 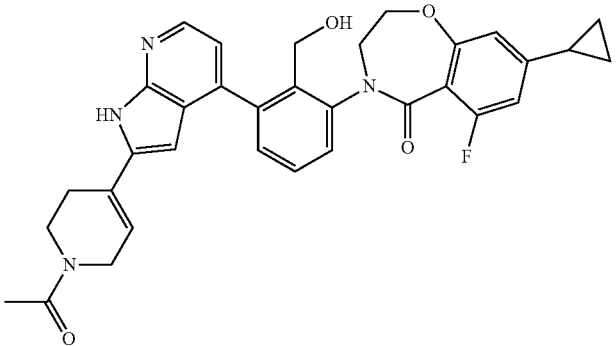 [SMILES: CC(=O)N1CC=C(c2cc3c(-c4cccc(N5CCOc6cc(C7CC7)cc(F)c6C5=O)c4CO)ccnc3[nH]2)CC1]<br>4-[3-[2-(1-acetyl-3,6-dihydro-2H-pyridin-4-yl)-1H-pyrrolo[2,3-b]pyridin-4-yl]-2-(hydroxymethyl)phenyl]-8-cyclopropyl-6-fluoro-2,3-dihydro-1,4-benzoxazepin-5-one | LCMS: m/z; 567.2 (M + 1)$^+$. $^1$H NMR (CD$_3$OD, 400 MHz) δ 0.78-0.82 (m, 2H); 1.06-1.12 (m, 2H); 1.94-2.04 (m, 1H); 2.16-2.20 (m, 3H); 2.50-2.64 (m, 2H); 3.16-3.22 (m, 1H); 3.70-3.80 (m, 2H); 3.86-3.94 (m, 1H); 3.98-4.10 (m, 1H); 4.22-4.30 (m, 2H); 4.40-4.60 (m, 4H); 6.30-6.34 (aromatics, 1H); 6.38-6.44 (aromatics, 1H); 6.74 (s, 1H); 6.79 (d, J = 11.0 Hz, 1H); 7.16-7.20 (aromatics, 1H); 7.44-7.50 (aromatics, 2H); 7.56-7.62 (aromatics, 1H); 8.20-8.26 (aromatics, 1H) | III-8-b |
| P-25 | 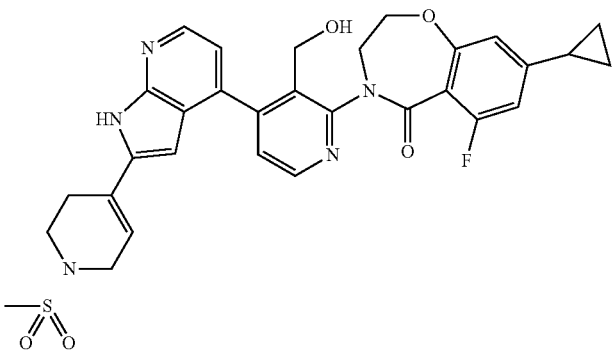<br>8-cyclopropyl-6-fluoro-4-[3-(hydroxymethyl)-4-[2-(1-methylsulfonyl-3,6-dihydro-2H-pyridin-4-yl)-1H-pyrrolo[2,3-b]pyridin-4-yl]-2-pyridyl]-2,3-dihydro-1,4-benzoxazepin-5-one | LCMS: m/z; 604.2 (M + 1)$^+$. $^1$H NMR (CD$_3$OD, 400 MHz) δ 0.68-0.76 (m, 2H); 1.00-1.06 (m, 2H); 1.86-1.96 (m, 1H); 2.57-2.62 (m, 2H); 2.89 (s, 3H); 3.44-3.50 (m, 2H); 3.88-4.24 (m, 6H); 4.28-4.32 (m, 1H); 4.40-4.48 (m, 1H); 6.25 (s, 1H); 6.44 (bs, 1H); 6.58 (d, J = 10.6 Hz, 1H); 6.74 (d, J = 4.9 Hz, 1H); 6.82 (s, 1H); 7.04 (d, J = 4.8 Hz, 1H); 8.16 (d, J = 5.3 Hz, 1H); 8.28 (d, J = 4.9 Hz, 1H) | III-10-b |

TABLE 31-continued

| No | Structure/IUPAC name | Characterization | INT used |
|---|---|---|---|
| P-26 | 8-cyclopropyl-6-fluoro-4-[2-(hydroxymethyl)-3-[2-(1-tetrahydropyran-4-yl-3,6-dihydro-2H-pyridin-4-yl)-1H-pyrrolo[2,3-b]pyridin-4-yl]phenyl]-2,3-dihydro-1,4-benzoxazepin-5-one | LCMS: m/z 609.3 (M + 1)$^+$. $^1$H NMR (DMSO-d$_6$, 400 MHz) δ 0.75-0.88 (m, 2H); 1.02-1.08 (m, 2H); 1.40-1.52 (m, 2H); 1.70-1.78 (m, 2H); 1.96-2.06 (m, 1H); 2.40-2.50 (m, 3H); 2.65-2.72 (m, 2H); 3.20-3.40 (m, 3H); 3.50-3.58 (m, 1H); 3.78-4.00 (m, 4H); 4.18-4.28 (m, 1H); 4.34-4.42 (m, 2H); 4.45-4.55 (m, 1H); 4.75-4.85 (m, 1H); 6.16 (s, 1H); 6.48-6.54 (aromatics, 1H); 6.77 (s, 1H); 6.84 (d, J = 11.5 Hz, 1H); 7.13 (bs, 1H); 7.38-7.46 (aromatics, 2H); 7.52-7.58 (aromatics, 1H); 8.23 (d, J = 4.6 Hz, 1H); 11.82 (bs, 1H) | III-9 |

Example P-27

3-[4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-3,6-dihydro-2H-pyridin-1-yl]-3-oxo-propanenitrile Step-I: tert-butyl 4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-3,6-dihydro-2H-pyridine-1-carboxylate (P-27-II)

Intermediate P-27-II was synthesized using P-27-I and III-9 by following procedure described for the synthesis of P-10. LCMS: m/z 625.4 (M+1)$^+$.

Step-II: 8-cyclopropyl-6-fluoro-4-[2-(hydroxymethyl)-3-[2-(1,2,3,6-tetrahydro pyridin-4-yl)-1H-pyrrolo[2,3-b]pyridin-4-yl]phenyl]-2,3-dihydro-1,4-benzoxazepin-5-one (P-27-III)

To a stirred solution of P-27-II (0.3 g) in anhydrous CH₂Cl₂ (6 mL) was added TFA (0.3 mL) at 0° C. and the reaction mixture was stirred at the same temperature for 2 h. After completion of the reaction, solvents were removed under reduced pressure and the residue was diluted using EtOAc (30 mL). The organic layer was washed with saturated NaHCO₃ solution (30 mL×2), water (30 mL), brine (30 mL), dried over anhydrous Na₂SO₄, filtered and concentrated under reduced pressure. The residue obtained was used without any further purification. LCMS: m/z 525.1 (M+1)⁺.

Step-III: 3-[4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-3,6-dihydro-2H-pyridin-1-yl]-3-oxo-propanenitrile (P-27)

To a stirred solution of P-27-III (0.25 g, 0.48 mmol), cyanoacetic acid (0.08 g, 0.95 mmol) and DIPEA (0.42 mL, 2.38 mmol) in DMF (2 mL) was added HATU (0.27 g, 0.71 mmol) and the reaction mixture was stirred at room temperature for 16 h. After completion of the reaction, it was diluted using water (30 mL) and extraction was carried out using EtOAc (30 mL×2). The combined organic layers were washed with water (50 mL), brine (50 mL), dried over anhydrous Na₂SO₄, filtered and concentrated under reduced pressure. The residue obtained was purified using silica gel column chromatography (5% MeOH in CH₂Cl₂ as eluent) to provide desired compound P-27. LCMS: m/z 592.1 (M+1)⁺. ¹H NMR (DMSO-d₆, 400 MHz) δ 0.74-0.84 (m, 2H); 1.00-1.08 (m, 2H); 1.20-1.28 (m, 2H); 1.96-2.06 (m, 1H); 2.56-2.60 (m, 1H); 3.30-3.36 (m, 1H); 3.62-3.68 (m, 1H); 3.76-3.86 (m, 1H); 3.92-4.02 (m, 1H); 4.06-4.26 (m, 4H); 4.34-4.42 (m, 2H); 4.46-4.56 (m, 1H); 4.76-4.86 (m, 1H); 6.24 (d, J=12.7 Hz, 1H); 6.48-6.55 (aromatic, 1H); 6.77 (s, 1H); 6.84 (d, J=11.3 Hz, 1H); 7.16 (bs, 1H); 7.41-7.57 (aromatics, 3H); 8.26 (d, J=4.9 Hz, 1H); 11.98 (d, J=7.6 Hz, 1H).

Using similar reaction sequence and conditions as described for the synthesis of P-27, following compounds were also synthesized.

TABLE 32

| No | Structure/IUPAC name | Characterization | INT used |
|---|---|---|---|
| P-28 | 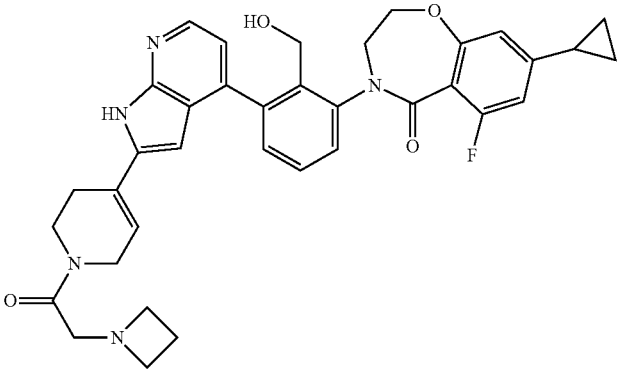 [SMILES: O=C(CN1CCC1)N1CC=C(c2cc3c(-c4cccc(N5CCOc6cc(C7CC7)cc(F)c6C5=O)c4CO)ccnc3[nH]2)CC1]<br>4-[3-[2-[1-[2-(azetidin-1-yl)acetyl]-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one | LCMS: m/z 622.3 (M + 1)⁺. ¹H NMR (DMSO-d₆,, 400 MHz) δ 0.74-0.82 (m, 2H); 1.00-1.08 (m, 2H); 1.20-1.28 (m, 4H); 1.96-2.06 (m, 3H); 3.20-3.30 (m, 2H); 3.36-3.40 (m, 2H); 3.56-3.66 (m, 2H); 3.76-3.86 (m, 1H); 3.90-4.00 (m, 1H); 4.08-4.14 (m, 1H); 4.16-4.26 (m, 2H); 4.34-4.42 (m, 2H); 4.46-4.56 (m, 1H); 4.84 (bs, 1H); 6.23 (s, 1H); 6.52 (s, 1H); 6.77 (s, 1H); 6.84 (d, J = 11.4 Hz, 1H); 7.16 (bs, 1H); 7.43 (t, J = 7.4 Hz, 2H); 7.52-7.58 (aromatics, 1H); 8.25 (d, J = 4.8 Hz, 1H); 11.99 (s, 1H) | Azetidine-acetic acid HCl salt |
| P-29 | 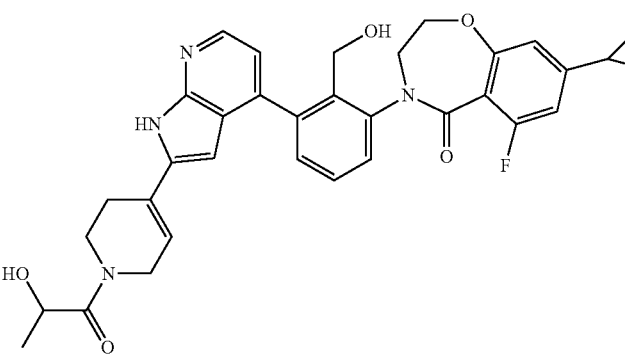<br>8-cyclopropyl-6-fluoro-4-[2-(hydroxymethyl)-3-[2-[1-(2-hydroxypropanoyl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z; 597.2 (M + 1)⁺. ¹H NMR (DMSO-d₆, 400 MHz) δ 0.78-0.82 (m, 2H); 1.06-1.12 (m, 2H); 1.24-1.34 (m, 3H); 1.94-2.04 (m, 1H); 2.54-2.64 (m, 2H); 3.14-3.20 (m, 2H); 3.45-3.51 (m, 1H); 3.76-3.80 (m, 1H); 3.86-3.94 (m, 1H); 3.98-4.08 (m, 1H); 4.22-4.30 (m, 2H); 4.40-4.60 (m, 4H); 6.30-6.36 (aromatics, 1H); 6.38-6.44 (aromatics, 1H); 6.74 (s, 1H); 6.78 (d, J = 11.1 Hz, 1H); 7.16-7.22 (aromatics, 1H); 7.42-7.50 (aromatics, 2H); 7.54-7.62 (aromatics, 1H); 8.22 (d, J = 4.8 Hz, 1H) | 2-hydroxypropionic acid |

TABLE 32-continued

| No | Structure/IUPAC name | Characterization | INT used |
|---|---|---|---|
| P-30 | 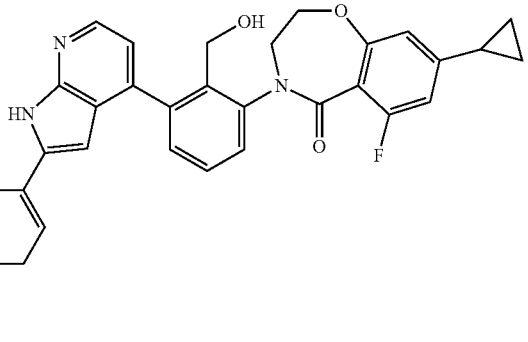

8-cyclopropyl-6-fluoro-4-[3-[2-[1-(2-hydroxyacetyl)-3,6-dihydro-2H-pyridin-4-yl]-1H-pyrrolo[2,3-b]pyridin-4-yl]-2-(hydroxymethyl)phenyl]-2,3-dihydro-1,4-benzoxazepin-5-one | LCMS: m/z; 583.2 (M + 1)+. 1H NMR (DMSO-$d_6$,, 400 MHz) δ 0.78-0.82 (m, 2H); 1.02-1.08 (m, 2H); 1.94-2.04 (m, 1H); 2.44-2.54 (m, 2H); 3.45-3.55 (m, 2H); 3.64-3.70 (m, 1H); 3.76-3.88 (m, 1H); 3.90-4.00 (m, 1H); 4.10-4.25 (m, 4H); 4.34-4.40 (m, 2H); 4.46-4.70 (m, 2H); 6.20-6.25 (aromatics, 1H); 6.50-6.55 (aromatics, 1H); 6.77 (s, 1H); 6.84 (d, J = 11.5 Hz, 1H); 7.16 (bs, 1H); 7.40-7.60 (aromatics, 3H); 8.25 (d, J = 4.8 Hz, 1H); 11.96-12.00 (aromatics, 1H) | 2-hydroxy-acetic acid |

Example P-31

2-[4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-3,6-dihydro-2H-pyridin-1-yl]acetamide

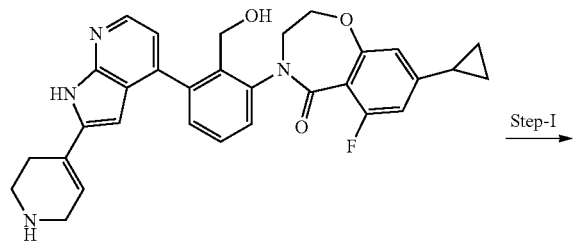

P-27-III

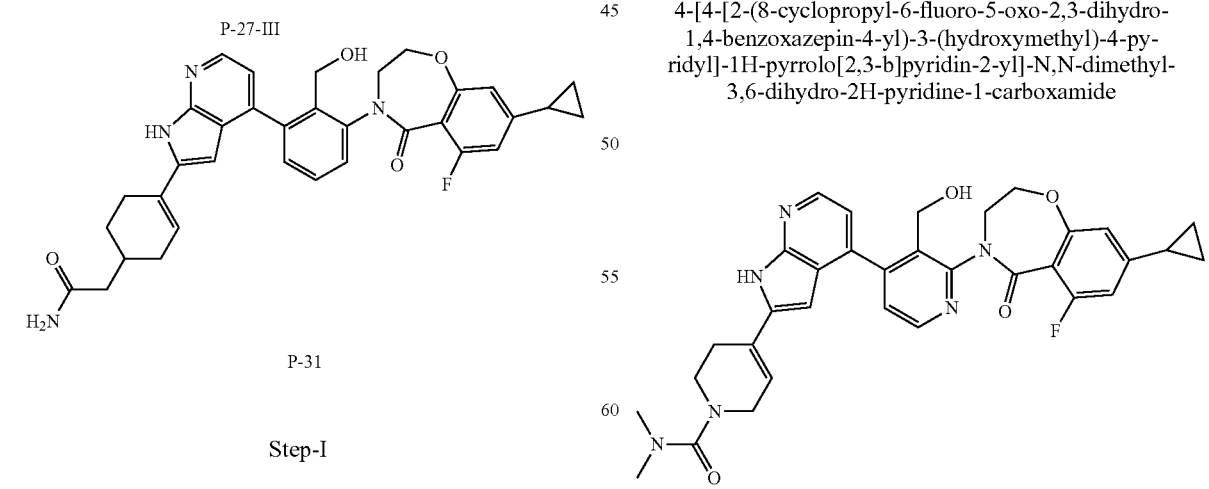

P-31

Step-I

To a stirred solution of P-27-III (0.05 g, 0.095 mmol) and TEA (0.026 mL) in anhydrous $CH_2Cl_2$ (3 mL) was added 2-bromoacetamide (0.017 g, 0.123 mmol); and the reaction mixture was stirred at room temperature for 16 h. After completion of the reaction, it was diluted using $CH_2Cl_2$ (30 mL) and washed using water (30 mL); brine (30 mL); dried over anhydrous $Na_2SO_4$, filtered and concentrated under reduced pressure. The residue obtained was purified using silica gel column chromatography (5% MeOH in $CH_2Cl_2$) to provide desired compound P-31. LCMS: m/z; 582.2 (M+1)+. 1H NMR (CD$_3$OD, 400 MHz) δ 0.78-0.84 (m, 2H); 1.06-1.12 (m, 2H); 1.94-2.04 (m, 1H); 2.56-2.66 (m, 2H); 2.78-2.86 (m, 2H); 3.17 (s, 2H); 3.30-3.40 (m, 2H); 3.86-3.96 (m, 1H); 3.98-4.10 (m, 1H); 4.44-4.64 (m, 4H); 6.28 (s, 1H); 6.39 (bs, 1H); 6.74 (s, 1H); 6.79 (d, J=11.0 Hz, 1H); 7.17 (d, J=4.8 Hz, 1H); 7.44-7.50 (aromatics, 2H); 7.56-7.62 (aromatics, 1H); 8.21 (d, J=4.8 Hz, 1H).

Example P-32

4-[4-[2-(8-cyclopropyl-6-fluoro-5-oxo-2,3-dihydro-1,4-benzoxazepin-4-yl)-3-(hydroxymethyl)-4-pyridyl]-1H-pyrrolo[2,3-b]pyridin-2-yl]-N,N-dimethyl-3,6-dihydro-2H-pyridine-1-carboxamide This example was synthesized using similar reaction sequence and conditions as described for the synthesis of P-25 and P-14.

LCMS: m/z 597.1 (M+1)+. $^1$H NMR (400 MHz; CDCl$_3$): δ 0.76-0.80 (m, 2H); 1.07-1.12 (m, 2H); 1.88-1.95 (m, 1H); 2.58-2.64 (m, 2H); 2.87 (s, 6H); 3.47 (t, J=5.3 Hz, 2H); 4.02-4.20 (m, 5H); 4.46-4.54 (m, 3H); 6.27 (bs, 1H); 6.37 (s, 1H); 6.66 (s, 1H); 6.69 (d, J=11.0 Hz, 1H); 7.40-7.46 (aromatics, 2H); 8.30-8.34 (aromatics, 1H); 8.61 (d, J=4.3 Hz, 1H); 11.22 (bs, 1H).
Example Q-1
Synthesis of 8-cyclopropyl-6-fluoro-4-[2-(hydroxymethyl)-3-[2-[5-(2-morpholinoethoxy)-2-pyridyl]-1H-pyrrolo[2,3-b]pyridin-4-yl]phenyl]-2,3-dihydro-1,4-benzoxazepin-5-one
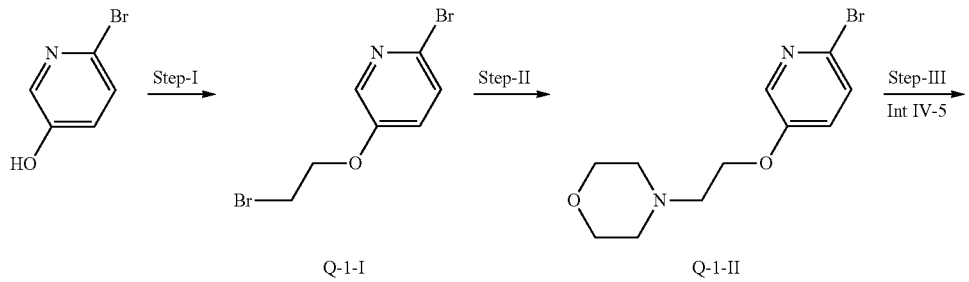
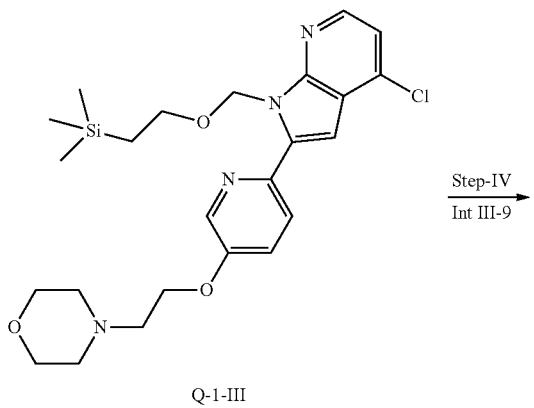
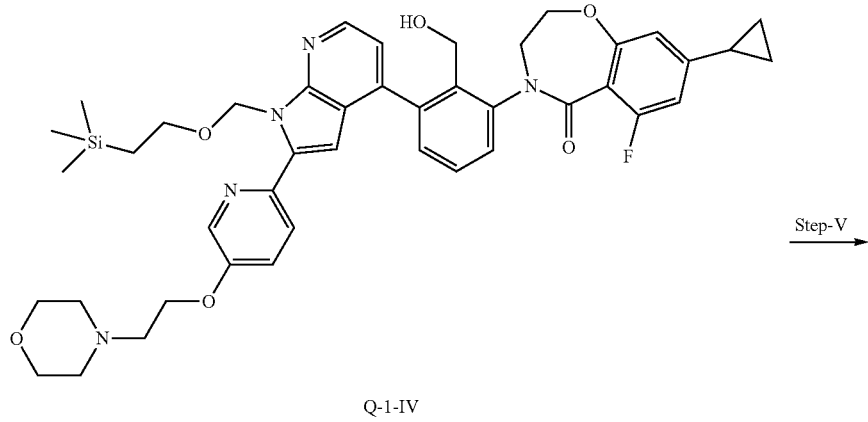

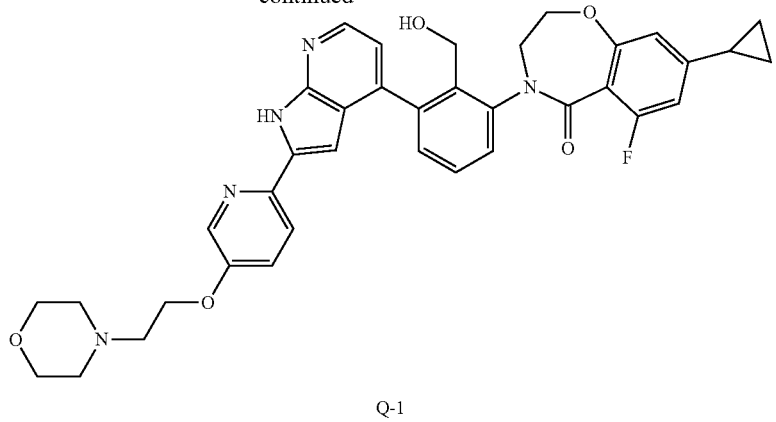

Q-1

Step-I: 2-bromo-5-(2-bromoethoxy)pyridine (Q-1-I)

6-Bromo-3-hydroxypyridine (2 g, 11.56 mmol) was dissolved in anhydrous DMF (20 mL); to which 1,2-dibromoethane (10 g, 57.82 mmol) was added and the reaction mixture was stirred at room temperature for 16 h. After completion of the reaction, water (100 mL) was added to it and extraction was carried out using EtOAc (30 mL×3). The combined organic layers were washed with water (100 mL), brine (100 mL), dried over anhydrous Na$_2$SO$_4$, filtered and concentrated under reduced pressure. The residue was purified using silica gel column chromatography to provide Q-1-I (2.7 g, 86% yield). LCMS: m/z; 280.0 (M+1)$^+$.

Step-II: 4-[2-[(6-bromo-3-pyridyl)oxy]ethyl]morpholine (Q-1-II)

To a solution of Q-1-I (1.2 g, 4.3 mmol) in anhydrous DMF (10 mL) was added morpholine (1.1 g, 12.8 mmol) and the reaction mixture was stirred at room temperature for 16 h. After completion of the reaction, water (100 mL) was added to it and extraction was carried out using EtOAc (30 mL×3). The combined organic layers were washed with water (100 mL), brine (100 mL), dried over anhydrous Na$_2$SO$_4$, filtered and concentrated under reduced pressure. The residue was purified using silica gel column chromatography (2% MeOH in CH$_2$Cl$_2$ as eluent) to provide Q-1-II (2.7 g, quantitative yield). LCMS: m/z; 287.1 (M+1)$^+$.

Step-III: 2-[[4-chloro-2-[5-(2-morpholinoethoxy)-2-pyridyl]pyrrolo[2,3-b]pyridin-1-yl]methoxy]ethyl-trimethyl-silane (Q-1-III)

This intermediate was synthesized using intermediates Q-1-II and IV-5, following procedure described for the synthesis of XI-3. (58% yield). LCMS: m/z; 489.3 (M+1)$^+$.

Step-IV: 8-cyclopropyl-6-fluoro-4-[2-(hydroxymethyl)-3-[2-[5-(2-morpholinoethoxy)-2-pyridyl]-1-(2-trimethylsilylethoxymethyl)pyrrolo[2,3-b]pyridin-4-yl]phenyl]-2,3-dihydro-1,4-benzoxazepin-5-one (Q-1-IV)

This intermediate was synthesized using intermediates Q-1-III and III-9, following procedure described for the synthesis of I-1 (step-I). LCMS: m/z; 780.4 (M+1)$^+$.

Step-V: 8-cyclopropyl-6-fluoro-4-[2-(hydroxymethyl)-3-[2-[5-(2-morpholinoethoxy)-2-pyridyl]-1H-pyrrolo[2,3-b]pyridin-4-yl]phenyl]-2,3-dihydro-1,4-benzoxazepin-5-one (Q-1)

As described for the synthesis of L-1 (step-II).

LCMS: m/z; 650.3 (M+1)$^+$. $^1$H NMR (DMSO-d$_6$, 400 MHz) δ 0.76-0.82 (m, 2H); 1.01-1.09 (m, 2H); 1.95-2.05 (m, 1H); 2.40-2.50 (m, 4H), 2.71 (t, J=6.0 Hz, 2H); 3.58 (t, J=4.4 Hz, 4H); 3.78-3.88 (m, 1H); 3.90-4.00 (m, 1H); 4.22 (t, J=6.0 Hz, 2H); 4.25-4.30 (m, 1H); 4.35-4.45 (m, 2H); 4.48-4.58 (m, 1H); 4.80 (bs, 1H); 6.76-6.80 (aromatics, 2H); 6.84 (d, J=11.2 Hz, 1H); 7.19 (d, J=4.0 Hz, 1H); 7.42-7.54 (aromatics, 3H); 7.54-7.60 (aromatics, 1H); 8.00 (d, J=8.8 Hz, 1H); 8.29 (d, J=5.2 Hz, 1H); 8.34 (d, J=2.8 Hz, 1H); 12.20 (bs, 1H).

Using similar reaction sequence and conditions as described for the synthesis of Q-1, following examples were also synthesized.

TABLE 33

| No | Structure/IUPAC name | Characterization | INT used |
|---|---|---|---|
| Q-2 | 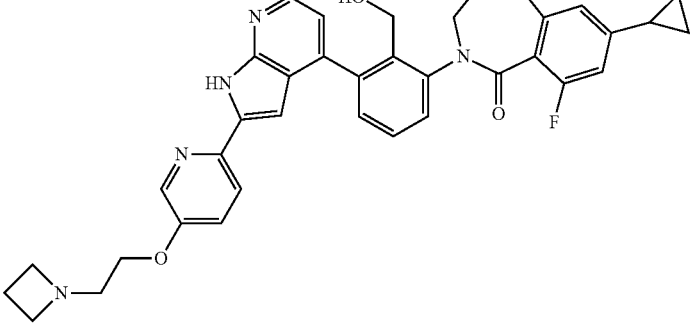<br>4-[3-[2-[5-[2-(azetidin-1-yl)ethoxy]-2-pyridyl]-1H-pyrrolo[2,3-b]pyridin-4-yl]-2-(hydroxymethyl)phenyl]-8-cyclopropyl-6-fluoro-2,3-dihydro-1,4-benzoxazepin-5-one | LCMS: m/z; 620.3 (M + 1)$^+$. $^1$H NMR (DMSO-d$_6$, 400 MHz) δ 0.74-0.80 (m, 2H); 0.98-1.06 (m, 2H); 1.95-2.05 (m, 3H); 2.40-2.50 (m, 4H); 2.65-2.75 (m, 2H); 3.76-3.86 (m, 1H); 3.90-4.00 (m, 1H); 4.04 (t, J = 5.2 Hz, 2H); 4.20-4.28 (m, 1H); 4.30-4.40 (m, 2H); 4.45-4.55 (m, 1H); 4.75-4.85 (m, 1H); 6.74-6.78 (aromatics, 2H); 6.82 (d, J = 11.2 Hz, 1H); 7.17 (d, J = 4.4 Hz, 1H); 7.40-7.48 (aromatics, 3H); 7.52-7.58 (aromatics, 1H); 7.97 (d, J = 8.8 Hz, 1H); 8.27 (d, J = 5.2 Hz, 1H); 8.30 (d, J = 2.8 Hz, 1H); 12.20 (bs, 1H). | Azetidine in step-II |
| Q3 | 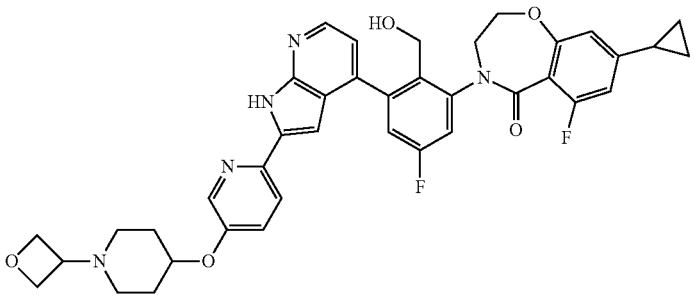 [SMILES: O=C1c2c(F)cc(C3CC3)cc2OCCN1c1cc(F)cc(-c2ccnc3[nH]c(-c4ccc(OC5CCN(C6COC6)CC5)cn4)cc23)c1CO]<br>8-cyclopropyl-6-fluoro-4-[5-fluoro-2-(hydroxymethyl)-3-[2-[5-[[1-(oxetan-3-yl)-4-piperidyl]oxy]-2-pyridyl]-1H-pyrrolo[2,3-b]pyridin-4-yl]phenyl]-2,3-dihydro-1,4-benzoxazepin-5-one | LCMS: m/z; 694.0 (M + 1)$^+$. $^1$H NMR (DMSO-d$_6$, 400 MHz) δ 0.74-0.82 (m, 2H); 1.00-1.10 (m, 2H); 1.60-1.72 (m, 2H); 1.94-2.04 (m, 3H); 2.06-2.14 (m, 2H); 2.50-2.60 (m, 2H); 3.40-3.44 (m, 1H); 3.80-4.00 (m, 2H); 4.16-4.30 (m, 1H); 4.30-4.45 (m, 4H); 4.50-4.60 (m, 4H); 4.75-4.85 (m, 1H); 6.77-6.82 (aromatics, 2H); 6.84 (d, J = 11.7 Hz, 1H); 7.18-7.22 (aromatics, 1H); 7.33 (d, J = 9.3 Hz, 1H); 7.38 (dd, J$_1$ = 2.5 Hz, J$_2$ = 9.3 Hz, 1H); 7.53 (dd, J$_1$ = 2.4 Hz, J$_2$ = 8.8 Hz, 1H); 8.01 (d, J = 8.8 Hz, 1H); 8.30 (d, J = 4.9 Hz, 1H); 8.33 (d, J = 2.4 Hz, 1H); 12.20 (bs, 1H). | III-12 for Suzuki coupling |

Example R-1

Synthesis of 4-[3-[2-[1-(1-acetylazetidin-3-yl)-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one

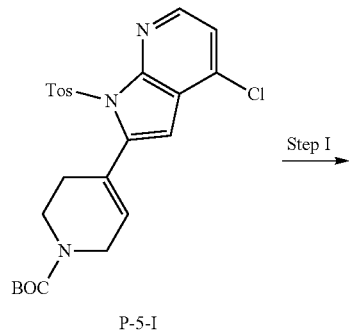

P-5-I

Step I →

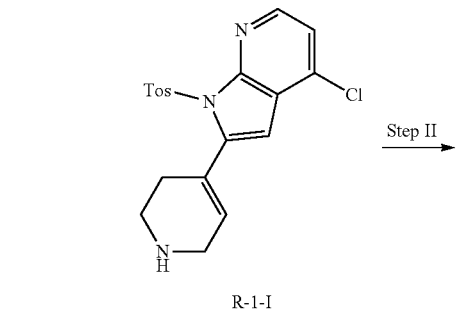

R-1-I

Step II →

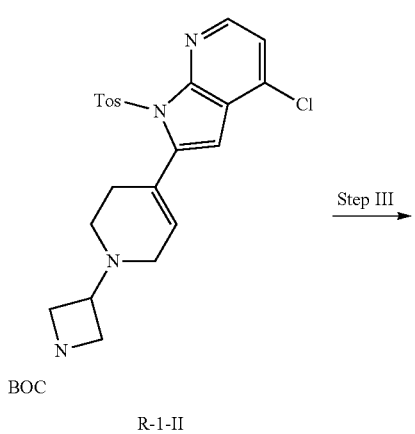

R-1-II

Step III →

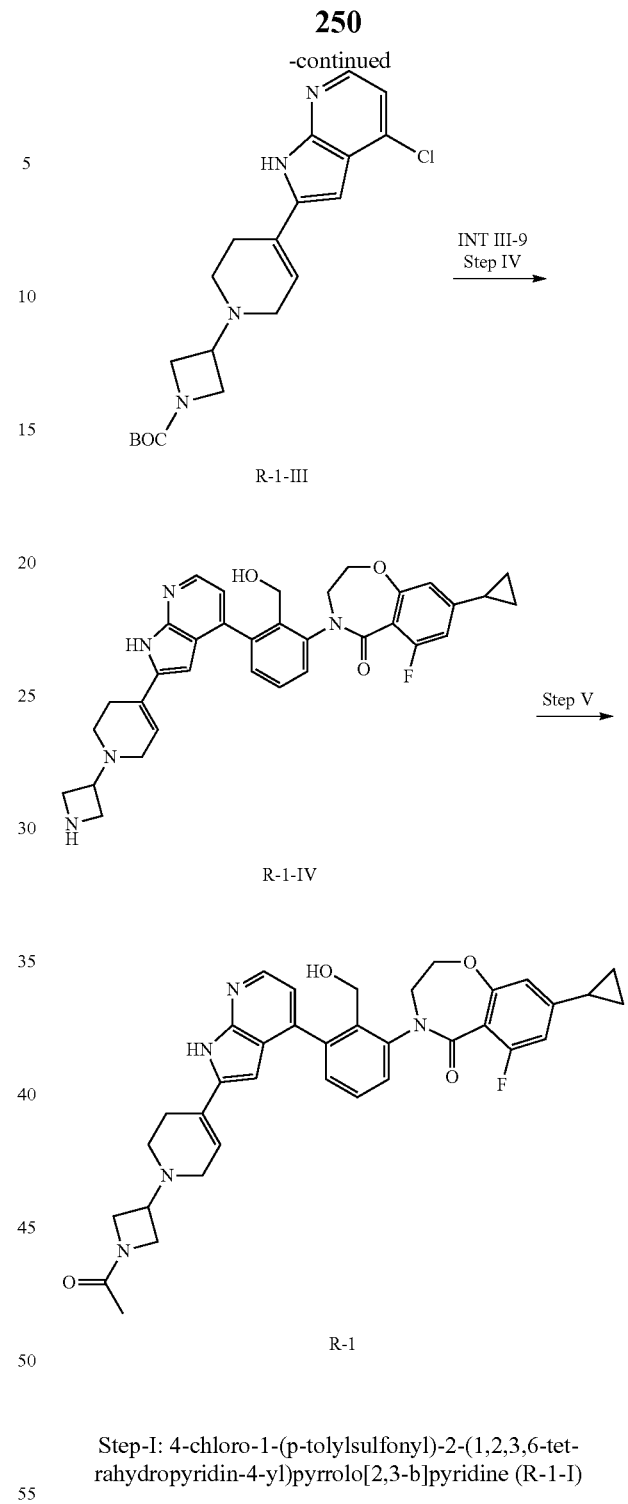

Step-I: 4-chloro-1-(p-tolylsulfonyl)-2-(1,2,3,6-tetrahydropyridin-4-yl)pyrrolo[2,3-b]pyridine (R-1-I)

Trifluoroacetic acid (5 mL) was added to a solution of P-5-I (2.4 g) in $CH_2Cl_2$ (20 mL) at 0° C. and the reaction mixture was stirred at room temperature for 3 h. After completion of the reaction, solvents were removed under reduced pressure and saturated $NaHCO_3$ (60 mL) solution was added to the residue. Extraction was carried out using EtOAc (50 mL×3); the combined organic layers were washed with water (100 mL); brine (100 mL); dried over anhydrous $Na_2SO_4$, filtered and concentrated under reduced pressure. The residue obtained (1.9 g, quantitative) was used without any purification. LCMS: m/z; 388.2 (M+1)⁺.

Step-II: tert-butyl 3-[4-[4-chloro-1-(p-tolylsulfonyl) pyrrolo[2,3-b]pyridin-2-yl]-3,6-dihydro-2H-pyridin-1-yl]azetidine-1-carboxylate (R-1-II)

A solution of R-1-I (2 g, 5.16 mmol), 1-Boc-3-azetidinone (2.65 g, 15.5 mmol) and ZnCl₂ (2.1 g, 15.5 mmol) in MeOH (60 mL) was stirred for 30 min. NaBH₃CN (0.98 g, 15.5 mmol) was added to it portion wise and the reaction mixture was stirred for 4 h. After completion of the reaction, MeOH was removed under reduced pressure and saturated NH₄Cl solution (60 mL) was added to the residue. Extraction was carried out using EtOAc (50 mL×3); the combined organic layers were washed with water (100 mL); brine (100 mL); dried over anhydrous Na₂SO₄, filtered and concentrated under reduced pressure. The residue obtained was stirred in hexane (60 mL) and filtered to provide desire R-1-II (2.6 g, 89%). LCMS: m/z; 543.1 (M+1)⁺.

Step-III: tert-butyl 3-[4-(4-chloro-1H-pyrrolo[2,3-b]pyridin-2-yl)-3,6-dihydro-2H-pyridin-1-yl]azetidine-1-carboxylate (R-1-III)

Similar procedure followed as described in the synthesis of P-5 (step-IV). LCMS: 389.1 (M+1)⁺.

Step-IV: 4-[3-[2-[1-(azetidin-3-yl)-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one (R-1-IV)

Suzuki coupling was done following reaction conditions described in the synthesis of P-10, using intermediates R-1-III and III-9. The Boc-protected compound was then treated with TFA (as described in step-I, R-1-I) to provide desired intermediate R-1-IV (17% yield for 2 steps). LCMS: m/z; 580.1 (M+1)⁺.

Step-V

To a solution of R-1-IV (0.25 g, 0.43 mmol) and pyridine (0.17 g, 2.15 mmol) in CH₂Cl₂ (6 mL) was added acetyl chloride (0.068 g, 0.86 mmol) at 0° C. and the reaction mixture was stirred for 30 min. Saturated NaHCO₃ solution (20 mL) was added to it and extraction was carried out using CH₂Cl₂ (20 mL×2). The combined organic layers were washed with water (50 mL); brine (50 mL); dried over anhydrous Na₂SO₄, filtered and concentrated under reduced pressure. The residue obtained was stirred in MeOH, to which K₂CO₃ (0.29 g, 2.15 mmol) was added. After stirring for 16 h, K₂CO₃ was then filtered off and MeOH was concentrated under reduced pressure. The residue obtained was subjected to silica gel column chromatography first and then to preparative HPLC purification to provide desired compound R-1 (35 mg, 13% yield). LCMS: m/z 622.3 (M+1)⁺. ¹H NMR (DMSO-d₆, 400 MHz) δ 0.75-0.82 (m, 2H); 0.98-1.04 (m, 2H); 1.73 (s, 3H); 1.94-2.02 (m, 1H); 2.40-2.50 (m, 4H); 3.07 (bs, 2H); 3.18-3.25 (m, 1H); 3.66-3.72 (m, 1H); 3.75-4.05 (m, 4H); 4.08-4.25 (m, 2H); 4.30-4.40 (m, 2H); 4.45-4.55 (m, 1H); 4.70-4.85 (m, 1H); 6.16 (s, 1H); 6.49 (bs, 1H); 6.75 (s, 1H); 6.82 (d, J=11.2 Hz, 1H); 7.10-7.16 (aromatics, 1H); 7.38-7.46 (aromatics, 2H); 7.50-7.58 (aromatics, 1H); 8.22 (d, J=4.8 Hz 1H); 11.82 (bs, 1H).

Example R-2

Synthesis of 8-cyclopropyl-4-[3-[2-[1-(1-ethylazetidin-3-yl)-3,6-dihydro-2H-pyridin-4-yl]-1H-pyrrolo[2,3-b]pyridin-4-yl]-2-(hydroxymethyl)phenyl]-6-fluoro-2,3-dihydro-1,4-benzoxazepin-5-one

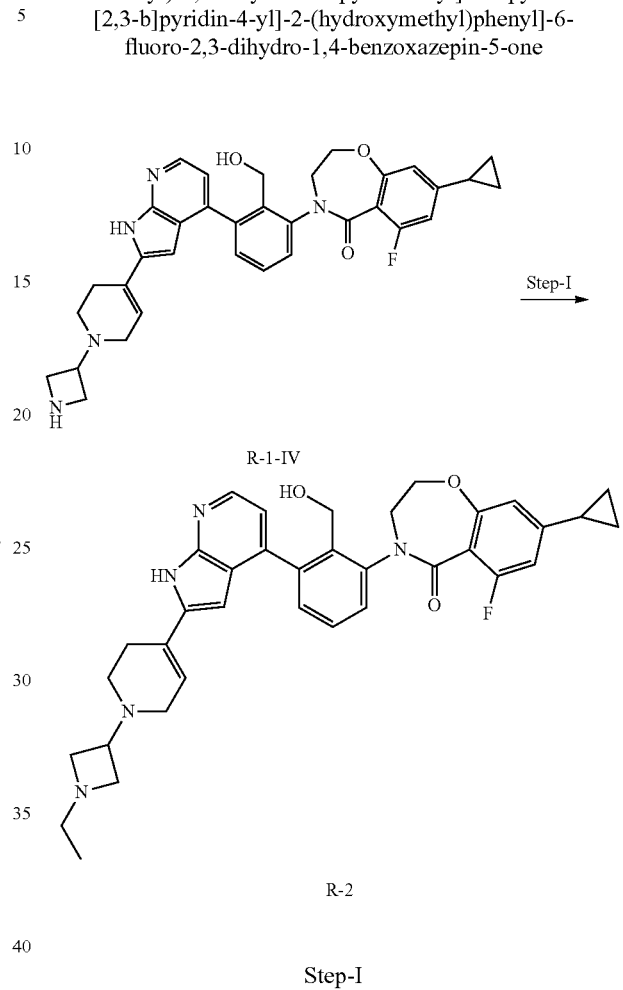

Step-I

To a solution of R-1-IV (0.4 g, 0.69 mmol) in CH₂Cl₂-MeOH (5 mL+5 mL) was added HOAc (2 drops) and it was cooled to 0° C. To this was added NaB(OAc)₃H (0.56 g, 2.64 mmol) followed by drop wise addition of acetaldehyde (0.4 mL, excess). The reaction mixture was stirred at room temperature for 1 h, before solvents were removed under reduced pressure. Saturated NaHCO₃ solution (30 mL) was, then, added to it and extraction was carried out using CH₂Cl₂ (20 mL×3). The combined organic layers were washed with water (50 mL); brine (50 mL); dried over anhydrous Na₂SO₄, filtered and concentrated under reduced pressure. The residue was purified using silica gel column chromatography, followed by crystallization from acetonitrile to provide desired compound R-2 (0.12 g, 28% yield). LCMS: m/z 608.3 (M+1)⁺. ¹H NMR (DMSO-d₆, 400 MHz) δ 0.76-0.82 (m, 2H); 0.87 (t, J=7.2 Hz, 3H); 1.00-1.09 (m, 2H); 1.96-2.04 (m, 1H); 2.38-2.50 (m, 6H); 2.81 (bs, 2H); 2.95-3.04 (m, 3H); 3.40-3.48 (m, 2H); 3.78-3.84 (m, 1H); 3.90-4.00 (m, 1H); 4.18-4.30 (m, 1H); 4.35-4.44 (m, 2H); 4.48-4.56 (m, 1H); 4.70-4.90 (m, 1H); 6.16 (s, 1H); 6.49 (bs, 1H); 6.77 (s, 1H); 6.83 (d, J=11.2 Hz, 1H); 7.10-7.16 (aromatics, 1H); 7.38-7.46 (aromatics, 2H); 7.52-7.58 (aromatics, 1H); 8.23 (d, J=4.9 Hz, 1H); 11.82 (bs, 1H).

Using similar reaction sequence and conditions as described for the synthesis of R-2, following examples were also synthesized.

TABLE 34

| No | Structure/IUPAC name | Characterization | INT used |
|---|---|---|---|
| R-3 | 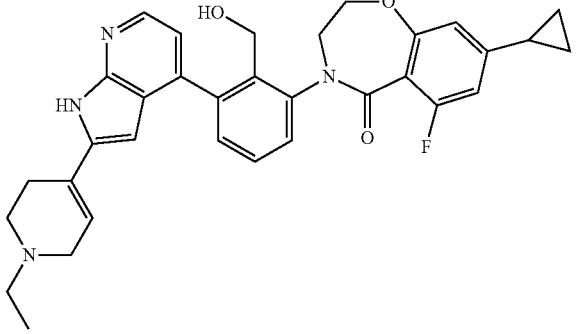<br>8-cyclopropyl-4-[3-[2-(1-ethyl-3,6-dihydro-2H-pyridin-4-yl)-1H-pyrrolo[2,3-b]pyridin-4-yl]-2-(hydroxymethyl)phenyl]-6-fluoro-2,3-dihydro-1,4-benzoxazepin-5-one | LCMS: m/z; 553.3 (M + 1)$^+$. $^1$H NMR (DMSO-d$_6$, 400 MHz) δ 0.75-0.82 (m, 2H); 1.00-1.10 (m, 2H); 1.20-1.25 (m, 3H); 1.94-2.04 (m, 1H); 2.40-2.60 (m, 6H); 3.06-3.16 (m, 2H); 3.78-3.86 (m, 1H); 3.90-4.00 (m, 1H); 4.18-4.28 (m, 1H); 4.34-4.42 (m, 2H); 4.48-4.56 (m, 1H); 4.75-4.85 (m, 1H); 6.17 (s, 1H); 6.46-6.54 (aromatics, 1H); 6.77 (s, 1H); 6.84 (d, J = 11.3 Hz, 1H); 7.12-7.16 (aromatics, 1H); 7.38-7.46 (aromatics, 2H); 7.52-7.58 (aromatics, 1H); 8.23 (d, J = 4.9 Hz 1H); 11.82 (bs, 1H) | P-27-III and CH$_3$CHO for reductive amination |
| R-4 | 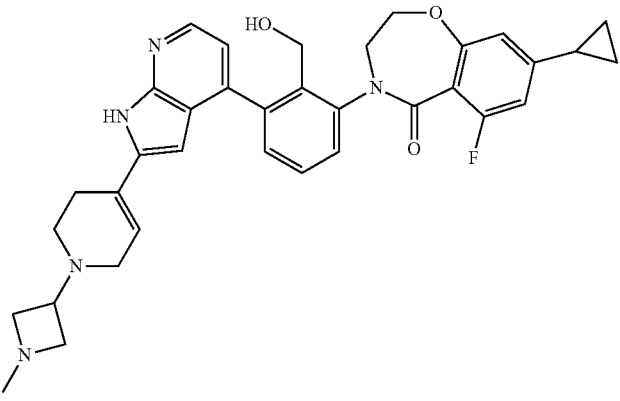 [SMILES: CN1CC(N2CC=C(c3cc4c(-c5cccc(N6CCOc7cc(C8CC8)cc(F)c7C6=O)c5CO)ccnc4[nH]3)CC2)C1]<br>8-cyclopropyl-6-fluoro-4-[2-(hydroxymethyl)-3-[2-[1-(1-methylazetidin-3-yl)-3,6-dihydro-2H-pyridin-4-yl]-1H-pyrrolo[2,3-b]pyridin-4-yl]phenyl]-2,3-dihydro-1,4-benzoxazepin-5-one | LCMS: m/z; 594.2 (M + 1)$^+$. $^1$H NMR (DMSO-d$_6$, 400 MHz) δ 0.70-0.80 (m, 2H); 0.98-1.08 (m, 2H); 1.92-2.02 (m, 1H); 2.32 (s, 3H); 2.38-2.48 (m, 5H); 2.95-3.10 (m, 4H); 3.50-3.60 (m, 2H); 3.75-3.85 (m, 1H); 3.90-4.00 (m, 1H); 4.15-4.25 (m, 1H); 4.34-4.42 (m, 2H); 4.45-4.55 (m, 1H); 4.70-4.90 (m, 1H); 6.16 (s, 1H); 6.48 (bs, 1H); 6.75 (s, 1H); 6.82 (d, J = 11.3 Hz, 1H); 7.10-7.16 (aromatics, 1H); 7.36-7.46 (aromatics, 2H); 7.50-7.56 (aromatics, 1H); 8.21 (d, J = 4.9 Hz, 1H); 11.82 (bs, 1H) | Formaldehyde for reductive amination |

Example R-5

Synthesis of 8-cyclopropyl-4-[3-[2-[1-(1-ethylazetidine-3-carbonyl)-3,6-dihydro-2H-pyridin-4-yl]-1H-pyrrolo[2,3-b]pyridin-4-yl]-2-(hydroxymethyl)phenyl]-6-fluoro-2,3-dihydro-1,4-benzoxazepin-5-one

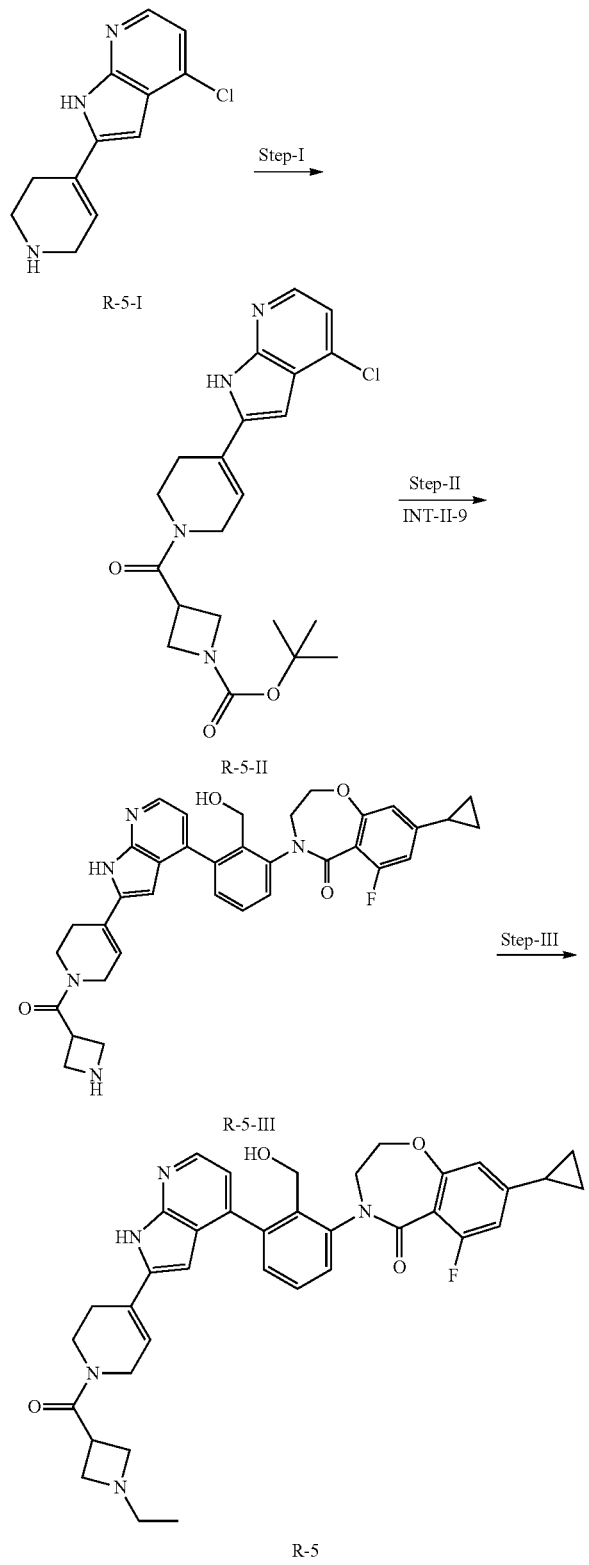

Step-I: tert-butyl 3-[4-(4-chloro-1H-pyrrolo[2,3-b]pyridin-2-yl)-3,6-dihydro-2H-pyridine-1-carbonyl]azetidine-1-carboxylate (R-5-II)

This intermediate was synthesized using R-5-I and N-Boc-azetidine-3-carboxylic acid using conditions described in the synthesis of P-27 (step-III). LCMS: m/z; 417.1 (M+1)$^+$.

Step-II: 4-[3-[2-[1-(azetidine-3-carbonyl)-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one (R-5-III)

This particular intermediate was synthesized using R-5-II and III-9 (Suzuki coupling following by Boc-deprotection using TFA), following conditions described in the synthesis of R-1-IV (step-IV). LCMS: m/z; 608.1 (M+1)$^+$.

Step-III

This particular conversion was performed as described for the synthesis of R-2. LCMS: m/z; 636.2 (M+1)$^+$. $^1$H NMR (DMSO-d$_6$, 400 MHz) δ 0.76-0.90 (m, 5H); 1.00-1.08 (m, 2H); 1.96-2.02 (m, 1H); 2.30-2.45 (m, 4H); 3.08-3.16 (m, 2H); 3.44-3.52 (m, 4H); 3.62-3.66 (m, 1H); 3.78-3.86 (m, 1H); 3.90-4.06 (m, 2H); 4.12-4.28 (m, 2H); 4.34-4.44 (m, 2H); 4.48-4.58 (m, 1H); 4.75-4.85 (m, 1H); 6.18-6.26 (aromatics, 1H); 6.46-6.56 (aromatics, 1H); 6.77 (s, 1H); 6.83 (d, J=11.3 Hz, 1H); 7.12-7.18 (aromatics, 1H); 7.40-7.46 (aromatics, 2H); 7.52-7.58 (aromatics, 1H); 8.25 (d, J=4.9 Hz, 1H); 11.92 (bs, 1H).

Example S-1

8-cyclopropyl-4-[2-(hydroxymethyl)-3-[6-[1-(1-prop-2-enoyl-3-piperidyl)pyrazol-4-yl]-7H-pyrrolo[2,3-d]pyrimidin-4-yl]phenyl]-2,3-dihydro-1,4-benzoxazepin-5-one

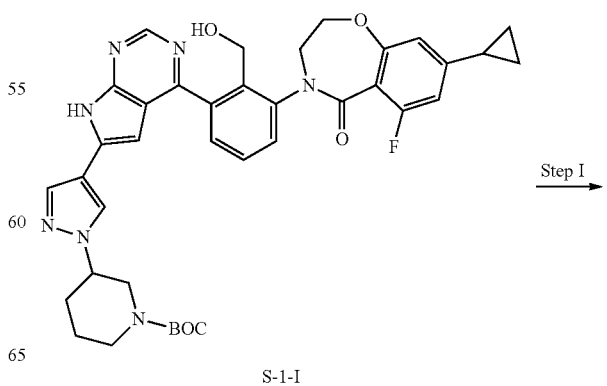

-continued

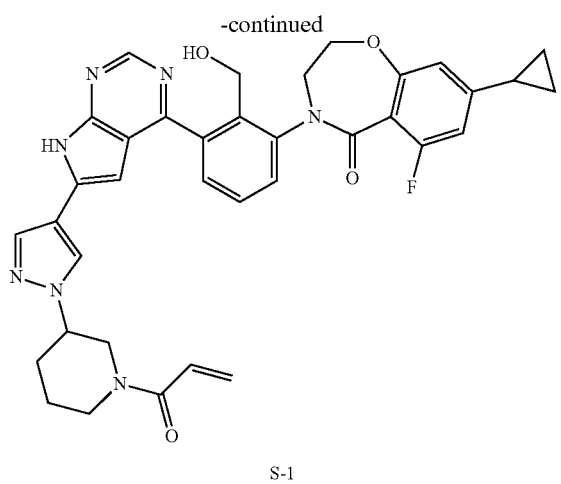

S-1

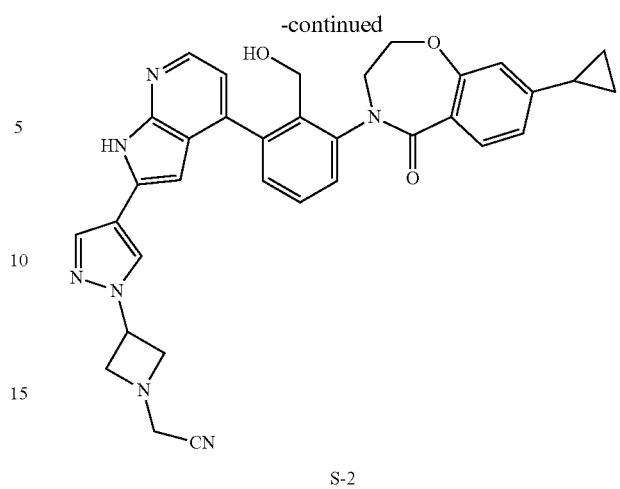

S-2

Step-I

Intermediate S-1-I (synthesized by following procedures described in step-I and step-III for the synthesis of D-1, using intermediates II-7 & III-5) (0.43 g, 0.64 mmol) was stirred in a mixture of $CH_2Cl_2$ (5 mL) and trifluoroacetic acid (1 mL) at room temperature for 1 h. After completion of the reaction, solvents were removed under reduced pressure and the residue was diluted using EtOAc (30 mL). The organic layer was washed with saturated $NaHCO_3$ solution (30 mL), brine (30 mL), dried over anhydrous $Na_2SO_4$, filtered and concentrated under reduced pressure. The residue obtained (0.3 g, 0.52 mmol) was dissolved in $CH_2Cl_2$ (5 mL) and cooled to 0° C. To this was added pyridine (0.05 mL, 0.57 mmol) and acryloyl chloride (0.05 mL, 0.625 mmol) and the reaction mixture was stirred for 30 min. It was diluted using $CH_2Cl_2$ (30 mL) and washed using saturated $NaHCO_3$ solution (30 mL); brine (30 mL); dried over anhydrous $Na_2SO_4$, filtered and concentrated under reduced pressure. The residue obtained was purified using preparative HPLC to provide the title compound S-1 (10 mg). LCMS: m/z; 630.2 $(M+1)^+$. $^1H$ NMR (DMSO-$d_6$, 400 MHz) δ 0.72-0.78 (m, 2H); 0.98-1.08 (m, 2H); 1.50-1.60 (m, 2H); 1.80-2.26 (m, 4H); 2.94-3.20 (m, 2H); 3.80-4.10 (m, 2H); 4.20-4.70 (m, 5H); 5.40-5.48 (m, 1H); 5.64-5.76 (m, 1H); 6.04-6.18 (aromatics, 1H); 6.77-6.92 (aromatics, 5H); 7.49 (d, J=7.5 Hz, 1H); 7.58-7.63 (aromatics, 2H); 7.74 (d, J=7.3 Hz, 1H); 8.14 (s, 1H); 8.45 (s, 1H); 8.79 (s, 1H); 12.68 (s, 1H).

Example S-2

2-[3-[4-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]pyrazol-1-yl]azetidin-1-yl]acetonitrile

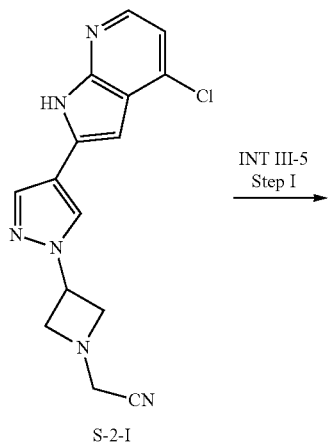

S-2-I

INT III-5
Step I →

Step-I

Example S-2 was synthesized following similar procedure as described in step-I for the synthesis of D-1, using intermediates S-2-1 and III-5. LCMS: m/z; 586.2 $(M+1)^+$. $^1H$ NMR (DMSO-$d_6$, 400 MHz) δ 0.73-0.77 (m, 2H); 1.20-1.28 (m, 2H); 1.94-2.00 (m, 1H); 3.58-3.66 (m, 2H); 3.76-3.80 (m, 4H); 3.88-3.96 (m, 2H); 4.16-4.38 (m, 2H); 4.52-4.58 (m, 2H); 4.72-4.82 (m, 1H); 5.02-5.10 (m, 1H); 6.41 (d, J=1.8 Hz, 1H); 6.81 (d, J=1.3 Hz, 1H); 6.88 (dd, $J_1$=1.4 Hz, $J_2$=8.2 Hz, 1H); 7.16 (d, J=3.8 Hz, 1H); 7.41 (d, J=7.7 Hz, 1H); 7.45 (d, J=7.1 Hz, 1H); 7.52-7.57 (aromatics, 1H); 7.66 (d, J=8.0 Hz, 1H); 8.08 (s, 1H); 8.19 (d, J=3.8 Hz, 1H); 8.42 (s, 1H); 12.09 (s, 1H).

Example S-3

8-cyclopropyl-4-[2-(hydroxymethyl)-3-[2-[5-(4-methylpiperazin-1-yl)-2-pyridyl]-1H-pyrrolo[2,3-b]pyridin-4-yl]phenyl]-2,3-dihydro-1,4-benzoxazepin-5-one

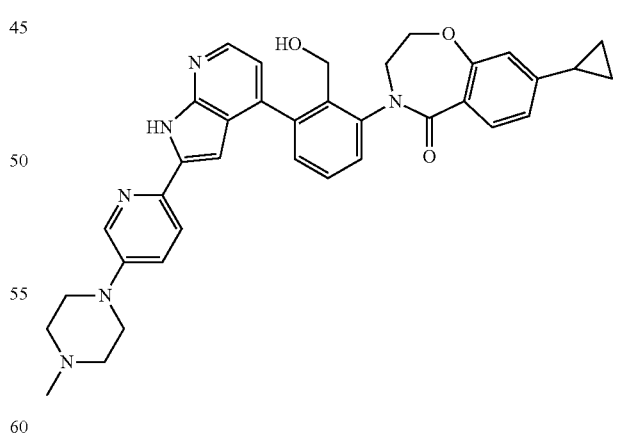

Example S-3 was synthesized following similar reaction sequence and conditions as described for the synthesis of example C-1. LCMS: m/z; 601.3 $(M+1)^+$. $^1H$ NMR (CDCl$_3$, 400 MHz) δ 0.76-0.80 (m, 2H); 1.01-1.09 (m, 2H); 1.91-1.95 (m, 1H); 2.39 (s, 3H); 2.58-2.48 (m, 4H); 3.31-3.43 (m, 4H); 3.91-3.99 (m, 3H); 4.41 (bs, 1H); 4.51-46.1 (m, 3H); 6.66 (s, 1H); 6.78 (d, J=1.6 Hz, 1H); 6.91-6.93 (aromatics, 1H); 7.10-

7.21 (aromatics, 2H); 7.35-7.38 (aromatics, 1H); 7.52-7.63 (aromatics, 3H); 7.82 (d, J=8.4 Hz, 1H); 8.30 (s, 1H); 8.37 (s, 1H); 10.01 (s, 1H).

The below list of examples, but not to be limited to these numbers, can also be synthesized by following the general synthesis described above:

6-fluoro-4-[5-fluoro-2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-8-(1-hydroxy-1-methylethyl)-2,3-dihydro-1,4-benzoxazepin-5-one;

6-fluoro-4-[5-fluoro-2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-8-(1-hydroxy-1-methylethyl)-2,3-dihydro-1,4-benzoxazepin-5-one;

4-[3-[2-[5-[[4-(2,2-difluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-8-(1-hydroxy-1-methylethyl)-2,3-dihydro-1,4-benzoxazepin-5-one;

4-[3-[2-[5-[[4-(2,2-difluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-8-(1-fluorocyclopropyl)-2,3-dihydro-1,4-benzoxazepin-5-one;

6-fluoro-8-(1-fluorocyclopropyl)-4-[5-fluoro-2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

6-fluoro-8-(1-fluorocyclopropyl)-4-[5-fluoro-2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[6-[5-[[4-(oxetan-3-yl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-[[4-(oxetan-3-yl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[6-[5-[[4-(2,2,2-trifluoroethyl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-[[4-(2,2,2-trifluoroethyl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-4-[3-[6-[5-[[4-(2,2-difluoroethyl)piperazin-1-yl]methyl]-2-pyridyl]-7H-pyrrolo[2,3-d]pyrimidin-4-yl]-5-fluoro-2-(hydroxymethyl)phenyl]-6-fluoro-2,3-dihydro-1,4-benzoxazepin-5-one;

8-cyclopropyl-4-[3-[6-[5-[[4-(2,2-difluoroethyl)piperazin-1-yl]methyl]-2-pyridyl]-7H-pyrrolo[2,3-d]pyrimidin-4-yl]-2-(hydroxymethyl)phenyl]-6-fluoro-2,3-dihydro-1,4-benzoxazepin-5-one;

8-cyclopropyl-6-fluoro-4-[2-(hydroxymethyl)-3-[6-[5-[(3-hydroxy-3-methyl-azetidin-1-yl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[6-[5-[(3-hydroxy-3-methyl-azetidin-1-yl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[2-[5-[(3-hydroxy-3-methyl-azetidin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(3-hydroxy-3-methyl-azetidin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(4-hydroxy-4-methyl-1-piperidyl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[(4-hydroxy-4-methyl-1-piperidyl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[6-[5-[(4-hydroxy-4-methyl-1-piperidyl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-[(4-hydroxy-4-methyl-1-piperidyl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-(morpholinomethyl)-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[6-[5-(morpholinomethyl)-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[2-[5-(morpholinomethyl)-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-(morpholinomethyl)-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[[3,5-dimethyl-4-(2,2,2-trifluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[3,5-dimethyl-4-(oxetan-3-yl)piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[4-(2,2-difluoroethyl)-3,5-dimethyl-piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[4-(2,2-difluoroethyl)-3-methyl-piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-6-fluoro-4-[5-fluoro-2-(hydroxymethyl)-3-[2-[5-[[3-methyl-4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[[3-methyl-4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[1-methyl-1-[4-(oxetan-3-yl)piperazin-1-yl]ethyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[1-methyl-1-[4-(2,2,2-trifluoroethyl)piperazin-1-yl]ethyl]-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[1-[4-(2,2-difluoroethyl)piperazin-1-yl]-1-methyl-ethyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[4-(2,2-difluoroethyl)piperazin-1-yl]methyl]-4-fluoro-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-6-fluoro-4-[5-fluoro-3-[2-[4-fluoro-5-[[4-(2,2,2-trifluoroethyl)piperazin-1-yl]methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-6-fluoro-4-[5-fluoro-3-[2-[4-fluoro-5-[[4-(oxetan-3-yl)piperazin-1-yl]methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-6-fluoro-4-[5-fluoro-2-(hydroxymethyl)-3-[2-[5-[[4-(oxetan-3-ylmethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[[4-(oxetan-3-ylmethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[6-[5-[[4-(oxetan-3-ylmethyl)piperazin-1-yl]methyl]-2-pyridyl]-7H-pyrrolo[2,3-d]pyrimidin-4-yl]phenyl]-2,3-dihydro-1,4-benzoxazepin-5-one;

1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]piperidine-4-carbonitrile;

4-[3-[6-[4-(4-aminopiperidine-1-carbonyl)phenyl]-7H-pyrrolo[2,3-d]pyrimidin-4-yl]-2-methyl-phenyl]-8-cyclopropyl-2,3-dihydro-1,4-benzoxazepin-5-one;

4-[3-[6-[4-(3-aminopiperidine-1-carbonyl)phenyl]-7H-pyrrolo[2,3-d]pyrimidin-4-yl]-2-methyl-phenyl]-8-cyclopropyl-2,3-dihydro-1,4-benzoxazepin-5-one;

8-cyclopropyl-4-[2-methyl-3-[6-[4-(3-oxopiperazine-1-carbonyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-(4-methyl-3-oxo-piperazine-1-carbonyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-[(4-methyl-3-oxo-piperazin-1-yl)methyl]phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-[(3-oxopiperazin-1-yl)methyl]phenyl]-7H-pyrrolo[2,3-d]pyrimidin-4-yl]phenyl]-2,3-dihydro-1,4-benzoxazepin-5-one;

1-[[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]phenyl]methyl]piperidine-4-carbonitrile;

1-[[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]phenyl]methyl]piperidine-3-carbonitrile;

6-cyclopropyl-2-[3-[6-[4-[(4-ethylpiperazin-1-yl)methyl]phenyl]-7H-pyrrolo[2,3-d]pyrimidin-4-yl]-2-methyl-phenyl]-3,4-dihydroisoquinolin-1-one;

6-cyclopropyl-2-[3-[6-[4-[(4-cyclopropylpiperazin-1-yl)methyl]phenyl]-7H-pyrrolo[2,3-d]pyrimidin-4-yl]-2-methyl-phenyl]-3,4-dihydroisoquinolin-1-one;

6-cyclopropyl-2-[2-methyl-3-[6-[4-[(4-methylpiperazin-1-yl)methyl]phenyl]-7H-pyrrolo[2,3-d]pyrimidin-4-yl]phenyl]isoquinolin-1-one;

6-cyclopropyl-2-[2-methyl-3-[6-[4-[(4-methyl-3-oxo-piperazin-1-yl)methyl]phenyl]-7H-pyrrolo[2,3-d]pyrimidin-4-yl]phenyl]isoquinolin-1-one;

6-cyclopropyl-2-[2-(hydroxymethyl)-3-[6-[4-[(4-methyl-3-oxo-piperazin-1-yl)methyl]phenyl]-7H-pyrrolo[2,3-d]pyrimidin-4-yl]phenyl]isoquinolin-1-one;

6-cyclopropyl-2-[3-[6-[4-[(4-cyclopropylpiperazin-1-yl)methyl]phenyl]-7H-pyrrolo[2,3-d]pyrimidin-4-yl]-2-(hydroxymethyl)phenyl]isoquinolin-1-one;

6-cyclopropyl-2-[3-[6-[4-[(4-ethylpiperazin-1-yl)methyl]phenyl]-7H-pyrrolo[2,3-d]pyrimidin-4-yl]-2-(hydroxymethyl)phenyl]isoquinolin-1-one;

6-cyclopropyl-2-[2-(hydroxymethyl)-3-[6-[4-(piperazin-1-ylmethyl)phenyl]-7H-pyrrolo[2,3-d]pyrimidin-4-yl]phenyl]phthalazin-1-one;

6-cyclopropyl-2-[2-(hydroxymethyl)-3-[6-[4-[(4-methylpiperazin-1-yl)methyl]phenyl]-7H-pyrrolo[2,3-d]pyrimidin-4-yl]phenyl]phthalazin-1-one;

2-[3-[6-[4-[(4-amino-1-piperidyl)methyl]phenyl]-7H-pyrrolo[2,3-d]pyrimidin-4-yl]-2-methyl-phenyl]-6-cyclopropyl-phthalazin-1-one;

2-[3-[6-[4-[(3-amino-1-piperidyl)methyl]phenyl]-7H-pyrrolo[2,3-d]pyrimidin-4-yl]-2-methyl-phenyl]-6-cyclopropyl-phthalazin-1-one;

6-cyclopropyl-2-[2-methyl-3-[6-[4-(4-methylpiperazine-1-carbonyl)phenyl]-7H-pyrrolo[2,3-d]pyrimidin-4-yl]phenyl]phthalazin-1-one;

6-cyclopropyl-2-[2-methyl-3-[6-(4-morpholinophenyl)-7H-pyrrolo[2,3-d]pyrimidin-4-yl]phenyl]phthalazin-1-one;

6-cyclopropyl-2-[2-methyl-3-[6-[4-(4-methylpiperazin-1-yl)phenyl]-7H-pyrrolo[2,3-d]pyrimidin-4-yl]phenyl]phthalazin-1-one;

6-cyclopropyl-2-[3-[6-[4-(1,4-dimethylpiperazin-2-yl)phenyl]-7H-pyrrolo[2,3-d]pyrimidin-4-yl]-2-methyl-phenyl]phthalazin-1-one;

2-[3-[2-amino-6-[4-(4-methylpiperazin-1-yl)phenyl]-7H-pyrrolo[2,3-d]pyrimidin-4-yl]-2-methyl-phenyl]-6-cyclopropyl-phthalazin-1-one;

2-[3-[2-amino-6-(4-morpholinophenyl)-7H-pyrrolo[2,3-d]pyrimidin-4-yl]-2-methyl-phenyl]-6-cyclopropyl-phthalazin-1-one;

2-[3-[2-amino-6-(4-morpholinophenyl)-7H-pyrrolo[2,3-d]pyrimidin-4-yl]-2-methyl-phenyl]-6-cyclopropyl-isoquinolin-1-one;

2-[3-[2-amino-6-(4-piperazin-1-ylphenyl)-7H-pyrrolo[2,3-d]pyrimidin-4-yl]-2-methyl-phenyl]-6-cyclopropyl-isoquinolin-1-one;

2-[3-[2-amino-6-[4-(4-methylpiperazin-1-yl)phenyl]-7H-pyrrolo[2,3-d]pyrimidin-4-yl]-2-methyl-phenyl]-6-cyclopropyl-isoquinolin-1-one;

2-[3-[2-amino-6-(1-methylpyrazol-4-yl)-7H-pyrrolo[2,3-d]pyrimidin-4-yl]-2-methyl-phenyl]-6-cyclopropyl-isoquinolin-1-one;

2-[3-[2-amino-6-[1-(2-hydroxyethyl)pyrazol-4-yl]-7H-pyrrolo[2,3-d]pyrimidin-4-yl]-2-methyl-phenyl]-6-cyclopropyl-isoquinolin-1-one;

2-[3-[2-amino-6-(5-methyl-6,7-dihydro-4H-pyrazolo[1,5-a]pyrazin-3-yl)-7H-pyrrolo[2,3-d]pyrimidin-4-yl]-2-methyl-phenyl]-6-cyclopropyl-isoquinolin-1-one;

2-[3-[2-amino-6-(6,7-dihydro-4H-pyrazolo[5,1-c][1,4]oxazin-3-yl)-7H-pyrrolo[2,3-d]pyrimidin-4-yl]-2-methyl-phenyl]-6-cyclopropyl-isoquinolin-1-one;

3-[2-[2-methyl-3-[6-[4-[(4-methylpiperazin-1-yl)methyl]phenyl]-7H-pyrrolo[2,3-d]pyrimidin-4-yl]phenyl]-1-oxo-3,4-dihydroisoquinolin-6-yl]butanoic acid;

2-[1-[2-[2-methyl-3-[6-[4-[(4-methylpiperazin-1-yl)methyl]phenyl]-7H-pyrrolo[2,3-d]pyrimidin-4-yl]phenyl]-1-oxo-3,4-dihydroisoquinolin-6-yl]cyclopropyl]acetic acid;

2-[2-methyl-3-[6-[4-[(4-methylpiperazin-1-yl)methyl]phenyl]-7H-pyrrolo[2,3-d]pyrimidin-4-yl]phenyl]-6-[1-(1,2,5-oxadiazol-3-yl)cyclopropyl]-3,4-dihydroisoquinolin-1-one;

2-[2-methyl-3-[6-(4-morpholinophenyl)-7H-pyrrolo[2,3-d]pyrimidin-4-yl]phenyl]-6-[1-(1,2,5-oxadiazol-3-yl)cyclopropyl]-3,4-dihydroisoquinolin-1-one;

2-[1-[4-[2-methyl-3-[6-[4-[(4-methylpiperazin-1-yl)methyl]phenyl]-7H-pyrrolo[2,3-d]pyrimidin-4-yl]phenyl]-5-oxo-2,3-dihydro-1,4-benzoxazepin-8-yl]cyclopropyl]acetic acid;

2-[1-[4-[2-methyl-3-[6-[4-(4-methylpiperazine-1-carbonyl)phenyl]-7H-pyrrolo[2,3-d]pyrimidin-4-yl]phenyl]-5-oxo-2,3-dihydro-1,4-benzoxazepin-8-yl]cyclopropyl]acetic acid;

8-cyclopropyl-4-[2-methyl-3-[6-[5-methyl-1-[(1-methyl-2-oxo-4-piperidyl)methyl]imidazol-4-yl]-7H-pyrrolo[2,3-d]pyrimidin-4-yl]phenyl]-2,3-dihydro-1,4-benzoxazepin-5-one;

2-cyclopropyl-6-[2-methyl-3-[6-(6-morpholino-3-pyridyl)-7H-pyrrolo[2,3-d]pyrimidin-4-yl]phenyl]-7,8-dihydropyrimido[5,4-f][1,4]oxazepin-5-one;

2-cyclopropyl-6-[2-methyl-3-[6-[6-(4-methylpiperazin-1-yl)-3-pyridyl]-7H-pyrrolo[2,3-d]pyrimidin-4-yl]phenyl]-7,8-dihydropyrimido[5,4-f][1,4]oxazepin-5-one;

8-cyclopropyl-4-[2-methyl-3-[6-[4-[(3-methyl-3,8-diazabicyclo[3.2.1]octan-8-yl)methyl]phenyl]-7H-pyrrolo[2,3-d]pyrimidin-4-yl]phenyl]-2,3-dihydro-1,4-benzoxazepin-5-one;

8-cyclopropyl-4-[3-[6-[4-[[4-(2-hydroxyethyl)piperazin-1-yl]methyl]phenyl]-7H-pyrrolo[2,3-d]pyrimidin-4-yl]-2-methyl-phenyl]-2,3-dihydro-1,4-benzoxazepin-5-one;

4-[3-[6-[4-(3-azabicyclo[3.3.2]decan-3-ylmethyl)phenyl]-7H-pyrrolo[2,3-d]pyrimidin-4-yl]-2-methyl-phenyl]-8-cyclopropyl-2,3-dihydro-1,4-benzoxazepin-5-one;

8-cyclopropyl-4-[2-methyl-3-[6-[5-(5-methyl-2,5-diazabicyclo[2.2.1]heptan-2-yl)-2-pyridyl]-7H-pyrrolo[2,3-d]pyrimidin-4-yl]phenyl]-2,3-dihydro-1,4-benzoxazepin-5-one;

7-cyclopropyl-2-methyl-3-[2-methyl-3-[6-[4-[(4-methylpiperazin-1-yl)methyl]phenyl]-7H-pyrrolo[2,3-d]pyrimidin-4-yl]phenyl]quinazolin-4-one;

7-cyclopropyl-2-methyl-3-[2-methyl-3-[6-[4-(4-methylpiperazine-1-carbonyl)phenyl]-7H-pyrrolo[2,3-d]pyrimidin-4-yl]phenyl]quinazolin-4-one;

6-cyclopropyl-2-[2-(hydroxymethyl)-3-[6-[1-[(3R)-1-methyl-3-piperidyl]pyrazol-4-yl]-7H-pyrrolo[2,3-d]pyrimidin-4-yl]phenyl]phthalazin-1-one;

6-cyclopropyl-2-[3-[6-[1-[(3R)-1-ethyl-3-piperidyl]pyrazol-4-yl]-7H-pyrrolo[2,3-d]pyrimidin-4-yl]-2-(hydroxymethyl)phenyl]phthalazin-1-one;

6-cyclopropyl-2-[3-[6-[5-[(1-ethyl-4-piperidyl)oxy]-2-pyridyl]-7H-pyrrolo[2,3-d]pyrimidin-4-yl]-2-(hydroxymethyl)phenyl]phthalazin-1-one;

6-cyclopropyl-2-[3-[6-[5-(1-ethylazetidin-3-yl)oxy-2-pyridyl]-7H-pyrrolo[2,3-d]pyrimidin-4-yl]-2-(hydroxymethyl)phenyl]phthalazin-1-one;

6-cyclopropyl-2-[3-[6-[1-(1-ethyl-4-piperidyl)-3,6-dihydro-2H-pyridin-4-yl]-7H-pyrrolo[2,3-d]pyrimidin-4-yl]-2-(hydroxymethyl)phenyl]phthalazin-1-one;

8-cyclopropyl-4-[3-[6-[1-(1-ethyl-4-piperidyl)-3,6-dihydro-2H-pyridin-4-yl]-7H-pyrrolo[2,3-d]pyrimidin-4-yl]-2-(hydroxymethyl)phenyl]-2,3-dihydro-1,4-benzoxazepin-5-one;

8-cyclopropyl-4-[2-(hydroxymethyl)-3-[6-[5-(1-methyl-4-piperidyl)-2-pyridyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[6-[5-(1-methyl-3-piperidyl)-2-pyridyl]-7H-pyrrolo[2,3-d]pyrimidin-4-yl]phenyl]-2,3-dihydro-1,4-benzoxazepin-5-one;

6-cyclopropyl-2-[2-(hydroxymethyl)-3-[6-[5-(1-methyl-3-piperidyl)-2-pyridyl]-7H-pyrrolo[2,3-d]pyrimidin-4-yl]phenyl]phthalazin-1-one;

6-cyclopropyl-2-[2-(hydroxymethyl)-3-[6-[5-(1-methyl-4-piperidyl)-2-pyridyl]-7H-pyrrolo[2,3-d]pyrimidin-4-yl]phenyl]phthalazin-1-one;

8-Cyclopropyl-6-fluoro-4-[3-[2-[1-(2-hydroxyethyl)-3,6-dihydro-2H-pyridin-4-yl]-1H-pyrrolo[2,3-b]pyridin-4-yl]-2-(hydroxymethyl)phenyl]-2,3-dihydro-1,4-benzoxazepin-5-one;

8-cyclopropyl-6-fluoro-4-[2-(hydroxymethyl)-3-[2-(1-methylsulfonyl-3,6-dihydro-2H-pyridin-4-yl)-1H-pyrrolo[2,3-b]pyridin-4-yl]phenyl]-2,3-dihydro-1,4-benzoxazepin-5-one;

8-cyclopropyl-6-fluoro-4-[3-[6-[1-(3-hydroxyazetidine-1-carbonyl)-3,6-dihydro-2H-pyridin-4-yl]-7H-pyrrolo[2,3-d]pyrimidin-4-yl]-2-(hydroxymethyl)phenyl]-2,3-dihydro-1,4-benzoxazepin-5-one;

4-[4-[3-[8-(1-fluorocyclopropyl)-5-oxo-2,3-dihydro-1,4-benzoxazepin-4-yl]-2-(hydroxymethyl)phenyl]-1H-pyrrolo[2,3-b]pyridin-2-yl]-N,N-dimethyl-3,6-dihydro-2H-pyridine-1-carboxamide;

4-[4-[3-[8-(1-hydroxycyclopropyl)-5-oxo-2,3-dihydro-1,4-benzoxazepin-4-yl]-2-(hydroxymethyl)phenyl]-1H-pyrrolo[2,3-b]pyridin-2-yl]-N,N-dimethyl-3,6-dihydro-2H-pyridine-1-carboxamide;

4-[4-[3-(8-cyclopropyl-6-fluoro-5-oxo-2,3-dihydropyrido[3,2-f][1,4]oxazepin-4-yl)-5-fluoro-2-(hydroxymethyl)phenyl]-7H-pyrrolo[2,3-d]pyrimidin-6-yl]-N,N-dimethyl-3,6-dihydro-2H-pyridine-1-carboxamide;

8-(1-hydroxy-1-methyl-ethyl)-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydropyrido[3,2-f][1,4]oxazepin-5-one;

8-cyclopropyl-6-fluoro-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1H-1,4-benzodiazepin-5-one;

8-cyclopropyl-4-[3-[2-[5-[(2,4-dimethylpiperazin-1-yl)methyl]-2-pyridyl]-1H-pyrrolo[2,3-b]pyridin-4-yl]-2-(hydroxymethyl)phenyl]-6-fluoro-2,3-dihydro-1,4-benzoxazepin-5-one;

8-cyclopropyl-4-[3-[2-[5-[(2,4-dimethylpiperazin-1-yl)methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[1-(3,4-dimethylpiperazin-1-yl)ethyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

6-fluoro-8-(1-hydroxycyclopropyl)-4-[2-(hydroxymethyl)-3-[2-[5-(4-methylpiperazin-1-yl)-2-pyridyl]-1H-pyrrolo[2,3-b]pyridin-4-yl]phenyl]-2,3-dihydro-1,4-benzoxazepin-5-one;

6-fluoro-8-(1-hydroxy-1-methyl-ethyl)-4-[2-(hydroxymethyl)-3-[2-[5-(4-methylpiperazin-1-yl)-2-pyridyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[6-[1-(oxetan-3-yl)imidazol-4-yl]-7H-pyrrolo[2,3-d]pyrimidin-4-yl]phenyl]-2,3-dihydro-1,4-benzoxazepin-5-one;
8-cyclopropyl-4-[2-(hydroxymethyl)-3-[2-[1-(oxetan-3-yl)imidazol-4-yl]-1H-pyrrolo[2,3-b]pyridin-4-yl]phenyl]-2,3-dihydro-1,4-benzoxazepin-5-one;
8-(1-hydroxy-1-methyl-ethyl)-4-[2-(hydroxymethyl)-3-[2-[1-(oxetan-3-yl)imidazol-4-yl]-1H-pyrrolo[2,3-b]pyridin-4-yl]phenyl]-2,3-dihydro-1,4-benzoxazepin-5-one;
8-cyclopropyl-6-fluoro-4-[2-(hydroxymethyl)-3-[2-[1-(oxetan-3-yl)imidazol-4-yl]-1H-pyrrolo[2,3-b]pyridin-4-yl]phenyl]-2,3-dihydro-1,4-benzoxazepin-5-one;
8-cyclopropyl-6-fluoro-4-[2-(hydroxymethyl)-3-[6-[1-(oxetan-3-yl)imidazol-4-yl]-7H-pyrrolo[2,3-d]pyrimidin-4-yl]phenyl]-2,3-dihydro-1,4-benzoxazepin-5-one;
6-fluoro-8-(1-hydroxy-1-methyl-ethyl)-4-[2-(hydroxymethyl)-3-[6-[1-(oxetan-3-yl)imidazol-4-yl]-7H-pyrrolo[2,3-d]pyrimidin-4-yl]phenyl]-2,3-dihydro-1,4-benzoxazepin-5-one;
8-cyclopropyl-6-fluoro-4-[2-(hydroxymethyl)-3-[2-(1-tetrahydropyran-4-ylimidazol-4-yl)-1H-pyrrolo[2,3-b]pyridin-4-yl]phenyl]-2,3-dihydro-1,4-benzoxazepin-5-one;
6-fluoro-8-(1-hydroxy-1-methyl-ethyl)-4-[2-(hydroxymethyl)-3-[2-[1-(3-hydroxy-3-methyl-azetidine-1-carbonyl)-3,6-dihydro-2H-pyridin-4-yl]-1H-pyrrolo[2,3-b]pyridin-4-yl]phenyl]-2,3-dihydro-1,4-benzoxazepin-5-one;
8-cyclopropyl-6-fluoro-4-[2-(hydroxymethyl)-3-[2-[1-(3,3,3-trifluoropropanoyl)-3,6-dihydro-2H-pyridin-4-yl]-1H-pyrrolo[2,3-b]pyridin-4-yl]phenyl]-2,3-dihydro-1,4-benzoxazepin-5-one;
6-fluoro-8-(1-hydroxy-1-methyl-ethyl)-4-[2-(hydroxymethyl)-3-[2-[1-(3,3,3-trifluoropropanoyl)-3,6-dihydro-2H-pyridin-4-yl]-1H-pyrrolo[2,3-b]pyridin-4-yl]phenyl]-2,3-dihydro-1,4-benzoxazepin-5-one;
4-[4-[2-(8-cyclopropyl-6-fluoro-5-oxo-2,3-dihydro-1,4-benzoxazepin-4-yl)-3-(hydroxymethyl)-4-pyridyl]-1H-pyrrolo[2,3-b]pyridin-2-yl]-N,N-dimethyl-3,6-dihydro-2H-pyridine-1-carboxamide;
4-[4-[5-fluoro-3-[6-fluoro-8-(1-hydroxy-1-methyl-ethyl)-5-oxo-2,3-dihydro-1,4-benzoxazepin-4-yl]-2-(hydroxymethyl)phenyl]-1H-pyrrolo[2,3-b]pyridin-2-yl]-N,N-dimethyl-3,6-dihydro-2H-pyridine-1-carboxamide;
4-[3-[2-[1-(azetidine-1-carbonyl)-3,6-dihydro-2H-pyridin-4-yl]-1H-pyrrolo[2,3-b]pyridin-4-yl]-5-fluoro-2-(hydroxymethyl)phenyl]-8-cyclopropyl-6-fluoro-2,3-dihydro-1,4-benzoxazepin-5-one;
3-[4-[4-[5-fluoro-3-[6-fluoro-8-(1-hydroxy-1-methyl-ethyl)-5-oxo-2,3-dihydro-1,4-benzoxazepin-4-yl]-2-(hydroxymethyl)phenyl]-1H-pyrrolo[2,3-b]pyridin-2-yl]-3,6-dihydro-2H-pyridin-1-yl]-3-oxo-propanenitrile;
3-[4-[4-[3-(8-cyclopropyl-6-fluoro-5-oxo-2,3-dihydro-1,4-benzoxazepin-4-yl)-5-fluoro-2-(hydroxymethyl)phenyl]-1H-pyrrolo[2,3-b]pyridin-2-yl]-3,6-dihydro-2H-pyridin-1-yl]-3-oxo-propanenitrile.

Biological Activity
Recombinant Human Bruton's Tyrosine Kinase (Btk) Inhibition Assay.

Full length human BTK (hBTK, Genbank#NM_000061.2) was cloned into pFastBac-HTB vector (Invitrogen, cat#10359-016). hBTK gene was expressed with N'-terminal 6×His tag in Sf9 cells using Bac-to-Bac® Baculovirus expression system (Invitrogen, cat#10359-016) and the recombinant protein was purified by Ni-NTA method. The elution buffer for hBTK consisted of 50 mM Hepes pH 8.0, 300 mM NaCl, 10% glycerol, 1 mM dithiothreitol and 200 mM imidazole.

The inhibition assays were performed using the generic tyrosine kinase assay kit from Cis Bio (HTRF® KinEASE—TK™ #62TK0PEB). The assay is based on the principle of fluorescence resonance energy transfer (FRET) between the Europium Cryptate labeled anti-phosphotyrosine antibody and streptavidin labeled fluorophore, XL-665. In an uninhibited kinase reaction the biotinylated peptide substrate (Tk-Biotin) gets phosphorylated at an intermediate tyrosine site which is captured by anti-phosphotyrosine antibody which eventually acts as a FRET donor. The streptavidin labeled XL-665 binds strongly to the Tk-Biotin substrate and act as a FRET acceptor. The resultant FRET signal is measured at 665 nm. A ratio of this specific fluorescence (665 nm) to the background fluorescence (620 nm), conferred by the free antibody, is directly proportional to the kinase activity. Inhibition of the kinase activity by a pharmacological intervention such as a Btk inhibitor of the present disclosure will result into decreased FRET signal.

The Btk inhibition assays were performed using 20 ng/ml of rhBtk in a final volume of 100 reaction buffer containing 77 µM ATP and 1 µM TK-Biotin Substrate in 50 mM HEPES pH 7.0, 5 mM MgCl2, 1 mM DTT, 0.01% Tween 20 and 50 nM SEB®; with a range of concentrations of the inhibitors. The kinase reaction was carried out at the $K_M$ of ATP (77 µM) as well as that of Tk-Biotin substrate (1 µM). After 90 min, the reaction was stopped by addition of SA-XL665 at a concentration of 62.5 nM in HTRF® detection buffer containing EDTA. Finally 50 of TK antibody-cryptate was added to the reaction and the plate was incubated for additional 60 min. The fluorescence was read using the Flexstation (Molecular Devices) with excitation at 340 nm and emissions at 620 nm (for Cryptate) and 665 nm (for FRET). A ratio of the 2 emissions was calculated for each well and expressed as follows:

Specific signal=Ratio(Sample)−Ratio(Negative)

Ratio=(665 nm/620 nm)×10$^4$

Mean Ratio=ΣRatio/3(triplicates)

For each data point, % inhibition is calculated based on uninhibited reaction which is considered as 100% activity over no enzyme or substrate controls. Dose response data is then fit using a four parameter logistic equation using Graphpad Prism 5 software to determine inhibition constant 50 ($IC_{50}$).

Compounds of present disclosure are considered to be active if $IC_{50}$ of the recombinant human Btk (hBtk) enzyme inhibition is below 10 µM, and more specifically below 1.0 µM.

Inhibition of B Cell Activation as Measured by CD69 Expression in Mouse Splenocytes:

To test the effect of BTK inhibitors in suppressing B-cell receptor (BCR) mediated activation of B cells, we developed a flow cytometry based assay to analyze CD69 expression in B cell population among total splenocyte from the mouse. C57/BL6 mouse spleens were dissected out and splenocytes were isolated by mincing the tissue with a syringe plunger followed by RBC lysis (0.85% ammonium chloride) and several washes in PBS. Finally, cell were cultured in RPMI medium with 10% FBS.

Test compounds were diluted half log starting from 2 mM in 100% DMSO (200×). 1×10$^5$ splenocytes were incubated with 1 uL of diluted test compounds in 200 uL culture medium in a U-bottom 96 well plate (Greiner) at 37° C. with 5% CO$_2$ for 30 mins. Control wells received 1 uL of 100% DMSO without any compound. The cells were stimulated with 3 ug/mL goat anti-mouse IgM (Sigma, cat#M8644) and incubated for 18-20 hrs. After the stimulation, cells were washed in cold PBS with 1% FBS and stained with 1:100 dilutions of anti-CD69-PE (eBioscience, cat#12-0691-83) and anti-CD19-PeCy5 (eBioscience, cat#15-0193-83) for 1 hr on ice. Then the cells were washed 3 times with PBS with 1% FBS and analyzed by Guava Easycyte Mini flow cytometer system (Millipore). Flow cytometry data were analyzed using Weasel software (WEHI, Melbourne). First B cells were gated using CD19 markers. Then expression of CD69 was analyzed as percentage of CD69+ve cells within CD19. Percent activity for each data point was calculated using following formula:

$$\% \text{ Activity} = 100 \times \frac{(\text{Experimental} - \text{No stimulation control})}{(\text{No compound control} - \text{No stimulation control})}$$

Percentage activity was fit using sigmoid dose response with variable slope logistic equation in Graph-pad Prism 5 software to determine inhibition constant 50 ($IC_{50}$).

Compounds of present disclosure are considered to be active in the B-cell specific functional assay (inhibition of CD69 expression) if $IC_{50}$ values are less than 10 μM.

Data for representative compounds of the present disclosure are given below in Table 1:

TABLE 1 hBTK and mouse spleenocyte $IC_{50}$ values:

| Example No | hBTK $IC_{50}$ (nM) | Mouse spleenocyte $IC_{50}$ (nM) |
|---|---|---|
| A-1 | 7 | 99 |
| A-2 | 7 | 165 |
| A-3 | 515 | — |
| A-4 | 396 | — |
| A-5 | 92 | — |
| A-6 | 143 | — |
| A-7 | 415 | — |
| A-8 | 825 | — |
| B-1 | 6 | 40 |
| B-2 | 31 | 200 |
| B-3 | 30 | — |
| B-4 | 41 | — |
| B-5 | 8 | 60 |
| B-6 | 7 | 81 |
| B-7 | 6 | 52 |
| B-8 | 7 | — |
| B-9 | 10 | — |
| B-10 | 2 | 20 |
| B-11 | 254 | — |
| B-12 | 115 | — |
| B-13 | 3 | 9 |
| B-14 | 7 | 96 |
| B-15 | 103 | — |
| B-16 | 4 | 17 |
| B-17 | 6 | 74 |
| B-18 | 9 | — |
| B-19 | 190 | — |
| B-20 | 7 | 67 |
| B-21 | 8 | — |
| B-22 | 32.5 | 137 |
| C-1 | 5 | 9 |
| C-2 | 12 | 36 |
| C-3 | 21 | 175 |
| C-4 | 11 | — |
| C-5 | 3 | 125 |
| D-1 | 6 | 32 |
| D-2 | 13 | — |
| D-3 | 5 | 43 |
| D-4 | 3 | 19 |
| D-5 | 5 | 38 |
| D-6 | 5 | 53 |
| D-7 | 4 | 43 |
| D-8 | 6.5 | 97 |
| D-9 | 2 | 33 |
| D-10 | 7 | 76 |
| D-11 | 14 | 80 |
| D-12 | 11 | 261 |
| D-13 | 3 | 65 |
| D-14 | 1.7 | 8 |
| E-1 | 9 | — |
| F-1 | 3 | 70 |
| F-2 | 43 | — |
| F-3 | 3.8 | 92 |
| G-1 | 3 | 51 |
| G-2 | 5 | 54 |
| H-1 | 13 | — |
| I-1 | 5 | 14 |
| I-2 | 1 | 5 |
| I-3 | 35 | — |
| I-4 | 2 | 23 |
| I-5 | 3 | 30 |
| I-6 | 3 | 36 |
| I-7 | 2 | 21 |
| I-8 | 9 | 85 |
| I-9 | 8 | 47 |
| I-10 | 7 | 31 |
| I-11 | >1000 | — |
| I-12 | 2 | 46 |
| I-13 | 2 | 8 |
| I-14 | 1.7 | 7.5 |
| I-15 | 1.5 | 18 |
| I-16 | 1.6 | 7.7 |
| I-17 | 1.3 | 2.7 |
| I-18 | 1.9 | 2.7 |
| I-19 | 0.65 | 2.4 |
| I-20 | 0.55 | — |
| J-1 | 9 | 179 |
| J-2 | 3.5 | 77 |
| K-1 | 20 | 147 |
| K-2 | 32 | 815 |
| K-3 | 42 | — |
| K-4 | 51 | 129 |
| K-5 | 171 | — |
| K-6 | 9.7 | 189 |
| K-7 | >1000 | — |
| K-8 | 360 | — |
| K-9 | 137 | — |
| K-10 | 233 | — |
| K-11 | 162 | — |
| K-12 | 114 | — |
| K-13 | 133 | — |
| K-14 | >1000 | — |
| K-15 | 130 | — |
| K-16 | 21 | >1000 |
| K-17 | 41 | — |
| K-18 | 208 | — |
| K-19 | 36 | >1000 |
| K-20 | 44 | 195 |
| K-21 | >1000 | — |
| K-22 | 2 | 8 |
| L-1 | 8 | 67 |
| L-2 | 9 | 87 |
| L-3 | 8 | 21 |
| L-4 | 43 | — |
| M-1 | >1000 | — |
| M-2 | >1000 | — |
| M-3 | >1000 | — |
| N-1 | 33 | 61 |
| N-2 | 181 | — |
| O-1 | 55 | 171 |
| P-1 | 272 | — |
| P-2 | 611 | — |
| P-3 | >1000 | — |

TABLE 1-continued hBTK and mouse spleenocyte IC$_{50}$ values:

| Example No | hBTK IC$_{50}$ (nM) | Mouse spleenocyte IC$_{50}$ (nM) |
|---|---|---|
| P-4 | >1000 | — |
| P-5 | 2 | 14.6 |
| P-6 | 82 | — |
| P-7 | 46 | — |
| P-8 | 25 | — |
| P-9 | 7 | 104.4 |
| P-10 | 6 | 94 |
| P-11 | 10 | — |
| P-12 | 22 | — |
| P-13 | 1 | — |
| P-14 | 1 | 5.8 |
| P-15 | 1 | 14.7 |
| P-16 | 1.3 | 9 |
| P-17 | 2.5 | 47 |
| P-18 | 1.7 | 5.4 |
| P-19 | 14.6 | 20 |
| P-20 | 4 | 27 |
| P-21 | 4 | 59 |
| P-22 | 1.2 | 57 |
| P-23 | 1.4 | 75 |
| P-24 | 3.6 | 11 |
| P-25 | 618 | — |
| P-26 | 3.4 | 162 |
| P-27 | 1.2 | 50 |
| P-28 | 3.1 | 63 |
| P-29 | 1.3 | 8 |
| P-30 | 1 | 11 |
| P-31 | 5.3 | 52 |
| Q-1 | 2.9 | — |
| Q-2 | 3.1 | — |
| Q-3 | 1.15 | — |
| R-1 | 2.2 | 75 |
| R-2 | 1.5 | 21 |
| R-3 | 22 | 85 |
| R-4 | 1.6 | 70 |
| R-5 | 0.75 | 51 |
| S-1 | 4 | 130 |
| S-2 | 12 | 126 |
| S-3 | 3 | — |

Although the subject matter has been described in considerable detail with reference to certain preferred embodiments thereof, other embodiments are possible. As such, the spirit and scope of the present disclosure should not be limited to the description of the preferred embodiment contained therein.

We claim:

1. A compound of formula (I) or a pharmaceutically acceptable salt thereof,

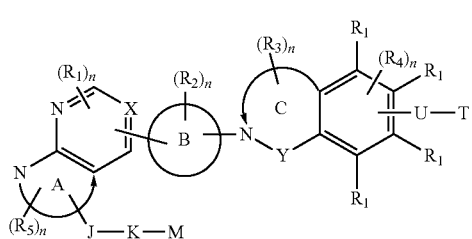

I wherein,
ring A is pyrrole;
ring B is phenyl or pyridine;
ring C represents a 7 membered ring which is unsaturated or partially unsaturated having one, two or three hetero atoms independently selected from O, N or S;
each X independently represents N or C(R$^1$);
Y represents —C(O);
J is absent or is selected from the group consisting of (C$_{1-6}$)alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene and tetrahydropyridylene;
K is a bond or (C$_{1-6}$)alkylene wherein optionally one or more than one methylene groups of alkylene are independently replaced by hetero atoms or groups selected from —O—, —N(R$^6$)— and —C(O)—;
M is selected from hydrogen, cyano, halogen, haloalkyl, perhaloalkyl, alkyl, cyanoalkyl, C$_{1-6}$ alkanoyl, —(CR$^a$R$^b$)$_m$OR$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, thiocarbonyl, —S(O)$_p$R$^6$, —SO$_3$H, cyclopropyl, cyclobutyl, cyclopentyl, cyclohexyl, cycloheptyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl and pyrimidinyl;
J, K and M is optionally substituted with one or more substituents independently selected from cyano, nitro, oxo, halogen, haloalkyl, perhaloalkyl, hydroxyamino, —(CR$^a$R$^b$)$_m$OR$^6$, —(CR$^a$R$^b$)$_m$C(O)R$^6$, —OC(O)R$^6$, —SR$^6$, —(CR$^a$R$^b$)$_m$COOR$^6$, —(CR$^a$R$^b$)$_m$NR$^7$R$^8$, —(CR$^a$R$^b$)$_m$C(O)NR$^7$R$^8$, —(CR$^a$R$^b$)$_m$NR$^6$C(O) NR$^7$R$^8$, —NR$^6$C(O)R$^6$, thiocarbonyl, —S(O)$_2$NR$^7$R$^8$, —NR$^6$S(O)$_2$R$^6$, —S(O)$_p$R$^6$, —SO$_3$H, alkyl, alkenyl, alkynyl, C$_{3-10}$cycloalkyl, C$_{3-10}$cycloalkenyl, C$_{3-10}$cycloalkylalkyl, C$_{3-10}$ aryl, C$_{3-10}$heterocyclyl and C$_{3-10}$heteroaryl;
wherein alkyl, alkenyl, alkynyl, cycloalkyl, cycloalkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O) R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ and —NR$^6$S(O)$_2$R$^6$;
U is a bond or is selected from the group consisting of cyclopropylene, cyclobutylene, cyclohexylene and (C$_{1-6}$)alkylene;
T is selected from hydrogen, cyano, halogen, haloalkyl, perhaloalkyl alkyl and —(CR$^a$R$^b$)$_m$OR$^6$;
R$^1$, R$^2$, R$^3$, R$^4$ and R$^5$ are independently selected from hydrogen, alkyl, alkoxy, C$_{1-6}$ alkanoyl, acylamino, acyloxy, —(CR$^a$R$^b$)$_m$C(O)R$^6$, —(CR$^a$R$^b$)$_m$NR$^7$R$^8$, —(CR$^a$R$^b$)$_m$O(CR$^a$R$^b$)$_n$Si(R$^7$)$_3$, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, alkylthio, aminosulfonyl, alkylsulfonyl, and nitro;
R$^6$ is selected from the group consisting of hydrogen, halogen, alkyl, haloalkyl, and C$_{3-10}$ cycloalkyl;
R$^7$ and R$^8$ are independently selected from the group consisting of hydrogen, haloalkyl and alkyl;
R$^a$ and R$^b$ are independently selected from the group consisting of hydrogen, —OR$^6$, halogen, haloalkyl, perhaloalkyl and alkyl;
m is 0-3;
n is 0-3;
p is 0, 1 or 2; and
q is 1 or 2.

2. A compound of formula (Ia) according to claim 1 or a pharmaceutically acceptable salt thereof,

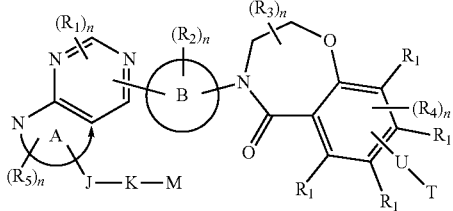

(Ia)

wherein,
ring A is pyrrole;
ring B is phenyl or pyridine;
J is absent or is selected from the group consisting of $(C_{1-6})$alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene and tetrahydropyridylene;
K is a bond or $(C_{1-6})$alkylene wherein optionally one or more than one methylene groups of alkylene are independently replaced by hetero atoms or groups selected from —O—, —N($R^6$)— and —C(O)—;
M is selected from hydrogen, cyano, halogen, haloalkyl, perhaloalkyl, alkyl, cyanoalkyl, $C_{1-6}$ alkanoyl, —$(CR^aR^b)_mOR^6$, —$SR^6$, —$(CR^aR^b)_mCOOR^6$, —$(CR^aR^b)_mNR^7R^8$, —$(CR^aR^b)_mC(O)NR^7R^8$, thiocarbonyl, —$S(O)_pR^6$, —$SO_3H$, cyclopropyl, cyclohexyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl and pyrimidinyl;
J, K and M is optionally substituted with one or more substituents independently selected from cyano, nitro, oxo, halogen, haloalkyl, perhaloalkyl, hydroxyamino, —$(CR^aR^b)_mOR^6$, —$(CR^aR^b)_mC(O)R^6$, —$OC(O)R^6$, —$SR^6$, —$(CR^aR^b)_mCOOR^6$, —$(CR^aR^b)_mNR^7R^8$, —$(CR^aR^b)_mC(O)NR^7R^8$, —$(CR^aR^b)_mNR^6C(O)$ $NR^7R^8$, —$NR^6C(O)R^6$, thiocarbonyl, —$S(O)_2NR^7R^8$, —$NR^6S(O)_2R^6$, —$S(O)_pR^6$, —$SO_3H$, alkyl, alkenyl, alkynyl, $C_{3-10}$ cycloalkyl, $C_{3-10}$ cycloalkenyl, $C_{3-10}$ cycloalkylalkyl, $C_{3-10}$ aryl, $C_{3-10}$ heterocyclyl and $C_{3-10}$ heteroaryl;
wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —$OC(O)R^6$, —$(CR^aR^b)_mC(O)NR^7R^8$, —$NR^6C(O)R^6$, —$SR^6$, —$S(O)_pR^6$, —$S(O)_2NR^7R^8$ and —$NR^6S(O)_2R^6$;
U is a bond or is selected from the group consisting of cyclopropylene, cyclobutylene, cyclohexylene and $(C_{1-6})$alkylene;
T is selected from hydrogen, cyano, halogen, haloalkyl, perhaloalkyl, alkyl, and —$(CR^aR^b)_mOR^6$;
$R^1$, $R^2$, $R^3$, $R^4$ and $R^5$ are independently selected from hydrogen, alkyl, alkoxy, $C_{1-6}$ alkanoyl, acylamino, acyloxy, —$(CR^aR^b)_mNR^7R^8$, —$(CR^aR^b)_mO(CR^aR^b)_nSi$ $(R^7)_3$, azido, cyano, halogen, hydroxy, hydroxyalkyl, haloalkyl, perhaloalkyl, carboxy, alkylcarboxy, carboxyalkyl, carboxyalkyloxy, —$SO_3H$, alkylthio, alkylsulfonyl, and nitro;
$R^6$ is selected from the group consisting of hydrogen, —$(CR^aR^b)_mOR^6$, halogen, haloalkyl, —$(CR^aR^b)_mC(O)$ $R^6$, alkyl, and $C_{3-10}$ cycloalkyl;
$R^7$ and $R^8$ are independently selected from the group consisting of hydrogen, —$(CR^aR^b)_mOR^6$, haloalkyl, —$(CR^aR^b)_mC(O)R^6$, and alkyl;
$R^a$ and $R^b$ are independently selected from the group consisting of hydrogen, —$OR^6$, halogen, haloalkyl, perhaloalkyl and alkyl;
m is 0-3;
n is 0-3;
p is 0, 1 or 2; and
q is 1 or 2.

3. A compound of formula (Ia) according to claim 1 or a pharmaceutically acceptable salt thereof,

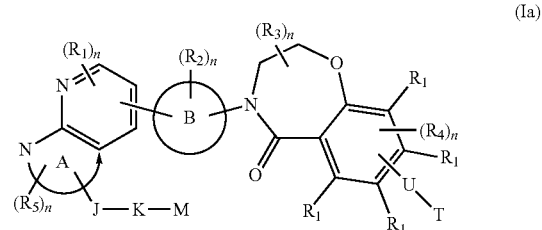

(Ia)

wherein,
ring A is pyrrole;
ring B is phenyl or pyridine;
J is absent or is selected from the group consisting of $(C_{1-6})$alkylene, phenylene, pyrazolylene, imidazolylene, thienylene, furanylene, thiazolylene, oxazolylene, triazolylenene, pyridylene, pyridazinylene, pyrazinylene, dihydropyrazolylene, dihydroimidazolylene and tetrahydropyridylene;
K is a bond or $(C_{1-6})$alkylene wherein optionally one or more than one methylene groups of alkylene are independently replaced by hetero atoms or groups selected from —O—, —N($R^6$)— and —C(O)—;
M is selected from hydrogen, cyano, halogen, haloalkyl, perhaloalkyl, alkyl, cyanoalkyl, $C_{1-6}$ alkanoyl, —$(CR^aR^b)_mOR^6$, —$SR^6$, —$(CR^aR^b)_mCOOR^6$, —$(CR^aR^b)_mNR^7R^8$, —$(CR^aR^b)_mC(O)NR^7R^8$, thiocarbonyl, —$S(O)_pR^6$, —$SO_3H$, cyclopropyl, cyclohexyl, phenyl, azetidinyl, oxetanyl, pyrrolidinyl, dihydroimidazolyl, tetrahydrofuranyl, piperidinyl, piperazinyl, morpholinyl, thiomorpholinyl, thiazinyl-dioxide, tetrahydropyranyl, tetrahydropyridinyl, pyrrolyl, imidazolyl, furanyl, thiazolyl, oxazolyl, pyranyl, pyridyl and pyrimidinyl;
J, K and M is optionally substituted with one or more substituents independently selected from cyano, nitro, oxo, halogen, haloalkyl, perhaloalkyl, hydroxyamino, —$(CR^aR^b)_mOR^6$, —$(CR^aR^b)_mC(O)R^6$, —$OC(O)R^6$, —$SR^6$, —$(CR^aR^b)_mCOOR^6$, —$(CR^aR^b)_mNR^7R^8$, —$(CR^aR^b)_mC(O)NR^7R^8$, —$(CR^aR^b)_mNR^6C(O)$ $NR^7R^8$, —$NR^6C(O)R^6$, thiocarbonyl, —$S(O)_2NR^7R^8$, —$NR^6S(O)_2R^6$, —$S(O)_pR^6$, —$SO_3H$, alkyl, alkenyl, alkynyl, $C_{3-10}$ cycloalkyl, $C_{3-10}$ cyclkenyl, $C_{3-10}$ cycloalkylalkyl, $C_{3-10}$ aryl, $C_{3-10}$ heterocyclyl and $C_{3-10}$ heteroaryl;

wherein alkyl, alkenyl or alkynyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^6$, —(CR$^a$R$^b$)$_m$C(O)NR$^7$R$^8$, —NR$^6$C(O)R$^6$, —SR$^6$, —S(O)$_p$R$^6$, —S(O)$_2$NR$^7$R$^8$ and —NR$^6$S(O)$_2$R$^6$;

U is a bond or is selected from the group consisting of cyclopropylene, cyclobutylene, cyclohexylene and (C$_{1-6}$)alkylene;

T is selected from hydrogen, cyano, halogen, haloalkyl, perhaloalkyl alkyl, and —(CR$^a$R$^b$)$_m$OR$^6$;

R$^1$, R$^2$, R$^3$, R$^4$ and R$^5$ are independently selected from hydrogen, alkyl, alkoxy, C$_{1-6}$ alkanoyl, acylamino, acyloxy, —(CR$^a$R$^b$)$_m$NR$^7$R$^8$, —(CR$^a$R$^b$)$_m$O(CR$^a$R$^b$)$_m$Si(R$^7$)$_3$, azido, cyano, halogen, hydroxy, hydroxyalkyl, haloalkyl, perhaloalkyl, carboxy, alkylcarboxy, carboxyalkyl, carboxyalkyloxy, —SO$_3$H, alkylthio, alkylsulfonyl, and nitro;

R$^6$ is selected from the group consisting of hydrogen, —(CR$^a$R$^b$)$_m$OR$^6$, halogen, haloalkyl, —(CR$^a$R$^b$)$_m$C(O)R$^6$, alkyl, and C$_{3-10}$ cycloalkyl;

R$^7$ and R$^8$ are independently selected from the group consisting of hydrogen, —(CR$^a$R$^b$)$_m$OR$^6$, haloalkyl, —(CR$^a$R$^b$)$_m$C(O)R$^6$, and alkyl;

R$^a$ and R$^b$ are independently selected from the group consisting of hydrogen, —OR$^6$, halogen, haloalkyl, perhaloalkyl and alkyl;

m is 0-3;

n is 0-3;

p is 0, 1 or 2; and q is 1 or 2.

4. A compound selected from a group consisting of:

8-cyclopropyl-4-[2-methyl-3-[6-[4-(piperazin-1-ylmethyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[3-(piperazin-1-ylmethyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-(morpholinomethyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[3-(morpholinomethyl)phenyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[6-[4-[(4-methylpiperazin-1-yl)methyl]phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-[(4-methylpiperazin-1-yl)methyl]phenyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[6-[4-(morpholinomethyl)phenyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[6-[4-[(4-hydroxy-4-methyl-1-piperidyl)methyl]phenyl]-7H-pyrrolo[2,3-d]pyrimidin-4-yl]phenyl]-2,3-dihydro-1,4-benzoxazepin-5-one;

8-cyclopropyl-4-[3-[6-[4-[(4-ethylpiperazin-1-yl)methyl]phenyl]-7H-pyrrolo[2,3-d]pyrimidin-4-yl]-2-(hydroxymethyl)phenyl]-2,3-dihydro-1,4-benzoxazepin-5-one;

8-cyclopropyl-4-[2-(hydroxymethyl)-3-[2-[4-[(4-methylpiperazin-1-yl)methyl]phenyl]-1H-pyrrolo[2,3-b]pyridin-4-yl]phenyl]-2,3-dihydro-1,4-benzoxazepin-5-one;

1-[[4-[4-[3-(8-cyclopropyl-5-oxo-2,3-dihydro-1,4-benzoxazepin-4-yl)-2-(hydroxymethyl)phenyl]-7H-pyrrolo[2,3-d]pyrimidin-6-yl]phenyl]methyl]piperidine-4-carbonitrile;

8-cyclopropyl-4-[2-methyl-3-[2-[4-[(4-methylpiperazin-1-yl)methyl]phenyl]-1H-pyrrolo[2,3-b]pyridin-4-yl]phenyl]-2,3-dihydro-1,4-benzoxazepin-5-one;

8-cyclopropyl-4-[3-[2-[4-[(4-ethylpiperazin-1-yl)methyl]phenyl]-1H-pyrrolo[2,3-b]pyridin-4-yl]-2-(hydroxymethyl)phenyl]-2,3-dihydro-1,4-benzoxazepin-5-one;

8-cyclopropyl-4-[2-(hydroxymethyl)-3-[2-[4-[(3-hydroxy-3-methyl-azetidin-1-yl)methyl]phenyl]-1H-pyrrolo[2,3-b]pyridin-4-yl]phenyl]-2,3-dihydro-1,4-benzoxazepin-5-one;

8-cyclopropyl-4-[3-[2-[2-fluoro-4-[(4-methylpiperazin-1-yl)methyl]phenyl]-1H-pyrrolo[2,3-b]pyridin-4-yl]-2-(hydroxymethyl)phenyl]-2,3-dihydro-1,4-benzoxazepin-5-one;

8-cyclopropyl-4-[3-[2-[3-fluoro-4-[(4-methylpiperazin-1-yl)methyl]phenyl]-1H-pyrrolo[2,3-b]pyridin-4-yl]-2-methyl-phenyl]-2,3-dihydro-1,4-benzoxazepin-5-one;

8-cyclopropyl-4-[2-(hydroxymethyl)-3-[2-[6-[(4-methylpiperazin-1-yl)methyl]-3-pyridyl]-1H-pyrrolo[2,3-b]pyridin-4-yl]phenyl]-2,3-dihydro-1,4-benzoxazepin-5-one;

8-cyclopropyl-4-[3-[2-[6-[(4-ethylpiperazin-1-yl)methyl]-3-pyridyl]-1H-pyrrolo[2,3-b]pyridin-4-yl]-2-(hydroxymethyl)phenyl]-2,3-dihydro-1,4-benzoxazepin-5-one;

8-cyclopropyl-4-[2-(hydroxymethyl)-3-[6-[4-(4-methylpiperazin-1-yl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-(4-methylpiperazin-1-yl)phenyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[2-[4-(1-methyl-3,6-dihydro-2H-pyridin-4-yl)phenyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[4-(4-methylmorpholin-2-yl)phenyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[6-[1-(1-methyl-4-piperidyl)pyrazol-4-yl]-7H-pyrrolo[2,3-d]pyrimidin-4-yl]phenyl]-2,3-dihydro-1,4-benzoxazepin-5-one;

8-cyclopropyl-4-[2-methyl-3-[6-[1-(1-methyl-4-piperidyl)pyrazol-4-yl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[2-[1-(1-methyl-4-piperidyl)pyrazol-4-yl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[6-[1-(1-methyl-3-piperidyl)pyrazol-4-yl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[2-[1-(1-methylazetidin-3-yl)pyrazo-4-yl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[1-(1-isopropylazetidin-3-yl)pyrazo-4-yl]-1H-pyrrolo[2,3-b]pyridin-4-yl]phenyl]-2,3-dihydro-1,4-benzoxazepin-5-one;

8-cyclopropyl-4-[3-[2-[1-(1-ethylazetidin-3-yl)pyrazo]-4-yl]-1H-pyrrolo[2,3-b]pyridin-4-yl]-2-(hydroxymethyl)phenyl]-2,3-dihydro-1,4-benzoxazepin-5-one;

8-cyclopropyl-4-[2-(hydroxymethyl)-3-[2-[6-(4-methylpiperazin-1-yl)-3-pyridyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[6-(1-isopropylazetidin-3-yl)oxy-3-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[1-[1-(oxetan-3-yl)-4-piperidyl]pyrazol-4-yl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[3-methyl-1-(1-methylazetidin-3-yl)pyrazol-4-yl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[1-(oxetan-3-yl)pyrazol-4-yl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-(1-tetrahydropyran-4-ylpyrazol-4-yl)-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[1-(4-hydroxy-4-methyl-cyclohexyl)pyrazol-4-yl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[6-[4-[(1-methyl-4-piperidyl)oxy]phenyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[6-[4-(1-methylazetidin-3-yl)oxyphenyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[5-[(4-methylpiperazin-1-yl)methyl]-2-pyridyl]-1H-pyrrolo[2,3-b]pyridin-4-yl]phenyl]-2,3-dihydropyrido[2,3-f][1,4]oxazepin-5-one;

8-cyclopropyl-4-[3-[2-[5-[(4-ethylpiperazin-1-yl)methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-4-[3-[2-[5-[(4-cyclopropylpiperazin-1-yl)methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-4-[2-(hydroxymethyl)-3-[2-[5-[(4-methylsulfonylpiperazin-1-yl)methyl]-2-pyridyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[5-[(4-isopropylpiperazin-1-yl)methyl]-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[(1,1-dioxo-1,4-thiazinan-4-yl)methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-4-[2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[(4-cyclopropylsulfonylpiperazin-1-yl)methyl]-2-pyridyl]-1H-pyrrolo[2,3-b]pyridin-4-yl]-2-(hydroxymethyl)phenyl]-2,3-dihydro-1,4-benzoxazepin-5-one;

4-[[6-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]-3-pyridyl]methyl]-N,N-dimethyl-piperazine-1-carboxamide;

8-cyclopropyl-4-[3-[2-[5-[(4-ethylpiperazin-1-yl)methyl]-2-pyridyl]-1H-pyrrolo[2,3-b]pyridin-4-yl]-2-(hydroxymethyl)phenyl]-6-fluoro-2,3-dihydro-1,4-benzoxazepin-5-one;

8-cyclopropyl-6-fluoro-4-[2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(3,4,5-trimethylpiperazin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(4-methyl-3-oxo-piperazin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[[4-(2,2-difluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-6-fluoro-4-[5-fluoro-2-(hydroxymethyl)-3-[2-[5-(morpholinomethyl)-2-pyridyl]-1H-pyrrolo[2,3-b]pyridin-4-yl]phenyl]-2,3-dihydro-1,4-benzoxazepin-5-one;

8-cyclopropyl-4-[3-[2-[4-(4-fluoro-1-methyl-4-piperidyl)phenyl]-1H-pyrrolo[2,3-b]pyridin-4-yl]-2-(hydroxymethyl)phenyl]-2,3-dihydro-1,4-benzoxazepin-5-one;

8-cyclopropyl-4-[3-[2-[4-(3-fluoro-1-methyl-3-piperidyl)phenyl]-1H-pyrrolo[2,3-b]pyridin-4-yl]-2-(hydroxymethyl)phenyl]-2,3-dihydro-1,4-benzoxazepin-5-one;

8-cyclopropyl-4-[2-methyl-3-[6-[4-(4-methylpiperazine-1-carbonyl)phenyl]-7H-pyrrolo[2,3-d]pyrimidin-4-yl]phenyl]-2,3-dihydro-1,4-benzoxazepin-5-one;

8-cyclopropyl-4-[3-[6-[4-(4-hydroxypiperidine-1-carbonyl)phenyl]-7H-pyrrolo[2,3-d]pyrimidin-4-yl]-2-methyl-phenyl]-2,3-dihydro-1,4-benzoxazepin-5-one;

8-cyclopropyl-4-[3-[6-[4-(3-hydroxypiperidine-1-carbonyl)phenyl]-7H-pyrrolo[2,3-d]pyrimidin-4-yl]-2-methyl-phenyl]-2,3-dihydro-1,4-benzoxazepin-5-one;

8-cyclopropyl-4-[3-[6-[4-(4-hydroxy-4-methyl-piperidine-1-carbonyl)phenyl]-7H-pyrrolo[2,3-d]pyrimidin-4-yl]-2-methyl-phenyl]-2,3-dihydro-1,4-benzoxazepin-5-one;

8-cyclopropyl-4-[2-methyl-3-[6-[4-(piperidine-1-carbonyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-(piperazine-1-carbonyl)phenyl]-7H-pyrrolo[2,3-d]pyrimidin-4-yl]phenyl]-2,3-dihydro-1,4-benzoxazepin-5-one;

4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]-N-(2,2,2-trifluoroethyl)benzamide;

8-cyclopropyl-4-[3-[6-[4-(3-hydroxyazetidine-1-carbonyl)phenyl]-7H-pyrrolo[2,3-d]pyrimidin-4-yl]-2-methyl-phenyl]-2,3-dihydro-1,4-benzoxazepin-5-one;

8-cyclopropyl-4-[2-methyl-3-[6-[4-(pyrrolidine-1-carbonyl)phenyl]-7H-pyrrolo[2,3-d]pyrimidin-4-yl]phenyl]-2,3-dihydro-1,4-benzoxazepin-5-one;

8-cyclopropyl-4-[3-[6-[4-(4-methoxypiperidine-1-carbonyl)phenyl]-7H-pyrrolo[2,3-d]pyrimidin-4-yl]-2-methyl-phenyl]-2,3-dihydro-1,4-benzoxazepin-5-one;

8-cyclopropyl-4-[3-[6-[4-(3-methoxyazetidine-1-carbonyl)phenyl]-7H-pyrrolo[2,3-d]pyrimidin-4-yl]-2-methyl-phenyl]-2,3-dihydro-1,4-benzoxazepin-5-one;

1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]pyrrolidine-2-carboxylic acid;

1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]piperidine-3-carboxylic acid;

1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]piperidine-4-carboxylic acid;

8-cyclopropyl-4-[3-[6-[4-(4-hydroxypiperidine-1-carbonyl)phenyl]-7H-pyrrolo[2,3-d]pyrimidin-4-yl]-2-methyl-phenyl]-2,3-dihydro-1,4-benzoxazepin-5-one (hydrochloride salt);

6-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]pyridine-3-carboxamide;

8-cyclopropyl-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[2-[4-(4-hydroxy-4-methyl-piperidine-1-carbonyl)phenyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-(3-hydroxy-3-methyl-azetidine-1-carbonyl)-2-pyridyl]-1H-pyrrolo[2,3-b]pyridin-4-yl]phenyl]-2,3-dihydro-1,4-benzoxazepin-5-one;

7-cyclopropyl-2-[2-methyl-3-(6-phenyl-7H-pyrrolo[2,3-d]pyrimidin-4-yl)phenyl]-4,5-dihydro-3H-2-benzazepin-1-one;

8-cyclopropyl-4-[2-methyl-3-[6-(4-morpholinophenyl)-7H-pyrrolo[2,3-d]pyrimidin-4-yl]phenyl]-2,3-dihydro-1,4-benzoxazepin-5-one;

2-[3-[2-amino-6-[4-[(4-methylpiperazin-1-yl)methyl]phenyl]-7H-pyrrolo[2,3-d]pyrimidin-4-yl]-2-methyl-phenyl]-7-cyclopropyl-4,5-dihydro-3H-2-benzazepin-1-one;

4-[3-[2-amino-6-(6-morpholino-3-pyridyl)-7H-pyrrolo[2,3-d]pyrimidin-4-yl]-2-methyl-phenyl]-8-cyclopropyl-2,3-dihydro-1,4-benzoxazepin-5-one;

4-[3-[2-amino-6-[4-(morpholine-4-carbonyl)phenyl]-7H-pyrrolo[2,3-d]pyrimidin-4-yl]-2-methyl-phenyl]-8-cyclopropyl-2,3-dihydro-1,4-benzoxazepin-5-one;

8-cyclopropyl-4-[3-[6-[1-(3-hydroxypropyl)-3,6-dihydro-2H-pyridin-4-yl]-7H-pyrrolo[2,3-d]pyrimidin-4-yl]-2-methyl-phenyl]-2,3-dihydro-1,4-benzoxazepin-5-one;

7-cyclopropyl-2-[3-[6-[1-(2-hydroxyethyl)-3,6-dihydro-2H-pyridin-4-yl]-7H-pyrrolo[2,3-d]pyrimidin-4-yl]-2-methyl-phenyl]-4,5-dihydro-3H-2-benzazepin-1-one;

8-cyclopropyl-4-[3-[6-[1-(3-hydroxypropyl)-4-piperidyl]-7H-pyrrolo[2,3-d]pyrimidin-4-yl]-2-methyl-phenyl]-2,3-dihydro-1,4-benzoxazepin-5-one;

8-cyclopropyl-4-[2-methyl-3-[6-(1,2,3,6-tetrahydropyridin-5-yl)-7H-pyrrolo[2,3-d]pyrimidin-4-yl]phenyl]-2,3-dihydro-1,4-benzoxazepin-5-one;

4-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]-N,N-dimethyl-3,6-dihydro-2H-pyridine-1-carboxamide;

4-[3-(8-cyclopropyl-5-oxo-2,3-dihydro-1,4-benzoxazepin-4-yl)phenyl]-2-[4-[(4-methylpiperazin-1-yl)methyl]phenyl]-1H-pyrrolo[2,3-b]pyridine-5-carbonitrile;

6-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]pyridine-3-carboxylic acid;

8-cyclopropyl-4-[3-[2-[4-(1,2-dihydroxyethyl)phenyl]-1H-pyrrolo[2,3-b]pyridin-4-yl]-2-(hydroxymethyl)phenyl]-2,3-dihydro-1,4-benzoxazepin-5-one;

8-cyclopropyl-4-[2-(hydroxymethyl)-3-[2-[1-(1-isopropylazetidin-3-yl)imidazol-4-yl]-1H-pyrrolo[2,3-b]pyridin-4-yl]phenyl]-2,3-dihydro-1,4-benzoxazepin-5-one;

4-[4-[2-(hydroxymethyl)-3-[8-(1-hydroxy-1-methyl-ethyl)-5-oxo-2,3-dihydro-1,4-benzoxazepin-4-yl]phenyl]-1H-pyrrolo[2,3-b]pyridin-2-yl]-N,N-dimethyl-3,6-dihydro-2H-pyridine-1-carboxamide;

8-cyclopropyl-6-fluoro-4-[2-(hydroxymethyl)-3-[2-(1-methylsulfonyl-3,6-dihydro-2H-pyridin-4-yl)-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[1-(oxetan-3-yl)-3,6-dihydro-2H-pyridin-4-yl]-1H-pyrrolo[2,3-b]pyridin-4-yl]phenyl]-2,3-dihydro-1,4-benzoxazepin-5-one;

4-[3-[2-[1-(azetidine-1-carbonyl)-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one;

4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-N,N-dimethyl-3,6-dihydro-2H-pyridine-1-carboxamide;

8-cyclopropyl-6-fluoro-4-[2-(hydroxymethyl)-3-[2-[1-(3-hydroxy-3-methyl-azetidine-1-carbonyl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[1-(oxetan-3-yl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-4-[5-fluoro-2-(hydroxymethyl)-3-[2-[1-(oxetan-3-yl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[1-(morpholine-4-carbonyl)-3,6-dihydro-2H-pyridin-4-yl]-1H-pyrrolo[2,3-b]pyridin-4-yl]phenyl]-2,3-dihydro-1,4-benzoxazepin-5-one;

4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-N,N-diethyl-3,6-dihydro-2H-pyridine-1-carboxamide;

8-cyclopropyl-4-[5-fluoro-2-(hydroxymethyl)-3-[2-[1-(2-hydroxy-2-methyl-propyl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-(1-tetrahydrofuran-3-yl-3,6-dihydro-2H-pyridin-4-yl)-1H-pyrrolo[2,3-b]pyridin-4-yl]phenyl]-2,3-dihydro-1,4-benzoxazepin-5-one;

4-[3-[2-[1-[2-(azetidin-1-yl)-2-oxo-ethyl]-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one;

8-cyclopropyl-6-fluoro-4-[2-(hydroxymethyl)-3-[2-[1-(2-hydroxy-2-methyl-propyl)-3,6-dihydro-2H-pyridin-4-yl]-1H-pyrrolo[2,3-b]pyridin-4-yl]phenyl]-2,3-dihydro-1,4-benzoxazepin-5-one;

4-[3-[2-(1-acetyl-3,6-dihydro-2H-pyridin-4-yl)-1H-pyrrolo[2,3-b]pyridin-4-yl]-2-(hydroxymethyl)phenyl]-8-cyclopropyl-6-fluoro-2,3-dihydro-1,4-benzoxazepin-5-one;

8-cyclopropyl-6-fluoro-4-[3-(hydroxymethyl)-4-[2-(1-methylsulfonyl-3,6-dihydro-2H-pyridin-4-yl)-1H-pyrrolo[2,3-b]pyridin-4-yl]-2-pyridyl]-2,3-dihydro-1,4-benzoxazepin-5-one;

8-cyclopropyl-6-fluoro-4-[2-(hydroxymethyl)-3-[2-(1-tetrahydropyran-4-yl-3,6-dihydro-2H-pyridin-4-yl)-1H-pyrrolo[2,3-b]pyridin-4-yl]phenyl]-2,3-dihydro-1,4-benzoxazepin-5-one;

3-[4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-3,6-dihydro-2H-pyridin-1-yl]-3-oxo-propanenitrile;

8-cyclopropyl-6-fluoro-4-[2-(hydroxymethyl)-3-[2-(1,2,3,6-tetrahydro pyridin-4-yl)-1H-pyrrolo[2,3-b]pyridin-4-yl]phenyl]-2,3-dihydro-1,4-benzoxazepin-5-one;

4-[3-[2-[1-[2-(azetidin-1-yl)acetyl]-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one;

8-cyclopropyl-6-fluoro-4-[2-(hydroxymethyl)-3-[2-[1-(2-hydroxypropanoyl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-6-fluoro-4-[3-[2-[1-(2-hydroxyacetyl)-3,6-dihydro-2H-pyridin-4-yl]-1H-pyrrolo[2,3-b]pyridin-4-yl]-2-(hydroxymethyl)phenyl]-2,3-dihydro-1,4-benzoxazepin-5-one;

2-[4-[4-[3-(8-cyclopropyl-6-fluoro-5-oxo-2,3-dihydro-1,4-benzoxazepin-4-yl)-2-(hydroxymethyl)phenyl]-1H-pyrrolo[2,3-b]pyridin-2-yl]-3,6-dihydro-2H-pyridin-1-yl]acetamide;

4-[4-[2-(8-cyclopropyl-6-fluoro-5-oxo-2,3-dihydro-1,4-benzoxazepin-4-yl)-3-(hydroxymethyl)-4-pyridyl]-1H-pyrrolo[2,3-b]pyridin-2-yl]-N,N-dimethyl-3,6-dihydro-2H-pyridine-1-carboxamide;

8-cyclopropyl-6-fluoro-4-[2-(hydroxymethyl)-3-[2-[5-(2-morpholinoethoxy)-2-pyridyl]-1H-pyrrolo[2,3-b]pyridin-4-yl]phenyl]-2,3-dihydro-1,4-benzoxazepin-5-one;

4-[3-[2-[5-[2-(azetidin-1-yl)ethoxy]-2-pyridyl]-1H-pyrrolo[2,3-b]pyridin-4-yl]-2-(hydroxymethyl)phenyl]-8-cyclopropyl-6-fluoro-2,3-dihydro-1,4-benzoxazepin-5-one;

8-cyclopropyl-6-fluoro-4-[5-fluoro-2-(hydroxymethyl)-3-[2-[5-[[1-(oxetan-3-yl)-4-piperidyl]oxy]-2-pyridyl]-1H-pyrrolo[2,3-b]pyridin-4-yl]phenyl]-2,3-dihydro-1,4-benzoxazepin-5-one;

4-[3-[2-[1-(1-acetylazetidin-3-yl)-3,6-dihydro-2H-pyridin-4-yl]-1H-pyrrolo[2,3-b]pyridin-4-yl]-2-(hydroxymethyl)phenyl]-8-cyclopropyl-6-fluoro-2,3-dihydro-1,4-benzoxazepin-5-one;

8-cyclopropyl-4-[3-[2-[1-(1-ethylazetidin-3-yl)-3,6-dihydro-2H-pyridin-4-yl]-1H-pyrrolo[2,3-b]pyridin-4-yl]-2-(hydroxymethyl)phenyl]-6-fluoro-2,3-dihydro-1,4-benzoxazepin-5-one;

8-cyclopropyl-4-[3-[2-(1-ethyl-3,6-dihydro-2H-pyridin-4-yl)-1H-pyrrolo[2,3-b]pyridin-4-yl]-2-(hydroxymethyl)phenyl]-6-fluoro-2,3-dihydro-1,4-benzoxazepin-5-one;

8-cyclopropyl-6-fluoro-4-[2-(hydroxymethyl)-3-[2-[1-(1-methylazetidin-3-yl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-4-[3-[2-[1-(1-ethylazetidine-3-carbonyl)-3,6-dihydro-2H-pyridin-4-yl]-1H-pyrrolo[2,3-b]pyridin-4-yl]-2-(hydroxymethyl)phenyl]-6-fluoro-2,3-dihydro-1,4-benzoxazepin-5-one;

8-cyclopropyl-4-[2-(hydroxymethyl)-3-[6-[1-(1-prop-2-enoyl-3-piperidyl)pyrazol-4-yl]-7H-pyrrolo[2,3-d]pyrimidin-4-yl]phenyl]-2,3-dihydro-1,4-benzoxazepin-5-one;

2-[3-[4-[4-[3-(8-cyclopropyl-5-oxo-2,3-dihydro-1,4-benzoxazepin-4-yl)-2-(hydroxymethyl)phenyl]-1H-pyrrolo[2,3-b]pyridin-2-yl]pyrazol-1-yl]azetidin-1-yl]acetonitrile;

8-cyclopropyl-4-[2-(hydroxymethyl)-3-[2-[5-(4-methylpiperazin-1-yl)-2-pyridyl]-1H-pyrrolo[2,3-b]pyridin-4-yl]phenyl]-2,3-dihydro-1,4-benzoxazepin-5-one;

6-fluoro-4-[5-fluoro-2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-8-(1-hydroxy-1-methyl-ethyl)-2,3-dihydro-1,4-benzoxazepin-5-one;

6-fluoro-4-[5-fluoro-2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-8-(1-hydroxy-1-methyl-ethyl)-2,3-dihydro-1,4-benzoxazepin-5-one;

4-[3-[2-[5-[[4-(2,2-difluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-8-(1-hydroxy-1-methyl-ethyl)-2,3-dihydro-1,4-benzoxazepin-5-one;

4-[3-[2-[5-[[4-(2,2-difluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-8-(1-fluorocyclopropyl)-2,3-dihydro-1,4-benzoxazepin-5-one;

6-fluoro-8-(1-fluorocyclopropyl)-4-[5-fluoro-2-(hydroxymethyl)-3-[2-[5-[[4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

6-fluoro-8-(1-fluorocyclopropyl)-4-[5-fluoro-2-(hydroxymethyl)-3-[2-[5-[[4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[6-[5-[[4-(oxetan-3-yl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-[[4-(oxetan-3-yl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[6-[5-[[4-(2,2,2-trifluoroethyl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-[[4-(2,2,2-trifluoroethyl)piperazin-1-yl]methyl]-2-pyridyl]-7H-pyrrolo[2,3-d]pyrimidin-4-yl]phenyl]-2,3-dihydro-1,4-benzoxazepin-5-one;

8-cyclopropyl-4-[3-[6-[5-[[4-(2,2-difluoroethyl)piperazin-1-yl]methyl]-2-pyridyl]-7H-pyrrolo[2,3-d]pyrimidin-4-yl]-5-fluoro-2-(hydroxymethyl)phenyl]-6-fluoro-2,3-dihydro-1,4-benzoxazepin-5-one;

8-cyclopropyl-4-[3-[6-[5-[[4-(2,2-difluoroethyl)piperazin-1-yl]methyl]-2-pyridyl]-7H-pyrrolo[2,3-d]pyrimidin-4-yl]-2-(hydroxymethyl)phenyl]-6-fluoro-2,3-dihydro-1,4-benzoxazepin-5-one;

8-cyclopropyl-6-fluoro-4-[2-(hydroxymethyl)-3-[6-[5-[(3-hydroxy-3-methyl-azetidin-1-yl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[6-[5-[(3-hydroxy-3-methyl-azetidin-1-yl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[2-[5-[(3-hydroxy-3-methyl-azetidin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(3-hydroxy-3-methyl-azetidin-1-yl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[(4-hydroxy-4-methyl-1-piperidyl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[(4-hydroxy-4-methyl-1-piperidyl)methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[6-[5-[(4-hydroxy-4-methyl-1-piperidyl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-[(4-hydroxy-4-methyl-1-piperidyl)methyl]-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[6-[5-(morpholinomethyl)-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[6-[5-(morpholinomethyl)-2-pyridyl]-7H-pyrrolo[2,3-d]pyrimidin-4-yl]phenyl]-2,3-dihydro-1,4-benzoxazepin-5-one;

8-cyclopropyl-6-fluoro-4-[5-fluoro-2-(hydroxymethyl)-3-[2-[5-(morpholinomethyl)-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-(morpholinomethyl)-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[[3,5-dimethyl-4-(2,2,2-trifluoroethyl)piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[3,5-dimethyl-4-(oxetan-3-yl)piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[4-(2,2-difluoroethyl)-3,5-dimethyl-piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[4-(2,2-difluoroethyl)-3-methyl-piperazin-1-yl]methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-6-fluoro-4-[5-fluoro-2-(hydroxymethyl)-3-[2-[5-[[3-methyl-4-(2,2,2-trifluoroethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[[3-methyl-4-(oxetan-3-yl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[1-methyl-1-[4-(oxetan-3-yl)piperazin-1-yl]ethyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[2-[5-[1-methyl-1-[4-(2,2,2-trifluoroethyl)piperazin-1-yl]ethyl]-2-pyridyl]-1H-pyrrolo[2,3-b]pyridin-4-yl]phenyl]-2,3-dihydro-1,4-benzoxazepin-5-one;

8-cyclopropyl-4-[3-[2-[5-[1-[4-(2,2-difluoroethyl)piperazin-1-yl]-1-methyl-ethyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[[4-(2,2-difluoroethyl)piperazin-1-yl]methyl]-4-fluoro-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-6-fluoro-4-[5-fluoro-3-[2-[4-fluoro-5-[[4-(2,2,2-trifluoroethyl)piperazin-1-yl]methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-6-fluoro-4-[5-fluoro-3-[2-[4-fluoro-5-[[4-(oxetan-3-yl)piperazin-1-yl]methyl]-2-pyridyl]-1H-pyrrolo[2,3-b]pyridin-4-yl]-2-(hydroxymethyl)phenyl]-2,3-dihydro-1,4-benzoxazepin-5-one;

8-cyclopropyl-6-fluoro-4-[5-fluoro-2-(hydroxymethyl)-3-[2-[5-[[4-(oxetan-3-ylmethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-[[4-(oxetan-3-ylmethyl)piperazin-1-yl]methyl]-2-pyridyl]-1H-pyrrolo[2,3-b]pyridin-4-yl]phenyl]-2,3-dihydro-1,4-benzoxazepin-5-one;

8-cyclopropyl-6-fluoro-4-[5-fluoro-2-(hydroxymethyl)-3-[6-[5-[[4-(oxetan-3-ylmethyl)piperazin-1-yl]methyl]-2-pyridyl]-7H-pyrrolo[2,3-d]pyrimidin-4-yl]phenyl]-2,3-dihydro-1,4-benzoxazepin-5-one;

1-[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]benzoyl]piperidine-4-carbonitrile;

4-[3-[6-[4-(4-aminopiperidine-1-carbonyl)phenyl]-7H-pyrrolo[2,3-d]pyrimidin-4-yl]-2-methyl-phenyl]-8-cyclopropyl-2,3-dihydro-1,4-benzoxazepin-5-one;

4-[3-[6-[4-(3-aminopiperidine-1-carbonyl)phenyl]-7H-pyrrolo[2,3-d]pyrimidin-4-yl]-2-methyl-phenyl]-8-cyclopropyl-2,3-dihydro-1,4-benzoxazepin-5-one;

8-cyclopropyl-4-[2-methyl-3-[6-[4-(3-oxopiperazine-1-carbonyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-(4-methyl-3-oxo-piperazine-1-carbonyl)phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-[(4-methyl-3-oxo-piperazin-1-yl)methyl]phenyl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-[(3-oxopiperazin-1-yl)methyl]phenyl]-7H-pyrrolo[2,3-d]pyrimidin-4-yl]phenyl]-2,3-dihydro-1,4-benzoxazepin-5-one;

1-[[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]phenyl]methyl]piperidine-4-carbonitrile;

1-[[4-[4-[3-(8-cyclopropyl-5-oxo-2,3-dihydro-1,4-benzoxazepin-4-yl)-2-methyl-phenyl]-7H-pyrrolo[2,3-d]pyrimidin-6-yl]phenyl]methyl]piperidine-3-carbonitrile;

2-[1-[4-[2-methyl-3-[6-[4-[(4-methylpiperazin-1-yl)methyl]phenyl]-7H-pyrrolo[2,3-d]pyrimidin-4-yl]phenyl]-5-oxo-2,3-dihydro-1,4-benzoxazepin-8-yl]cyclopropyl]acetic acid;

2-[1-[4-[2-methyl-3-[6-[4-(4-methylpiperazine-1-carbonyl)phenyl]-7H-pyrrolo[2,3-d]pyrimidin-4-yl]phenyl]-5-oxo-2,3-dihydro-1,4-benzoxazepin-8-yl]cyclopropyl]acetic acid;

8-cyclopropyl-4-[2-methyl-3-[6-[5-methyl-1-[(1-methyl-2-oxo-4-piperidyl)methyl]imidazol-4-yl]-7H-pyrrolo[2,3-d]pyrimidin-4-yl]phenyl]-2,3-dihydro-1,4-benzoxazepin-5-one;

8-cyclopropyl-4-[2-methyl-3-[6-[4-[(3-methyl-3,8-diazabicyclo[3.2.1]octan-8-yl)methyl]phenyl]-7H-pyrrolo[2,3-d]pyrimidin-4-yl]phenyl]-2,3-dihydro-1,4-benzoxazepin-5-one;

8-cyclopropyl-4-[3-[6-[4-[[4-(2-hydroxyethyl)piperazin-1-yl]methyl]phenyl]-7H-pyrrolo[2,3-d]pyrimidin-4-yl]-2-methyl-phenyl]-2,3-dihydro-1,4-benzoxazepin-5-one;

4-[3-[6-[4-(3-azabicyclo[3.3.2]decan-3-ylmethyl)phenyl]-7H-pyrrolo[2,3-d]pyrimidin-4-yl]-2-methyl-phenyl]-8-cyclopropyl-2,3-dihydro-1,4-benzoxazepin-5-one;

8-cyclopropyl-4-[2-methyl-3-[6-[5-(5-methyl-2,5-diazabicyclo[2.2.1]heptan-2-yl)-2-pyridyl]-7H-pyrrolo[2,3-d]pyrimidin-4-yl]phenyl]-2,3-dihydro-1,4-benzoxazepin-5-one;

8-cyclopropyl-4-[3-[6-[1-(1-ethyl-4-piperidyl)-3,6-dihydro-2H-pyridin-4-yl]-7H-pyrrolo[2,3-d]pyrimidin-4-yl]-2-(hydroxymethyl)phenyl]-2,3-dihydro-1,4-benzoxazepin-5-one;

8-cyclopropyl-4-[2-(hydroxymethyl)-3-[6-[5-(1-methyl-4-piperidyl)-2-pyridyl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[6-[5-(1-methyl-3-piperidyl)-2-pyridyl]-7H-pyrrolo[2,3-d]pyrimidin-4-yl]phenyl]-2,3-dihydro-1,4-benzoxazepin-5-one;

8-Cyclopropyl-6-fluoro-4-[3-[2-[1-(2-hydroxyethyl)-3,6-dihydro-2H-pyridin-4-yl]-1H-pyrrolo[2,3-b]pyridin-4-yl]-2-(hydroxymethyl)phenyl]-2,3-dihydro-1,4-benzoxazepin-5-one;

8-cyclopropyl-6-fluoro-4-[2-(hydroxymethyl)-3-[2-(1-methylsulfonyl-3,6-dihydro-2H-pyridin-4-yl)-1H-pyrrolo[2,3-b]pyridin-4-yl]phenyl]-2,3-dihydro-1,4-benzoxazepin-5-one;

8-cyclopropyl-6-fluoro-4-[3-[6-[1-(3-hydroxyazetidine-1-carbonyl)-3,6-dihydro-2H-pyridin-4-yl]-7H-pyrrolo[2,3-d]pyrimidin-4-yl]-2-(hydroxymethyl)phenyl]-2,3-dihydro-1,4-benzoxazepin-5-one;

4-[4-[3-[8-(1-fluorocyclopropyl)-5-oxo-2,3-dihydro-1,4-benzoxazepin-4-yl]-2-(hydroxymethyl)phenyl]-1H-pyrrolo[2,3-b]pyridin-2-yl]-N,N-dimethyl-3,6-dihydro-2H-pyridine-1-carboxamide;

4-[4-[3-[8-(1-hydroxycyclopropyl)-5-oxo-2,3-dihydro-1,4-benzoxazepin-4-yl]-2-(hydroxymethyl)phenyl]-1H-pyrrolo[2,3-b]pyridin-2-yl]-N,N-dimethyl-3,6-dihydro-2H-pyridine-1-carboxamide;

8-(1-hydroxy-1-methyl-ethyl)-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[5-(4-hydroxy-4-methyl-piperidine-1-carbonyl)-2-pyridyl]-1H-pyrrolo[2,3-b]pyridin-4-yl]phenyl]-2,3-dihydro-1H-1,4-benzodiazepin-5-one;

8-cyclopropyl-4-[3-[2-[5-[(2,4-dimethylpiperazin-1-yl)methyl]-2-pyridyl]-1H-pyrrolo[2,3-b]pyridin-4-yl]-2-(hydroxymethyl)phenyl]-6-fluoro-2,3-dihydro-1,4-benzoxazepin-5-one;

8-cyclopropyl-4-[3-[2-[5-[(2,4-dimethylpiperazin-1-yl)methyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

8-cyclopropyl-4-[3-[2-[5-[1-(3,4-dimethylpiperazin-1-yl)ethyl]-2-pyridyl]-1H-pyrrolo[2,3-b]pyridin-4-yl]-5-fluoro-2-(hydroxymethyl)phenyl]-6-fluoro-2,3-dihydro-1,4-benzoxazepin-5-one;

6-fluoro-8-(1-hydroxycyclopropyl)-4-[2-(hydroxymethyl)-3-[2-[5-(4-methylpiperazin-1-yl)-2-pyridyl]-1H-pyrrolo[2,3-b]pyridin-4-yl]phenyl]-2,3-dihydro-1,4-benzoxazepin-5-one;

6-fluoro-8-(1-hydroxy-1-methyl-ethyl)-4-[2-(hydroxymethyl)-3-[2-[5-(4-methylpiperazin-1-yl)-2-pyridyl]-1H-pyrrolo[2,3-b]pyridin-4-yl]phenyl]-2,3-dihydro-1,4-benzoxazepin-5-one;

8-cyclopropyl-4-[2-(hydroxymethyl)-3-[6-[1-(oxetan-3-yl)imidazol-4-yl]-7H-pyrrolo[2,3-d]pyrimidin-4-yl]phenyl]-2,3-dihydro-1,4-benzoxazepin-5-one;

8-cyclopropyl-4-[2-(hydroxymethyl)-3-[2-[1-(oxetan-3-yl)imidazol-4-yl]-1H-pyrrolo[2,3-b]pyridin-4-yl]phenyl]-2,3-dihydro-1,4-benzoxazepin-5-one;

8-(1-hydroxy-1-methyl-ethyl)-4-[2-(hydroxymethyl)-3-[2-[1-(oxetan-3-yl)imidazol-4-yl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[1-(oxetan-3-yl)imidazol-4-yl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[6-[1-(oxetan-3-yl)imidazol-4-yl]-7H-pyrrolo[2,3-d]pyrimidin-4-yl]phenyl]-2,3-dihydro-1,4-benzoxazepin-5-one;

6-fluoro-8-(1-hydroxy-1-methyl-ethyl)-4-[2-(hydroxymethyl)-3-[6-[1-(oxetan-3-yl)imidazol-4-yl]-7H-pyrrolo[2,3-d]pyrimidin-4-yl]phenyl]-2,3-dihydro-1,4-benzoxazepin-5-one;

8-cyclopropyl-6-fluoro-4-[2-(hydroxymethyl)-3-[2-(1-tetrahydropyran-4-ylimidazol-4-yl)-1H-pyrrolo[2,3-b]pyridin-4-yl]phenyl]-2,3-dihydro-1,4-benzoxazepin-5-one;

6-fluoro-8-(1-hydroxy-1-methyl-ethyl)-4-[2-(hydroxymethyl)-3-[2-[1-(3-hydroxy-3-methyl-azetidine-1-carbonyl)-3,6-dihydro-2H-pyridin-4-yl]-1H-pyrrolo[2,3-b]pyridin-4-yl]phenyl]-2,3-dihydro-1,4-benzoxazepin-5-one;

8-cyclopropyl-6-fluoro-4-[2-(hydroxymethyl)-3-[2-[1-(3,3,3-trifluoropropanoyl)-3,6-dihydro-2H-pyridin-4-yl]-1H-pyrrolo[2,3-b]pyridin-4-yl]phenyl]-2,3-dihydro-1,4-benzoxazepin-5-one;

6-fluoro-8-(1-hydroxy-1-methyl-ethyl)-4-[2-(hydroxymethyl)-3-[2-[1-(3,3,3-trifluoropropanoyl)-3,6-dihydro-2H-pyridin-4-yl]-1H-pyrrolo[2,3-b]pyridin-4-yl]phenyl]-2,3-dihydro-1,4-benzoxazepin-5-one;

4-[4-[2-(8-cyclopropyl-6-fluoro-5-oxo-2,3-dihydro-1,4-benzoxazepin-4-yl)-3-(hydroxymethyl)-4-pyridyl]-1H-pyrrolo[2,3-b]pyridin-2-yl]-N,N-dimethyl-3,6-dihydro-2H-pyridine-1-carboxamide;

4-[4-[5-fluoro-3-[6-fluoro-8-(1-hydroxy-1-methyl-ethyl)-5-oxo-2,3-dihydro-1,4-benzoxazepin-4-yl]-2-(hydroxymethyl)phenyl]-1H-pyrrolo[2,3-b]pyridin-2-yl]-N,N-dimethyl-3,6-dihydro-2H-pyridine-1-carboxamide;

4-[3-[2-[1-(azetidine-1-carbonyl)-3,6-dihydro-2H-pyridin-4-yl]-1H-pyrrolo[2,3-b]pyridin-4-yl]-5-fluoro-2-(hydroxymethyl)phenyl]-8-cyclopropyl-6-fluoro-2,3-dihydro-1,4-benzoxazepin-5-one;

3-[4-[4-[5-fluoro-3-[6-fluoro-8-(1-hydroxy-1-methyl-ethyl)-5-oxo-2,3-dihydro-1,4-benzoxazepin-4-yl]-2-(hydroxymethyl)phenyl]-1H-pyrrolo[2,3-b]pyridin-2-yl]-3,6-dihydro-2H-pyridin-1-yl]-3-oxo-propanenitrile; and 3-[4-[4-[3-(8-cyclopropyl-6-fluoro-5-oxo-2,3-dihydro-1,4-benzoxazepin-4-yl)-5-fluoro-2-(hydroxymethyl)phenyl]-1H-pyrrolo[2,3-b]pyridin-2-yl]-3,6-dihydro-2H-pyridin-1-yl]-3-oxo-propanenitrile.

5. A process of preparation of a compounds of formula (I) according to claim 1 comprising the step of,
reacting a compound of formula II

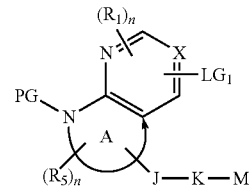

with a compound of formula III

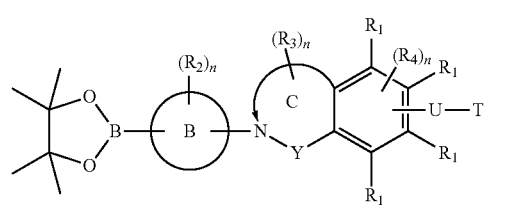

to form the compound of formula (I),
wherein,
PG is selected from the group consisting of H, tosyl, [2-(Trimethylsilyl)ethoxy]methyl acetal (SEM), and 2-Methoxyethoxymethyl ether (MEM);
LG1 is halogen or triflate; and
A, B, C, X, Y, J, K, M, U, T, $R_1$, $R_2$, $R_3$, $R_4$, $R_5$ and n are each as defined in claim 1.

6. A pharmaceutical composition comprising at least one compound of formula (I) according to claim 1 and one or more pharmaceutically acceptable excipients.

* * * * *